US011667699B2

(12) United States Patent
Sun et al.

(10) Patent No.: US 11,667,699 B2
(45) Date of Patent: Jun. 6, 2023

(54) ANTI-MS4A4A ANTIBODIES AND METHODS OF USE THEREOF

(71) Applicant: Alector LLC, South San Francisco, CA (US)

(72) Inventors: Jeonghoon Sun, San Francisco, CA (US); Wei-Hsien Ho, Belmont, CA (US); Muhammad A. Alhawagri, San Francisco, CA (US); Philip Ling Kong, San Francisco, CA (US); Herve Rhinn, San Francisco, CA (US); Hua Long, San Carlos, CA (US); Karpagam Srinivasan, San Jose, CA (US); Ananya Mitra, Menlo Park, CA (US); Daniel P. Bermingham, San Francisco, CA (US); Klaus-Dieter Heger, San Mateo, CA (US); Santiago Viveros Salazar, San Carlos, CA (US); Francesca Cignarella, South San Francisco, CA (US); Ilaria Tassi, San Francisco, CA (US); Tina Schwabe, San Francisco, CA (US); Angie Grace Yee, San Francisco, CA (US); Arnon Rosenthal, Woodside, CA (US)

(73) Assignee: Alector LLC, South San Francisco, CA (US)

( * ) Notice: Subject to any disclaimer, the term of this patent is extended or adjusted under 35 U.S.C. 154(b) by 0 days.

(21) Appl. No.: 16/943,123

(22) Filed: Jul. 30, 2020

(65) Prior Publication Data
US 2021/0079074 A1 Mar. 18, 2021

Related U.S. Application Data

(60) Provisional application No. 63/057,142, filed on Jul. 27, 2020, provisional application No. 62/960,606, filed on Jan. 13, 2020, provisional application No. 62/947,449, filed on Dec. 12, 2019, provisional application No. 62/892,467, filed on Aug. 27, 2019, provisional application No. 62/881,187, filed on Jul. 31, 2019.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/31* (2013.01); *C07K 2317/34* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| 2009/0011409 A1 | 1/2009 | Sharma et al. |
| 2016/0376359 A1 | 12/2016 | Wang et al. |
| 2017/0355756 A1* | 12/2017 | Julien ............... A61P 21/02 |
| 2021/0040200 A1 | 2/2021 | Kong et al. |
| 2021/0122817 A1 | 4/2021 | Kong et al. |

FOREIGN PATENT DOCUMENTS

| CN | 105759057 A | 7/2016 |
| WO | WO-02062946 A2 | 8/2002 |
| WO | WO 2008068048 * | 6/2008 |
| WO | WO-2017143036 A1 | 8/2017 |
| WO | WO-2019152706 A1 | 8/2019 |
| WO | WO-2019152715 A1 | 8/2019 |
| WO | WO-2021022083 A2 | 2/2021 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Reitz "Toward precision medicine in Alzheimer's disease" Ann Transl Med 2016;4(6):107 (Year: 2016).*
Stanford "Alzheimer's Prevention, Treatment and Research—A Q&A with Dr. Frank Longo" accessed from stanfordhealthcare.org on May 3, 2016 (Year: 2016).*
Al-Shawi, R., et al., "Neurotoxic and Neurotrophic Roles of ProNGF and the Receptor Sortilin in the Adult and Ageing Nervous System," *European Journal of Neuroscience* 28(9):2103-2114, Wiley-Blackwell Publishing Ltd., United Kingdom (Dec. 2008).
Allen, M., et al., "Novel late-onset Alzheimer disease loci variants associate with brain gene expression," *Neurology* 79(3):221-228, Lippincott Williams and Wilkins Ltd., United States (Jul. 2012).
Antúnez, C., et al., "The membrane-spanning 4-domains, subfamily A (*MS4A*) gene cluster contains a common variant associated with Alzheimer's disease," *Genome Medicine* 3:33, BioMed Central Ltd., United Kingdom (May 2011).
Arnett, M.J., et al., "Pro-NGF, Sortilin, and p75$^{NTR}$: Potential Mediators of Injury-induced Apoptosis in the Mouse Dorsal Root Ganglion," *Brain Research* 1183:32-42, Elsevier, Netherlands (Dec. 2007).
Barber, R.C., "The Genetics of Alzheimer's Disease," *Scientifica (Cairo)* 2012:246210, 14 pages, Hindawi Publishing Corporation, Egypt (Dec. 2012).

(Continued)

*Primary Examiner* — Adam Weidner
(74) *Attorney, Agent, or Firm* — Sterne, Kessler, Goldstein & Fox P.L.L.C

(57) ABSTRACT

The present disclosure is generally directed to compositions that include antibodies, e.g., monoclonal antibodies, humanized antibodies and antibody fragments, that specifically bind a MS4A4A polypeptide, e.g., a mammalian MS4A4A or human MS4A4A, and use of such compositions in preventing, reducing risk, or treating an individual in need thereof.

93 Claims, 50 Drawing Sheets

Specification includes a Sequence Listing.

(56) References Cited

OTHER PUBLICATIONS

Beattie, M.S., et al., "ProNGF Induces p75-mediated Death of Oligodendrocytes Following Spinal Cord Injury," *Neuron* 36(3):375-386, Cell Press, United States (Oct. 2002).

Bubien, J.K., et al., "Transfection of the CD20 Cell Surface Molecule Into Ectopic Cell Types Generates a $Ca^{2+}$Conductance Found Constitutively in B Lymphocytes," *The Journal of Cell Biology* 121(5):1121-1132, Rockefeller University Press, United States (Jun. 1993).

Cruse, G., et al., "The CD20 Homologue MS4A4 Directs Trafficking of KIT Toward Clathrin-independent Endocytosis Pathways and Thus Regulates Receptor Signaling and Recycling," *Molecular Biology of the Cell* 26(9):1711-1727, American Society for Cell Biology, United States (May 2015).

Deming, Y., et al., "The *MS4A* gene cluster is a key regulator of soluble TREM2 and Alzheimer disease risk," *Science Translational Medicine* 11(505):eaau2291, 34 pages, American Association for the Advancement of Science, United States (Aug. 14, 2019).

Denardo, D.G., et al., "Leukocyte Complexity Predicts Breast Cancer Survival and Functionally Regulates Response to Chemotherapy," *Cancer Discovery I* (1):54-67, American Association for Cancer Research, United States (Jun. 2011).

Drake, A.W., and Klakamp, S.L., "A Rigorous Multiple Independent Binding Site Model for Determining Cell-based Equilibrium Dissociation Constants," *Journal of Immunological Methods* 318(1-2):147-152, Elsevier, Netherlands (Jan. 2007).

Efthymiou, A.G., and Goate, A.M., "Late Onset Alzheimer's Disease Genetics Implicates Microglial Pathways in Disease Risk," *Molecular Neurodegeneration* 12:A3, BioMed Central Ltd., United Kingdom (May 2017).

Elias-Sonnenschein, L.S., et al., "Genetic loci associated with Alzheimer's disease and cerebrospinal fluid biomarkers in a Finnish case-control cohort," *PLoS One* 8(4):e59676, 9 pages, Public Library of Science, United States (Apr. 2013).

Engle, S.J., et al., "Best Practices For Translational Disease Modeling Using Human iPSC-derived Neurons," *Neuron* 100(4):783-797, Cell Press, United States (Nov. 2018).

Fahnestock, M., et al., "The Precursor Pro-nerve Growth Factor is the Predominant Form of Nerve Growth Factor in Brain and is Increased in Alzheimer's Disease," *Molecular and Cellular Neuroscience* 18(2):210-220, Academic Press, United States (Aug. 2001).

Fan, Y.J., et al., "Differential Effects of Pro-BDNF on Sensory Neurons After Sciatic Nerve Transection in Neonatal Rats," *European Journal of Neuroscience* 27(9):2380-2390, Wiley-Blackwell, France (May 2008).

Greer, P.L., et al., "A Family of Non-GPCR Chemosensors Defines an Alternative Logic for Mammalian Olfaction," *Cell* 165(7):1734-1748, Cell Press, United States (Jun. 2016).

Harrington, A.W., et al., "Secreted ProNGF is a Pathophysiological Death-inducing Ligand After Adult CNS Injury," *Proceedings of the National Academy of Sciences of the United States of America* 101(16):6226-6230, National Academy of Sciences, United States (Apr. 2004).

Hollingworth, P., et al., "Common Variants at *ABCA7, MS4A6A/ MS4A4E, EPHA1, CD33* and *CD2AP* are Associated With Alzheimer's Disease," *Nature Genetics* 43(5):429-435, Nature Publishing Group, United Kingdom (May 2011).

Idusogie, E.E., et al., "Mapping of the C1q Binding Site on Rituxan, A Chimeric Antibody with a Human IgG1 Fc," *The Journal of Immunology* 164(8):4178-4184, American Association of Immunologists, United States (2000).

Ishibashi, K., et al., "Identification of a New Multigene Four-transmembrane Family (MS4A) Related to CD20, HTm4 and β Subunit of the High-affinity IgE Receptor," *Gene* 264(1):87-93, Elsevier, Netherlands (Feb. 2001).

International Search Report and Written Opinion for Application No. PCT/US2019/016156, European Patent Office, Netherlands, dated Apr. 23, 2019, 13 pages.

Jansen, P., et al., "Roles for the Pro-neurotrophin Receptor Sortilin in Neuronal Development, Aging and Brain Injury," *Nature Neuroscience* 10(11):1449-1457, Nature Publishing Group, United Kingdom (Nov. 2007).

Karch, C.M., et al., "Expression of novel Alzheimer's disease risk genes in control and Alzheimer's disease brains," *PLoS One* 7(11):e50976, Public Library of Science, United States (Nov. 2012).

Karch, C.M., et al., "Alzheimer's disease risk genes and mechanisms of disease pathogenesis," *Biol Psychiatry* 77(1):43-51, Elsevier Inc., Netherlands (Jan. 2015).

Kay, B.K., et al., "The Importance of Being Proline: the Interaction of Proline-rich Motifs in Signaling Proteins With Their Cognate Domains," *FASEB* 14(2):231-241, The Federation of American Societies for Experimental Biology, United States (Feb. 2000).

Koslowski, M., et al., "MS4A12 is a Colon-selective Store-operated Calcium Channel Promoting Malignant Cell Processes," *Cancer Research* 68(9):3458-3466, American Association for Cancer Research, United States (May 2008).

Kuek, L.E., et al., "The MS4A family: counting past 1, 2 and 3," *Immunology and Cell Biology* 94:11-23, American Society for Immunology Inc., United States (Apr. 2015).

Lambert, J.C., et al., "Meta-analysis of 74,046 Individuals Identifies 11 New Susceptibility Loci for Alzheimer's Disease," *Nature Genetics* 45(12):1452-1458, Nature Publishing Group, United Kingdom (Dec. 2013).

Liang, Y., and Tedder, T.F., "Identification of a CD20-, FcεRIβ-, and HTm4-related Gene Family: Sixteen New MS4A Family Members Expressed in Human and Mouse," *Genomics* 72(2):119-127, Academic Press, United States (Mar. 2001).

Liang, C.C., et al., "In Vitro Scratch Assay: a Convenient and Inexpensive Method for Analysis of Cell Migration in Vitro" *Nature Protocols* 2(2):329-333, Nature Publishing Group, United Kingdom (2007).

Ma, J., et al., "MS4A6A genotypes are associated with the atrophy rates of Alzheimer's disease related brain structures," *Oncotarget* 7(37):58779-58788, Impact Journals LLC, United States (Sep. 2016).

Murthy, M.N., et al., "Increased Brain Expression of *GPNMB* is Associated with Genome Wide Significant Risk for Parkinson's Disease on Chromosome 7p15.3," *Neurogenetics* 18(3):121-133, Springer-Verlag, Germany (Jul. 2017).

Naj, A.C., et al., "Common Variants at *MS4A4/MS4A6E, CD2AP, CD33* and *EPHA1* are Associated With Late-onset Alzheimer's Disease," *Nature Genetics* 43(5):436-441, Nature Publishing Group, United Kingdom (May 2011).

Nakamura, K., et al., "Intracellular Sortilin Expression Pattern Regulates ProNGF-induced Naturally Occurring Cell Death During Development," *Cell Death and Differentiation* 74(8):1552-1554, Nature Publishing Group, United Kingdom (Aug. 2007).

Nykjaer, A., et al., "Sortilin is Essential for ProNGF-induced Neuronal Cell Death," *Nature* 427(6977):843-848, Nature Publishing Group, United Kingdom (Feb. 2004).

Nykjaer, A., et al., "P75$^{NTR}$ —Live or Let Die," *Current Opinion in Neurobiology* 15(1):49-57, Elsevier Ltd., Netherlands (Feb. 2005).

Peng, X., et al., "Preclinical Evaluation of 3D185, a Novel Potent Inhibitor of FGFR1/2/3 and CSF-1R, in FGFR-Dependent and Macrophage-Dominant Cancer models," *Journal of Experimental & Clinical Cancer Research* 38(1):372, BioMed Central, United Kingdom (Aug. 2019).

Piccio, L., et al., "Cerebrospinal Fluid Soluble TREM2 is Higher in Alzheimer Disease and Associated With Mutation Status," *Acta Neuropathologica* 131(6):925-933, Springer Verlag, Germany (Jun. 2016).

Pocock, J.M., et al., "Modelling Microglial Function With Induced Pluripotent Stem Cells: An Update," *Nature Reviews Neuroscience* 19(8):445-452, Nature Publishing Group, United Kingdom (Aug. 2018).

Provenzano, M.J., et al., "P75NTR and Sortilin Increase After Facial Nerve Injury," *Laryngoscope* 118(1):87-93, Wiley-Blackwell, United States (Jan. 2008).

(56) References Cited

OTHER PUBLICATIONS

Salimi, A., et al., "Comparison of Different Protocols For Neural Differentiation of Human Induced Pluripotent Stem Cells," *Molecular Biology Reports* 41(3):1713-1721, Springer, Netherlands (Mar. 2014).

Sanyal, R., et al., "MS4A4A: a novel cell surface marker for M2 macrophages and plasma cells," *Immunology and Cell Biology* 95(7):611-619, American Society for Immunology Inc., United States (Apr. 2017).

Shang, L., et al., "Selective Antibody Intervention of Toll-like Receptor 4 Activation through Fc γ Receptor Tethering," *The Journal of Biological Chemistry* 289(22):15309-15318, American Society for Biochemistry and Molecular Biology, United States (May 2014).

Tcw, J., et al., "An Efficient Platform for Astrocyte Differentiation From Human Induced Pluripotent Stem Cells," *Stem Cell Reports* 9(2):600-614, Cell Press, United States (Aug. 2017).

Teng, H.K., et al., "ProBDNF Induces Neuronal Apoptosis via Activation of a Receptor Complex of $P75^{NTR}$ and Sortilin," *The Journal of Neuroscience* 25(22):5455-5463, Society for Neuroscience, United States (Jun. 2005).

Thornton, P., et al., "TREM2 shedding by cleavage at the H157-S158 bond is accelerated for the Alzheimer's disease-associated H157Y variant," *EMBO Mol Med* 9:1366-1378, Wiley-Blackwell, United Kingdom (Oct. 2017).

Volosin, M., et al., "Interaction of Survival and Death Signaling in Basal Forebrain Neurons: Roles of Neurotrophins and Proneurotrophins," *The Journal of Neuroscience* 26(29):7756-7766, Society for Neuroscience, United States (Jul. 2006).

Volosin, M., et al., "Induction of Proneurotrophins and Activation of $P75^{NTR}$—mediated Apoptosis via Neurotrophin Receptor—interacting Factor in Hippocampal Neurons After Seizures," *The Journal of Neuroscience* 28(39):9870-9879, Society for Neuroscience, United States (Sep. 2008).

U.S. Appl. No. 16/943,123, inventors Sun J., et al., filed Jul. 30, 2020 (Not Published).

Co-pending, U.S. Appl. No. 16/965,675, inventors Kong, P., et al., International filing date: Jan. 31, 2019 (Not Published).

Koeing, P., et al., "Mutational landscape of antibody variable domains reveals a switch modulating the interdomain conformational dynamics and antigen binding," *PNAS* 114(4):E486-E496, National Academy of Sciences, United States (2017).

International Search Report and Written Opinion dated Jan. 28, 2021, in Application No. PCT/US2020/044335, EPO, Netherlands, 15 pages.

International Search Report and Written Opinion dated May 30, 2019, in Application No. PCT/US2019/016141, Korean Intellectual Property Office, Korea, 11 pages.

Proitsi, P., et al., "Alzheimer's disease susceptibility variants in the MS4A6A gene are associated with altered levels of MS4A6A expression in blood," Neurobiology of Aging 35:279-290, Elsevier, Netherlands (Sep. 2013).

Puri, M., et al., "The Evaluation of MS4A4A and MS4A8B Expression in Hematopoietic Cells," retrieved from: https://prism.ucalgary.ca/bitstream/handle/11023/1791/ucalgary2014purmandip.pdf;jsessionid=cda23b615634fb7f5836e43810707090?sequence=2, retrieved Oct. 21, 2020, Thesis, 160 pages (Sep. 2014).

Tomay, F., "Regulation and function of the tetraspanin-like molecule MS4A4A in alternatively activated and tumor-associated macrophages," XP055578452, Retrieved from the Internet: https://air.unimi.it/retrieve/handle/2434/248877/338927/phd_unimi_R09505.pdf, Thesis, Feb. 10, 2015, pp. 1-160.

Wei, Y., et al., "Enhanced Protein Expressions of Sortilin and $P75^{NTR}$ in Retina of Rat Following Elevated Intraocular Pressure-induced Retinal Ischemia," Neuroscience Letters 429(2-3):169-174, Elsevier, Ireland (Dec. 2007).

Yano, H., et al., "Proneurotrophin-3 Is a Neuronal Apoptotic Ligand: Evidence for Retrograde-Directed Cell Killing," The Journal of Neuroscience 29(47):14790-14802, Society for Neuroscience, United States (Nov. 2009).

\* cited by examiner

FIG. 1

MHQTYSRHCRPEESTFSAAMTTMQGMEQAMPGAGPGVPQLGNMAVIHSHLWKGLQEKFLKGEP
KVLGVVQILTALMSLSMGITMMCMASNTYGSNPISVYIGYTIWGSVMFIISGSLSI*AAGIRTTKG
LVRGSLGMN*ITSSVLAASGILINTFSLAFYSFHHPYCNYYGNSNNCHGTMSILMGLDGMVLLL
SVLEFCIAV*SLSAFGCKVLCCTPGGVVLILPSHSHMAETASPTPLNEV*

1P68 (SEQ ID NO:181)

MYGKLNDLLEDLQEVLKNLHKNWHGGKDNLHDVDNHLQNVIEDIHDFMQGGGSGGKLQE
MMKEFQQVLDELNNHLQGGKHTVHHIEQNIKEIFHHLEELVHR

1M6T (SEQ ID NO:182)

ADLEDNWETLNDNLKVIEKADNAAQVKDALTKMRAAALDAQKATPPKLEDKSPDSPEMKD
FRHGFDILVGQIDDALKLANEGKVKEAQAAAEQLKTTRNAYIQKYL

FIG. 3A

JS1 (SEQ ID NO:172)

MGWSCIILFLVATATGVHSMYGKLNDLLEDLQEVLKNLHKNCMASNTYGSNPISKDNLHD
VDNHLQNVIEDIHDFMQGGGSGGKLQEMMKEFQQVLDELNNHSFHHPYCNYYGNSNNCH
GTMSHTVHHIEQNIKEIFHHLEELVHRHHHHHHHHGGGLNDIFEAQKIEWHE

JS5 (SEQ ID NO:173)

MGWSCIILFLVATATGVHSADLEDNWETLNDNLKVIECMASNTYGSNPISAAQVKDALTKM
RAAALDAQKATPPKLEDKSPDSPEMKDFRHGFDILVGQIDDALKLANSFHHPYCNYYGNSN
NCHGTMSVKEAQAAAEQLKTTRNAYIQKYLHHHHHHHHGGGLNDIFEAQKIEWHE

JS6 (SEQ ID NO:174)

MGWSCIILFLVATATGVHSADLEDNWETLNDNLKVIEGPCMASNTYGSNPISAAQVKDALT
KMRAAALDAQKATPPKLEDKSPDSPEMKDFRHGFDILVGQIDDALKLANSFHHPYCNYYG
NSNNCHGTMSVKEAQAAAEQLKTTRNAYIQKYLHHHHHHHHGGGLNDIFEAQKIEWHE

FIG. 3B

JS4 (SEQ ID NO:175)

MGWSCIILFLVATATGVHSMYGKLNDLLEDLQEVLKNLHKNWHGGKDNLHDVDNHLQNVI
EDIHDFMQGGGSGGKLQEMMKEFQQVLDELNNHLQGGKHTVHHIEQNIKEIFHHLEELVHR
HHHHHHHHGGGLNDIFEAQKIEWHE

JS10 (SEQ ID NO:176)

MGWSCIILFLVATATGVHSADLEDNWETLNDNLKVIEKADNAAQVKDALTKMRAAALDAQ
KATPPKLEDKSPDSPEMKDFRHGFDILVGQIDDALKLANEGKVKEAQAAAEQLKTTRNAYIQ
KYLHHHHHHHHGGGLNDIFEAQKIEWHE

ANTI-MS4A4A ANTIBODIES AND METHODS OF USE THEREOF

CROSS-REFERENCE TO RELATED APPLICATIONS

This application claims the priority benefit of U.S. Provisional Application No. 62/881,187, filed Jul. 31, 2019, U.S. Provisional Application No. 62/892,467, filed Aug. 27, 2019, U.S. Provisional Application No. 62/947,449, filed Dec. 12, 2019, U.S. Provisional Application No. 62/960,606, filed Jan. 13, 2020, and U.S. Provisional Application No. 63/057,142, filed Jul. 27, 2020.

Submission of Sequence Listing on ASCII Text File

The content of the following submission on ASCII text file is incorporated herein by reference in its entirety: a computer readable form (CRF) of the Sequence Listing (file name: 4503_0080007_Seqlisting_ST25.TXT; date of creation: Jul. 28, 2020; size: 289,867 bytes).

FIELD OF THE PRESENT DISCLOSURE

The present disclosure relates to anti-MS4A4A antibodies and therapeutic uses of such antibodies.

BACKGROUND OF THE PRESENT DISCLOSURE

The membrane-spanning 4-domain subfamily A (MS4A) gene cluster is present on chromosome 11q12 and includes eighteen genes. The MS4A gene family encodes membrane proteins typically having tetra-spanning topology (Ishibashi et al, 2001, Gene, 265:87-93; Liang and Tedder, 2001, Genomics, 72:119-127; Efthymiou and Goate, 2017, Molecular Neurodegeneration, 12:43). The membrane spanning domains are interconnected by one intracellular loop and two extracellular loops with both N- and C-termini residing within the cytosol. Most MS4A proteins share amino acid sequence homology to that of MS4A1 (CD20) (20-30% similarity), with the highest degree of sequence identity occurring in the first three transmembrane domains. The highly conserved motifs within these transmembrane regions across different MS4A proteins suggest that the membrane spanning domains have an important general role in MS4A protein function. The regions of greatest variation between MS4A proteins occur within their N- and C-terminal cytoplasmic domains and the putative second extracellular loop (Ishibashi et al, 2001, Gene, 265:87-93), suggesting that these regions impart unique functional properties.

Despite this diversity, the MS4A domains possess some shared elements. For instance, one notable feature conserved in MS4A proteins (with the exception of MS4A8B and MS4A12) is the conservation of two cysteine residues in the putative second extracellular loop that may form a disulfide bridge. The N- and C-terminal domains of MS4A proteins are also rich in proline residues, although the functional significance of this remains to be elucidated (Hulett et al, 2001, Genomics, 72:119-127). Proline rich regions are, however, commonly involved in various cellular processes such as cytoskeletal rearrangement, initiation of transcription, signaling cascades, and association with SH3 domains as part of an adaptor system to facilitate protein-protein interactions (Kay et al, 2000, FASEB J, 14:231-241).

The MS4A protein family is relatively uncharacterized functionally, with some important exceptions: MS4A1 (CD20) is expressed exclusively in B lymphocytes, where the protein has a function in signaling by the B cell antigen receptor, and calcium influx. CD20 is the target of immunotherapeutic antibodies used to deplete pathogenic B cells in chronic lymphocytic leukemia, lymphomas, autoimmune diseases, and in solid organ transplantation. MS4A2 (FcεRβ) is a signaling subunit of the high affinity IgE receptor (FcεRI) and the low affinity IgG receptor (FcεRIII) on mast cells, having a key role in hypersensitivity and allergic reactions. MS4A2 is an ITAM-domain protein that amplifies signals through a 4-protein high affinity IgE receptor complex. MS4A3 (Htm4) is expressed on intracellular membranes of lymphoid and myeloid cells, and functions as an adaptor protein in cell cycle regulation.

While the majority of MS4A family members are uncharacterized, reports suggest MS4A proteins act as chemosensors and chemoreceptors for a variety of exogenous and endogenous ligands, including fatty acids, peptides, and sulfated steroids, and have been implicated in mediating calcium influx, regulating endocytosis, trafficking, and may act as adapters for signal transduction complexes (Cruse et al, 2015, Mol Biol Cell, 26:1711-1727; Greer et al, 2016, Cell, 165:1734-1748; Eon Kuek et al, 2016, Cell, 165:1734-1748; Koslowski et al, 2008, Cancer Res, 68:3458-3466; Bubien et al, 1993; J Cell Biol, 121:1121-1132).

Certain MS4A genes have been genetically linked to various disorders and diseases, in particular neurodegenerative disorders. For example, genome-wide significance association analyses have identified the MS4A gene cluster, located on chromosome 11q12, as one of the most significant Alzheimer's disease loci. One gene of particular interest identified is MS4A4A (Lambert et al, 2013, Nat Genet, 45:1452-1458; Hollingworth et al, 2011, Nat Genet, 43:429-435; Naj et al, 2011, Nat Genet, 43:436-441).

Accordingly, there is a need for therapies targeting MS4A4A, including antibodies that specifically bind to MS4A4A, and/or therapies that are capable of modulating (e.g., inhibiting or reducing; activating or enhancing) the activity of MS4A4A, such as by reducing or increasing MS4A4A protein levels or activity, in order to treat various diseases, disorders, and conditions associated with MS4A4A activity.

All references cited herein, including patent applications and publications, are hereby incorporated by reference in their entirety.

SUMMARY OF THE PRESENT DISCLOSURE

The present disclosure is generally directed to anti-MS4A4A antibodies and methods of using such antibodies. The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disease, disorder, or condition selected from Alzheimer's disease, late onset Alzheimer's disease, dementia, and cognitive impairment, the method including administering to the individual in need thereof a therapeutically effective amount of an anti-MS4A4A antibody. In some embodiments, the present disclosure provides a method for preventing, reducing risk, or treating an individual having a disease, disorder, or condition associated with increased expression or activity of MS4A4A, the method including administering to the individual in need thereof a therapeutically effective amount of an anti-MS4A4A antibody.

In one aspect, the present disclosure relates to an isolated antibody that binds to a MS4A4A protein, wherein the antibody includes a heavy chain variable region and a light chain variable region, wherein the heavy chain variable region includes: an HVR-H1 including an amino acid sequence selected from SEQ ID NOs:94, 108, 116, 146, 147, 308, and 311; an HVR-H2 including an amino acid sequence selected from SEQ ID NOs:96, 97, 98, 99, 110, 111, 118, 119, 120, 121, 122, 149, 150, 151, 152, 153, 309, and 312; and an HVR-H3 including an amino acid sequence selected from SEQ ID NOs:100, 101, 102, 112, 123, 124, 125, 126, 127, 128, 129, 154, 310, and 313; and the light chain variable region includes: an HVR-L1 including an amino acid sequence selected from SEQ ID NOs:103, 104, 113, 130, 131, 132, 133, 134, 135, 136, 137, 138, 156, 157, 158, 314, and 317; an HVR-L2 including an amino acid sequence selected from SEQ ID NOs:105, 106, 114, 139, 140, 141, 142, 143, 159, 160, 161, 315, and 318; and an HVR-L3 including an amino acid sequence selected from SEQ ID NOs:107, 115, 144, 145, 163, 316, and 319.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO:94; an HVR-H2 including an amino acid sequence selected from SEQ ID NOs:96-99; and an HVR-H3 including an amino acid sequence selected from SEQ ID NOs:100-102; and the light chain variable region includes: an HVR-L1 including an amino acid sequence selected from SEQ ID NOs:103-104; an HVR-L2 including an amino acid sequence selected from SEQ ID NOs:105-106; and an HVR-L3 including the amino acid sequence of SEQ ID NO:107.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO:308; an HVR-H2 including the amino acid sequence of SEQ ID NO:309; and an HVR-H3 including the amino acid sequence of SEQ ID NO:310; and the light chain variable region includes: an HVR-L1 including the amino acid sequence of SEQ ID NO:314; an HVR-L2 including the amino acid sequence of SEQ ID NO:315; and an HVR-L3 including the amino acid sequence of SEQ ID NO:316.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO:311; an HVR-H2 including the amino acid sequence of SEQ ID NO:312; and an HVR-H3 including the amino acid sequence of SEQ ID NO:313; and the light chain variable region includes: an HVR-L1 including the amino acid sequence of SEQ ID NO:317; an HVR-L2 including the amino acid sequence of SEQ ID NO:318; and an HVR-L3 including the amino acid sequence of SEQ ID NO:319.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO:108; an HVR-H2 including an amino acid sequence selected from SEQ ID NOs:110-111; and an HVR-H3 including the amino acid sequence of SEQ ID NO:112; and the light chain variable region includes: an HVR-L1 including the amino acid sequence of SEQ ID NO:113; an HVR-L2 including the amino acid sequence of SEQ ID NO:114; and an HVR-L3 including the amino acid sequence of SEQ ID NO:115.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including the amino acid sequence of SEQ ID NO:116; an HVR-H2 including an amino acid sequence selected from SEQ ID NOs:118-122; and an HVR-H3 including an amino acid sequence selected from SEQ ID NOs:123-129; and the light chain variable region includes: an HVR-L1 including an amino acid sequence selected from SEQ ID NOs:130-138; an HVR-L2 including an amino acid sequence selected from SEQ ID NOs:139-143; and an HVR-L3 including an amino acid sequence selected from SEQ ID NOs:144-145.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes: an HVR-H1 including an amino acid sequence selected from SEQ ID NOs:146-147; an HVR-H2 including an amino acid sequence selected from SEQ ID NOs:149-153; and an HVR-H3 including the amino acid sequence of SEQ ID NO:154; and the light chain variable region includes: an HVR-L1 including an amino acid sequence selected from SEQ ID NOs:156-158; an HVR-L2 including an amino acid sequence selected from SEQ ID NOs:159-161; and an HVR-L3 including the amino acid sequence of SEQ ID NO:163.

In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs:5-15, 304, and 306. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs:24-30. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs:40-53. In some embodiments that may be combined with any of the embodiments herein, an anti-MS4A4A antibody of the present disclosure is an isolated antibody that binds to a MS4A4A protein, wherein the antibody includes a heavy chain variable region, wherein the heavy chain variable region includes an amino acid sequence selected from SEQ ID NOs:76-84.

In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs:17-22, 305, and 307. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs:32-36. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs:55-74. In some embodiments that may be combined with any of the embodiments herein, an anti-MS4A4A antibody of the present disclosure is an isolated antibody that binds to a MS4A4A protein, wherein the antibody includes a light chain variable region, wherein the light chain variable region includes an amino acid sequence selected from SEQ ID NOs:86-93.

In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 5-15, 304, and 306, and the light chain variable region includes an amino acid sequence selected from SEQ ID NOs: 17-22, 305, and 307. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 24-30, and the light chain variable region includes an amino acid sequence selected from SEQ ID NOs: 32-36. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 40-53, and the light chain variable region includes an amino acid sequence selected from SEQ ID NOs: 55-74. In some embodiments that may be combined with any of the embodiments herein, an anti-MS4A4A antibody of the present disclosure is an isolated antibody that binds to a MS4A4A protein, wherein the antibody includes a heavy chain variable region and a light chain variable region, wherein the heavy chain variable region includes an amino acid sequence selected from SEQ ID NOs: 76-84, and the light chain variable region includes an amino acid sequence selected from SEQ ID NOs: 86-93.

In some embodiments that may be combined with any of the embodiments herein, an anti-MS4A4A antibody of the present disclosure is an isolated antibody that binds to a MS4A4A protein, wherein the antibody includes a heavy chain and a light chain, wherein the heavy chain includes an amino acid sequence selected from SEQ ID NOs: 320-343. In some embodiments, the heavy chain includes an amino acid sequence selected from SEQ ID NOs:336-343 (optionally wherein the light chain comprises a light chain variable region comprising the amino acid sequence of SEQ ID NO:22, further optionally wherein the light chain further comprises a constant region comprising the amino acid sequence of SEQ ID NO: 344). In some embodiments, the heavy chain includes an amino acid sequence selected from SEQ ID NOs:320-327 (optionally wherein the light chain comprises a light chain variable region comprising the amino acid sequence of SEQ ID NO:304, further optionally wherein the light chain further comprises a constant region comprising the amino acid sequence of SEQ ID NO: 344). In some embodiments, the heavy chain includes an amino acid sequence selected from SEQ ID NOs:328-335 (optionally wherein the light chain comprises a light chain variable region comprising the amino acid sequence of SEQ ID NO:305, further optionally wherein the light chain further comprises a constant region comprising the amino acid sequence of SEQ ID NO: 344).

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises an HVR-H1 comprising the amino acid sequence of SEQ ID NO:94, an HVR-H2 comprising the amino acid sequence of SEQ ID NO:96, and an HVR-H3 comprising the amino acid sequence of SEQ ID NO:102; and the light chain variable region comprises an HVR-L1 comprising the amino acid sequence of SEQ ID NO:104, an HVR-L2 comprising the amino acid sequence of SEQ ID NO:105, and an HVR-L3 comprising the amino acid sequence of SEQ ID NO:107. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO:14, and the light chain variable region comprises the amino acid sequence of SEQ ID NO:22. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 359 or 360, and the light chain comprises the amino acid sequence of SEQ ID NO:365.

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises: an HVR-H1 comprising the amino acid sequence of SEQ ID NO:308; an HVR-H2 comprising the amino acid sequence of SEQ ID NO:309; and an HVR-H3 comprising the amino acid sequence of SEQ ID NO:310; and the light chain variable region comprises: an HVR-L1 comprising the amino acid sequence of SEQ ID NO:314; an HVR-L2 comprising the amino acid sequence of SEQ ID NO:315; and an HVR-L3 comprising the amino acid sequence of SEQ ID NO:316. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO:304, and the light chain variable region comprises the amino acid sequence of SEQ ID NO:305. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 324 or 325, and the light chain comprises the amino acid sequence of SEQ ID NO:363.

In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises: an HVR-H1 comprising the amino acid sequence of SEQ ID NO:311; an HVR-H2 comprising the amino acid sequence of SEQ ID NO:312; and an HVR-H3 comprising the amino acid sequence of SEQ ID NO:313; and the light chain variable region comprises: an HVR-L1 comprising the amino acid sequence of SEQ ID NO:317; an HVR-L2 comprising the amino acid sequence of SEQ ID NO:318; and an HVR-L3 comprising the amino acid sequence of SEQ ID NO:319. In some embodiments that may be combined with any of the embodiments herein, an anti-MS4A4A antibody of the present disclosure is an isolated antibody that binds to a MS4A4A protein, wherein the antibody comprises a heavy chain variable region and a light chain variable region, wherein the heavy chain variable region comprises the amino acid sequence of SEQ ID NO:306, and the light chain variable region comprises the amino acid sequence of SEQ ID NO:307. In some embodiments that may be combined with any of the embodiments herein, an anti-MS4A4A antibody of the present disclosure is an isolated antibody that binds to a MS4A4A protein, wherein the antibody comprises a heavy chain and a light chain wherein the heavy chain comprises the amino acid sequence of SEQ ID NO: 332 or 333, and the light chain comprises the amino acid sequence of SEQ ID NO:364.

In one aspect, the present disclosure relates to an isolated antibody that binds to a MS4A4A protein, wherein the antibody competitively inhibits binding with one or more of the antibodies of any of the embodiments herein for binding to MS4A4A.

In another aspect, the present disclosure relates to an isolated antibody that binds to a MS4A4A protein, wherein the antibody binds essentially the same or an overlapping epitope on MS4A4A as the antibody of any of the embodiments herein.

In some embodiments that may be combined with any of the embodiments herein, an anti-MS4A4A antibody of the present disclosure is an isolated antibody that binds to a MS4A4A protein, wherein the antibody binds to extracellular domain 1 of human MS4A4A. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence CMASNTYGSNPIS (SEQ ID NO:177) of SEQ ID NO:1. In some embodiments that may be combined with any of the embodiments herein, an anti-MS4A4A antibody of the present disclosure is an isolated antibody that binds to a MS4A4A protein, wherein the antibody binds to extracellular domain 2 of human MS4A4A. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence SFHHPYCNYYGNSNNCHGTMS (SEQ ID NO:178) of SEQ ID NO:1. In some embodiments that may be combined with any of the embodiments herein, an anti-MS4A4A antibody of the present disclosure is an isolated antibody that binds to a MS4A4A protein, wherein the antibody binds to one or more amino acid residues within the amino acid sequence SFFIHPYCNYYGNSNNCHGTMS (SEQ ID NO:178) of SEQ ID NO:1, and further wherein the antibody does not bind to amino acid residue proline 163 (P163) of SEQ ID NO:1. In some embodiments that may be combined with any of the embodiments herein, the anti-MS4A4A antibody is a human anti-MS4A4A antibody or a humanized anti-MS4A4A antibody.

In some embodiments that may be combined with any of the embodiments herein, an anti-MS4A4A antibody of the present disclosure is an isolated antibody that binds to a MS4A4A protein, wherein the antibody decreases cell surface levels of MS4A4A or decreases intracellular levels of MS4A4A.

In certain embodiments that may be combined with any of the embodiments herein, the MS4A4A protein is a mammalian protein or a human protein. In certain embodiments that may be combined with any of the embodiments herein, the MS4A4A protein is a wild-type protein. In certain embodiments that may be combined with any of the embodiments herein, the MS4A4A protein is a naturally occurring variant.

In some embodiments that may be combined with any of the embodiments herein, an anti-MS4A4A antibody of the present disclosure increases soluble TREM2 levels, increases membrane TREM2 levels, or increases soluble TREM2 and increases membrane TREM2 levels in myeloid cells. In some embodiments that may be combined with any of the embodiments herein, an anti-MS4A4A antibody of the present disclosure increases soluble TREM2 levels. In some embodiments that may be combined with any of the embodiments herein, an anti-MS4A4A antibody of the present disclosure increases membrane TREM2 levels. In some embodiments that may be combined with any of the embodiments herein, an anti-MS4A4A antibody of the present disclosure increases soluble TREM2 levels and membrane TREM2 levels. In some embodiments that may be combined with any of the embodiments herein, an anti-MS4A4A antibody of the present disclosure increases soluble TREM2 levels in vivo. In some embodiments that may be combined with any of the embodiments herein, an anti-MS4A4A antibody of the present disclosure increases soluble TREM2 levels in serum in vivo. In some embodiments that may be combined with any of the embodiments herein, an anti-MS4A4A antibody of the present disclosure increases soluble TREM2 levels in cerebrospinal fluid (CSF) in vivo. In some embodiments that may be combined with any of the embodiments herein, an anti-MS4A4A antibody of the present disclosure increases soluble TREM2 levels in serum and in CSF in vivo.

In some embodiments that may be combined with any of the embodiments herein, an anti-MS4A4A antibody of the present disclosure reduces expression of M2 cell surface markers (e.g., receptors) on myeloid cells. In some embodiments that may be combined with any of the embodiments herein, an anti-MS4A4A antibody of the present disclosure decreases or reduces the levels of M2 cell surface markers in a myeloid cell, e.g., a macrophage.

In some embodiments that may be combined with any of the embodiments herein, an anti-MS4A4A antibody of the present disclosure reduces expression of CD200R, Dectin-1, or CD163 on myeloid cells. In some embodiments that may be combined with any of the embodiments herein, an anti-MS4A4A antibody of the present disclosure decreases or reduces cell surface levels of CD200R, Dectin-1, and/or CD163 in myeloid cells, e.g., a macrophage.

In some embodiments that may be combined with any of the embodiments herein, an anti-MS4A4A antibody of the present disclosure increases mRNA and/or protein expression of gelsolin and/or osteopontin on myeloid cells. In some embodiments that may be combined with any of the embodiments herein, an anti-MS4A4A antibody of the present disclosure increases mRNA and/or protein levels of IL1RN on myeloid cells. In some embodiments that may be combined with any of the embodiments herein, an anti-MS4A4A antibody of the present disclosure increases mRNA and/or protein levels of CSF1R on myeloid cells. In some embodiments that may be combined with any of the embodiments herein, an anti-MS4A4A antibody of the present disclosure decreases mRNA and/or protein levels of purinergic receptor P2RY12 and/or CX3C chemokine receptor 1 (CX3CR1) on myeloid cells. In some embodiments that may be combined with any of the embodiments herein, an anti-MS4A4A antibody of the present disclosure increases mRNA and/or protein levels of 1-phosphotidylinositol-4,5-bisphosphate phosphodiesterase gamma-2 (PLCG2), C-type lectin domain family 7 member A (CLEC7A), inositol 1,4,5-triphosphate receptor 2 (ITPR2), and/or antigen KI-67 (MK167) on myeloid cells. In some embodiments that may be combined with any of the embodiments herein, an anti-MS4A4A antibody of the present disclosure decreases mRNA and/or protein levels of transmembrane glycoprotein NMB (GPNMB) on myeloid cells.

In one aspect, the present disclosure relates to an isolated antibody that binds to a MS4A4A protein, wherein the antibody increases mRNA and/or protein expression of gelsolin and/or osteopontin on myeloid cells. In some embodiments that may be combined with any of the embodiments herein, the myeloid cells are human macrophages. In certain embodiments that may be combined with any of the embodiments herein, the isolated antibody that binds to a MS4A4A protein is human or humanized. In certain embodiments that may be combined with any of the embodiments herein, the isolated antibody that binds to a MS4A4A protein is a human antibody, a humanized antibody, a bispecific antibody, a monoclonal antibody, a multivalent antibody, a conjugated antibody, or a chimeric antibody. In certain embodiments that may be combined with any of the embodiments herein, the isolated antibody that binds to a MS4A4A protein binds to the same epitope as an antibody selected from 4A-18, 4A-25, 4A-214, 4A-21 and 4A-202. In certain embodiments that may be combined with any of the embodiments herein, the isolated antibody that binds to a MS4A4A protein reduces expression of M2 markers on myeloid cells. In certain embodiments that may be combined with any of the embodiments herein, the myeloid cells are human macrophages. In certain embodiments that may be combined with any of the embodiments herein, the M2 markers are CD200R, Dectin-1, and/or CD163. In certain embodiments that may be combined with any of the embodiments herein, the isolated antibody that binds to a MS4A4A protein increases plasma-membrane or cell surface TREM2 on human macrophages by at least 50%, 90%, 100%, 150%, 200% or 250%. In certain embodiments that may be combined with any of the embodiments herein, the isolated antibody that binds to a MS4A4A protein increases soluble TREM2 in human macrophage supernatant by at least 15%, 20%, 25%, 30%, 40%, 50%, 60%, or 70%.

In certain embodiments that may be combined with any of the embodiments herein, the anti-MS4A4A antibody is a bispecific antibody recognizing a first antigen and a second antigen. In certain embodiments that may be combined with any of the embodiments herein, the first antigen is MS4A4A and the second antigen is an antigen facilitating transport across the blood-brain-barrier. In certain embodiments that may be combined with any of the embodiments herein, the second antigen is selected from MS4A4A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

In some embodiments that may be combined with any of the embodiments herein, the anti-MS4A4A antibody of the present disclosure is a monoclonal antibody. In some embodiments that may be combined with any of the embodiments herein, the antibody is a human antibody. In some embodiments that may be combined with any of the embodiments herein, the antibody is a humanized antibody. In some embodiments that may be combined with any of the embodiments herein, the antibody is a bispecific antibody. In some embodiments that may be combined with any of the embodiments herein, the antibody is a multivalent antibody. In some embodiments that may be combined with any of the embodiments herein, the antibody is a chimeric antibody.

In some embodiments that may be combined with any of the embodiments herein, the anti-MS4A4A antibody of the present disclosure is of the IgG class, the IgM class, or the IgA class. In some embodiments, the antibody is of the IgG class and has an IgG1, IgG2, or IgG4 isotype. In certain embodiments that may be combined with any of the embodiments herein, the antibody is an antibody fragment. In certain embodiments that may be combined with any of the embodiments herein, antibody is an antibody fragment that binds to an epitope including amino acid residues on human MS4A4A or a mammalian MS4A4A protein. In certain embodiments that may be combined with any of the embodiments herein, the antibody fragment is a Fab, Fab', Fab'-SH, F(ab')2, Fv, or scFv fragment.

In some embodiments that may be combined with any of the embodiments herein, the antibody is a bispecific antibody recognizing a first antigen and a second antigen. In some embodiments that may be combined with any of the embodiments herein, the first antigen is MS4A4A and the second antigen is:

(a) an antigen facilitating transport across the blood-brain-barrier;
(b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005;
(c) a disease-causing agent selected from disease-causing peptides or proteins or, disease-causing nucleic acids, wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;

(d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; or (e) a protein, lipid, polysaccharide, or glycolipid expressed on one or more tumor cells.

In another aspect, the present disclosure relates to an isolated nucleic acid including a nucleic acid sequence encoding the antibody of any of the preceding embodiments. In some embodiments, the present disclosure relates to a vector including the nucleic acid of any of the preceding embodiments. In some embodiments, the present disclosure relates to an isolated host cell including the vector of any of the preceding embodiments.

In another aspect, the present disclosure relates to a method of producing an antibody that binds to human MS4A4A antibody, including culturing the host cell of any of the preceding embodiments so that the anti-MS4A4A antibody is produced. In certain embodiments, the method further includes recovering the anti-MS4A4A antibody produced by the cell.

In another aspect, the present disclosure relates to a pharmaceutical composition including the antibody of any one of the preceding embodiments and a pharmaceutically acceptable carrier.

In one aspect, the present disclosure relates to a method of preventing, reducing risk, or treating an individual having a disease, disorder, or injury selected from Alzheimer's disease, late onset Alzheimer's disease, and cognitive impairment, the method including administering to an individual in need thereof a therapeutically effective amount of the antibody of any one of the preceding embodiments. In another aspect, the present disclosure relates to a method of preventing, reducing risk, or treating an individual having a disease, disorder, condition, or injury caused by or associated with over expression or increased activity of MS4A4A, the method including administering to an individual in need thereof a therapeutically effective amount of the antibody of any one of the preceding embodiments. In some embodiments of the present disclosure, the method further includes detecting levels of osteopontin, gelsolin, plasma-membrane or cell surface TREM2, and/or soluble TREM2 before and/or after the administration of the antibody.

In one aspect, the present disclosure relates to a method of preventing, reducing risk, or treating an individual having a CSF1R-deficient disease or disorder, the method including administering to an individual in need thereof a therapeutically effective amount of the antibody of any one of the preceding embodiments. In some embodiments, the CSF1R-deficient disease or disorder is adult-onset leukoencephalopathy with axonal spheroids and pigmented glia (ALSP) or hereditary diffuse leukoencephalopathy (HDLS).

Other aspects of the present disclosure relate to an isolated anti-MS4A4A antibody produced by the method of any of the preceding embodiments. Other aspects of the present disclosure relate to a pharmaceutical composition including the anti-MS4A4A antibody of any of the preceding embodiments, and a pharmaceutically acceptable carrier.

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, or 4A-450 (as shown in Table 1, Table 5, Table 30, and Table 31).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, or 4A-331 (as shown in Table 2 and Table 6).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, or 4A-381 (as shown in Table 3 and Table 7).

In another aspect, the present disclosure relates to an antibody that binds to a MS4A4A protein, wherein the antibody includes a heavy chain variable region and a light chain variable region, wherein the heavy chain variable region includes the HVR-H1, HVR-H2, and HVR-H3 of antibody 4A-382, 4A-383, 4A-384, 4A-385, 4A-386, 4A-387, 4A-388, 4A-389, or 4A-390 (as shown in Table 4 and Table 8).

In another aspect, the present disclosure relates to an antibody that binds to a MS4A4A protein, wherein the antibody includes a heavy chain variable region and a light chain variable region, wherein the light chain variable region includes the HVR-L1, HVR-L2, and HVR-L3 of antibody 4A-382, 4A-383, 4A-384, 4A-385, 4A-386, 4A-387, 4A-388, 4A-389, or 4A-390 (as shown in Table 4 and Table 8).

In another aspect, the present disclosure relates to an antibody that bind to a MS4A4A protein, wherein the antibody includes a heavy chain variable region including an HVR-H1, HVR-H2, and HVR-H3 and a light chain variable region including an HVR-L1, HVR-L2, and HVR-L3, wherein the antibody includes the HVR-H1, HVR-H2, HVR-H3, HVR-L1, HVR-L2, and HVR-L3 of antibody 4A-382, 4A-383, 4A-384, 4A-385, 4A-386, 4A-387, 4A-388, 4A-389, or 4A-390 (as shown in Table 4 and Table 8).

In certain embodiments that may be combined with any of the embodiments herein, the present disclosure relates to an antibody that binds to a MS4A4A protein, wherein the antibody increases mRNA and/or protein expression of gelsolin and/or osteopontin on myeloid cells. In some embodiments, the myeloid cells are macrophages.

In certain embodiments that may be combined with any of the embodiments herein, the anti-MS4A4A antibody binds specifically to human MS4A4A, mouse MS4A4A, cyno MS4A4A, or a combination thereof.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1 shows the primary amino acid sequence of human MS4A4A (SEQ ID NO:1). Intracellular domain are italicized, transmembrane domains are underlined, extracellular loops are bold italicized.

FIG. 3A shows the primary amino acid sequences of soluble four helix bundle scaffolds JS1, JS5, and JS6, into which the two extracellular loops of human MS4A4A were added (shown as bold underlined). FIG. 3B shows the primary amino acid sequences of soluble four helix bundle scaffolds JS4 and JS10 used as negative control variants.

FIG. 10A provides the levels (ng/mL) of sTREM2 in the serum of cynomolgus monkeys at the indicated times (hours) following administration of anti-MS4A4A antibody 4A-202 or isotype control antibody (huIgG1), both at a dose of 80 mg/kg. FIG. 10B provides the levels of sTREM2 (percent of baseline) in the serum of cynomolgus monkeys at the indicated times (hours) following administration of anti-MS4A4A antibody 4A-202 or isotype control antibody (huIgG1), both at a dose of 80 mg/kg.

FIG. 11A provides the levels (ng/mL) of sTREM2 in the CSF of cynomolgus monkeys at the indicated times (hours) following administration of anti-MS4A4A antibody 4A-202 or isotype control antibody (huIgG1), both at a dose of 80 mg/kg. FIG. 11B provides the levels of sTREM2 (percent of baseline) in the CSF of cynomolgus monkeys at the indicated times (hours) following administration of anti-MS4A4A antibody 4A-202 or isotype control antibody (huIgG1), both at a dose of 80 mg/kg.

DETAILED DESCRIPTION OF THE PRESENT DISCLOSURE

Figures 2A, 2B, 2C:
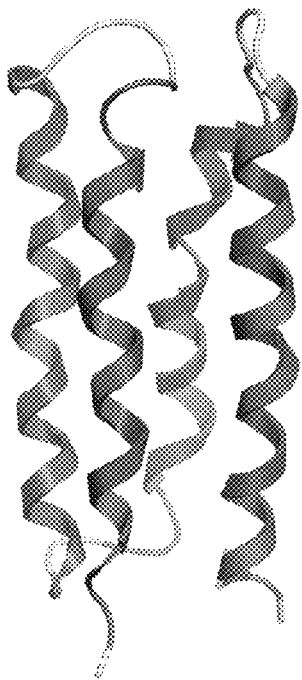
FIG. 2A shows a structure schematic of a soluble four helix bundle scaffold (PDB_ID:1P68) obtained from the RCSB Protein Data Bank having four transmembrane domains shown as helical ribbons in the structure.
FIG. 2B and FIG. 2C show the primary amino acid sequence of soluble four helix bundle scaffold PDB-ID:1P68 and PDB_ID:1M6T, respectively; the four transmembrane domains are underlined in the amino acid sequences.

The present disclosure relates to anti-MS4A4A antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "MS4A4A" or "MS4A4A polypeptide" are used interchangeably herein refer herein to any native MS4A4A from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed MS4A4A as well as any form of MS4A4A that results from processing in the cell. In some embodiments, the MS4A4A is human MS4A4A. In some embodiments, the amino acid sequence of an exemplary MS4A4A is Uniprot Accession No. Q96JQ5 as of Dec. 1, 2001. In some embodiments, the amino acid sequence of an exemplary human MS4A4A is SEQ ID NO: 1.

The terms "anti-MS4A4A antibody," an "antibody that binds to MS4A4A," and "antibody that specifically binds MS4A4A" refer to an antibody that is capable of binding MS4A4A with sufficient affinity such that the antibody is useful as a diagnostic and/or therapeutic agent in targeting MS4A4A. In one embodiment, the extent of binding of an anti-MS4A4A antibody to an unrelated, non-MS4A4A polypeptide is less than about 10% of the binding of the antibody to MS4A4A as measured, e.g., by a radioimmunoassay (RIA). In certain embodiments, an antibody that binds to MS4A4A has a dissociation constant (KD) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MS4A4A antibody binds to an epitope of MS4A4A that is conserved among MS4A4A from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Ten and Tristram G. Parslow (eds.), Appleton & Lange, Norwalk, Conn., 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody, such as an anti-MS4A4A antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MS4A4A antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MS4A4A antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MS4A4A antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-MS4A4A antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MS4A4A antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MS4A4A antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MS4A4A antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of each HVR (e.g., CDRs) correspond to those of a non-human antibody, and all or substantially all of each FR correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is an antibody, such as an anti-MS4A4A antibody of the present disclosure, possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MS4A4A antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |

-continued

| Loop | Kabat | AbM | Chothia | Contact |
|---|---|---|---|---|
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ framework sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MS4A4A antibody of the present disclosure, refers to the substitution or deletion of the specified residue, or the insertion of at least one amino acid residue adjacent the specified residue. "Adjacent" to a specified residue means insertion within one to two residues thereof. The insertion may be N-terminal or C-terminal to the specified residue. A preferred amino acid modification herein is a substitution.

An "affinity-matured" antibody, such as an affinity matured anti-MS4A4A antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., MS4A4A or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MS4A4A polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-MS4A4A antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MS4A4A antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

The terms "membrane TREM2", "plasma membrane TREM2", and "cell surface TREM2", as used herein, are used interchangeably.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-MS4A4A Antibodies

Provided herein are anti-MS4A4A antibodies. Antibodies provided herein are useful, e.g., for the diagnosis or treatment of MS4A4A-associated disorders.

In one aspect, the present disclosure provides isolated (e.g., monoclonal) antibodies that bind to an epitope within a MS4A4A protein of the present disclosure. MS4A4A proteins of the present disclosure include, without limitation, a mammalian MS4A4A protein, human MS4A4A protein, mouse MS4A4A protein, and cyno MS4A4A protein. MS4A4A proteins of the present disclosure include naturally-occurring variants of MS4A4A.

Human MS4A4A is a 239-amino acid protein that encodes a membrane glycoprotein. The amino acid sequence of human MS4A4A is set forth in SEQ ID NO:1:

```
MHQTYSRHCRPEESTFSAAMTTMQGMEQAMPGAGPGVPQLGNMAVIHSHL

WKGLQEKFLKGEPKVLGVVQILTALMSLSMGITMMCMASNTYGSNPISVY

IGYTIWGSVMFIISGSLSIAAGIRTTKGLVRGSLGMNITSSVLAASGILI

NTFSLAFYSFHHPYCNYYGNSNNCHGTMSILMGLDGMVLLLSVLEFCIAV

SLSAFGCKVLCCTPGGVVLILPSHSHMAETASPTPLNEV
```

Additionally, the amino acid sequence of mouse MS4A4A is set forth in SEQ ID NO:2:

MLVIQGTEQSALEAGYGAQQNGQPLYVNSHSWKRMTEKFLKGEPKILGIV

QIVIAIMNLSIGIMMIIATVSTGEIPPSSVYIGYPIWGSLMFIISGSFSI

VAGRRTTKGLVRSSLGLNITSSVFAFSGIVISSLSPGIYSFHVYYCTYRG

SSEGCHMTLSILMGLDIVVVVLSVLEFCIGVSLSAFGCRVMCCNPGGVMI

IMPSNPTKAETANPVTLQSGLMPPEHQERNVPENMH

Additionally, the amino acid sequence of cynomolgus (cyno) MS4A4A is set forth in SEQ ID NO:3:

HQTYRRHCRPEESTFSAAMTTMQGMEQATPGAGPGVPQLGNMAVVHSHLW

KGLQEKFLKGEPKVLGVVQILIALMSLSMGITMMCVAFSAYGHYPISVYI

GYTIWGSVMFIISGSLSIAAGIRTTKGLVRGSLGMNITSSVLAVSAILIN

TISLTIYSFYHRYCNYYGNPNNCHGTVSILMGMDGMVLLLSVLEFCIAVS

LSAFGCKAICCTPGGVVLIIPSNSHMAEAAPLTPLNEV

In some embodiments, MS4A4A is expressed in a cell. In some embodiments, MS4A4A is expressed in myeloid cells. In some embodiments, MS4A4A is expressed in brain cells. In some embodiments, MS4A4A is expressed in astrocytes, including without limitation mature astrocytes. In some embodiments, MS4A4A is expressed in oligodendrocytes. In some embodiments, MS4A4A is expressed in microglial cells. In some embodiments, MS4A4A is expressed in immune cells, including without limitation, macrophages, eosinophils, mast cells, dendritic cells, natural killer cells, neutrophils, and T cells. In some embodiment, MS4A4A is expressed in olfactory cells. In some embodiments, MS4A4A is expressed on the cell surface.

MS4A4A proteins of the present disclosure include several domains, including without limitation, a cytoplasmic domain (amino acid residues 1-64 of human MS4A4A; see SEQ ID NO:1); a transmembrane domain (amino acid residues 65-85 of human MS4A4A); an extracellular domain (extracellular domain 1; ECL1), corresponding to amino acid residues 86-98 of human MS4A4A; a transmembrane domain (amino acid residues 99-119 of human MS4A4A); a cytoplasmic domain (amino acid residues 120-137 of human MS4A4A); a transmembrane domain (amino acid residues 138-158 of human MS4A4A); an extracellular domain (extracellular domain 2; ECL2), corresponding to amino acid residues 159-179; a transmembrane domain (amino acid residues 180-200 of human MS4A4A); and a cytoplasmic domain (amino acid residues 201-239 of human MS4A4A). Additionally, MS4A4A proteins of the present disclosure are expressed in a number of tissues and cells, including without limitation, the brain, neurons, glial cells, endothelial cells, perivascular cells, pericytes, etc.

MS4A4A in Macrophage and Microglial Cell Function

Macrophages and myeloid cells of the central nervous system (CNS), such as microglia, are inherently plastic in their phenotype and function. Macrophages in vitro can be divided into M1 macrophages and M2 macrophages, which have differing phagocytic and inflammatory potentials, phenotypes, and activities. For example, in peripheral organs, macrophages having an M1 phenotype are considered to have pro-inflammatory and anti-microbial phenotype and function, while macrophages having an M2 phenotype are considered to be in a more homeostatic state, having an anti-inflammatory phenotype and function.

Microglia associated with healthy, homeostatic conditions express more M2 markers on their cell surface (e.g., CD200R, CD163 and CD115) compared to that of M1 markers (e.g., CD16, MHC Class II, CD86) (Ginhoux and Prinz, 2015, Cold Spring Harb Perspect Biol, 7:a020537). However, disease associated microglia (DAM) in both mouse models of Alzheimer's disease and in human Alzheimer's disease are in a proinflammatory or activated state. Disease associated microglia in proinflammatory or activated states are considered beneficial by playing an active role in reducing the pathology associated with Alzheimer's disease and other neurodegenerative disorders.

MS4A4A expression is elevated in M2 macrophages in vitro, and it has been suggested that MS4A4A is a novel cell surface marker for M2 macrophages. Additionally, MS4A4A has also been shown to regulate cell surface transport of cKit on mast cells, suggesting a role of MS4A4A in modulating mast cell degranulation and survival (Cruse et al, 2015, Molecular Biol Cell, 26:1711-1727). Taken together, these reported findings suggest that targeting MS4A4A may affect the recycling, expression, and/or degradation of various macrophage cell surface receptors associated with M1 and M2 macrophage phenotypes, thus affecting their functions and activities.

Anti-MS4A4A antibodies of the present disclosure affect the expression of M2 macrophage cell surface markers. In particular, anti-MS4A4A antibodies of the present disclosure reduce the cell surface expression of CD200R, Dectin-1, and CD163 in macrophages, suggesting that anti-MS4A4A antibodies modulate macrophage polarization, function, and/or activity by reducing expression of M2 macrophage cell surface receptors. Anti-MS4A4A antibodies of the present disclosure reduce M2 macrophage cell surface receptors, suggesting that anti-MS4A4A antibodies of the present disclosure are effective at altering the physiological state of microglial cells to that of a more protective phenotype, such as to a more proinflammatory or activated state (e.g., to a more M1 phenotype). Accordingly, anti-MS4A4A antibodies of the present disclosure are useful in treating Alzheimer's disease and other neurodegenerative disorders, in part, by altering the phenotype of macrophages and microglia to a proinflammatory and activated state.

Anti-MS4A4A antibodies of the present disclosure affect the activation state of microglia. Anti-MS4A4A antibodies of the present disclosure increased mRNA levels of proteins associated with microglia activation (e.g., C-type lectin domain family 7 member A (CLEC7A)), microglia migration (e.g., inositol 1,4,5-triphosphate receptor 2 (ITPR2)), and microglia proliferation (e.g., antigen KI-67 (MKI67)) in vivo. Additionally, anti-MS4A4A antibodies of the present disclosure increased mRNA levels of microglia activation markers IL1RN, SPP1, and PLCG2. Anti-MS4A4A antibodies of the present dislsoure also decreased mRNA levels of homeostatic microglia markers purinergic receptor P2RY12 and CX3C chemokine receptor 1 (CX3CR1). Accordingly, anti-MS4A4A antibodies of the present disclosure are effective at activating microglia in vivo as evidenced by increases in various mRNA levels of proteins associated with microglia activation, migration, and proliferation; and by decreases in various mRNA levels of proteins associated with microglia homeostasis.

MS4A4A and TREM2 Expression

Neurodegenerative diseases are characterized, in part, by defective immune function in the central nervous system (CNS). For example, a decrease in viability and function in the CNS myeloid cell compartment, including but not restricted to microglia, is thought to contribute to susceptibility to neurodegenerative disorders, such as Alzheimer's disease. Pharmacological intervention that enhances viability and/or function of myeloid cells would provide effective treatment to ameliorate the onset, severity, or progression of such neurodegenerative diseases and disorders.

Triggering receptor expressed on myeloid cells-2 (TREM2) is an immunoglobulin-like receptor that is expressed primarily on myeloid cells, such as macrophages, dendritic cells, monocytes, Langerhans cells of skin, Kupffer cells, osteoclasts, and microglia. TREM2 is highly expressed on microglia and infiltrating macrophages in the CNS during experimental autoimmune encephalomyelitis and Alzheimer's disease (Piccio et al, 2007, Eur J Immunol, 37:1290-1301; Wang, 2015, Cell, 160:1061-1071). The TREM2 pathway is considered a key modulator of CNS myeloid cell viability and function.

Data from human genetics studies have suggested strong genetic links between MS4A4A and TREM2 and with susceptibility to Alzheimer's disease (Piccio et al., 2016, Acta Neuropathol, 131:925-9330). In particular, MS4A4A alleles protective for Alzheimer's disease are linked to increased sTREM2 levels in the cerebrospinal fluid in patients.

Anti-MS4A4A antibodies of the present invention increase cellular ATP levels in macrophages, indicating that anti-MA4A4A antibodies are effective at increasing, maintaining, or enhancing cell (e.g., macrophages, myeloid cells, microglia) viability and function. Additionally, anti-MS4A4A antibodies of the present invention increased sTREM2 and mTREM2 levels in macrophages, in contrast to that previously reported in which commercially available anti-MS4A4A antibody 5C12 reduced sTREM2 levels in supernatants of cultured human macrophages (Deming et al, 2018, bioRxiv, doi: dx doi org/10.1101/352179). As MS4A4A protective alleles for Alzheimer's disease are linked to increased sTREM2 levels, the results provided herein indicated that anti-MS4A4A antibodies of the present invention mimic or replicate a protective phenotype in neurodegenerative diseases and disorders, such as Alzheimer's disease, by increasing sTREM2 and mTREM2 levels. In some embodiments, an anti-MS4A4A antibody of the present disclosure increases cell surface expression of TREM2 in myeloid cells (e.g., macrophages, human macrophages, microglia) by at least 10%, by at least 20%, by at least 25%, by at least 50%, by at least 75%, by at least 90%, by at least 100%, by at least 125%, by at least 150%, by at least 200%, or by at least 250%. In some embodiments, an anti-MS4A4A antibody of the present disclosure increases soluble TREM2 levels in myeloid cells (e.g., macrophages, human macrophages, microglia) by at least 10%, by at least 20%, by at least 30%, by at least 40%, by at least 50%, by at least 60%, by at least 70%, by at least 80%, by at least 90%, or by at least 100%.

In some embodiments, an anti-MS4A4A antibody of the present disclosure increases mTREM protein levels in myeloid cells (e.g., macrophages, human macrophages, microglia) with an EC50 of about 0.028 µg/ml to about 0.039 µg/ml. In some embodiments, an anti-MS4A4A antibody of the present disclosure increases sTREM protein levels in myeloid cells (e.g., macrophages, human macrophages, microglia) with an EC50 of about 0.025 µg/ml to about 0.069 µg/ml. In yet other embodiments, an anti-MS4A4A antibody of the present disclosure increases ATP levels in myeloid cells (e.g., macrophages, human macrophages, microglia) with an EC50 of about 0.010 µg/ml to about 0.021 µg/ml. In some embodiments, an anti-MS4A4A antibody of the present disclosure increases ATP levels in myeloid cells (e.g., macrophages, human macrophages, microglia) by about 1.2-fold, about 1.4-fold, or about 1.7-fold over the level of ATP in such cells in the absence of anti-MS4A4A antibody.

In some embodiments, an anti-MS4A4A antibody of the present disclosure increases soluble TREM2 levels in vivo (e.g., in a non-human primate or in a human). In some embodiments, an anti-MS4A4A antibody of the present disclosure increases soluble TREM2 levels in serum in vivo by at least 10%, by at least 20%, by at least 25%, by at least 50%, by at least 75%, by at least 90%, by at least 100%, by at least 125%, or by at least 150% from the baseline soluble TREM2 levels in serum in vivo prior to administration of an anti-MS4A4A antibody of the present disclosure. In some embodiments, an anti-MS4A4A antibody of the present disclosure increases soluble TREM2 levels in serum in vivo by about 50% from the baseline soluble TREM2 levels in serum in vivo prior to administration of an anti-MS4A4A antibody of the present disclosure.

In some embodiments, an anti-MS4A4A antibody of the present disclosure increases soluble TREM2 levels in serum in vivo by at least 1.1-fold, by at least 1.2-fold, by at least 1.3-fold, by at least 1.4-fold, by at least 1.5-fold, by at least 1.6-fold, by at least 1.7-fold, by at least 1.8-fold, by at least 1.9-fold, or by at least 2-fold relative to the soluble TREM2 levels in serum in vivo prior to administration of an anti-MS4A4A antibody of the present disclosure. In some embodiments, an anti-MS4A4A antibody of the present disclosure increases soluble TREM2 levels in serum in vivo by about 1.5-fold relative to the soluble TREM2 levels in serum in vivo prior to administration of an anti-MS4A4A antibody of the present disclosure.

In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 1 day, at least 2 days, at least 3 days, at least 4 days, at least 5 days, at least 6 days, at least 7 days, at least 8 days, at least 9 days, at lead 10 days, at least 11 days, at least 12 days, at least 13 days, at least 14 days, at least 15, at least 16 days, at least 17 days, at least 18 days, at least 19 days, or at least 20 days. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 20 days. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 24 hours, at least 48 hours, at least 72 hours, at least 96 hours, at least 120 hours, at least 144 hours, at least 168 hours, at least 192 hours, at least 216 hours, at least 240 hours, at least 264 hours, at least 288 hours, at least 312 hours, at least 336 hours, at least 360 hours, at least 384 hours, at least 408 hours, at 432 hours, at least 456 hours, or at least 480 hours. In some embodiments, an anti-MS4A4A antibody of the present disclosure increases soluble TREM2 levels in serum in vivo compared to the soluble TREM2 levels in serum in vivo prior to administration of an anti-MS4A4A antibody of the present disclosure for at least 480 hours.

In some embodiments, an anti-MS4A4A antibody of the present disclosure increases soluble TREM2 levels in CSF in vivo by at least 10%, by at least 20%, by at least 25%, by at least 50%, by at least 75%, by at least 90%, by at least 100%, by at least 125%, by at least 150%, by at least 200%, by at least 225%, by at least 250%, by at least 275%, by at least 300%, by at least 325%, by at least 350%, by at least 375%, or by at least 400% from the baseline soluble TREM2 levels in CSF in vivo prior to administration of an anti-MS4A4A antibody of the present disclosure. In some embodiments, an anti-MS4A4A antibody of the present disclosure increases soluble TREM2 levels in CSF in vivo by about 300% from the baseline soluble TREM2 levels in CSF in vivo prior to administration of an anti-MS4A4A antibody of the present disclosure.

In some embodiments, an anti-MS4A4A antibody of the present disclosure increases soluble TREM2 levels in CSF in vivo by at least 1.4-fold, by at least 1.6-fold, by at least 1.8-fold, by at least 2.0-fold, by at least 2.2-fold, by at least 2.4-fold, by at least 2.6-fold, by at least 2.8-fold, by at least 3.0-fold, by at least 3.2-fold, by at least 3.4-fold, by at least 3.6-fold, by at least 3.8-fold, or by at least 4.0-fold relative to the soluble TREM2 levels in CSF in vivo prior to administration of an anti-MS4A4A antibody of the present disclosure. In some embodiments, an anti-MS4A4A antibody of the present disclosure increases soluble TREM2 levels in CSF in vivo by between about 2-fold to about 4-fold relative to the soluble TREM2 levels in CSF in vivo prior to administration of an anti-MS4A4A antibody of the present disclosure.

In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 1 day, at least 2 days, at least 3 days, or at least 4 days. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 4 days. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 24 hours, at least 48 hours, at least 72 hours, or at least 96 hours. In some embodiments, an anti-MS4A4A antibody of the present disclosure increases soluble TREM2 levels in CSF in vivo compared to the soluble TREM2 levels in CSF in vivo prior to administration of an anti-MS4A4A antibody of the present disclosure for at least 96 hours.

The evidence provided herein demonstates that the anti-MS4A4A antibodies of the present disclosure affect TREM2, but does not exclude the antibodies acting through other pathways.

Antagonist Antibodies

In some embodiments, antibodies that bind a MS4A4A protein may include antagonist antibodies that bind MS4A4A inhibit one or more MS4A4A activities, either by preventing interaction between MS4A4A and its ligand(s), or by preventing the transduction of signal of MS4A4A into the cell cytoplasm in the presence of ligand. In some embodiments, antagonist antibodies of the present disclosure may have the epitope specificity of an agonist antibody of the present disclosure, but have an Fc domain that is not capable of binding Fcg receptors and thus is unable to, for example, cluster MS4A4A receptor.

In some embodiments, an antibody of the present disclosure is an antagonist antibody. In some embodiments, the antagonist antibody inhibits one or more MS4A4A activities. In some embodiments, the antagonist antibody decreases activity of one or more MS4A4A-dependent genes. In some embodiments, the antagonist antibody inhibits interaction between MS4A4A and one or more MS4A4A ligands. In some embodiments, the antagonist antibody inhibits MS4A4A signal transduction. In some embodiments, the antagonist antibody inhibits interaction between MS4A4A and one or more MS4A4A ligands and inhibits MS4A4A signal transduction.

In some embodiments, down-regulation of MS4A4A protein levels or reducing MS4A4A activity is accomplished by an anti-MS4A4A antibody that down-regulates or reduces MS4A4A protein levels in a cell. In some embodiments, down-regulation of MS4A4A protein levels or reducing MS4A4A activity is accomplished by down-regulation of MS4A4A nucleic acid expression or levels, by, e.g., use of antisense methodologies, gene therapy, etc, using methods known and available to one of skill in the art. Accordingly, in some embodiments, reducing MS4A4A protein levels or activity is accomplished with an anti-MS4A4A antibody of the present disclosure or by reducing MS4A4A nucleic acid (e.g., mRNA) expression or levels.

In some embodiments, antibody cross-linking is required for agonist antibody function. Antibody cross-linking can occur through binding to a secondary antibody in vitro or through binding to Fc receptors in vivo. For example, antagonistic antibodies can be converted to agonistic antibodies via biotin/streptavidin cross-linking or secondary antibody binding in vitro (see for example Gravestein et al., 1996, J. Exp. Med. 184:675-685; Gravestein et al., 1994, International Immunol, 7:551-557). Agonistic antibodies may exert their activity by mimicking the biological activity of the receptor ligand or by enhancing receptor aggregation, thereby activating receptor signaling. In some embodiments, the absence of antibody cross-linking is required for antagonistic activity. Antagonistic antibodies may exert their activity by blocking receptor-ligand interactions.

Gelsolin, Osteopontin, and Phenocopy of Alzheimer's Disease Protective Allele

There are three SNPs in the MS4A gene cluster that have been associated with an increased risk of late-onset Alzheimer's disease. These include rs4938933 in MS4A4A, rs670139 in MS4A4E, and rs610932 in MS4A6A (Hollingworth et al, 2011, Nat Genetics, 43:429-435; Naj et al 2011, Nature Genetics, 43:436-441; Antunez et al, 2011, Genome Medicine, 3, article 33). Additionally, MS4A4A locus SNPs (rs2304933 and rs2304935) are associated with higher levels of MS4A4A and increased Alzheimer's disease risk, including late-onset Alzheimer's disease (LOAD) (Allen et al, 2012, Neurology, 79:221-228).

Alzheimer's disease-associated genetic variants (SNPs) associated with the MS4A gene cluster have been identified. One of those variant alleles is rs1582763, which is associated with elevated CSF sTREM2 levels and with reduced Alzheimer's disease risk and delayed age-at-onset, and thus considered a protective allele. (Deming et al, 2018, bioRxiv, doi: dx doi org/10.1101/352179). The rs1582763 protective allele is associated with decreased MS4A4A mRNA levels in blood. These findings further suggest that the rs1582763 allele performs a protective role by reducing MS4A4A levels, and decreasing Alzheimer's disease risk or severity. The protective rs1582763 is associated also with increased expression levels of osteopontin and with increased levels of gelsolin. Anti-MS4A4A antibodies of the present invention are effective at phenocopying these aspects of the protective alleles, at least with respect to decreasing MS4A4A expression, increasing osteopontin expression, increasing gelsolin expression, and/or increasing sTREM levels. In some aspects of the present disclosure, anti-MS4A4A antibodies are provided wherein the antibodies phenocopy one or more alleles of MS4A that are associated with reduced Alzheimer's disease risk and/or delayed age-at-onset of Alzheimer's disease.

Anti-MS4A4A antibodies of the present disclosure increased mRNA levels of osteopontin (SPP1) and increased mRNA levels of gelsolin (GSN) in human peripheral blood mononuclear cell-derived macrophages. In some embodiments, anti-MS4A4A antibodies of the present disclosure increase mRNA and/or protein levels of osteopontin. In some embodiments, anti-MS4A4A antibodies of the present disclosure increase mRNA and/or protein levels of gelsolin. In some embodiments, an anti-MS4A4A antibody of the present disclosure increases mRNA and/or protein levels of osteopontin in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases gelsolin mRNA and/or protein levels in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%.

Anti-MS4A4A antibodies of the present disclosure increased osteopontin (SSP1) levels in non-human primates. In some embodiments, anti-MS4A4A antibodies of the present disclosure increase mRNA and/or protein levels of osteopontin in vivo (e.g., in non-human primates or in humans). In some embodiments, an anti-MS4A4A antibody of the present disclosure increases mRNA and/or protein levels of osteopontin in serum and/or in CSF. In some embodiments, an anti-MS4A4A antibody of the present disclosure increases mRNA and/or protein levels of osteopontin in serum and/or in CSF by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases protein levels of osteopontin in the brain. In some embodiments, an anti-MS4A4A antibody of the present disclosure increases protein levels of osteopontin in the frontal cortex and/or in the hippocampus.

In some embodiments, anti-MS4A4A antibodies of the present disclosure phenocopy the protective rs1582763 allele with respect to increasing expression of osteopontin and gelsolin. In other aspects, anti-MS4A4A antibodies of the present disclosure are effective at increasing expression of osteopontin, of gelsolin, and /or of sTREM2 and are biologically active in decreasing Alzhemier's disease risk and/or severity, similar to that of the protective rs1582763 allele. The data indicated that SPP1 and GSN are pharmacodynamic markers for the protective biological activity associated with the rs158273 allele.

CSFR1 and IL1RN Expression

Anti-MS4A4A antibodies of the present disclosure increased CSF1R levels in non-human primates. In some embodiments, anti-MS4A4A antibodies of the present disclosure increase mRNA and/or protein levels of CSF1R in vivo (e.g., in non-human primates or in humans). In some embodiments, an anti-MS4A4A antibody of the present disclosure increases mRNA and/or protein levels of CSF1R in serum and/or in CSF. In some embodiments, an anti-MS4A4A antibody of the present disclosure increases mRNA and/or protein levels of CSF1R in serum and/or in CSF by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%. In some embodiments, an anti-MS4A4A antibody of the present disclosure increases protein levels of CSF1R in the brain. In some embodiments, an anti-MS4A4A antibody of the present disclosure increases protein levels of CSF1R in the frontal cortex and/or in the hippocampus.

CSF1R deficiency negatively impacts the development of microglia in the brain (Swerdlow et al (2000) Neurology, 111:300-311; Baba et al (2006) Acta Neuropath, 111:300-311) and recent research has linked mutations in the CSF1R gene to various disorders, including adult-onset leukoencephalopathy with axonal spheroids and pigmented glia (ALSP) and hereditary diffuse leukoencephalopathy with spheroids (HDLS) (Oosterhof et al (2019) Am J Hum Genet, 104:936-947; Rademaker et al (2011) Nat Genet, 44:200-205; Nicholson et al (2013) Neurology, 80:1033-1040). Anti-MS4A4A antibodies of the present disclosure reduced cell death and sustained survival of human macrophages following CSF1R inhibition. Accordingly, in some embodiments, anti-MS4A4A antibodies of the present disclosure are useful for treating an individual having a CSF1R-deficient disease or disorder, such as ALSP or HDLS.

Anti-MS4A4A antibodies of the present disclosure increased IL1RN levels in human peripheral blood mononuclear cell-derived macrophages. In some embodiments, anti-MS4A4A antibodies of the present disclosure increase mRNA and/or protein levels of IL1RN. In some embodiments, anti-MS4A4A antibodies of the present disclosure increase mRNA and/or protein levels of IL1RN. In some embodiments, an anti-MS4A4A antibody of the present disclosure increases mRNA and/or protein levels of IL1RN in myeloid cells (e.g., macrophages, human macrophages, microglia) by at least 10%, by at least 20%, by at least 25%, by at least 30%, by at least 40%, by at least 50%, by at least 60%, by at least 70%, by at least 75%, by at least 80%, by at least 90%, by at least 100%, by at least 125%, by at least 150%, by at least 200%, or by at least 250%.

GPNMB Expression

GPNMB (glycoprotein nonmetastatic melanoma protein B); is a surface glycoprotein expressed in multiple cell types including tissue macrophages and microglia. Several genetic variants have been associated with Parkinson's disease (PD) risk. GPNMB protein levels are elevated in the substantia nigra of PD patients and GPNMB levels are increased following lysosomal stress (Moloney et.al., 2018, Neurobio Dis. 120: 1-11). Additionally, increased expression of GPNMB was linked to SNP rs199347, this risk SNP being located withing the GPNMB gene (Murthy et al, Neurogenetics, 2017, 18:121-133).

Anti-MS4A4A antibodies of the present disclosure reduced GPNMB cell surface protein levels in human primary macrophages. In some embodiments, an anti-MS4A4A antibody of the present disclosure decreases GPNMB cell surface protein levels in myeoid cells (e.g., macrophages, human macrophages, microglia) by at least 10%, by at least 20%, by at least 30%, by at least 40%, or by at least 50%. As increased GPNMB levels are associated with risk alleles for PD, a reduction in GPNMB following anti-MS4A4A antibody addition may provide a means for treatment of PD.

A. Exemplary Antibodies and Certain Other Antibody Embodiments

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs:94, 108, 116, 146, 147, 308, and 311, or an amino acid with at least about 95% homology to an amino acid selected from the group consisting of SEQ ID NOs:94, 108, 116, 146, 147, 308, and 311; (b) HVR-H2 comprising an amino acid sequence selected from the group consisting of SEQ ID NOs:96, 97, 98, 99, 110, 111, 118, 119, 120, 121, 122, 149, 150, 151, 152, 153, 309, and 312, or an amino acid with at least about 95% homology to an amino acid selected from the group consisting of SEQ ID NOs: 96, 97, 98, 99, 110, 111, 118, 119, 120, 121, 122, 149, 150, 151, 152, 153, 309, and 312; (c) HVR-H3 comprising an amino acid sequence selected from the group consisting of SEQ ID NOs:100, 101, 102, 112, 123, 124, 125, 126, 127, 128, 129, 154, 310, and 313, or an amino acid with at least about 95% homology to an amino acid selected from the group consisting of SEQ ID NOs: 100, 101, 102, 112, 123, 124, 125, 126, 127, 128, 129, 154, 310, and 313; (d) HVR-L1 comprising an amino acid sequence selected from the group consisting of SEQ ID NOs:103, 104, 113, 130, 131, 132, 133, 134, 135, 136, 137, 138, 156, 157, 158, 314, and 317, or an amino acid with at least about 95% homology to an amino acid selected from the group consisting of SEQ ID NOs: 103, 104, 113, 130, 131, 132, 133, 134, 135, 136, 137, 138, 156, 157, 158, 314, and 317; (e) HVR-L2 comprising an amino acid sequence selected from the group consisting of SEQ ID NOs:105, 106, 114, 139, 140, 141, 142, 143, 160, 161, 315, and 318, or an amino acid with at least about 95% homology to an amino acid selected from the group consisting of SEQ ID NOs: 105, 106, 114, 139, 140, 141, 142, 143, 160, 161, 315, and 318; and (f) HVR-L3 comprising an amino acid sequence selected from the group consisting of SEQ ID NOs:107, 115, 144, 145, 163, 316, and 319, or an amino acid with at least about 95% homology to an amino acid selected from the group consisting of SEQ ID Nos:107, 115, 144, 145, 163, 316, and 319.

In some embodiments, provided herein are anti-MS4A4A antibodies comprising at least one, two, three, four, five, or six HVRs selected from: (a) FIVR-H1 comprising the amino acid sequence selected from the group consisting of SEQ ID NO:94 and 308, or an amino acid with at least about 95% homology to the amino acid sequence selected from the group consisting of SEQ ID NO:94 and 308; (b) HVR-H2 comprising an amino acid sequence selected from the group consisting of SEQ ID NOs:96, 97, 98, 99, and 309, or an amino acid with at least about 95% homology to an amino acid selected from the group consisting of SEQ ID NOs: 96, 97, 98, 99, and 309; (c) HVR-H3 comprising an amino acid sequence selected from the group consisting of SEQ ID NOs:100, 101, 102, and 310, or an amino acid with at least about 95% homology to an amino acid selected from the group consisting of SEQ ID NOs: 100, 101, 102, and 310; (d) HVR-L1 comprising an amino acid sequence selected from the group consisting of SEQ ID NOs:103 104, and 314, or an amino acid with at least about 95% homology to an amino acid selected from the group consisting of SEQ ID NOs: 103, 104, and 314; (e) HVR-L2 comprising an amino acid sequence selected from the group consisting of SEQ ID NOs:105, 106, and 315, or an amino acid with at least about 95% homology to an amino acid selected from the group consisting of SEQ ID NOs: 105, 106, and 315; and (f) HVR-L3 comprising the amino acid sequence selected from the group consisting of SEQ ID NO:107 and 316, or an amino acid with at least about 95% homology to an amino acid sequence selected from the group consisting of SEQ ID NO:107 and 316.

In some embodiments, provided herein are anti-MS4A4A antibodies comprising at least one, two, three, four, five, or six HVRs selected from: (a) HVR-H1 comprising the amino acid sequence of SEQ ID NO:108, or an amino acid with at least about 95% homology to the amino acid of SEQ ID NO: 108; (b) HVR-H2 comprising an amino acid sequence selected from the group consisting of SEQ ID NOs:110 and 111, or an amino acid with at least about 95% homology to an amino acid selected from the group consisting of SEQ ID NOs:110 and 111; (c) HVR-H3 comprising the amino acid sequence of SEQ ID NO:112, or an amino acid with at least about 95% homology to the amino acid of SEQ ID NO: 112; (d) HVR-L1 comprising the amino acid sequence of SEQ ID NO:113, or an amino acid with at least about 95% homology to the amino acid of SEQ ID NO:113; (e) HVR-L2 comprising the amino acid sequence of SEQ ID NO:114, or an amino acid with at least about 95% homology to the amino acid of SEQ ID NO: 114; and (f) HVR-L3 comprising the amino acid sequence of SEQ ID NO:115, or an amino acid with at least about 95% homology to the amino acid of SEQ ID NO:115.

In some embodiments, provided herein are anti-MS4A4A antibodies comprising at least one, two, three, four, five, or six HVRs selected from: (a) HVR-H1 comprising the amino acid sequence of SEQ ID NO:116, or an amino acid with at least about 95% homology to the amino acid of SEQ ID NO:116; (b) HVR-H2 comprising an amino acid sequence selected from the group consisting of SEQ ID NOs: 118, 119, 120, 121, and 122, or an amino acid with at least about 95% homology to an amino acid selected from the group consisting of SEQ ID NOs: 118, 119, 120, 121, and 122; (c) HVR-H3 comprising an amino acid sequence selected from the group consisting of SEQ ID NOs:123, 124, 125, 126, 127, 128, and 129, or an amino acid with at least about 95% homology to an amino acid selected from the group consisting of SEQ ID NOs: 123, 124, 125, 126, 127, 128, and 129; (d) HVR-L1 comprising an amino acid sequence selected from the group consisting of SEQ ID NOs:130, 131, 132, 133, 134, 135, 136, 137, and 138, or an amino acid with at least about 95% homology to an amino acid selected from the group consisting of SEQ ID NOs:130, 131, 132, 133, 134, 135, 136, 137, and 138; (e) HVR-L2 comprising an amino acid sequence selected from the group consisting of SEQ ID NOs:139, 140, 141, 142, and 143, or an amino acid with at least about 95% homology to an amino acid selected from the group consisting of SEQ ID NOs:139, 140, 141, 142, and 143; and (f) HVR-L3 comprising an amino acid sequence selected from the group consisting of SEQ ID Nos:144 and 145, or an amino acid with at least about 95% homology to an amino acid selected from the group consisting of SEQ ID Nos:144 and 145.

In some embodiments, provided herein are anti-MS4A4A antibodies comprising at least one, two, three, four, five, or six HVRs selected from: (a) HVR-H1 comprising an amino acid sequence selected from the group consisting of SEQ ID NOs:146 and 147, or an amino acid with at least about 95% homology to an amino acid selected from the group consisting of SEQ ID NOs:146 and 147; (b) HVR-H2 comprising an amino acid sequence selected from the group consisting of SEQ ID NOs:149, 150, 151, 152, and 153, or an amino acid with at least about 95% homology to an amino acid selected from the group consisting of SEQ ID NOs: 149, 150, 151, 152, and 153; (c) HVR-H3 comprising the amino acid sequence of SEQ ID NO:154, or an amino acid with at least about 95% homology to the amino acid of SEQ ID NO: 154; (d) HVR-L1 comprising an amino acid sequence selected from the group consisting of SEQ ID NOs:156, 157, and 158, or an amino acid with at least about 95% homology to an amino acid selected from the group consisting of SEQ ID NOs: 156, 157, and 158; (e) HVR-L2 comprising an amino acid sequence selected from the group consisting of SEQ ID NOs: 159, 160, and 161, or an amino acid with at least about 95% homology to an amino acid selected from the group consisting of SEQ ID NOs: 159, 160, and 161; and (f) HVR-L3 comprising the amino acid sequence selected from the group consisting of SEQ ID NO:163, or an amino acid with at least about 95% homology to the amino acid selected from the group consisting of SEQ ID NO:163.

In some embodiments, provided herein are anti-MS4A4A antibodies comprising: (a) HVR-H1 comprising the amino acid sequence of SEQ ID NO:94; (b) HVR-H2 comprising the amino acid sequence of SEQ ID NO:96; (c) HVR-H3 comprising the amino acid sequence of SEQ ID NO:100; (d) HVR-L1 comprising the amino acid sequence of SEQ ID NO:103; (e) HVR-L2 comprising the amino acid sequence of SEQ ID NO:105; and (f) HVR-L3 comprising the amino acid sequence of SEQ ID NO:107; (a) HVR-H1 comprising the amino acid sequence of SEQ ID NO:94; (b) HVR-H2 comprising the amino acid sequence of SEQ ID NO:97; (c) HVR-H3 comprising the amino acid sequence of SEQ ID NO:100; (d) HVR-L1 comprising the amino acid sequence of SEQ ID NO:103; (e) HVR-L2 comprising the amino acid sequence of SEQ ID NO:105; and (f) HVR-L3 comprising the amino acid sequence of SEQ ID NO:107;(a) HVR-H1 comprising the amino acid sequence of SEQ ID NO:94; (b) HVR-H2 comprising the amino acid sequence of SEQ ID NO:98; (c) HVR-H3 comprising the amino acid sequence of SEQ ID NO:100; (d) HVR-L1 comprising the amino acid sequence of SEQ ID NO:103; (e) HVR-L2 comprising the amino acid sequence of SEQ ID NO:105; and (f) HVR-L3 comprising the amino acid sequence of SEQ ID NO:107; (a) HVR-H1 comprising the amino acid sequence of SEQ ID NO:94; (b) HVR-H2 comprising the amino acid sequence of SEQ ID NO:96; (c) HVR-H3 comprising the amino acid sequence of SEQ ID NO:101; (d) HVR-L1 comprising the amino acid sequence of SEQ ID NO:103; (e) HVR-L2 comprising the amino acid sequence of SEQ ID NO:106; and (f) HVR-L3 comprising the amino acid sequence of SEQ ID NO:107; (a) HVR-H1 comprising the amino acid sequence of SEQ ID NO:94; (b) HVR-H2 comprising the amino acid sequence of SEQ ID NO:96; (c) HVR-H3 comprising the amino acid sequence of SEQ ID NO:102; (d) HVR-L1 comprising the amino acid sequence of SEQ ID NO:104; (e) HVR-L2 comprising the amino acid sequence of SEQ ID NO:105; and (f) HVR-L3 comprising the amino acid sequence of SEQ ID NO:107; or (a) HVR-H1 comprising the amino acid sequence of SEQ ID NO:94; (b) HVR-H2 comprising the amino acid sequence of SEQ ID NO:99; (c) HVR-H3 comprising the amino acid sequence of SEQ ID NO:100; (d) HVR-L1 comprising the amino acid sequence of SEQ ID NO:104; (e) HVR-L2 comprising the amino acid sequence of SEQ ID NO:105; and (f) HVR-L3 comprising the amino acid sequence of SEQ ID NO:107.

In some embodiments, provided herein are anti-MS4A4A antibodies comprising: (a) HVR-H1 comprising the amino acid sequence of SEQ ID NO:308; (b) HVR-H2 comprising the amino acid sequence of SEQ ID NO:309; (c) HVR-H3 comprising the amino acid sequence of SEQ ID NO:310; (d) HVR-L1 comprising the amino acid sequence of SEQ ID NO:314; (e) HVR-L2 comprising the amino acid sequence of SEQ ID NO:315; and (f) HVR-L3 comprising the amino acid sequence of SEQ ID NO:316; or (a) HVR-H1 comprising the amino acid sequence of SEQ ID NO:311; (b) HVR-H2 comprising the amino acid sequence of SEQ ID NO:312; (c) HVR-H3 comprising the amino acid sequence of SEQ ID NO:313; (d) HVR-L1 comprising the amino acid sequence of SEQ ID NO:317; (e) HVR-L2 comprising the amino acid sequence of SEQ ID NO:318; and (f) HVR-L3 comprising the amino acid sequence of SEQ ID NO:319.

In some embodiments, provided herein are anti-MS4A4A antibodies comprising: (a) HVR-H1 comprising the amino acid sequence of SEQ ID NO:108; (b) HVR-H2 comprising the amino acid sequence of SEQ ID NO:110; (c) HVR-H3 comprising the amino acid sequence of SEQ ID NO:112; (d) HVR-L1 comprising the amino acid sequence of SEQ ID NO:113; (e) HVR-L2 comprising the amino acid sequence of SEQ ID NO:114; and (f) HVR-L3 comprising the amino acid sequence of SEQ ID NO:115; or (a) HVR-H1 comprising the amino acid sequence of SEQ ID NO:108; (b) HVR-H2 comprising the amino acid sequence of SEQ ID NO:111; (c) HVR-H3 comprising the amino acid sequence of SEQ ID NO:112; (d) HVR-L1 comprising the amino acid sequence of SEQ ID NO:113; (e) HVR-L2 comprising the amino acid sequence of SEQ ID NO:114; and (f) HVR-L3 comprising the amino acid sequence of SEQ ID NO:115.

In some embodiments, provided herein are anti-MS4A4A antibodies comprising: (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:123; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:119; (c) HVR-H3 comprising the amino acid sequence of SEQ ID NO:123; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:120; (c) HVR-H3 comprising the amino acid sequence of SEQ ID NO:123; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:121; (c) HVR-H3 comprising the amino acid sequence of SEQ ID NO:123; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:132; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:133; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:134; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:135; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:136; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:140; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:145; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:137; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:138; (e) HVR-L2 comprising the amino acid sequence of SEQ ID NO:141; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:142; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:141; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:124; (d) HVR-L1 comprising the amino acid sequence of SEQ ID NO:130; (e) HVR-L2 comprising the amino acid sequence of SEQ ID NO:143; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:137; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:130; (e) HVR-L2 comprising the amino acid sequence of SEQ ID NO:143; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:130; (e) HVR-L2 comprising the amino acid sequence of SEQ ID NO:142; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:125; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:145; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:126; (d) HVR-L1 comprising the amino acid sequence of SEQ ID NO:138; (e) HVR-L2 comprising the amino acid sequence of SEQ ID NO:141; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:126; (d) HVR-L1 comprising the amino acid sequence of SEQ ID NO:130; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:126; (d) HVR-L1 comprising the amino acid sequence of SEQ ID NO:130; (e) HVR-L2 comprising the amino acid sequence of SEQ ID NO:141; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:127; (d) HVR-L 1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:122; (c) HVR-H3 comprising the amino acid sequence of SEQ ID NO:127; (d) HVR-L1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:128; (d) HVR-L 1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L1 comprising the amino acid sequence of SEQ ID NO:131; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L1 comprising the amino acid sequence of SEQ ID NO:132; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L1 comprising the amino acid sequence of SEQ ID NO:133; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L1 comprising the amino acid sequence of SEQ ID NO:134; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L1 comprising the amino acid sequence of SEQ ID NO:135; (e) HVR-L2 comprising the amino acid sequence of SEQ ID NO:139; and (f) HVR-L3 comprising the amino acid sequence of SEQ ID NO:144; (a) HVR-H1 comprising the amino acid sequence of SEQ ID NO:116; (b) HVR-H2 comprising the amino acid sequence of SEQ ID NO:118; (c) HVR-H3 comprising the amino acid sequence of SEQ ID NO:129; (d) HVR-L 1 comprising the amino acid sequence of SEQ ID NO:136; (e) HVR-L2 comprising the amino acid sequence of SEQ ID NO:139; and (f) HVR-L3 comprising the amino acid sequence of SEQ ID NO:144.

In some embodiments, provided herein are anti-MS4A4A antibodies comprising: (a) HVR-H1 comprising the amino acid sequence of SEQ ID NO:147; (b) HVR-H2 comprising the amino acid sequence of SEQ ID NO:149; (c) HVR-H3 comprising the amino acid sequence of SEQ ID NO:154; (d) HVR-L1 comprising the amino acid sequence of SEQ ID NO:156; (e) HVR-L2 comprising the amino acid sequence of SEQ ID NO:160; and (f) HVR-L3 comprising the amino acid sequence of SEQ ID NO:163; (a) HVR-H1 comprising the amino acid sequence of SEQ ID NO:146; (b) HVR-H2 comprising the amino acid sequence of SEQ ID NO:150; (c) HVR-H3 comprising the amino acid sequence of SEQ ID NO:154; (d) HVR-L1 comprising the amino acid sequence of SEQ ID NO:156; (e) HVR-L2 comprising the amino acid sequence of SEQ ID NO:160; and (f) HVR-L3 comprising the amino acid sequence of SEQ ID NO:163; (a) HVR-H1 comprising the amino acid sequence of SEQ ID NO:147; (b) HVR-H2 comprising the amino acid sequence of SEQ ID NO:149; (c) HVR-H3 comprising the amino acid sequence of SEQ ID NO:154; (d) HVR-L1 comprising the amino acid sequence of SEQ ID NO:157; (e) HVR-L2 comprising the amino acid sequence of SEQ ID NO:159; and (f) HVR-L3 comprising the amino acid sequence of SEQ ID NO:163; (a) HVR-H1 comprising the amino acid sequence of SEQ ID NO:147; (b) HVR-H2 comprising the amino acid sequence of SEQ ID NO:151; (c) HVR-H3 comprising the amino acid sequence of SEQ ID NO:154; (d) HVR-L1 comprising the amino acid sequence of SEQ ID NO:156; (e) HVR-L2 comprising the amino acid sequence of SEQ ID NO:160; and (f) HVR-L3 comprising the amino acid sequence of SEQ ID NO:163; (a) HVR-H1 comprising the amino acid sequence of SEQ ID NO:147; (b) HVR-H2 comprising the amino acid sequence of SEQ ID NO:151; (c) HVR-H3 comprising the amino acid sequence of SEQ ID NO:154; (d) HVR-L1 comprising the amino acid sequence of SEQ ID NO:158; (e) HVR-L2 comprising the amino acid sequence of SEQ ID NO:159; and (f) HVR-L3 comprising the amino acid sequence of SEQ ID NO:163; (a) HVR-H1 comprising the amino acid sequence of SEQ ID NO:146; (b) HVR-H2 comprising the amino acid sequence of SEQ ID NO:152; (c)

HVR-H3 comprising the amino acid sequence of SEQ ID NO:154; (d) HVR-L1 comprising the amino acid sequence of SEQ ID NO:156; (e) HVR-L2 comprising the amino acid sequence of SEQ ID NO:161; and (f) HVR-L3 comprising the amino acid sequence of SEQ ID NO:163; (a) HVR-H1 comprising the amino acid sequence of SEQ ID NO:146; (b) HVR-H2 comprising the amino acid sequence of SEQ ID NO:153; (c) HVR-H3 comprising the amino acid sequence of SEQ ID NO:154; (d) HVR-L1 comprising the amino acid sequence of SEQ ID NO:158; (e) HVR-L2 comprising the amino acid sequence of SEQ ID NO:159; and (f) HVR-L3 comprising the amino acid sequence of SEQ ID NO:163.

In some embodiments, provided herein are anti-MS4A4A antibodies comprising at least one, at least two, or all three $V_H$ HVR sequences selected from (a) HVR-H1 comprising the amino acid sequence of SEQ ID NO:94, or an amino acid sequence with at least about 95% homology to the amino acid sequence of SEQ ID NO:94; (b) HVR-H2 comprising an amino acid sequence selected from the group consisting of SEQ ID NOs:96, 97, 98, and 99, or an amino acid sequence with at least about 95% homology to an amino acid sequence selected from the group consisting of SEQ ID Nos:96, 97, 98, and 99; and (c) HVR-H3 comprising an amino acid sequence selected from the group consisting of SEQ ID NOs: 100, 101, and 102, or an amino acid sequence with at least about 95% homology to an amino acid sequence selected from the group consisting of SEQ ID NOs: 100, 101, and 102.

In some embodiments, provided herein are anti-MS4A4A antibodies comprising at least one, at least two, or all three $V_H$ HVR sequences selected from (a) HVR-H1 comprising the amino acid sequence of SEQ ID NO:308, or an amino acid sequence with at least about 95% homology to the amino acid sequence of SEQ ID NO:308; (b) HVR-H2 comprising the amino acid sequence of SEQ ID NO:309, or an amino acid sequence with at least about 95% homology to the amino acid sequence of SEQ ID No:309; and (c) HVR-H3 comprising the amino acid sequence of SEQ ID NO:310, or an amino acid sequence with at least about 95% homology to the amino acid sequence of SEQ ID NO:310.

In some embodiments, provided herein are anti-MS4A4A antibodies comprising at least one, at least two, or all three $V_H$ HVR sequences selected from (a) HVR-H1 comprising the amino acid sequence of SEQ ID NO:311, or an amino acid sequence with at least about 95% homology to the amino acid sequence of SEQ ID NO:311; (b) HVR-H2 comprising the amino acid sequence of SEQ ID NO:312, or an amino acid sequence with at least about 95% homology to the amino acid sequence of SEQ ID No:312; and (c) HVR-H3 comprising the amino acid sequence of SEQ ID NO:313, or an amino acid sequence with at least about 95% homology to the amino acid sequence of SEQ ID NO:313.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs:103 and 104, or an amino acid sequence with at least about 95% homology to an amino acid sequence selected from the group consisting of SEQ ID NOs: 103 and 104; (b) HVR-L2 comprising an amino acid sequence selected from the group consisting of SEQ ID NOs: 105 and 106, or an amino acid sequence with at least about 95% homology to an amino acid sequence selected from the group consisting of SEQ ID NOs:105 and 106; and (c) HVR-L3 comprising the amino acid sequence of SEQ ID NO:107, or an amino acid sequence with at least about 95% homology to the amino acid sequence of SEQ ID NO:107.

In some embodiments, provided herein are anti-MS4A4A antibodies comprising at least one, at least two, or all three $V_L$ HVR sequences selected from (a) HVR-L1 comprising the amino acid sequence selected of SEQ ID NO:314, or an amino acid sequence with at least about 95% homology to the amino acid sequence selected of SEQ ID NO:314; (b) HVR-L2 comprising the amino acid sequence of SEQ ID NO: 315, or an amino acid sequence with at least about 95% homology to the amino acid sequence of SEQ ID NO:315; and (c) HVR-L3 comprising the amino acid sequence of SEQ ID NO:316, or an amino acid sequence with at least about 95% homology to the amino acid sequence of SEQ ID NO:316.

In some embodiments, provided herein are anti-MS4A4A antibodies comprising at least one, at least two, or all three $V_L$ HVR sequences selected from (a) HVR-L1 comprising the amino acid sequence selected of SEQ ID NO:317, or an amino acid sequence with at least about 95% homology to the amino acid sequence selected of SEQ ID NO:317; (b) HVR-L2 comprising the amino acid sequence of SEQ ID NO: 318, or an amino acid sequence with at least about 95% homology to the amino acid sequence of SEQ ID NO:318; and (c) HVR-L3 comprising the amino acid sequence of SEQ ID NO:319, or an amino acid sequence with at least about 95% homology to the amino acid sequence of SEQ ID NO:319.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO:94, or an amino acid sequence with at least about 95% homology to the amino acid sequence of SEQ ID NO:94, (ii) HVR-H2 comprising an amino acid sequence selected from the group consisting of SEQ ID NOs: 96, 97, 98, and 99, or an amino acid sequence with at least about 95% homology to an amino acid sequence selected from the group consisting of SEQ ID NOs: 96, 97, 98, and 99, and (iii) HVR-H3 comprising an amino acid sequence selected from the group consisting of SEQ ID NOs: 100, 101, and 102, or an amino acid sequence with at least about 95% homology to an amino acid sequence selected from the group consisting of SEQ ID NOs: 100, 101, and 102, and (b) a $V_L$ domain comprising at least one, at least two, or all three $V_L$ HVR sequences selected from (i) HVR-L1 comprising an amino acid sequence selected from the group consisting of SEQ ID NOs: 103 and 104, or an amino acid sequence with at least about 95% homology to an amino acid sequence selected from the group consisting of SEQ ID NOs: 103 and 104, (ii) HVR-L2 comprising an amino acid sequence selected from the group consisting of SEQ ID NOs: 105 and 106, or an amino acid sequence with at least about 95% homology to an amino acid sequence selected from the group consisting of SEQ ID NOs: 105 and 106, and (iii) HVR-L3 comprising the amino acid sequence of SEQ ID NO: 107, or an amino acid sequence with at least about 95% homology to the amino acid sequence of SEQ ID NO:107.

In some embodiments, provided herein are anti-MS4A4A antibodies comprising (a) a $V_H$ domain comprising at least one, at least two, or all three $V_H$ HVR sequences selected from (i) HVR-H1 comprising the amino acid sequence of SEQ ID NO:308, or an amino acid sequence with at least about 95% homology to the amino acid sequence of SEQ ID NO:308, (ii) HVR-H2 comprising the amino acid of SEQ ID NO: 309, or an amino acid sequence with at least about 95% homology to the amino acid sequence of SEQ ID NO: 309, and (iii) HVR-H3 comprising the amino acid sequence of SEQ ID NO: 310, or an amino acid sequence with at least about 95% homology to the amino acid sequence of SEQ ID NO: 310, and (b) a V$_L$ domain comprising at least one, at least two, or all three V$_L$ HVR sequences selected from (i) HVR-L1 comprising the amino acid sequence of SEQ ID NO: 314, or an amino acid sequence with at least about 95% homology to the amino acid sequence of SEQ ID NO: 314 (ii) HVR-L2 comprising the amino acid sequence of SEQ ID NO: 315, or an amino acid sequence with at least about 95% homology to the amino acid sequence selected of SEQ ID NO: 315, and (iii) HVR-L3 comprising the amino acid sequence of SEQ ID NO: 316, or an amino acid sequence with at least about 95% homology to the amino acid sequence of SEQ ID NO:316.

In some embodiments, provided herein are anti-MS4A4A antibodies comprising (a) a V$_H$ domain comprising at least one, at least two, or all three V$_H$ HVR sequences selected from (i) HVR-H1 comprising the amino acid sequence of SEQ ID NO:311, or an amino acid sequence with at least about 95% homology to the amino acid sequence of SEQ ID NO:311, (ii) HVR-H2 comprising the amino acid of SEQ ID NO: 312, or an amino acid sequence with at least about 95% homology to the amino acid sequence of SEQ ID NO: 312, and (iii) HVR-H3 comprising the amino acid sequence of SEQ ID NO: 313, or an amino acid sequence with at least about 95% homology to the amino acid sequence of SEQ ID NO: 313, and (b) a V$_L$ domain comprising at least one, at least two, or all three V$_L$ HVR sequences selected from (i) HVR-L1 comprising the amino acid sequence of SEQ ID NO: 317, or an amino acid sequence with at least about 95% homology to the amino acid sequence of SEQ ID NO: 317 (ii) HVR-L2 comprising the amino acid sequence of SEQ ID NO: 318, or an amino acid sequence with at least about 95% homology to the amino acid sequence selected of SEQ ID NO: 318, and (iii) HVR-L3 comprising the amino acid sequence of SEQ ID NO: 316, or an amino acid sequence with at least about 95% homology to the amino acid sequence of SEQ ID NO:316.

In some embodiments, provided herein are anti-MS4A4A antibodies comprising at least one, at least two, or all three V$_H$ HVR sequences selected from (a) HVR-H1 comprising an amino acid sequence selected from the group consisting of SEQ ID NOs:24, 25, 26, 27, 28, 29, and 30, or an amino acid sequence with at least about 95% homology to an amino acid sequence selected from the group consisting of SEQ ID NOs: 24, 25, 26, 27, 28, 29, and 30; (b) HVR-H2 comprising an amino acid sequence selected from the group consisting of SEQ ID NOs:110 and 111, or an amino acid sequence with at least about 95% homology to an amino acid sequence selected from the group consisting of SEQ ID NOs: 110 and 111; and (c) HVR-H3 comprising the amino acid sequence of SEQ ID NO: 112, or an amino acid sequence with at least about 95% homology to the amino acid sequence of SEQ ID NO: 112.

In some embodiments, provided herein are anti-MS4A4A antibodies comprising at least one, at least two, or all three V$_L$ HVR sequences selected from (a) HVR-L1 comprising the amino acid sequence of SEQ ID NO: 113, or an amino acid sequence with at least about 95% homology to the amino acid sequence of SEQ ID NO: 113; (b) HVR-L2 comprising the amino acid sequence of SEQ ID NO: 114, or an amino acid sequence with at least about 95% homology to the amino acid sequence of SEQ ID NO:114; and (c) HVR-L3 comprising the amino acid sequence of SEQ ID NO:115, or an amino acid sequence with at least about 95% homology to the amino acid sequence of SEQ ID NO:115.

In some embodiments, provided herein are anti-MS4A4A antibodies comprising (a) a V$_H$ domain comprising at least one, at least two, or all three V$_H$ HVR sequences selected from (i) HVR-H1 comprising the amino acid sequence of SEQ ID NO:108, or an amino acid sequence with at least about 95% homology to the amino acid sequence of SEQ ID NO:108, (ii) HVR-H2 comprising an amino acid sequence selected from the group consisting of SEQ ID NOs: 110 and 111, or an amino acid sequence with at least about 95% homology to an amino acid sequence selected from the group consisting of SEQ ID NOs: 110 and 111, and (iii) HVR-H3 comprising the amino acid sequence of SEQ ID NO: 112, or an amino acid sequence with at least about 95% homology to the amino acid sequence of SEQ ID NO: 112, and (b) a V$_L$ domain comprising at least one, at least two, or all three V$_L$ HVR sequences selected from (i) HVR-L1 comprising the amino acid sequence of SEQ ID NO: 113, or an amino acid sequence with at least about 95% homology to the amino acid sequence of SEQ ID NO: 113, (ii) HVR-L2 comprising the amino acid sequence of SEQ ID NO: 114, or an amino acid sequence with at least about 95% homology to the amino acid sequence of SEQ ID NO: 114, and (iii) HVR-L3 comprising the amino acid sequence of SEQ ID NO: 115, or an amino acid sequence with at least about 95% homology to the amino acid sequence of SEQ ID NO:115.

In some embodiments, provided herein are anti-MS4A4A antibodies comprising at least one, at least two, or all three V$_H$ HVR sequences selected from (a) HVR-H1 comprising the amino acid sequence of SEQ ID NO:116, or an amino acid sequence with at least about 95% homology to the amino acid sequence of SEQ ID NO:116; (b) HVR-H2 comprising an amino acid sequence selected from the group consisting of SEQ ID NOs:118, 119, 120, 121, and 122, or an amino acid sequence with at least about 95% homology to an amino acid sequence selected from the group consisting of SEQ ID NOs: 118, 119, 120 121, and 122; and (c) HVR-H3 comprising an amino acid sequence selected from the group consisting of SEQ ID NOs: 123, 124, 125, 126, 127, 128, and 129, or an amino acid sequence with at least about 95% homology to an amino acid sequence selected from the group consisting of SEQ ID NOs: 123, 124, 125, 126, 127, 128, and 129.

In some embodiments, provided herein are anti-MS4A4A antibodies comprising at least one, at least two, or all three V$_L$ HVR sequences selected from (a) HVR-L1 comprising an amino acid sequence selected from the group consisting of SEQ ID NOs: 130, 131, 132, 133, 134, 135, 136, 137, and 138, or an amino acid sequence with at least about 95% homology to an amino acid sequence selected from the group consisting of SEQ ID NOs: 130, 131, 132, 133, 134, 135, 136, 137, and 138; (b) HVR-L2 comprising an amino acid sequence selected from the group consisting of SEQ ID NOs:139, 140, 141, 142, and 143, or an amino acid sequence with at least about 95% homology to an amino acid sequence selected from the group consisting of SEQ ID NOs:139, 140, 141, 142, and 143; and (c) HVR-L3 comprising an amino acid sequence selected from the group consisting of SEQ ID NOs:144 and 145, or an amino acid sequence with at least about 95% homology to an amino acid sequence selected from the group consisting of SEQ ID NOs:144 and 145.

In some embodiments, provided herein are anti-MS4A4A antibodies comprising (a) a V$_H$ domain comprising at least one, at least two, or all three V$_H$ HVR sequences selected from (i) HVR-H1 comprising the amino acid sequence of SEQ ID NO:116, or an amino acid sequence with at least about 95% homology to the amino acid sequence of SEQ ID NO:116, (ii) HVR-H2 comprising an amino acid sequence selected from the group consisting of SEQ ID NOs: 118, 119, 120, 121, and 122, or an amino acid sequence with at least about 95% homology to an amino acid sequence selected from the group consisting of SEQ ID NOs: 118, 119, 120, 121, and 122, and (iii) HVR-H3 comprising an amino acid sequence selected from the group consisting of SEQ ID NOs: 123, 124, 125, 126, 127, 128, and 129, or an amino acid sequence with at least about 95% homology to an amino acid sequence selected from the group consisting of SEQ ID NOs: 123, 124, 125, 126, 127, 128, and 129, and (b) a $V_L$ domain comprising at least one, at least two, or all three $V_L$ HVR sequences selected from (i) HVR-L1 comprising an amino acid sequence selected from the group consisting of SEQ ID NOs: 130, 131, 132, 133, 134, 135, 136, 137, and 138, or an amino acid sequence with at least about 95% homology to an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, or an amino acid sequence with at least about 95% homology to an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145, or an amino acid sequence with at least about 95% homology to an amino acid sequence selected from the group consisting of SEQ ID NOs: 144 and 145.

In some embodiments, provided herein are anti-MS4A4A antibodies comprising at least one, at least two, or all three $V_H$ HVR sequences selected from (a) HVR-H1 comprising an amino acid sequence selected from the group consisting of SEQ ID NOs:146 and 147, or an amino acid sequence with at least about 95% homology to an amino acid sequence selected from the group consisting of SEQ ID NOs:146 and 147; (b) HVR-H2 comprising an amino acid sequence selected from the group consisting of SEQ ID NOs:149, 150, 151, 152, and 153, or an amino acid sequence with at least about 95% homology to an amino acid sequence selected from the group consisting of SEQ ID NOs: 149, 150, 151, 152, and 153; and (c) HVR-H3 comprising the amino acid sequence of SEQ ID NO: 154, or an amino acid sequence with at least about 95% homology to the amino acid sequence of SEQ ID NO: 154.

In some embodiments, provided herein are anti-MS4A4A antibodies comprising at least one, at least two, or all three $V_L$ HVR sequences selected from (a) HVR-L1 comprising an amino acid sequence selected from the group consisting of SEQ ID NOs: 156, 157, and 158, or an amino acid sequence with at least about 95% homology to an amino acid sequence selected from the group consisting of SEQ ID NOs: 156, 157, and 158; (b) HVR-L2 comprising an amino acid sequence selected from the group consisting of SEQ ID NOs:160 and 161, or an amino acid sequence with at least about 95% homology to an amino acid sequence selected from the group consisting of SEQ ID NOs:160 and 161; and (c) HVR-L3 comprising the amino acid sequence of SEQ ID NO:163, or an amino acid sequence with at least about 95% homology to the amino acid sequence of SEQ ID NO:163.

In some embodiments, provided herein are anti-MS4A4A antibodies comprising (a) a $V_H$ domain comprising at least one, at least two, or all three $V_H$ HVR sequences selected from (i) HVR-H1 comprising an amino acid sequence selected from the group consisting of SEQ ID NOs:146 and 147, or an amino acid sequence with at least about 95% homology to an amino acid sequence selected from the group consisting of SEQ ID NOs:146 and 147, (ii) HVR-H2 comprising an amino acid sequence selected from the group consisting of SEQ ID NOs: 149, 150, 151, 152, and 153, or an amino acid sequence with at least about 95% homology to an amino acid sequence selected from the group consisting of SEQ ID NOs: 149, 150, 151, 152, and 153, and (iii) HVR-H3 comprising the amino acid sequence of SEQ ID NO: 154, or an amino acid sequence with at least about 95% homology to the amino acid sequence of SEQ ID NO: 154, and (b) a $V_L$ domain comprising at least one, at least two, or all three $V_L$ HVR sequences selected from (i) HVR-L1 comprising an amino acid sequence selected from the group consisting of SEQ ID NOs: 156, 157, and 158, or an amino acid sequence with at least about 95% homology to an amino acid sequence selected from the group consisting of SEQ ID NOs: 156, 157, and 158, (ii) HVR-L2 comprising an amino acid sequence selected from the group consisting of SEQ ID NOs: 160 and 161, or an amino acid sequence with at least about 95% homology to an amino acid sequence selected from the group consisting of SEQ ID NOs: 160 and 161, and (iii) HVR-L3 comprising the amino acid sequence of SEQ ID NO: 163, or an amino acid sequence with at least about 95% homology to the amino acid sequence of SEQ ID NO: 163.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, and 306. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, and 306 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. In certain embodiments, a total of 1 to 5 amino acids have been substituted, inserted and/or deleted in SEQ ID NO: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. In certain embodiments, substitutions, insertions, or deletions occur in regions outside the HVRs (i.e., in the FRs). Optionally, the anti-MS4A4A antibody comprises the $V_H$ sequence of SEQ ID NO: 5, 6, 7, 8, 9, 10, 11, 12, 13, 14, 15, 24, 25, 26, 27, 28, 29, 30, 40, 41, 42, 43, 44, 45, 46, 47, 48, 49, 50, 51, 52, 53, 76, 77, 78, 79, 80, 81, 82, 83, 84, 304, or 306. including post-translational modifications of that sequence. In a particular embodiment, the $V_H$ comprises one, two or three HVRs selected from: (a) HVR-H1 comprising an amino acid sequence selected from the group consisting of SEQ ID NOs:94, 108, 116, 146, 147, and 308, and 311, (b) HVR-H2 comprising an amino acid sequence selected from the group consisting of SEQ ID NOs:96, 97, 98, 99, 110, 111, 118, 119, 120, 121, 122, 149, 150, 151, 152, 153, 309, and 312, and (c) HVR-H3 comprising an amino acid sequence selected from the group consisting of SEQ ID NOs: 100, 101, 102, 112, 123, 124, 125, 126, 127, 128, 129, 154, 310, and 313.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, and 307. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, and 307 and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307. In certain embodiments, a total of 1 to 5 amino acids have been substituted, inserted and/or deleted in SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307. In certain embodiments, the substitutions, insertions, or deletions occur in regions outside the HVRs (i.e., in the FRs). Optionally, the anti-MS4A4A antibody comprises the $V_L$ sequence of SEQ ID NO: 17, 18, 19, 20, 21, 22, 32, 33, 34, 35, 36, 55, 56, 57, 58, 59, 60, 61, 62, 63, 64, 65, 66, 67, 68, 69, 70, 71, 72, 73, 74, 86, 87, 88, 89, 90, 91, 92, 93, 305, or 307, including post-translational modifications of that sequence. In a particular embodiment, the $V_L$ comprises one, two or three HVRs selected from (a) HVR-L1 comprising an amino acid sequence selected from the group consisting of SEQ ID NOs: 103, 104, 113, 130, 131, 132, 133, 134, 135, 136, 137, 138, 156, 157, 158, 314 and 317, (b) HVR-L2 comprising an amino acid sequence selected from the group consisting of SEQ ID NOs: 105, 106, 114, 139, 140, 141, 142, 143, 160, 161, 315 and 318, and (c) HVR-L3 comprising an amino acid sequence selected from the group consisting of SEQ ID NOs: 107, 115, 144, 145, 163, 316 and 319.

In some embodiments, an anti-MS4A4A antibody is provided, wherein the antibody comprises a $V_H$ as in any of the embodiments provided above, and a $V_L$ as in any of the embodiments provided above. In some embodiments, provided herein are anti-MS4A4A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:5-15 and SEQ ID NOs:17-22, respectively, including post-translational modifications of those sequences. In one embodiment, the antibody comprises the $V_H$ and $V_L$ sequences in SEQ ID NOs:24-30 and SEQ ID NOs:32-36, respectively, including post-translational modifications of those sequences. In one embodiment, the antibody comprises the $V_H$ and $V_L$ sequences in SEQ ID NOs:40-53 and SEQ ID NOs:55-74, respectively, including post-translational modifications of those sequences. In one embodiment, the antibody comprises the $V_H$ and $V_L$ sequences in SEQ ID NOs:76-84 and SEQ ID NOs:86-93, respectively, including post-translational modifications of those sequences. In one embodiment, the antibody comprises the $V_H$ and $V_L$ sequences in SEQ ID NO:304 and SEQ ID NO:305, respectively, including post-translational modifications of those sequences. In one embodiment, the antibody comprises the $V_H$ and $V_L$ sequences in SEQ ID NO:306 and SEQ ID NO:307, respectively, including post-translational modifications of those sequences.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:5 and $V_L$ comprising the amino acid sequence of SEQ ID NO:17; $V_H$ comprising the amino acid sequence of SEQ ID NO:5 and $V_L$ comprising the amino acid sequence of SEQ ID NO:18; $V_H$ comprising the amino acid sequence of SEQ ID NO:6 and $V_L$ comprising the amino acid sequence of SEQ ID NO:17; $V_H$ comprising the amino acid sequence of SEQ ID NO:5 and $V_L$ comprising the amino acid sequence of SEQ ID NO:19; $V_H$ comprising the amino acid sequence of SEQ ID NO:7 and $V_L$ comprising the amino acid sequence of SEQ ID NO:17; $V_H$ comprising the amino acid sequence of SEQ ID NO:5 and $V_L$ comprising the amino acid sequence of SEQ ID NO:20; $V_H$ comprising the amino acid sequence of SEQ ID NO:8 and $V_L$ comprising the amino acid sequence of SEQ ID NO:17; $V_H$ comprising the amino acid sequence of SEQ ID NO:9 and $V_L$ comprising the amino acid sequence of SEQ ID NO:17; $V_H$ comprising the amino acid sequence of SEQ ID NO:10 and $V_L$ comprising the amino acid sequence of SEQ ID NO:18; $V_H$ comprising the amino acid sequence of SEQ ID NO:11 and $V_L$ comprising the amino acid sequence of SEQ ID NO:17; $V_H$ comprising the amino acid sequence of SEQ ID NO:12 and $V_L$ comprising the amino acid sequence of SEQ ID NO:17; $V_H$ comprising the amino acid sequence of SEQ ID NO:13 and $V_L$ comprising the amino acid sequence of SEQ ID NO:21; $V_H$ comprising the amino acid sequence of SEQ ID NO:14 and $V_L$ comprising the amino acid sequence of SEQ ID NO:22; $V_H$ comprising the amino acid sequence of SEQ ID NO:15 and $V_L$ comprising the amino acid sequence of SEQ ID NO:122; $V_H$ comprising the amino acid sequence of SEQ ID NO:304 and $V_L$ comprising the amino acid sequence of SEQ ID NO:305; and $V_H$ comprising the amino acid sequence of SEQ ID NO:306 and $V_L$ comprising the amino acid sequence of SEQ ID NO:307.

In some embodiments, provided herein are anti-MS4A4A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:24 and $V_L$ comprising the amino acid sequence of SEQ ID NO:32; $V_H$ comprising the amino acid sequence of SEQ ID NO:25 and $V_L$ comprising the amino acid sequence of SEQ ID NO:33; $V_H$ comprising the amino acid sequence of SEQ ID NO:25 and $V_L$ comprising the amino acid sequence of SEQ ID NO:32; $V_H$ comprising the amino acid sequence of SEQ ID NO:26 and $V_L$ comprising the amino acid sequence of SEQ ID NO:33; $V_H$ comprising the amino acid sequence of SEQ ID NO:26 and $V_L$ comprising the amino acid sequence of SEQ ID NO:32; $V_H$ comprising the amino acid sequence of SEQ ID NO:27 and $V_L$ comprising the amino acid sequence of SEQ ID NO:32; $V_H$ comprising the amino acid sequence of SEQ ID NO:27 and $V_L$ comprising the amino acid sequence of SEQ ID NO:34; $V_H$ comprising the amino acid sequence of SEQ ID NO:28 and $V_L$ comprising the amino acid sequence of SEQ ID NO:33; $V_H$ comprising the amino acid sequence of SEQ ID NO:28 and $V_L$ comprising the amino acid sequence of SEQ ID NO:32; $V_H$ comprising the amino acid sequence of SEQ ID NO:28 and V$_L$ comprising the amino acid sequence of SEQ ID NO:35; V$_H$ comprising the amino acid sequence of SEQ ID NO:28 and V$_L$ comprising the amino acid sequence of SEQ ID NO:34; V$_H$ comprising the amino acid sequence of SEQ ID NO:29 and V$_L$ comprising the amino acid sequence of SEQ ID NO:32; V$_H$ comprising the amino acid sequence of SEQ ID NO:29 and V$_L$ comprising the amino acid sequence of SEQ ID NO:36; V$_H$ comprising the amino acid sequence of SEQ ID NO:30 and V$_L$ comprising the amino acid sequence of SEQ ID NO:37; V$_H$ comprising the amino acid sequence of SEQ ID NO:30 and V$_L$ comprising the amino acid sequence of SEQ ID NO:32; V$_H$ comprising the amino acid sequence of SEQ ID NO:30 and V$_L$ comprising the amino acid sequence of SEQ ID NO:38; and V$_H$ comprising the amino acid sequence of SEQ ID NO:30 and V$_L$ comprising the amino acid sequence of SEQ ID NO:36.

In some embodiments, provided herein are anti-MS4A4A antibodies comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:40 and V$_L$ comprising the amino acid sequence of SEQ ID NO:55; V$_H$ comprising the amino acid sequence of SEQ ID NO:41 and V$_L$ comprising the amino acid sequence of SEQ ID NO:55; V$_H$ comprising the amino acid sequence of SEQ ID NO:40 and V$_L$ comprising the amino acid sequence of SEQ ID NO:56; V$_H$ comprising the amino acid sequence of SEQ ID NO:40 and V$_L$ comprising the amino acid sequence of SEQ ID NO:57; V$_H$ comprising the amino acid sequence of SEQ ID NO:40 and V$_L$ comprising the amino acid sequence of SEQ ID NO:58; V$_H$ comprising the amino acid sequence of SEQ ID NO:41 and V$_L$ comprising the amino acid sequence of SEQ ID NO:56; V$_H$ comprising the amino acid sequence of SEQ ID NO:41 and V$_L$ comprising the amino acid sequence of SEQ ID NO:57; V$_H$ comprising the amino acid sequence of SEQ ID NO:41 and V$_L$ comprising the amino acid sequence of SEQ ID NO:58; V$_H$ comprising the amino acid sequence of SEQ ID NO:42 and V$_L$ comprising the amino acid sequence of SEQ ID NO:59; V$_H$ comprising the amino acid sequence of SEQ ID NO:43 and V$_L$ comprising the amino acid sequence of SEQ ID NO:59; V$_H$ comprising the amino acid sequence of SEQ ID NO:44 and V$_L$ comprising the amino acid sequence of SEQ ID NO:60; V$_H$ comprising the amino acid sequence of SEQ ID NO:45 and V$_L$ comprising the amino acid sequence of SEQ ID NO:60; V$_H$ comprising the amino acid sequence of SEQ ID NO:46 and V$_L$ comprising the amino acid sequence of SEQ ID NO:60; V$_H$ comprising the amino acid sequence of SEQ ID NO:43 and V$_L$ comprising the amino acid sequence of SEQ ID NO:61; V$_H$ comprising the amino acid sequence of SEQ ID NO:46 and V$_L$ comprising the amino acid sequence of SEQ ID NO:61; V$_H$ comprising the amino acid sequence of SEQ ID NO:42 and V$_L$ comprising the amino acid sequence of SEQ ID NO:61; V$_H$ comprising the amino acid sequence of SEQ ID NO:44 and V$_L$ comprising the amino acid sequence of SEQ ID NO:61; V$_H$ comprising the amino acid sequence of SEQ ID NO:45 and V$_L$ comprising the amino acid sequence of SEQ ID NO:61; V$_H$ comprising the amino acid sequence of SEQ ID NO:47 and V$_L$ comprising the amino acid sequence of SEQ ID NO:55; V$_H$ comprising the amino acid sequence of SEQ ID NO:47 and V$_L$ comprising the amino acid sequence of SEQ ID NO:62; V$_H$ comprising the amino acid sequence of SEQ ID NO:47 and V$_L$ comprising the amino acid sequence of SEQ ID NO:63; V$_H$ comprising the amino acid sequence of SEQ ID NO:47 and V$_L$ comprising the amino acid sequence of SEQ ID NO:64; V$_H$ comprising the amino acid sequence of SEQ ID NO:47 and V$_L$ comprising the amino acid sequence of SEQ ID NO:65; V$_H$ comprising the amino acid sequence of SEQ ID NO:47 and V$_L$ comprising the amino acid sequence of SEQ ID NO:66; V$_H$ comprising the amino acid sequence of SEQ ID NO:47 and V$_L$ comprising the amino acid sequence of SEQ ID NO:67; V$_H$ comprising the amino acid sequence of SEQ ID NO:47 and V$_L$ comprising the amino acid sequence of SEQ ID NO:68; V$_H$ comprising the amino acid sequence of SEQ ID NO:47 and V$_L$ comprising the amino acid sequence of SEQ ID NO:69; V$_H$ comprising the amino acid sequence of SEQ ID NO:47 and V$_L$ comprising the amino acid sequence of SEQ ID NO:70; V$_H$ comprising the amino acid sequence of SEQ ID NO:47 and V$_L$ comprising the amino acid sequence of SEQ ID NO:71; V$_H$ comprising the amino acid sequence of SEQ ID NO:47 and V$_L$ comprising the amino acid sequence of SEQ ID NO:72; V$_H$ comprising the amino acid sequence of SEQ ID NO:47 and V$_L$ comprising the amino acid sequence of SEQ ID NO:73; V$_H$ comprising the amino acid sequence of SEQ ID NO:47 and V$_L$ comprising the amino acid sequence of SEQ ID NO:74; V$_H$ comprising the amino acid sequence of SEQ ID NO:48 and V$_L$ comprising the amino acid sequence of SEQ ID NO:70; V$_H$ comprising the amino acid sequence of SEQ ID NO:48 and V$_L$ comprising the amino acid sequence of SEQ ID NO:74; V$_H$ comprising the amino acid sequence of SEQ ID NO:48 and V$_L$ comprising the amino acid sequence of SEQ ID NO:62; V$_H$ comprising the amino acid sequence of SEQ ID NO:48 and V$_L$ comprising the amino acid sequence of SEQ ID NO:55; V$_H$ comprising the amino acid sequence of SEQ ID NO:48 and V$_L$ comprising the amino acid sequence of SEQ ID NO:72; V$_H$ comprising the amino acid sequence of SEQ ID NO:48 and V$_L$ comprising the amino acid sequence of SEQ ID NO:69; V$_H$ comprising the amino acid sequence of SEQ ID NO:49 and V$_L$ comprising the amino acid sequence of SEQ ID NO:71; V$_H$ comprising the amino acid sequence of SEQ ID NO:49 and V$_L$ comprising the amino acid sequence of SEQ ID NO:55; V$_H$ comprising the amino acid sequence of SEQ ID NO:49 and V$_L$ comprising the amino acid sequence of SEQ ID NO:73; V$_H$ comprising the amino acid sequence of SEQ ID NO:50 and V$_L$ comprising the amino acid sequence of SEQ ID NO:62; V$_H$ comprising the amino acid sequence of SEQ ID NO:51 and V$_L$ comprising the amino acid sequence of SEQ ID NO:62; V$_H$ comprising the amino acid sequence of SEQ ID NO:52 and V$_L$ comprising the amino acid sequence of SEQ ID NO:62; V$_H$ comprising the amino acid sequence of SEQ ID NO:53 and V$_L$ comprising the amino acid sequence of SEQ ID NO:62; V$_H$ comprising the amino acid sequence of SEQ ID NO:53 and V$_L$ comprising the amino acid sequence of SEQ ID NO:63; V$_H$ comprising the amino acid sequence of SEQ ID NO:53 and V$_L$ comprising the amino acid sequence of SEQ ID NO:64; V$_H$ comprising the amino acid sequence of SEQ ID NO:53 and V$_L$ comprising the amino acid sequence of SEQ ID NO:65; V$_H$ comprising the amino acid sequence of SEQ ID NO:53 and V$_L$ comprising the amino acid sequence of SEQ ID NO:66; and V$_H$ comprising the amino acid sequence of SEQ ID NO:53 and V$_L$ comprising the amino acid sequence of SEQ ID NO:67.

In some embodiments, provided herein are anti-MS4A4A antibodies comprising a heavy chain variable domain (V$_H$) and a light chain variable domain (V$_L$), wherein the V$_H$ and V$_L$ are selected from the group consisting of: V$_H$ comprising the amino acid sequence of SEQ ID NO:76 and V$_L$ comprising the amino acid sequence of SEQ ID NO:86; V$_H$ comprising the amino acid sequence of SEQ ID NO:77 and V$_L$ comprising the amino acid sequence of SEQ ID NO:87;

V$_H$ comprising the amino acid sequence of SEQ ID NO:78 and V$_L$ comprising the amino acid sequence of SEQ ID NO:88; V$_H$ comprising the amino acid sequence of SEQ ID NO:79 and V$_L$ comprising the amino acid sequence of SEQ ID NO:89; V$_H$ comprising the amino acid sequence of SEQ ID NO:80 and V$_L$ comprising the amino acid sequence of SEQ ID NO:90; V$_H$ comprising the amino acid sequence of SEQ ID NO:81 and V$_L$ comprising the amino acid sequence of SEQ ID NO:91; V$_H$ comprising the amino acid sequence of SEQ ID NO:82 and V$_L$ comprising the amino acid sequence of SEQ ID NO:91; V$_H$ comprising the amino acid sequence of SEQ ID NO:83 and V$_L$ comprising the amino acid sequence of SEQ ID NO:92; and V$_H$ comprising the amino acid sequence of SEQ ID NO:84 and V$_L$ comprising the amino acid sequence of SEQ ID NO:93.

In another aspect, an anti-MS4A4A antibody comprises a heavy chain variable domain (V$_H$) sequence having at least 90%, 91%, 92%, 93%, 94%, 95%, 96%, 97%, 98%, 99%, or 100% sequence identity to an amino acid sequence selected from the group consisting of SEQ ID NOs: 5, 6, 7, 8, 9, 10, 11, 12, 13, 14, 15, 304, and 306. In certain embodiments, a V$_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 304, and 306 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 5, 6, 7, 8, 9, 10, 11, 12, 13, 14, 15, 304, or 306. In certain embodiments, a total of 1 to 5 amino acids have been substituted, inserted and/or deleted in SEQ ID NO: 5, 6, 7, 8, 9, 10, 11, 12, 13, 14, 15, 304, or 306. In certain embodiments, substitutions, insertions, or deletions occur in regions outside the HVRs (i.e., in the FRs). Optionally, the anti-MS4A4A antibody comprises the V$_H$ sequence of SEQ ID NO: 5, 6, 7, 8, 9, 10, 11, 12, 13, 14, 15, 304, or 306, including post-translational modifications of that sequence. In a particular embodiment, the VH comprises one, two or three HVRs selected from: (a) HVR-H1 comprising the amino acid sequence selected from the group consisting of SEQ ID NO: 94 and 308, (b) HVR-H2 comprising an amino acid sequence selected from the group consisting of SEQ ID NOs: 96, 97, 98, 99, and 309, and (c) HVR-H3 comprising an amino acid sequence selected from the group consisting of SEQ ID NOs:100, 101, 102, and 310.

In another aspect, an anti-MS4A4A antibody is provided, wherein the antibody comprises a light chain variable domain (V$_L$) having at least 90%, 91%, 92%, 93%, 94%, 95%, 96%, 97%, 98%, 99%, or 100% sequence identity to an amino acid sequence selected from the group consisting of SEQ ID NOs:17, 18, 19, 20, 21, 22, 305, and 307. In certain embodiments, a V$_L$ sequence having at least 90%, 91%, 92%, 93%, 94%, 95%, 96%, 97%, 98%, or 99% identity to an amino acid sequence selected from the group consisting of SEQ ID NOs: 17, 18, 19, 20, 21, 22, 305, and 307, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 17, 18, 19, 20, 21, 22, 305 or 307. In certain embodiments, a total of 1 to 5 amino acids have been substituted, inserted and/or deleted in SEQ ID NO: 17, 18, 19, 20, 21, 22, 305 or 307. In certain embodiments, the substitutions, insertions, or deletions occur in regions outside the HVRs (i.e., in the FRs). Optionally, the anti-MS4A4A antibody comprises the V$_L$ sequence of SEQ ID NO: 17, 18, 19, 20, 21, 22, 305, or 307, including post-translational modifications of that sequence. In a particular embodiment, the V$_L$ comprises one, two or three HVRs selected from (a) HVR-L1 comprising an amino acid sequence selected from the group consisting of SEQ ID NOs: 103, 104, and 314, (b) HVR-L2 comprising an amino acid sequence selected from the group consisting of SEQ ID NOs: 105, 106, and 315, and (c) HVR-L3 comprising the amino acid sequence selected from the group consisting of SEQ ID NO: 107 and 316.

In another aspect, an anti-MS4A4A antibody comprises a heavy chain variable domain (V$_H$) sequence having at least 90%, 91%, 92%, 93%, 94%, 95%, 96%, 97%, 98%, 99%, or 100% sequence identity to an amino acid sequence selected from the group consisting of SEQ ID NOs: 24, 25, 26, 27, 28, 29, and 30. In certain embodiments, a VH sequence having at least 90%, 91%, 92%, 93%, 94%, 95%, 96%, 97%, 98%, or 99% identity to an amino acid sequence selected from the group consisting of SEQ ID NOs: 24, 25, 26, 27, 28, 29, and 30 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 24, 25, 26, 27, 28, 29, or 30. In certain embodiments, a total of 1 to 5 amino acids have been substituted, inserted and/or deleted in SEQ ID NO: 24, 25, 26, 27, 28, 29, or 30. In certain embodiments, substitutions, insertions, or deletions occur in regions outside the HVRs (i.e., in the FRs). Optionally, the anti-MS4A4A antibody comprises the V$_H$ sequence of SEQ ID NO: 24, 25, 26, 27, 28, 29, or 30, including post-translational modifications of that sequence. In a particular embodiment, the V$_H$ comprises one, two or three HVRs selected from: (a) HVR-H1 comprising the amino acid sequence of SEQ ID NO: 108, (b) HVR-H2 comprising an amino acid sequence selected from the group consisting of SEQ ID NOs: 110 and 111, and (c) HVR-H3 comprising the amino acid sequence of SEQ ID NO:112.

In another aspect, an anti-MS4A4A antibody is provided, wherein the antibody comprises a light chain variable domain (V$_L$) having at least 90%, 91%, 92%, 93%, 94%, 95%, 96%, 97%, 98%, 99%, or 100% sequence identity to an amino acid sequence selected from the group consisting of SEQ ID NOs:32, 33, 34, 35 and 36. In certain embodiments, a V$_L$ sequence having at least 90%, 91%, 92%, 93%, 94%, 95%, 96%, 97%, 98%, or 99% identity to an amino acid sequence selected from the group consisting of SEQ ID NOs: 32, 33, 34, 35, and 36, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 32, 33, 34, 35, or 36. In certain embodiments, a total of 1 to 5 amino acids have been substituted, inserted and/or deleted in SEQ ID NO: 32, 33, 34, 35, or 36. In certain embodiments, the substitutions, insertions, or deletions occur in regions outside the HVRs (i.e., in the FRs). Optionally, the anti-MS4A4A antibody comprises the V$_L$ sequence of SEQ ID NO: 32, 33, 34, 35, or 36, including post-translational modifications of that sequence. In a particular embodiment, the V$_L$ comprises one, two or three HVRs selected from (a) HVR-L1 comprising the amino acid sequence of SEQ ID NO: 113, (b) HVR-L2 comprising the amino acid sequence of SEQ ID NO: 114, and (c) HVR-L3 comprising the amino acid sequence of SEQ ID NO: 115.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 40, 41, 42, 43, 44, 45, 46, 47, 48, 49, 50, 51, 52, and 53. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 40, 41, 42, 43, 44, 45, 46, 47, 48, 49, 50, 51, 52, and 53 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 40, 41, 42, 43, 44, 45, 46, 47, 48, 49, 50, 51, 52, or 53. In certain embodiments, a total of 1 to 5 amino acids have been substituted, inserted and/or deleted in SEQ ID NO: 40, 41, 42, 43, 44, 45, 46, 47, 48, 49, 50, 51, 52, or 53. In certain embodiments, substitutions, insertions, or deletions occur in regions outside the HVRs (i.e., in the FRs). Optionally, the anti-MS4A4A antibody comprises the $V_H$ sequence of SEQ ID NO: 40, 41, 42, 43, 44, 45, 46, 47, 48, 49, 50, 51, 52, or 53, including post-translational modifications of that sequence. In a particular embodiment, the $V_H$ comprises one, two or three HVRs selected from: (a) HVR-H1 comprising the amino acid sequence of SEQ ID NO: 116, (b) HVR-H2 comprising an amino acid sequence selected from the group consisting of SEQ ID NOs: 118, 119, 120, 121, and 122, and (c) HVR-H3 comprising an amino acid sequence selected from the group consisting of SEQ ID NOs:123, 124, 125, 126, 127, 128, and 129.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:55, 56, 57, 58, 59, 60, 61, 62, 63, 64, 65, 66, 67, 68, 69, 70, 71, 72, 73, and 74. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 55, 56, 57, 58, 59, 60, 61, 62, 63, 64, 65, 66, 67, 68, 69, 70, 71, 72, 73, and 74, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 55, 56, 57, 58, 59, 60, 61, 62, 63, 64, 65, 66, 67, 68, 69, 70, 71, 72, 73, or 74. In certain embodiments, a total of 1 to 5 amino acids have been substituted, inserted and/or deleted in SEQ ID NO: 55, 56, 57, 58, 59, 60, 61, 62, 63, 64, 65, 66, 67, 68, 69, 70, 71, 72, 73, or 74. In certain embodiments, the substitutions, insertions, or deletions occur in regions outside the HVRs (i.e., in the FRs). Optionally, the anti-MS4A4A antibody comprises the $V_L$ sequence of SEQ ID NO: 55, 56, 57, 58, 59, 60, 61, 62, 63, 64, 65, 66, 67, 68, 69, 70, 71, 72, 73, or 74, including post-translational modifications of that sequence. In a particular embodiment, the $V_L$ comprises one, two or three HVRs selected from (a) HVR-L1 comprising an amino acid sequence selected from the group consisting of SEQ ID NOs: 130, 131, 132, 133, 134, 135, 136, 137, and 138, (b) HVR-L2 comprising an amino acid sequence selected from the group consisting of SEQ ID NOs: 139, 140, 141, 142, and 143, and (c) HVR-L3 comprising an amino acid sequence selected from the group consisting of SEQ ID NOs: 144 and 145.

In another aspect, an anti-MS4A4A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 76, 77, 78, 79, 80, 81, 82, 83, and 84. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 76, 77, 78, 79, 80, 81, 82, 83, and 84 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 76, 77, 78, 79, 80, 81, 82, 83, or 84. In certain embodiments, a total of 1 to 5 amino acids have been substituted, inserted and/or deleted in SEQ ID NO: 76, 77, 78, 79, 80, 81, 82, 83, or 84. In certain embodiments, substitutions, insertions, or deletions occur in regions outside the HVRs (i.e., in the FRs). Optionally, the anti-MS4A4A antibody comprises the $V_H$ sequence of SEQ ID NO: 76, 77, 78, 79, 80, 81, 82, 83, or 84, including post-translational modifications of that sequence. In a particular embodiment, the $V_H$ comprises one, two or three HVRs selected from: (a) HVR-H1 comprising an amino acid sequence selected from the group consisting of SEQ ID NOs: 146 and 147, (b) HVR-H2 comprising an amino acid sequence selected from the group consisting of SEQ ID NOs: 149, 150, 151, 152, and 153, and (c) HVR-H3 comprising the amino acid sequence of SEQ ID NO:154.

In another aspect, an anti-MS4A4A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:86, 87, 88, 89, 90, 91, 92, and 93. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 86, 87, 88, 89, 90, 91, 92, and 93, and contains substitutions (e.g., conservative substitutions), insertions, or deletions relative to the reference sequence, but an anti-MS4A4A antibody comprising that sequence retains the ability to bind to MS4A4A. In some embodiments, a total of 1 to 10 amino acids have been substituted, inserted and/or deleted in SEQ ID NO: 86, 87, 88, 89, 90, 91, 92, or 93. In certain embodiments, a total of 1 to 5 amino acids have been substituted, inserted and/or deleted in SEQ ID NO: 86, 87, 88, 89, 90, 91, 92, or 93. In certain embodiments, the substitutions, insertions, or deletions occur in regions outside the HVRs (i.e., in the FRs). Optionally, the anti-MS4A4A antibody comprises the $V_L$ sequence of SEQ ID NO: 86, 87, 88, 89, 90, 91, 92, or 93, including post-translational modifications of that sequence. In a particular embodiment, the $V_L$ comprises one, two or three HVRs selected from (a) HVR-L1 comprising an amino acid sequence selected from the group consisting of SEQ ID NOs: 156, 157, and 158, (b) HVR-L2 comprising an amino acid sequence selected from the group consisting of SEQ ID NOs: 160 and 161, and (c) HVR-L3 comprising the amino acid sequence of SEQ ID NO: 163.

In another aspect, an anti-MS4A4A antibody comprises a full length heavy chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 320-335 and 355-362. In certain embodiments, a full length heavy chain amino acid sequence having at least 90%, 91%, 92%, 93%, 94%, 95%, 96%, 97%, 98%, or 99% identity to an amino acid sequence selected from the group consisting of SEQ ID NOs: 320-335 and 355-362 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 320-335 and 355-362. In certain embodiments, a total of 1 to 5 amino acids have been substituted, inserted and/or deleted in SEQ ID NO: 320-335 and 355-362. In certain embodiments, substitutions, insertions, or deletions occur in regions outside the HVRs (i.e., in the FRs).

In another aspect, an anti-MS4A4A antibody comprises a full length light chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 363-365. In certain embodiments, a full length heavy chain amino acid sequence having at least 90%, 91%, 92%, 93%, 94%, 95%, 96%, 97%, 98%, or 99% identity to an amino acid sequence selected from the group consisting of SEQ ID NOs: 363-365 contains substitutions (e.g., conservative substitutions), insertions, or deletions relative to the reference sequence, but an anti-MS4A4A antibody comprising that sequence retains the ability to bind to MS4A4A. In certain embodiments, a total of 1 to 10 amino acids have been substituted, inserted, and/or deleted in SEQ ID NO: 363-365. In certain embodiments, a total of 1 to 5 amino acids have been substituted, inserted and/or deleted in SEQ ID NO: 363-365. In certain embodiments, substitutions, insertions, or deletions occur in regions outside the LVRs (i.e., in the FRs).

In some embodiments, the anti-MS4A4A antibody comprises a full length heavy chain amino acid sequence of SEQ ID NOs:355-362 and a full length light chain amino acid sequence of SEQ ID NO:365. In some embodiments, the anti-MS4A4A antibody comprises a full length heavy chain amino acid sequence of SEQ ID NOs:320-327 and a full length light chain amino acid sequence of SEQ ID NO:363. In some embodiments, the anti-MS4A4A antibody comprises a full length heavy chain amino acid sequence of SEQ ID NOs:328-335 and a full length light chain amino acid sequence of SEQ ID NO:364.

In some embodiments, an anti-MS4A4A antibody of the present disclosure competitively inhibits binding of at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450. In some embodiments, an anti-MS4A4A antibody of the present disclosure competitively inhibits binding of at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331. In some embodiments, an anti-MS4A4A antibody of the present disclosure competitively inhibits binding of at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381. In some embodiments, an anti-MS4A4A antibody of the present disclosure competitively inhibits binding of at least one reference antibody selected from 4A-25, 4A-382, 4A-383, 4A-384, 4A-385, 4A-386, 4A-387, 4A-388, 4A-389, 4A-390.

In some embodiments, an anti-MS4A4A antibody of the present disclosure binds to an epitope of human MS4A4A that is the same as or overlaps with the MS4A4A epitope bound by at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, 4A-331, 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, 4A-381, 4A-25, 4A-382, 4A-383, 4A-384, 4A-385, 4A-386, 4A-387, 4A-388, 4A-389, 4A-390, 4A-419, and 4A-450. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In some embodiments, an anti-MS4A4A antibody of the present disclosure competitively inhibits binding of at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450, and any combination thereof, for binding to MS4A4A. In some embodiments, an anti-MS4A4A antibody of the present disclosure competitively inhibits binding of at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331, and any combination thereof, for binding to MS4A4A. In some embodiments, an anti-MS4A4A antibody of the present disclosure competitively inhibits binding of at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381, and any combination thereof, for binding to MS4A4A. In some embodiments, an anti-MS4A4A antibody of the present disclosure competitively inhibits binding of at least one reference antibody selected from 4A-25, 4A-382, 4A-383, 4A-384, 4A-385, 4A-386, 4A-387, 4A-388, 4A-389, or 4A-390, and any combination thereof, for binding to MS4A4A.

In some embodiments, an anti-MS4A4A antibody of the present disclosure has the same or overlapping epitope on MS4A4A as at least one reference antibody selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-419, and 4A-450, and any combination thereof, for binding to MS4A4A. In some embodiments, an anti-MS4A4A antibody of the present disclosure has the same or overlapping epitope on MS4A4A as at least one reference antibody selected from 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, and 4A-331, and any combination thereof, for binding to MS4A4A. In some embodiments, an anti-MS4A4A antibody of the present disclosure has the same or overlapping epitope on MS4A4A as at least one reference antibody selected from 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, and 4A-381, and any combination thereof, for binding to MS4A4A. In some embodiments, an anti-MS4A4A antibody of the present disclosure has the same or overlapping epitope on MS4A4A as at least one reference antibody selected from 4A-25, 4A-382, 4A-383, 4A-384, 4A-385, 4A-386, 4A-387, 4A-388, 4A-389, and 4A-390, and any combination thereof, for binding to MS4A4A.

In some embodiments, an anti-MS4A4A antibody of the present disclosure binds to extracellular domain 1 (ECL1) of MS4A4A. In some embodiments, an anti-MS4A4A antibody of the present disclosure binds to one or more amino acids within the amino acid sequence CMASNTYGSNPIS (SEQ ID NO:177) of SEQ ID NO:1. In some embodiments, an anti-MS4A4A antibody of the present disclosure binds to extracellular domain 2 (ECL2) of MS4A4A. In some embodiments, an anti-MS4A4A antibody of the present disclosure binds to one or more amino acids within the amino acid sequence SFFIHPYCNYYGNSNNCHGTMS (SEQ ID NO:178) of SEQ ID NO:1

Any suitable competition assay or MS4A4A binding assay known in the art, such as BIAcore analysis, ELISA assays, or flow cytometry, may be utilized to determine whether an anti-MS4A4A antibody competes with (or competitively inhibits the binding of) one or more reference antibodies selected from 4A-202, 4A-301, 4A-302, 4A-303, 4A-304, 4A-305, 4A-306, 4A-307, 4A-308, 4A-309, 4A-310, 4A-311, 4A-312, 4A-313, 4A-314, 4A-18, 4A-315, 4A-316, 4A-317, 4A-318, 4A-319, 4A-320, 4A-321, 4A-322, 4A-323, 4A-324, 4A-325, 4A-326, 4A-327, 4A-328, 4A-329, 4A-330, 4A-331, 4A-21, 4A-332, 4A-333, 4A-334, 4A-335, 4A-336, 4A-337, 4A-338, 4A-339, 4A-340, 4A-341, 4A-342, 4A-343, 4A-344, 4A-345, 4A-346, 4A-347, 4A-348, 4A-349, 4A-350, 4A-351, 4A-352, 4A-353, 4A-354, 4A-355, 4A-356, 4A-357, 4A-358, 4A-359, 4A-360, 4A-361, 4A-361, 4A-363, 4A-364, 4A-365, 4A-366, 4A-367, 4A-368, 4A-369, 4A-370, 4A-371, 4A-372, 4A-373, 4A-374, 4A-375, 4A-376, 4A-377, 4A-378, 4A-379, 4A-380, 4A-381, 4A-25, 4A-382, 4A-383, 4A-384, 4A-385, 4A-386, 4A-387, 4A-388, 4A-389, 4A-390, 4A-419, and 4A-450, and any combination thereof for binding to MS4A4A. In an exemplary competition assay, immobilized MS4A4A or cells expressing MS4A4A on the cell surface are incubated in a solution comprising a first labeled antibody that binds to MS4A4A (e.g., human or non-human primate) and a second unlabeled antibody that is being tested for its ability to compete with the first antibody for binding to MS4A4A. The second antibody may be present in a hybridoma supernatant. As a control, immobilized MS4A4A or cells expressing MS4A4A is incubated in a solution comprising the first labeled antibody but not the second unlabeled antibody. After incubation under conditions permissive for binding of the first antibody to MS4A4A, excess unbound antibody is removed, and the amount of label associated with immobilized MS4A4A or cells expressing MS4A4A is measured. If the amount of label associated with immobilized MS4A4A or cells expressing MS4A4A is substantially reduced in the test sample relative to the control sample, then that indicates that the second antibody is competing with the first antibody for binding to MS4A4A. See, Harlow and Lane (1988) *Antibodies: A Laboratory Manual* ch.14 (Cold Spring Harbor Laboratory, Cold Spring Harbor, N.Y.).

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence selected from the group consisting of SEQ ID NO:94 and 308, (ii) HVR-H2 comprising an amino acid sequence selected from the group consisting of SEQ ID NOs: 96, 97, 98, 99, and 309, and (iii) HVR-H3 comprising an amino acid sequence selected from the group consisting of SEQ ID NOs: 100, 101, 102, and 310, and (b) a $V_L$ domain comprising (i) HVR-L1 comprising an amino acid sequence selected from the group consisting of SEQ ID NOs: 103, 104, and 314, (ii) HVR-L2 comprising an amino acid sequence selected from the group consisting of SEQ ID NOs: 105, 106, and 315, and (iii) HVR-L3 comprising the amino acid sequence selected from the group consisting of SEQ ID NOs: 107 and 316. In some embodiments, the antibody comprises the $V_H$ and $V_L$ sequences in SEQ ID NOs:5-15 and 304, and SEQ ID NOs:17-22 and 305, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence selected from the group consisting of SEQ ID NO:94 and 308, (ii) HVR-H2 comprising an amino acid sequence selected from the group consisting of SEQ ID NOs: 96, 97, 98, 99, and 309, and (iii) HVR-H3 comprising an amino acid sequence selected from the group consisting of SEQ ID NOs: 100, 101, 102, and 310, and (b) a $V_L$ domain comprising (i) HVR-L1 comprising an amino acid sequence selected from the group consisting of SEQ ID NOs: 103, 104, and 314, (ii) HVR-L2 comprising an amino acid sequence selected from the group consisting of SEQ ID NOs: 105, 106, and 315, and (iii) HVR-L3 comprising the amino acid sequence selected from the group consisting of SEQ ID NO: 107 and 316. In some embodiments, the antibody comprises the $V_H$ and $V_L$ sequences in SEQ ID NOs:5-15 and 304, and SEQ ID NOs:17-22 and 305, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence of SEQ ID NO: 108, (ii) HVR-H2 comprising an amino acid sequence selected from the group consisting of SEQ ID NOs: 110 and 111, and (iii) HVR-H3 comprising the amino acid sequence of SEQ ID NO: 112, and (b) a $V_L$ domain comprising (i) HVR-L1 comprising the amino acid sequence of SEQ ID NO: 113, (ii) HVR-L2 comprising the amino acid sequence of SEQ ID NO: 114, and (iii) HVR-L3 comprising the amino acid sequence of SEQ ID NO: 115. In some embodiments, the antibody comprises the $V_H$ and $V_L$ sequences in SEQ ID NOs:24-30 and SEQ ID NOs:32-36, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence of SEQ ID NO: 108, (ii) HVR-H2 comprising an amino acid sequence selected from the group consisting of SEQ ID NOs: 110 and 111, and (iii) HVR-H3 comprising the amino acid sequence of SEQ ID NO:112, and (b) a $V_L$ domain comprising (i) HVR-L1 comprising the amino acid sequence of SEQ ID NO: 113, (ii) HVR-L2 comprising the amino acid sequence of SEQ ID NO: 114, and (iii) HVR-L3 comprising the amino acid sequence of SEQ ID NO: 115. In some embodiments, the antibody comprises the $V_H$ and $V_L$ sequences in SEQ ID NOs:24-30 and SEQ ID NOs:32-36, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising the amino acid sequence of SEQ ID NO: 116, (ii) HVR-H2 comprising an amino acid sequence selected from the group consisting of SEQ ID NOs: 118, 119, 120, 121, and 122, and (iii) HVR-H3 comprising an amino acid sequence selected from the group consisting of SEQ ID NOs: 123, 124, 125, 126, 127, 128, and 129, and (b) a $V_L$ domain comprising (i) HVR-L1 comprising an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145. In some embodiments, the antibody comprises the $V_H$ and $V_L$ sequences in SEQ ID NOs:40-53 and SEQ ID NOs:55-74, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising the amino acid sequence of SEQ ID NO: 116, (ii) HVR-H2 comprising an amino acid sequence selected from the group consisting of SEQ ID NOs:118, 119, 120, 121, and 122, and (iii) HVR-H3 comprising an amino acid sequence selected from the group consisting of SEQ ID NOs: 123, 124, 125, 126, 127, 128, and 129, and (b) a $V_L$ domain comprising (i) HVR-L1 comprising an amino acid sequence selected from the group consisting of SEQ ID NOs: 130, 131, 132, 133, 134, 135, 136, 137, and 138, (ii) HVR-L2 comprising an amino acid sequence selected from the group consisting of SEQ ID NOs: 139, 140, 141, 142, and 143, and (iii) HVR-L3 comprising an amino acid sequence selected from the group consisting of SEQ ID NOs: 144 and 145. In some embodiments, the antibody comprises the $V_H$ and $V_L$ sequences in SEQ ID NOs:40-53 and SEQ ID NOs:55-74, respectively. In some embodiments, the epitope of human MS4A4A is the same epitope as bound by an anti-MS4A4A antibody.

Further provided herein are anti-MS4A4A antibodies which competitively inhibit binding of and/or compete for binding with an anti-MS4A4A antibody comprising (a) a $V_H$ domain comprising (i) HVR-H1 comprising an amino acid sequence selected from the group consisting of SEQ ID NOs: 146 and 147, (ii) HVR-H2 comprising an amino acid sequence selected from the group consisting of SEQ ID NOs: 149, 150, 151, 152, and 153, and (iii) HVR-H3 comprising the amino acid sequence of SEQ ID NO: 154, and (b) a $V_L$ domain comprising (i) HVR-L1 comprising an amino acid sequence selected from the group consisting of SEQ ID NOs: 156, 157, and 158, (ii) HVR-L2 comprising an amino acid sequence selected from the group consisting of SEQ ID NOs: 160 and 161, and (iii) HVR-L3 comprising the amino acid sequence of SEQ ID NO: 163. In some embodiments, the antibody comprises the $V_H$ and $V_L$ sequences in SEQ ID NOs:76-84 and SEQ ID NOs:86-93, respectively.

Provided herein are anti-MS4A4A antibodies which bind to an epitope of human MS4A4A that is the same as or overlaps with the epitope bound by an anti-MS4A4A antibody comprising (a) a $V_H$ domain comprising (i) HVR-H1 comprising an amino acid sequence selected from the group consisting of SEQ ID NOs: 146 and 147, (ii) HVR-H2 comprising an amino acid sequence selected from the group consisting of SEQ ID NOs: 149, 150, 151, 152, and 153, and (iii) HVR-H3 comprising the amino acid sequence of SEQ ID NO: 154, and (b) a $V_L$ domain comprising (i) HVR-L1 comprising an amino acid sequence selected from the group consisting of SEQ ID NOs: 156, 157 and 158, (ii) HVR-L2 comprising an amino acid sequence selected from the group consisting of SEQ ID NOs: 160 and 161, and (iii) HVR-L3 comprising the amino acid sequence of SEQ ID NO: 163. In some embodiments, the antibody comprises the $V_H$ and $V_L$ sequences in SEQ ID NOs:76-84 and SEQ ID Nos:86-93, respectively. In some embodiments, the epitope of human MS4A4A is the same epitope as bound by an anti-MS4A4A antibody.

In some embodiments, the anti-MS4A4A antibody according to any of the above embodiments is a monoclonal antibody, including a humanized and/or human antibody. In some embodiments, the anti-MS4A4A antibody is an antibody fragment, e.g., a Fv, Fab, Fab', scFv, diabody, or F(ab')2 fragment. In some embodiments, the anti-MS4A4A antibody is a substantially full-length antibody, e.g., an IgG1 antibody, IgG2a antibody or other antibody class or isotype as defined herein.

In some embodiments, an anti-MS4A4A antibody according to any of the above embodiments may incorporate any of the features, singly or in combination, as described in Sections 1-7 below:

(1) Anti-MS4A4A Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, Kd is measured using a BIACORE surface plasmon resonance assay, for example, an assay using a BIACORE-2000 or a BIACORE-3000 (BIAcore, Inc., Piscataway, N.J.) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

(2) Antibody Fragments

In some embodiments of any of the antibodies provided herein, the antibody is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol. 133:3001 (1984) and Boerner et al. J. Immunol. 147:86 (1991)). Human antibodies generated via human B-cell hybridoma technology are also described in Li et al. Proc. Natl. Acad. Sci. USA, 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. Histology and Histopathology 20(3) :927-937 (2005) and Vollmers et al. Methods and Findings in Experimental and Clinical Pharmacology 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MS4A4A activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, a human IgG1 light chain constant region comprises the amino acid sequence of SEQ ID NO: 344. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MS4A4A.

It may also be desirable to modify an anti-MS4A4A antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MS4A4A antibody of the present disclosure to modify effector function to increase finding selectivity toward the ITIM-containing FcgRIIb (CD32b) to increase clustering of MS4A4A antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more MS4A4A polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on MS4A4A and comprises a second antigen binding region which binds to a second site on MS4A4A. In some embodiment, the multispecific antibodies comprises a first antigen binding region which binds to MS4A4A and a second antigen binding region that binds to a second polypeptide.

Provided herein are multispecific antibodies comprises a first antigen binding region, wherein the first antigen binding region comprises the six HVRs of an antibody described herein, which binds to MS4A4A and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10):e13741 (2010)).

The multivalent antibodies may recognize the MS4A4A antigen as well as without limitation additional antigens Aβ peptide, antigen or an a-synuclein protein antigen or, Tau protein antigen or, TDP-43 protein antigen or, prion protein antigen or, huntingtin protein antigen, or RAN, translation Products antigen, including the DiPeptide Repeats,(DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is Aβ. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple MS4A4A (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Agr; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.*, 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant $V_H$ and $V_L$ sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modification. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises N297A mutation according to EU numbering. In some embodiments of any of the IgG1 modified Fc, the Fc comprises K322A mutation according to EU numbering. In some embodiments of any of the IgG1 modified Fc, the Fc comprises N297A mutation according to EU numbering. In some embodiments of any of the IgG1 modified Fc, the Fc comprises P331S mutation according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises the N325S and L328F mutations according to EU numbering (N325S/L328F). In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 ($C_H1$) and hinge region of IgG1 with $C_H1$ and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L234A, L235A, and P331S according to EU numbering. In some embodiments, the IgG1 modified Fc comprises an amino acid substitution at positions L234A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA*, 103:4005-4010 (2006)), or one or more of L234F, L235E, and/or P331S mutations (Sazinsky et al. *Proc Natl Acad Sci USA*, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MS4A4A antibody of the present disclosure with the correct epitope specificity can activate the target antigen, with minimal adverse effects, when the antibody has an Fc domain from a human IgG2 isotype ($C_H1$ and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol*, 200:16-26 (2000)); G237A (Cole et al. *Transplantation*, 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl.1):27 (2000); Armour et al. *The Haematology Journal* 1(Suppl.1):27 (2000)), C219S, and/or C220S (White et al. *Cancer Cell* 27, 138-148 (2015)); S267E, L328F (Chu et al. *Mol Immunol*, 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1($C_H1$) and hinge region (White et al. Cancer Cell 27:138-148 (2015)). In certain embodiments of any of the IgG2 modified Fc, the IgG2 isotype $C_H1$ and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. J Immunol 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. Mol Immunol. 30:105-108 (1993)) and/or with one or more mutations described in (Peters et al. J Biol Chem. 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In some embodiments of any of the IgG4 modified Fc, the Fc comprises S228P mutation according to EU numbering. In some embodiments of any of the IgG4 modified Fc, the Fc comprises S267E and L328F mutations according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

In some embodiments, an antibody comprises a heavy chain comprising the amino acid sequence of SEQ ID NO:336. In some embodiments, an antibody comprises a heavy chain comprising the amino acid sequence of SEQ ID NO:328. In some embodiments, an antibody comprises a heavy chain comprising the amino acid sequence of SEQ ID NO:320.

In some embodiments, an antibody has a human IgG1 heavy chain without a C-terminal lysine. In some embodiments, an antibody has a human IgG1 heavy chain with a P331S mutation. In some embodiments, an antibody has a human IgG1 heavy chain with a P331S mutation and without a C-terminal lysine. In some embodiments, an antibody has a human IgG1 heavy chain with N325S and L328F mutations (N325S/L328F). In some embodiments, an antibody has a human IgG1 heavy chain with a N325S/L328F mutation and without a C-terminal lysine. In some embodiments, an antibody has a human IgG1 heavy chain with a K322A mutation. In some embodiments, an antibody has a human IgG1 heavy chain with a K322A mutation and without a C-terminal lysine. In the foregoing embodiments, mutations are indicated according to EU numbering.

In some embodiments, an antibody comprises a heavy chain amino comprising the amino acid sequence of SEQ ID NO:337. In some embodiments, an antibody comprises a heavy chain comprising the amino acid sequence of SEQ ID NO:338. In some embodiments, an antibody comprises a heavy chain comprising the amino acid sequence of SEQ ID NO:339. In some embodiments, an antibody comprises a heavy chain comprising the amino acid sequence of SEQ ID NO:340. In some embodiments, an antibody comprises a heavy chain comprising the amino acid sequence of SEQ ID NO:341. In some embodiments, an antibody comprises a heavy chain comprising the amino acid sequence of SEQ ID NO:342. In some embodiments, an antibody comprises a heavy chain comprising the amino acid sequence of SEQ ID NO:343.

In some embodiments, an antibody comprises a heavy chain amino comprising the amino acid sequence of SEQ ID NO:329. In some embodiments, an antibody comprises a heavy chain comprising the amino acid sequence of SEQ ID NO:330. In some embodiments, an antibody comprises a heavy chain comprising the amino acid sequence of SEQ ID NO:331. In some embodiments, an antibody comprises a heavy chain comprising the amino acid sequence of SEQ ID NO:332. In some embodiments, an antibody comprises a heavy chain comprising the amino acid sequence of SEQ ID NO:333. In some embodiments, an antibody comprises a heavy chain comprising the amino acid sequence of SEQ ID NO:334. In some embodiments, an antibody comprises a heavy chain comprising the amino acid sequence of SEQ ID NO:335.

In some embodiments, an antibody comprises a heavy chain amino comprising the amino acid sequence of SEQ ID NO:321. In some embodiments, an antibody comprises a heavy chain comprising the amino acid sequence of SEQ ID NO:322. In some embodiments, an antibody comprises a heavy chain comprising the amino acid sequence of SEQ ID NO:323. In some embodiments, an antibody comprises a heavy chain comprising the amino acid sequence of SEQ ID NO:324. In some embodiments, an antibody comprises a heavy chain comprising the amino acid sequence of SEQ ID NO:325. In some embodiments, an antibody comprises a heavy chain comprising the amino acid sequence of SEQ ID NO:326. In some embodiments, an antibody comprises a heavy chain comprising the amino acid sequence of SEQ ID NO:327.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1,3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH- (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch Ann. Rev. Biochem., 61:387 (1992), incorporated herein by reference for any purpose); for example, by adding internal cysteine residues capable of forming intramolecular disulfide bridges which cyclize the peptide.

Drug conjugation involves coupling of a biological active cytotoxic payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. Bioconjugate Chemistry 21 (1):5-13 (2010).

II. Nucleic Acids, Vectors, and Host Cells

Anti-MS4A4A antibodies of the present disclosure may be produced using recombinant methods and compositions, e.g., as described in U.S. Pat. No. 4,816,567. In some embodiments, isolated nucleic acids having a nucleotide sequence encoding any of the anti-MS4A4A antibodies of the present disclosure are provided. Such nucleic acids may encode an amino acid sequence comprising the V$_L$ and/or an amino acid sequence comprising the V$_H$ of the anti-MS4A4A antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the V$_L$ of the antibody and an amino acid sequence comprising the V$_H$ of the antibody, or (2) a first vector comprising a nucleic acid that encodes an amino acid sequence comprising the V$_L$ of the antibody and a second vector comprising a nucleic acid that encodes an amino acid sequence comprising the V$_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MS4A4A antibody of the present disclosure are provided. In some embodiments, the method includes culturing a host cell of the present disclosure comprising a nucleic acid encoding the anti-MS4A4A antibody, under conditions suitable for expression of the antibody. In some embodiments, the antibody is subsequently recovered from the host cell (or host cell culture medium).

For recombinant production of an anti-MS4A4A antibody of the present disclosure, a nucleic acid encoding the anti-MS4A4A antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MS4A4A antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MS4A4A antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross Nat. Biotech. 22:1409-1414 (2004); and Li et al. Nat. Biotech. 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR- CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

III. Pharmaceutical Compositions/Formulations

Provided herein are pharmaceutical compositions and/or pharmaceutical formulations comprising the anti-MS4A4A antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, Langer, *Science* 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-MS4A4A antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid.

IV. Therapeutic Uses

As disclosed herein, anti-MS4A4A antibodies of the present disclosure may be used for preventing, reducing risk, or treating diseases and disorders. In some embodiments, an anti-MS4A4A antibody of the present disclosure is effective at preventing, reducing risk, or treating Alzheimer's disease, late onset Alzheimer's disease, and cognitive impairment.

MS4A4A as a Disease Target

Genome wide association studies have identified various members of the MS4A family are associated with Alzheimer's disease. These are MS4A2, MS4A3, MS4A4A, MS4A4E, MS4A6A, and MS4A6E. The associated SNPs are found in the 3' UTR of MS4A6A (rs610932) and the intergenic region between MS4A4E and MS4A6A (rs670139). There are three SNPs in the MS4A gene cluster that have been associated with an increased risk of late-onset Alzheimer's disease. These include rs4938933 in MS4A4A, rs670139 in MS4A4E, and rs610932 in MS4A6A (Hollingworth et al, 2011, Nat Genetics, 43:429-435; Naj et al, 2011, Nature Genetics, 43:436-441; Antunez et al, 2011, Genome Medicine, 3, article 33). Additionally, MS4A4A locus SNPs (rs2304933 and rs2304935) associated with higher levels of MS4A4A and increased Alzheimer's disease risk, including late-onset Alzheimer's disease (LOAD) (Allen et al, 2012, Neurology, 79:221-228).

The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disorder, the method comprising administering to the individual in need thereof a therapeutically effective amount of an anti-MS4A4A antibody.

In some embodiments, the present disclosure provides a method for preventing, reducing the risk, or treating an individual having Alzheimer's disease, the method comprising administering to the individual in need thereof a therapeutically effective amount of an anti-MS4A4A antibody.

In some embodiments, the present disclosure provides a method for preventing, reducing the risk, or treating an individual having late onset Alzheimer's disease, the method comprising administering to the individual in need thereof a therapeutically effective amount of an anti-MS4A4A antibody.

In some embodiments, the present disclosure provides a method for preventing, reducing the risk, or treating an individual having mild cognitive impairment, the method comprising administering to the individual in need thereof a therapeutically effective amount of an anti-MS4A4A antibody.

In some embodiments, the present disclosure provides a method for preventing, reducing risk, or treating an individual having a disease, disorder, or condition associated with over expression or increased activity of MS4A4A, the method comprising administering to an individual in need thereof a therapeutically effective amount of an anti-MS4A4A antibody.

In some embodiments, the present disclosure provides a method for preventing, reducing the risk, or treating an individual having a CSF1R-deficient disease or disorder, the method comprising administering to an individual in need thereof a therapeutically effective amount of an anti-MS4A4A antibody. In some embodiments, the CSF1R-deficient disease or disorder is adult-onset leukoencephalopathy with axonal spheroids and pigmented glia (ALSP) or hereditary diffuse leukoencephalopathy with spheroids (HDLS).

Other aspects of the present disclosure relate to a method of preventing, reducing risk, or treating an individual having a disease, disorder, or injury selected from the group consisting of frontotemporal dementia, Alzheimer's disease, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of older individual, and one or more undesirable symptoms of normal aging. Other aspects of the present disclosure relate to an anti-MS4A4A antibody of any of the preceding embodiments for use in preventing or reducing metastasis. Other aspects of the present disclosure relate to an anti-MS4A4A antibody of any of the preceding embodiments for use in preventing, reducing risk, or treating an individual having cancer.

Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, Alzheimer's disease, late-onset Alzheimer's disease, mild cognitive impairment, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitations inflammation, neuronal loss, and cognitive deficits, such as cognitive deficits in the absence of known brain disease, including cognitive deficits of the frontal cerebral cortex of older individual and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis, comprising administering to the individual a therapeutically effective amount of the anti-MS4A4A antibody of any of the preceding embodiments. Other aspects of the present disclosure relate to an anti-MS4A4A antibody of any of the preceding embodiments for use in preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. Other aspects of the present disclosure relate to use of an anti-MS4A4A antibody of any of the preceding embodiments in the manufacture of a medicament for preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 100 mg/kg of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 150 mg/kg, which may be administered to the patient intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose followed by one or more lower doses may be administered. However, other dosage regimens may be useful. The progress of this therapy is easily monitored by conventional techniques and assays.

V. Diagnostic Uses

In some embodiments of any of the antibodies, any of the anti-MS4A4A antibodies provided herein is useful for detecting the presence of MS4A4A in a sample or an individual. The term "detecting" as used herein encompasses quantitative or qualitative detection. Provided herein are methods of using the antibodies of this disclosure for diagnostic purposes, such as the detection of MS4A4A in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VI. Articles of Manufacture

Provided herein are articles of manufacture (e.g., kit) comprising an anti-MS4A4A antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MS4A4A antibody described herein) to prevent, reduce risk, or treat an individual having a disease, disorder, or injury selected from of frontotemporal dementia, Alzheimer's disease, late onset Alzheimer's disease, cognitive decline or impairment, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A4A antibody of any of the preceding embodiments.

In some embodiments, the instructions include instructions for use of the anti-MS4A4A antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1

Humanization of Murine Anti-MS4A4A Mouse Antibodies

The purpose of this example was to generate humanized variants of certain parental mouse anti-MS4A4A antibodies disclosed in international patent application serial number PCT/US2019/016156.

The parental mouse anti-MS4A4A antibody 4A-202 contains a heavy chain variable region comprising the amino acid sequence of:

QVQLQQSGAELARPGASVKLSCK-ASGYTFTNYWMQWVKQRPGQGLEWIGATH-PGHGDTRYTQ KFKGKATLSADKSSSTAYMQLSN-LASEDSAVYYCAREEVYYGFRSYWYFDVWGRGT-LVTVSS (SEQ ID NO:164), and a light chain variable region comprising the amino acid sequence of:

DIVLTQSPASLAVSLGQRATISCRAS-ESVDNYGVSFMNWFQQKPGQPPKWY-GASNQGSGVPARF SGSGSGTDFSLNIHPMEEDD-TAMYFCQQSKEVPPTFGGGTKLEIK (SEQ ID NO:165).

The parental mouse anti-MS4A4A 4A-18 contains a heavy chain variable region comprising the amino acid sequence of:

QVQLQQPGTELVKPGASVKLSCKASGYTFTSY-WIHWVKQRPGQGLEWIGNINPTNGGTNYNERF KSKATLTVDKSSSTAYMQLSSLTSEDSAVYYCAR-AYYYGSSLFAYWGQGTLVTVSS (SEQ ID NO:166), and a light chain variable region comprising the amino acid sequence of:

DIVMTQSQKFMSTTVGDRVSITCKASQNVGTA-
VAWSQQKPGQSPKLLIYSASYRHTGVPDRFTGS
GSGTDFTLTITNMQSEDLA-
DYFCQQYSTYPWTFGGGTKLEIK (SEQ ID NO:167).

The parental mouse anti-MS4A4A antibody 4A-21 contains a heavy chain variable region comprising the amino acid sequence of:
QIQLVQSGPELKKPGETVKISCKASGYIFT-
SYGLSWVKQTPGKGLKWMGWINTYSGVPTY-
ANDFK GRFAFSLETSASTTYLRINNLKNDD-
TATYFCARSLVDYWGQGTPLTVSS (SEQ ID NO:168),
and a light chain variable region comprising the amino acid sequence of:
DVVMTQTPFTLSVTIGQSASISCKSSQSLLYSDGK-
TYLSWLLQRPGQSPKRLIYLVSKLDSGVPDRF
TGSGSGTDFTLKISRVEAE-
DLGVYYCWQGIDFHQTFGGGTKLEIK (SEQ ID NO:169).

The parent mouse anti-MS4A4A antibody 4A-25 contains a heavy chain variable region comprising the amino acid sequence of:
QVTLKESGPGILQP-
SQTLSLTCSFSGFSLRTSDMGVGWVRQPSGEGLEW-
LADIWWDDNKYYNPSL
KSRLTISKDTSSNQVFLKITSVDTADTATYYCAR-
RANYGNLFDYWGQGTAVTVSS (SEQ ID NO:170), and
a light chain variable region comprising the amino acid sequence of:
DIVMTQSLKFMSTSVGDRVSITCKASQNVR-
SAVAWYQQKPGQSPKVLIYWASNRHTGVPDRFTG
SGSGTDFTLTISNVQSEDLADYFCLQHW-
NYLTFGSGTKLEIK (SEQ ID NO:171).

One method of humanizing non-human antibodies is to transplant the CDRs from a non-human (e.g., murine) antibody onto a human antibody acceptor framework. Such CDR transplantation may result in attenuation or complete loss of affinity of the humanized antibody to its target due to perturbation in its framework. As a result, certain amino acid residues in the human framework may need to be replaced by amino acid residues from the corresponding positions of the murine antibody framework (back mutations) in order to restore attenuated or lost affinity. Therefore, the amino acid residues to be replaced in the context of the selected human antibody germline acceptor framework must be determined so that the humanized antibody substantially retains functions and paratopes. In addition, retained or improved thermal stability and solubility are desired for good manufacturability and downstream development.

Accordingly, structure-based antibody modeling was applied in the process of humanizing mouse anti-MS4A4A monoclonal antibodies 4A-202, 4A-18, 4A-21, and 4A-25 utilizing the BioMOE module of MOE (Molecular Operating Environment, Chemical Computing Group, Montreal, Canada). Briefly, VH and VL amino acid sequences of the mouse monoclonal antibodies to be humanized were compared to human VL, VH, LJ, HJ functional germline amino acid sequences taken from IMGT. Pseudo-genes and ORFs were excluded from analysis. Per one mouse monoclonal antibody (query), five most similar VL and five most similar VH germline amino acid sequences were selected and combined with the most similar VJ and HJ genes, producing 25 humanized amino acid sequences. The CDRs to be transplanted onto the human framework were defined according to the AbM definition.

The query and the 25 humanized amino acid sequences were used to create Fv homology models using BioMOE module or the Antibody Modeler module of MOE (Molecular Operating Environment, Chemical Computing Group, Montreal, Canada). AMBER10:EHT force field analysis was used for energy minimization through the entire antibody homology modeling process. Based on the Fv homology models obtained, molecular descriptors such as interaction energy between VL and VH, coordinate-based isoelectric point (3D pI), hydrophobic patch, and charged surface area were calculated, analyzed, and sorted by scoring metrics provided by MOE. These molecular descriptors were utilized to prioritize the humanized monoclonal antibodies for downstream experimental procedures, including protein expression, purification, binding affinity studies, and functional assays.

The BioMOE module of MOE provides a tool, Mutation Site Properties, to visualize and classify potential residues for back-mutation. In this context, back-mutation is defined as amino acid substitution which is reverted to the original query amino acid sequence replacing the humanized amino acid sequence. Using this tool, the original query (reference) was compared individually to the selected humanized variants for both the primary amino acid sequence and the 3D structure of the 3D Fv homology model.

Changes between the reference (i.e., parental) antibody and the humanized variant were classified based on amino acid type difference, interaction potential with CDR residues, impact potential for VL/VH pairing, and potential change in hydrophobic and charged surface area in and near the CDRs.

Mutations near the CDRs or the VL/VH interface having a significant charge difference or containing strong H-bond interactions were individually evaluated and the significantly disrupting mutations were reverted to the original query residues. As a result, humanized amino acid sequences may contain up to five back mutations. Amino acid sequences for the variable heavy chain and variable light chain query mouse monoclonal antibodies (mouse anti-MS4A4A antibody 4A-202, mouse anti-MS4A4A antibody 4A-18, mouse anti-MS4A4A antibody 4A-21, and mouse anti-MS4A4A antibody 4A-25) and the humanized monoclonal antibodies with or without back mutations are provided in Tables 1-4 below. In Tables 1-4, the CDR sequences (Kabat) are underlined.

TABLE 1

| Antibody | Heavy Chain Variable | SEQ ID NO: | Light Chain Variable | SEQ ID NO: |
|---|---|---|---|---|
| 4A-202 | QVQLQQSGAELARPGASVKLS CKASGYTF<u>TNYWMQ</u>WVKQR PGQGLEWIG<u>ATHPGHGDTRYT QKFKG</u>KATLSADKSSSTAYM QLSNLASEDSAVYYCAR<u>EEVY YGFRSYWYFDV</u>WGRGTLVT VSS | 4 | DIVLTQSPASLAVSLGQRATISC<u>R ASESVDNYGVSFMN</u>WFQQKPGQ PPKLLIY<u>GASNQGS</u>GVPARFSGSG SGTDFSLNIHPMEEDDTAMYFC<u>Q QSKEVPPT</u>FGGGTKLEIK | 16 |

TABLE 1-continued

| Antibody | Heavy Chain Variable | SEQ ID NO: | Light Chain Variable | SEQ ID NO: |
|---|---|---|---|---|
| 4A-301 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-302 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | EIVLTQSPATLSLSPGERATLSCRASESVDNYGVSFMNWYQQKPGQAPRLLIYGASNQGSGIPARFSGSGSGTDFTLTISSLEPEDFAVYYCQQSKEVPPTFGGGTKVEIK | 18 |
| 4A-303 | EVQLVQSGAEVKKPGESLKISCKGSGYTFTNYWMQWVRQMPGKGLEWMGATHPGHGDTRYSPSFQGQVTISADKSISTAYLQWSSLKASDTAMYYCAREEVYYGFRSYWYFDVWGRGTLVTVSS | 6 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-304 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | EIVLTQSPGTLSLSPGERATLSCRASESVDNYGVSFMNWYQQKPGQAPRLLIYGASNQGSGIPDRFSGSGSGTDFTLTISRLEPEDFAVYYCQQSKEVPPTFGGGTKVEIK | 19 |
| 4A-305 | EVQLVQSGAEVKKPGATVKISCKVSGYTFTNYWMQWVQQAPGKGLEWMGATHPGHGDTRYAEKFQGRVTITADTSTDTAYMELSSLRSEDTAVYYCAREEVYYGFRSYWYFDVWGRGTLVTVSS | 7 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-306 | QVQLVQSGAEVKKPGASVKVSCKASGYTFTNYWMQWVRQAPGQGLEWMGATHPGHGDTRYAQKFQGRVTMTRDTSTSTVYMELSSLRSEDTAVYYCAREEVYYGFRSYWYFDVWGRGTLVTVSS | 5 | DIQMTQSPSSLSASVGDRVTITCRASESVDNYGVSFMNWYQQKPGKAPKLLIYGASNQGSGVPSRFSGSGSGTDFTLTISSLQPEDFATYYCQQSKEVPPTFGGGTKVEIK | 20 |
| 4A-307 | QVQLVQSGAEVKKPGASVKVSCKASGYTFTNYWMQWVRQAPGQGLEWMGATHPGHGDTRYAQKFQGRVTMTADKSTSTVYMELSSLRSEDTAVYYCAREEVYYGFRSYWYFDVWGRGTLVTVSS | 8 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-308 | QVQLVQSGAEVKKPGASVKVSCKASGYTFTNYWMQWVRQAPGQGLEWMGATHPGHGDTRYAQKFQGRVTMTADKSTSTAYMELSSLRSEDTAVYYCAREEVYYGFRSYWYFDVWGRGTLVTVSS | 9 | DIVMTQSPDSLAVSLGERATINCRASESVDNYGVSFMNWYQQKPGQPPKLLIYGASNQGSGVPDRFSGSGSGTDFTLTISSLQAEDVAVYYCQQSKEVPPTFGGGTKVEIK | 17 |
| 4A-309 | QVQLVQSGAEVKKPGASVKVSCKASGYTFTNYWMQWVRQAPGQGLEWMGATHPGHGDTRYAQKFQGRVTLTADKSISTAYMELSRLRSDDTVVYYCAREEVYYGFRSYWYFDVWGRGTLVTVSS | 10 | EIVLTQSPATLSLSPGERATLSCRASESVDNYGVSFMNWYQQKPGQAPRLLIYGASNQGSGIPARFSGSGSGTDFTLTISSLEPEDFAVYYCQQSKEVPPTFGGGTKVEIK | 18 |

TABLE 1-continued

| Antibody | Heavy Chain Variable | SEQ ID NO: | Light Chain Variable | SEQ ID NO: |
|---|---|---|---|---|
| 4A-310 | EVQLVQSGAEVKKPGESLKIS CKGSGYTFTNYWMQWVRQM PGKGLEWMGATHPGHGDTRY SPSFQGQVTISADKSSTAYLQ WSSLKASDTAMYYCAREEVY YGFRSYWYFDVWGRGTLVTV SS | 11 | DIVMTQSPDSLAVSLGERATINCR ASESVDNYGVSFMNWYQQKPGQ PPKLLIYGASNQGSGVPDRFSGSG SGTDFTLTISSLQAEDVAVYYCQQ SKEVPPTFGGGTKVEIK | 17 |
| 4A-311 | EVQLVQSGAEVKKPGATVKIS CKVSGYTFTNYWMQWVQQA PGKGLEWMGATHPGHGDTRY AEKFQGRVTITADKSTSTAYM ELSSLRSEDTAVYYCAREEVY YGFRSYWYFDVWGRGTLVTV SS | 12 | DIVMTQSPDSLAVSLGERATINCR ASESVDNYGVSFMNWYQQKPGQ PPKLLIYGASNQGSGVPDRFSGSG SGTDFTLTISSLQAEDVAVYYCQQ SKEVPPTFGGGTKVEIK | 17 |
| 4A-312 | QVQLVQSGAEVKKPGASVKV SCKASGYTFTNYWMQWVRQ APGQGLEWMGATHPGHGDTR YAQKFQGRVTMTRDTSTSTV YMELSSLRSEDTAVYYCAREE VDYGFRSYWYFDVWGRGTLV TVSS | 13 | EIVLTQSPATLSLSPGERATLSCRA SESVDNYGVSFMNWYQQKPGQA PRLLIYGASNQGSGIPARFSGSGSG TDFTLTISSLEPEDFAVYYCQQSK EVPPTFGGGTKVEIK | 21 |
| 4A-313 | QVQLVQSGAEVKKPGASVKV SCKASGYTFTNYWMQWVRQ APGQGLEWMGATHPGHGDTR YAQKFQGRVTMTRDTSTSTV YMELSSLRSEDTAVYYCAREE VYYGFRSYWYFDLWGRGTLV TVSS | 14 | EIVLTQSPATLSLSPGERATLSCRA SESVDNYGVSRMNWYQQKPGQA PRLLIYGASNQGSGIPARFSGSGSG TDFTLTISSLEPEDFAVYYCQQSK EVPPTFGGGTKVEIK | 22 |
| 4A-314 | QVQLVQSGAEVKKPGASVKV SCKASGYTFTNYWMQWVRQ APGQGLEWMGTTLPGHGDTR YAQKFQGRVTMTRDTSTSTV YMELSSLRSEDTAVYYCAREE VYYGFRSYWYFDVWGRGTLV TVSS | 15 | EIVLTQSPATLSLSPGERATLSCRA SESVDNYGVSRMNWYQQKPGQA PRLLIYGASNQGSGIPARFSGSGSG TDFTLTISSLEPEDFAVYYCQQSK EVPPTFGGGTKVEIK | 22 |

TABLE 2

| Antibody | Heavy Chain Variable | SEQ ID NO: | Light Chain Variable | SEQ ID NO: |
|---|---|---|---|---|
| 4A-18 | QVQLQQPGTELVKPGASVKLS CKASGYTFTSYWIHWVKQRP GQGLEWIGNINPTNGGTNYNE RFKSKATLTVDKSSSTAYMQL SSLTSEDSAVYYCARAYYYGS SLFAYWGQGTLVTVSS | 23 | DIVMTQSQKFMSTTVGDRVSITC KASQNVGTAVAWSQQKPGQSP KLLIYSASYRHTGVPDRFTGSGS GTDFTLTITNMQSEDLADYFCQ QYSTYPWTFGGGTKLEIK | 31 |
| 4A-315 | QVQLVQSGAEVKKPGASVKV SCKASGYTFTSYWIHWVRQAP GQGLEWMGNINPTNGGTNYA QKFQGRVTMTRDTSTSTVYM ELSSLRSEDTAVYYCARAYYY GSSLFAYWGQGTLVTVSS | 24 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-316 | QVQLVQSGAEVKKPGASVKV SCKASGYTFTSYWIHWVRQAP GQGLEWMGNINPTNGGTNYA QKFQGRVTMTVDKSTSTVYM ELSSLRSEDTAVYYCARAYYY GSSLFAYWGQGTLVTVSS | 25 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIKR | 33 |
| 4A-317 | QVQLVQSGAEVKKPGASVKV SCKASGYTFTSYWIHWVRQAP GQGLEWMGNINPTNGGTNYA QKFQGRVTMTVDKSTSTVYM ELSSLRSEDTAVYYCARAYYY GSSLFAYWGQGTLVTVSS | 25 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |

TABLE 2-continued

| Antibody | Heavy Chain Variable | SEQ ID NO: | Light Chain Variable | SEQ ID NO: |
|---|---|---|---|---|
| 4A-318 | QVQLVQSGAEVKKPGASVKV SCKASGYTFTSYWIHWVRQAP GQGLEWMGNINPTNGGTNYA QKFQGRVTMTVDKSTSTAYM ELSSLRSEDTAVYYCARAYYY GSSLFAYWGQGTLVTVSS | 26 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIKR | 33 |
| 4A-319 | QVQLVQSGAEVKKPGASVKV SCKASGYTFTSYWIHWVRQAP GQGLEWMGNINPTNGGTNYA QKFQGRVTMTVDKSTSTAYM ELSSLRSEDTAVYYCARAYYY GSSLFAYWGQGTLVTVSS | 26 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-320 | QVQLVQSGAEVKKPGASVKV SCKASGYTFTSYWIHWVRQAP GQGLEWMGNINPTNGGTNYA QKFQGRVTSTRDTSISTAYME LSRLRSDDTVVYYCARAYYY GSSLFAYWGQGTLVTVSS | 27 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-321 | QVQLVQSGAEVKKPGASVKV SCKASGYTFTSYWIHWVRQAP GQGLEWMGNINPTNGGTNYA QKFQGRVTSTRDTSISTAYME LSRLRSDDTVVYYCARAYYY GSSLFAYWGQGTLVTVSS | 27 | DIVMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 34 |
| 4A-322 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIKR | 33 |
| 4A-323 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-324 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIQMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 35 |
| 4A-325 | QVQLVQSGAEVKKPGASVKV SCKASGYTFTSYWIHWVRQAP GQGLEWMGNINPTNGGTNYA QKFQGRVTSTVDKSISTAYME LSRLRSDDTVVYYCARAYYY GSSLFAYWGQGTLVTVSS | 28 | DIVMTQSPSSLSASVGDRVTITC KASQNVGTAVAWYQQKPEKAP KSLIYSASYRHTGVPSRFSGSGS GTDFTLTISSLQPEDFATYYCQQ YSTYPWTFGGGTKVEIK | 34 |
| 4A-326 | QVQLVQSGAEVKKPGASVKV SCKASGYTFTSYWIHWVRQAP GQRLEWMGNINPTNGGTNYS QKFQGRVTITRDTSASTAYME LSSLRSEDTAVYYCARAYYYG SSLFAYWGQGTLVTVSS | 29 | DIVMTQSPSFLSASVGDRVTITC KASQNVGTAVAWYQQKPGKAP KLLIYSASYRHTGVPSRFSGSGS GTEFTLTISSLQPEDFATYYCQQ YSTYPWTFGGGTKVEIK | 32 |
| 4A-327 | QVQLVQSGAEVKKPGASVKV SCKASGYTFTSYWIHWVRQAP GQRLEWMGNINPTNGGTNYS QKFQGRVTITRDTSASTAYME LSSLRSEDTAVYYCARAYYYG SSLFAYWGQGTLVTVSS | 29 | AIQMTQSPSSLSASVGDRVTITC KASQNVGTAVAWYQQKPGKAP KLLIYSASYRHTGVPSRFSGSGS GTDFTLTISSLQPEDFATYYCQQ YSTYPWTFGGGTKVEIK | 36 |
| 4A-328 | QVQLVQSGAEVKKPGASVKV SCKASGYTFTSYWIHWVRQAP GQRLEWMGNINPTNGGTNYS QKFQGRVTITVDKSASTAYME LSSLRSEDTAVYYCARAYYYG SSLFAYWGQGTLVTVSS | 30 | DIQLTQSPSFLSASVGDRVTITCK ASQNVGTAVAWYQQKPGKAPK LLIYSASYRHTGVPSRFSGSGSG TEFTLTISSLQPEDFATYYCQQY STYPWTFGGGTKVEIK | 37 |

TABLE 2-continued

| Antibody | Heavy Chain Variable | SEQ ID NO: | Light Chain Variable | SEQ ID NO: |
|---|---|---|---|---|
| 4A-329 | QVQLVQSGAEVKKPGASVKVSCKASGYTFTSYWIHWVRQAPGQRLEWMGNINPTNGGTNYSQKFQGRVTITVDKSASTAYMELSSLRSEDTAVYYCARAYYYGSSLFAYWGQGTLVTVSS | 30 | DIVMTQSPSFLSASVGDRVTITCKASQNVGTAVAWYQQKPGKAPKLLIYSASYRHTGVPSRFSGSGSGTEFTLTISSLQPEDFATYYCQQYSTYPWTFGGGTKVEIK | 32 |
| 4A-330 | QVQLVQSGAEVKKPGASVKVSCKASGYTFTSYWIHWVRQAPGQRLEWMGNINPTNGGTNYSQKFQGRVTITVDKSASTAYMELSSLRSEDTAVYYCARAYYYGSSLFAYWGQGTLVTVSS | 30 | AIQLTQSPSSLSASVGDRVTITCKASQNVGTAVAWYQQKPGKAPKLLIYSASYRHTGVPSRFSGSGSGTDFTLTISSLQPEDFATYYCQQYSTYPWTFGGGTKVEIK | 38 |
| 4A-331 | QVQLVQSGAEVKKPGASVKVSCKASGYTFTSYWIHWVRQAPGQRLEWMGNINPTNGGTNYSQKFQGRVTITVDKSASTAYMELSSLRSEDTAVYYCARAYYYGSSLFAYWGQGTLVTVSS | 30 | AIQMTQSPSSLSASVGDRVTITCKASQNVGTAVAWYQQKPGKAPKLLIYSASYRHTGVPSRFSGSGSGTDFTLTISSLQPEDFATYYCQQYSTYPWTFGGGTKVEIK | 36 |

TABLE 3

| Antibody | Heavy Chain Variable | SEQ ID NO: | Light Chain Variable | SEQ ID NO: |
|---|---|---|---|---|
| 4A-21 | QIQLVQSGPELKKPGETVKISCKASGYIFTSYGLSWVKQTPGKGLKWMGWINTYSGVPTYANDFKGRFAFSLETSASTTYLRINNLKNDDTATYFCARSLVDYWGQGTPLTVSS | 39 | DVVMTQTPFTLSVTIGQSASISCKSSQSLLYSDGKTYLSWLLQRPGQSPKRLIYLVSKLDSGVPDRFTGSGSGTDFTLKISRVEAEDLGVYYCWQGIDFHQTFGGGTKLEIK | 54 |
| 4A-332 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYCARSLVDYWGQGTLVTVSS | 40 | DVVMTQSPLSLPVTLGQPASISCKSSQSLLYSDGKTYLSWFQQRPGQSPRRLIYLVSKLDSGVPDRFSGSGSGTDFTLKISRVEAEDVGVYYCWQGIDFHQTFGGGTKVEIK | 55 |
| 4A-333 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYCARSLVDYWGQGTLVTVSS | 41 | DVVMTQSPLSLPVTLGQPASISCKSSQSLLYSDGKTYLSWFQQRPGQSPRRLIYLVSKLDSGVPDRFSGSGSGTDFTLKISRVEAEDVGVYYCWQGIDFHQTFGGGTKVEIK | 55 |
| 4A-334 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYCARSLVDYWGQGTLVTVSS | 40 | DIVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 56 |
| 4A-335 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYCARSLVDYWGQGTLVTVSS | 40 | DVVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 57 |
| 4A-336 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYCARSLVDYWGQGTLVTVSS | 40 | DVVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 58 |

TABLE 3-continued

| Antibody | Heavy Chain Variable | SEQ ID NO: | Light Chain Variable | SEQ ID NO: |
|---|---|---|---|---|
| 4A-337 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DIVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 56 |
| 4A-338 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DVVMTQTPLSSPVTLGQPASISCKSSQSLLYSDGKTYLSWLQQRPGQPPRLLIYLVSKLDSGVPDRFSGSGAGTDFTLKISRVEAEDVGVYYCWQGIDFHQTFGGGTKVEIK | 57 |
| 4A-339 | QVQLVQSGSELKKPGASVKVSCKASGYIFTSYGLSWVRQAPGQGLEWMGWINTYSGVPTYAQGFTGRFVFSLDTSVSTTYLQISSLKAEDTAVYYCARSLVDYWGQGTLVTVSS | 41 | DVVMTQTPLSSPVTLGQPASISCKSSQSLLYSDGKTYLSWLQQRPGQPPRRLIYLVSKLDSGVPDRFSGSGAGTDFTLKISRVEAEDVGVYYCWQGIDFHQTFGGGTKVEIK | 58 |
| 4A-340 | QVQLVQSGAEVKKPGASVKVSCKASGYIFTSYGLSWVRQAPGQRLEWMGWINTYSGVPTYSQKFQGRVTITLDTSASTTYMELSSLRSEDTAVYYCARSLVDYWGQGTLVTVSS | 42 | DVVMTQTPLSLSVTPGQPASISCKSSQSLLYSDGKTYLSWYLQKPGQPPLLIYLVSKLDSGVPDRFSGSGSGTDFTLKISRVEAEDVGVYYCWQGIDFHQTFGGGTKVEIK | 59 |
| 4A-341 | QVQLVQSGAEVKKPGASVKVSCKASGYIFTSYGLSWVRQAPGQRLEWMGWINTYSGVPTYSQKFQGRVTITRDTSASTAYMELSSLRSEDTAVYYCARSLVDYWGQGTLVTVSS | 43 | DVVMTQTPLSLSVTPGQPASISCKSSQSLLYSDGKTYLSWYLQKPGQPPLLIYLVSKLDSGVPDRFSGSGSGTDFTLKISRVEAEDVGVYYCWQGIDFHQTFGGGTKVEIK | 59 |
| 4A-342 | QIQLVQSGAEVKKPGASVKVSCKASGYIFTSYGLSWVRQAPGQGLEWMGWINTYSGVPTYAQKFQGRVTMTRDTSTSTVYMELSSLRSEDTAVYYCARSLVDYWGQGTLVTVSS | 44 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-343 | QIQLVQSGAEVKKPGASVKVSCKASGYIFTSYGLSWVRQAPGQGLEWMGWINTYSGVPTYAQKFQGRVTMTLDTSTSTTYMELSSLRSEDTAVYYCARSLVDYWGQGTLVTVSS | 45 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-344 | QVQLVQSGAEVKKPGASVKVSCKASGYIFTSYGLSWVRQAPGQGLEWMGWINTYSGVPTYAQKFQGRVTMTRDTSTSTVYMELSSLRSEDTAVYYCARSLVDYWGQGTLVTVSS | 46 | DVVMTQTPLSLSVTPGQPASISCKSSQSLLYSDGKTYLSWYLQKPGQPPQRLIYLVSKLDSGVPDRFSGSGSGTDFTLKISRVEAEDVGVYYCWQGIDFHQTFGGGTKVEIK | 60 |
| 4A-345 | QVQLVQSGAEVKKPGASVKVSCKASGYIFTSYGLSWVRQAPGQRLEWMGWINTYSGVPTYSQKFQGRVTITRDTSASTAYMELSSLRSEDTAVYYCARSLVDYWGQGTLVTVSS | 43 | DIVMTQTPLSLSVTPGQPASISCKSSQSLLYSDGKTYLSWYLQKPGQPPLLIYLVSKLDSGVPDRFSGSGSGTDFTLKISRVEAEDVGVYYCWQGIDFHQTFGGGTKVEIK | 61 |
| 4A-346 | QVQLVQSGAEVKKPGASVKVSCKASGYIFTSYGLSWVRQAPGQGLEWMGWINTYS | 46 | DIVMTQTPLSLSVTPGQPASISCKSSQSLLYSDGKTYLSWYLQKPGQPPLLIYLVSKLDSGVPD | 61 |

TABLE 3-continued

| Antibody | Heavy Chain Variable | SEQ ID NO: | Light Chain Variable | SEQ ID NO: |
|---|---|---|---|---|
| | GVPTYAQKFQGRVTMTRD TSTSTVYMELSSLRSEDTAV YYCAR<u>SLVDY</u>WGQGTLVT VSS | | RFSGSGSGTDFTLKISRVEAED VGVYYC<u>WQGIDFHQT</u>FGGGT KVEIK | |
| 4A-347 | QVQLVQSGAEVKKPGASV KVSCKASGYIFT<u>SYGLS</u>WV RQAPGQRLEWMG<u>WINTYS GVPTYSQKFQG</u>RVTITLDTS ASTTYMELSSLRSEDTAVY YCAR<u>SLVDY</u>WGQGTLVTV SS | 42 | DIVMTQTPLSLSVTPGQPASIS C<u>KSSQSLLYSDGKTYLS</u>WYLQ KPGQPPQLLIY<u>LVSKLDS</u>GVPD RFSGSGSGTDFTLKISRVEAED VGVYYC<u>WQGIDFHQT</u>FGGGT KVEIK | 61 |
| 4A-348 | QIQLVQSGAEVKKPGASVK VSCKASGYIFT<u>SYGLS</u>WVR QAPGQGLEWMG<u>WINTYSG VPTYAQKFQG</u>RVTMTRDTS TSTVYMELSSLRSEDTAVY YCAR<u>SLVDY</u>WGQGTLVTV SS | 44 | DIVMTQTPLSLSVTPGQPASIS C<u>KSSQSLLYSDGKTYLS</u>WYLQ KPGQPPQLLIY<u>LVSKLDS</u>GVPD RFSGSGSGTDFTLKISRVEAED VGVYYC<u>WQGIDFHQT</u>FGGGT KVEIK | 61 |
| 4A-349 | QIQLVQSGAEVKKPGASVK VSCKASGYIFT<u>SYGLS</u>WVR QAPGQGLEWMG<u>WINTYSG VPTYAQKFQG</u>RVTMTLDTS TSTTYMELSSLRSEDTAVY YCAR<u>SLVDY</u>WGQGTLVTV SS | 45 | DIVMTQTPLSLSVTPGQPASIS C<u>KSSQSLLYSDGKTYLS</u>WYLQ KPGQPPQLLIY<u>LVSKLDS</u>GVPD RFSGSGSGTDFTLKISRVEAED VGVYYC<u>WQGIDFHQT</u>FGGGT KVEIK | 61 |
| 4A-350 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSQSLLYSDGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 55 |
| 4A-351 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSRSLLYSDGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 62 |
| 4A-352 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 63 |
| 4A-353 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSRSLLYSEGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 64 |
| 4A-354 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSRSLLYSAGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 65 |
| 4A-355 | QVQLVQSGSELKKPGASVK VSCKASGYIFT<u>SYGLS</u>WVR QAPGQGLEWMG<u>WINTYSG VPTYAQGFTG</u>RFVFSLDTS VSTAYLQISSLKAEDTAVY YCAR<u>TLADY</u>WGQGTLVTV SS | 47 | DVVMTQSPLSLPVTLGQPASIS C<u>KSSRSLLYSSGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 66 |

TABLE 3-continued

| Antibody | Heavy Chain Variable | SEQ ID NO: | Light Chain Variable | SEQ ID NO: |
|---|---|---|---|---|
| 4A-356 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSRSLLYSQGKTYLSWFQQRPGQSPRRLIYLVSKLDSGVPDRFSGSGSGTDFTLKISRVEAEDVGVYYCWQGIDFHQTFGGGTKVEIK | 67 |
| 4A-357 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYEVSKLDSGVPDRFSGSGSGTDFTLKISRVEAEDVGVYYCWQGIDFHQTFGGGTKVEIK | 68 |
| 4A-358 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLDSGVPDRFSGSGSGTDFTLKISRVEAEDVGVYYCWQGIRFHQTFGGGTKVEIK | 69 |
| 4A-359 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKASQSLLYSDGKTYLSWFQQRPGQSPRRLIYLVSKLDSGVPDRFSGSGSGADFTLKISRVEAEDVGVYYCWQGIDFHQTFGGGTKVEIK | 70 |
| 4A-360 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSGQSLLYSDGKTYLSWFQQRPGQSPRRLIYLVSRLDSGVPDRFSGSGSGTDFTLKISRVEAEDVGVYYCWQGIDFHQTFGGGTKVEIK | 71 |
| 4A-361 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLESGVPDRFSGSGSGTDFTLKISRVEAEDVGVYYCWQGIDFHQTFGGGTKVEIK | 72 |
| 4A-362 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSRLDSGVPDRFSGSGSGTDFTLKISRVEAEDVGVYYCWQGIDFHQTFGGGTKVEIK | 73 |
| 4A-363 | QVQLVQSGSELKKPGASVKVSCKASGYIFTSYGLSWVRQAPGQGLEWMGWINTYSGVPTYAQGFTGRFVFSLDTSVSTAYLQISSLKAEDTAVYYCARTLADYWGQGTLVTVSS | 47 | DVVMTQSPLSLPVTLGQPASISCKSSQSLLYSDGKTYLSWFQQRPGQSPRRLIYLVSKLSSGVPDRFSGSGSGTDFTLKISRVEAEDVGVYYCWQGIDFHQTFGGGTKVEIK | 74 |
| 4A-364 | QVQLVQSGSELKKPGASVKVSCKASGYTFTSYGLSWIRQAPGQGLEWMGWINTYSGVPTYAQGFTGRFVFSLDTSVSTAYLQISSLKAEDTAVYYCARTMVDYWGQGTLVTVSS | 48 | DVVMTQSPLSLPVTLGQPASISCKASQSLLYSDGKTYLSWFQQRPGQSPRRLIYLVSKLDSGVPDRFSGSGSGADFTLKISRVEAEDVGVYYCWQGIDFHQTFGGGTKVEIK | 70 |
| 4A-365 | QVQLVQSGSELKKPGASVKVSCKASGYTFTSYGLSWIRQAPGQGLEWMGWINTYSG | 48 | DVVMTQSPLSLPVTLGQPASISCKSSQSLLYSDGKTYLSWFQQRPGQSPRRLIYLVSKLSSGVPD | 74 |

TABLE 3-continued

| Antibody | Heavy Chain Variable | SEQ ID NO: | Light Chain Variable | SEQ ID NO: |
|---|---|---|---|---|
| | VPTYAQGFTGRFVFSLDTS VSTAYLQISSLKAEDTAVY YCARTMVDYWGQGTLVTV SS | | RFSGSGSGTDFTLKISRVEAED VGVYYCWQGIDFHQTFGGGT KVEIK | |
| 4A-366 | QVQLVQSGSELKKPGASVK VSCKASGYTFTSYGLSWIR QAPGQGLEWMGWINTYSG VPTYAQGFTGRFVFSLDTS VSTAYLQISSLKAEDTAVY YCARTMVDYWGQGTLVTV SS | 48 | DVVMTQSPLSLPVTLGQPASIS CKSSRSLLYSDGKTYLSWFQQ RPGQSPRRLIYLVSKLDSGVPD RFSGSGSGTDFTLKISRVEAED VGVYYCWQGIDFHQTFGGGT KVEIK | 62 |
| 4A-367 | QVQLVQSGSELKKPGASVK VSCKASGYTFTSYGLSWIR QAPGQGLEWMGWINTYSG VPTYAQGFTGRFVFSLDTS VSTAYLQISSLKAEDTAVY YCARTMVDYWGQGTLVTV SS | 48 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIDFHQTFGGGT KVEIK | 55 |
| 4A-368 | QVQLVQSGSELKKPGASVK VSCKASGYTFTSYGLSWIR QAPGQGLEWMGWINTYSG VPTYAQGFTGRFVFSLDTS VSTAYLQISSLKAEDTAVY YCARTMVDYWGQGTLVTV SS | 48 | DVVMTQSPLSLPVTLGQPASIS CKSSQSLLYSDGKTYLSWFQQ RPGQSPRRLIYLVSKLESGVPD RFSGSGSGTDFTLKISRVEAED VGVYYCWQGIDFHQTFGGGT KVEIK | 72 |
| 4A-369 | QVQLVQSGSELKKPGASVK VSCKASGYTFTSYGLSWIR QAPGQGLEWMGWINTYSG VPTYAQGFTGRFVFSLDTS VSTAYLQISSLKAEDTAVY YCARTMVDYWGQGTLVTV SS | 48 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIRFHQTFGGGT KVEIK | 69 |
| 4A-370 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLGDYWGQGTLVTV SS | 49 | DVVMTQSPLSLPVTLGQPASIS CKSGQSLLYSDGKTYLSWFQQ RPGQSPRRLIYLVSRLDSGVPD RFSGSGSGTDFTLKISRVEAED VGVYYCWQGIDFHQTFGGGT KVEIK | 71 |
| 4A-371 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLGDYWGQGTLVTV SS | 49 | DVVMTQSPLSLPVTLGQPASIS CKSSQSLLYSDGKTYLSWFQQ RPGQSPRRLIYLVSKLDSGVPD RFSGSGSGTDFTLKISRVEAED VGVYYCWQGIDFHQTFGGGT KVEIK | 55 |
| 4A-372 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLGDYWGQGTLVTV SS | 49 | DVVMTQSPLSLPVTLGQPASIS CKSSQSLLYSDGKTYLSWFQQ RPGQSPRRLIYLVSRLDSGVPD RFSGSGSGTDFTLKISRVEAED VGVYYCWQGIDFHQTFGGGT KVEIK | 73 |
| 4A-373 | QVQLVQSGSELKKPGASVK VSCKASGYIFTSYGLSWVR QAPGQGLEWMGWINTYSG VPTYAQGFTGRFVFSLDTS VSTAYLQISSLKAEDTAVY YCARTLVDYWGQGTLVTV SS | 50 | DVVMTQSPLSLPVTLGQPASIS CKSSRSLLYSDGKTYLSWFQQ RPGQSPRRLIYLVSKLDSGVPD RFSGSGSGTDFTLKISRVEAED VGVYYCWQGIDFHQTFGGGT KVEIK | 62 |
| 4A-374 | QVQLVQSGSELKKPGASVK VSCKASGYIFTSYGLSWVR QAPGQGLEWMGWINTYSG VPTYAQGFAGRFVFSLDTS VSTAYLQISSLKAEDTAVY YCARTLVDYWGQGTLVTV SS | 51 | DVVMTQSPLSLPVTLGQPASIS CKSSRSLLYSDGKTYLSWFQQ RPGQSPRRLIYLVSKLDSGVPD RFSGSGSGTDFTLKISRVEAED VGVYYCWQGIDFHQTFGGGT KVEIK | 62 |

TABLE 3-continued

| Antibody | Heavy Chain Variable | SEQ ID NO: | Light Chain Variable | SEQ ID NO: |
|---|---|---|---|---|
| 4A-375 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SLADY</u>WGQGTLVTV SS | 52 | DVVMTQSPLSLPVTLGQPASIS C<u>KSSRSLLYSDGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 62 |
| 4A-376 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSDGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 62 |
| 4A-377 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 63 |
| 4A-378 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 64 |
| 4A-379 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 65 |
| 4A-380 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 66 |
| 4A-381 | QVQLVQSGSELKKPGASVK VSCKASGYIFT<u>SYGLS</u>WVR QAPGQGLEWMG<u>WINTYSG VPTYAQG</u>FTGRFVFSLDTS VSTAYLQISSLKAEDTAVY YCAR<u>SMADY</u>WGQGTLVTV SS | 53 | DVVMTQSPLSLPVTLGQPASIS C<u>KSSRSLLYSGGKTYLS</u>WFQQ RPGQSPRRLIY<u>LVSKLDS</u>GVPD RFSGSGSGTDFTLKISRVEAED VGVYYC<u>WQGIDFHQT</u>FGGGT KVEIK | 67 |

TABLE 4

| Antibody | Heavy Chain Variable | SEQ ID NO: | Light Chain Variable | SEQ ID NO: |
|---|---|---|---|---|
| 4A-25 | QVTLKESGPGILQPSQTLSLTC SFSGFSLR<u>TSDMGVG</u>WVRQPS GEGLEWLA<u>DIWWDDNKYYNP SLKS</u>RLTISKDTSSNQVFLKITS VDTADTATYYCAR<u>RANYGNL FDY</u>WGQGTAVTVSS | 75 | DIVMTQSLKFMSTSVGDRVSIT C<u>KASQNVRSAVA</u>WYQQKPGQ SPKVLIY<u>WASNRHT</u>GVPDRFT GSGSGTDFTLTISNVQSEDLAD YFCL<u>QHWNYLT</u>FGSGTKLEIK | 85 |
| 4A-382 | QVTLKESGPALVQPTQTLTLT CTFSGFSLR<u>TSDMGVS</u>WIRQPP GEALEWLA<u>LIWWDDNKYYST</u> | 76 | DIVLTQSPSSLSASVGDRVTIT C<u>RASQNVRSALA</u>WYQQKPGQ APKVLIY<u>WASNRHS</u>GVPSRFS | 86 |

TABLE 4-continued

| Antibody | Heavy Chain Variable | SEQ ID NO: | Light Chain Variable | SEQ ID NO: |
|---|---|---|---|---|
| | SLKTRLTISKDTSSNQVVLTMT NMDPVDTATYYCARRANYGN LFDYWGQGTAVTVSS | | GSGSGTDFTLTISSLQPEDFAT YYCQQHWNYLTFGGGTKVEI K | |
| 4A-383 | QVTLKESGPTLVQPTQTLTLTC TFSGFSLRTSDMGVGWIRQPP GKALEWLALIWWDDNKYYSP SLKSRLTISKDTSSNQVVLTMT NMDPVDTATYYCARRANYGN LFDYWGQGTLVTVSS | 77 | DIVLTQSPSSLSASVGDRVTIT CRASQNVRSALAWYQQKPGQ APKLLIYWASNRHSGVPSRFS GSGSGTDFTLTISSLQPEDFAT YYCQQHWNYLTFGGGTKVEI K | 87 |
| 4A-384 | QVTLRESGPALVQPTQTLTLT CTFSGFSLRTSDMGVSWIRQPP GEALEWLALIWWDDNKYYST SLKTRLTISKDTSSNQVVLTMT NMDPVDTATYYCARRANYGN LFDYWGQGTLVTVSS | 78 | DIVMTQSPSSMSASVGDRVTIT CQASQNVRSAVAWYQQKPGK APKLLIYWASNRHTGVPSRFS GSGSGTDFTFTISSLQPEDIATY YCQQHWNYLTFGGGTKVEIK | 88 |
| 4A-385 | QVTLKESGPTLVKPTQTLTLTC TFSGFSLRTSDMGVGWIRQPP GKALEWLALIWWDDNKYYSP SLKSRLTITKDTSSNQVVLTMT NMDPVDTATYYCARRANYGN LFDYWGQGTLVTVSS | 79 | DIVMTQSPSSLSTSVGDRVTIT CRASQNVRSALAWYQQKPEK APKSLIYWASNRHSGVPSRFS GSGSGTDFTLTISSLQPEDFAT YYCQQHWNYLTFGGGTKVEI K | 89 |
| 4A-386 | QVTLKESGPGLVQPTETLTLTC TFSGFSLRTSDMGVSWIRQPPG KALEWLAHIWWDDNKSYSTS LKSRLTISKDTSSNQVVLTMT NMDPVDTATYYCARRANYGN LFDYWGQGTLVTVSS | 80 | DIVMTQSPSSLSASVGDRVTIT CRASQNVRSALAWYQQKPEQ APKSLIYWASNRHSGVPSRFS GSGSGTDFTLTISSLQPEDFAT YYCQQHWNYLTFGGGTKVEI K | 90 |
| 4A-387 | QVTLKESGPVLVKPTETLTLTC TFSGFSLRTSDMGVSWIRQPSG KALEWLAHIWWDDNKSYSTS LKSRLTISKDTSKNQVVLTMT NMDPVDTATYYCARRANYGN LFDYWGQGTLVTVSS | 81 | DIVMTQSPSSLSASVGDRVTIT CQASQNVRSALNWYQQKPGK APKLLIYWASNRHTGVPSRFS GSGSGTDFTFTISSLQSEDIATY YCQQHWNYLTFGGGTKVEIK | 91 |
| 4A-388 | QVTLKESGPVLVKPTETLTLTC TFSGFSLRTSDMGVSWIRQPSG EGLEWLAHIWWDDNKSYSTS LKSRLTISKDTSKNQVVLTMT NMDPVDTATYYCARRANYGN LFDYWGQGTLVTVSS | 82 | DIVMTQSPSSLSASVGDRVTIT CQASQNVRSALNWYQQKPGK APKLLIYWASNRHTGVPSRFS GSGSGTDFTFTISSLQSEDIATY YCQQHWNYLTFGGGTKVEIK | 91 |
| 4A-389 | QVTLQESGPGLVKPSETLSLTC AVSGFSLRTSDMGVGWIRQPP GEGLEWIGSIWWDDNKYYNP SLKSRVTISKDTSKNQVSLKLS SVDAADTAVYYCARRANYGN LFDYWGQGTLVTVSS | 83 | DIQMTQSPSSLSASVGDRVTIT CRASQNVRSALAWYQQKPEQ APKSLIYWASSLQSGVPSRFSG SGSGTDFTLTISNRHPEDFATY YCQQHWNYLTFGGGTKVEIK | 92 |
| 4A-390 | QVQLQESGPGLVQPSETLSLTC AVSGFSLRTSDMGVGWIRQPP GKGLEWIGSIWYDDNKYYNPS LKSRVTISKDTSSNQFSLKLSS VTAADTAVYYCARRANYGNL FDYWGQGTLVTVSS | 84 | DIQMTQSPSSLSTSVGDRVTIT CQASQNVRSALNWYQQKPGK APKLLIYWASNRHTGVPSRFS GSGSGTDFTFTISSLQSEDIATY YCQQHWNYLTFGGGTKVEIK | 93 |

The CDR sequences according to Kabat for the anti-MS4A4A antibodies of the present disclosure are provided below in Tables 5-8.

TABLE 5

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-202 | NYWMQ | 94 | ATHPGHG DTRYTQK FKG | 95 | EEVYYGFR SYWYFDV | 100 | RASESVDN YGVSFMN | 103 | GASNQGS | 105 | QQSKEVP PT | 107 |

TABLE 5-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-301 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-302 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-303 | NYWMQ | 94 | ATHPGHGDTRYSPSFQG | 97 | EEVYYGFRSYWYFDV | 100 | RASESVDNYGVSFMN | 103 | GASNQGS | 105 | QQSKEVPPT | 107 |
| 4A-304 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-305 | NYWMQ | 94 | ATHPGHGDTRYAEKFQG | 98 | EEVYYGFRSYWYFDV | 100 | RASESVDNYGVSFMN | 103 | GASNQGS | 105 | QQSKEVPPT | 107 |
| 4A-306 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-307 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-308 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-309 | NYWMQ | 94 | ATHPGHGDTRYAQKFQG | 96 | EEVYYGFRSYWYFDV | 100 | RASESVDNYGVSFMN | 103 | GASNQGS | 105 | QQSKEVPPT | 107 |
| 4A-310 | NYWMQ | 94 | ATHPGHGDTRYSPSFQG | 97 | EEVYYGFRSYWYFDV | 100 | RASESVDNYGVSFMN | 103 | GASNQGS | 105 | QQSKEVPPT | 107 |
| 4A-311 | NYWMQ | 94 | ATHPGHGDTRYAEKFQG | 98 | EEVYYGFRSYWYFDV | 100 | RASESVDNYGVSFMN | 103 | GASNQGS | 105 | QQSKEVPPT | 107 |
| 4A-312 | NYWMQ | 94 | ATHPGHGDTRYAQKFQG | 96 | EEVDYGFRSYWYFDV | 101 | RASESVDNYGVSFMN | 103 | GASNQQS | 106 | QQSKEVPPT | 107 |
| 4A-313 | NYWMQ | 94 | ATHPGHGDTRYAQKFQG | 96 | EEVYYGFRSYWYFDL | 102 | RASESVDNYGVSRMN | 104 | GASNQGS | 105 | QQSKEVPPT | 107 |
| 4A-314 | NYWMQ | 94 | TTLPGHGDTRYAQKFQG | 99 | EEVYYGFRSYWYFDV | 100 | RASESVDNYGVSRMN | 104 | GASNQGS | 105 | QQSKEVPPT | 107 |

TABLE 6

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-18 | SYWIH | 108 | NINPTNGGTNYNERFKS | 109 | AYYYGSSLFAY | 112 | KASQNVGTAVA | 113 | SASYRHT | 114 | QQYSTYPWT | 115 |
| 4A-315 | SYWIH | 108 | NINPTNGGTNYAQKFQG | 110 | AYYYGSSLFAY | 112 | KASQNVGTAVA | 113 | SASYRHT | 114 | QQYSTYPWT | 115 |
| 4A-316 | SYWIH | 108 | NINPTNGGTNYAQKFQG | 110 | AYYYGSSLFAY | 112 | KASQNVGTAVA | 113 | SASYRHT | 114 | QQYSTYPWT | 115 |

TABLE 6-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-317 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-318 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-319 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-320 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-321 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-322 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-323 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-324 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-325 | SYWIH | 108 | NINPTNGGTNYAQKFQG | 110 | AYYYGSLFAY | 112 | KASQNVGTAVA | 113 | SASYRHT | 114 | QQYSTYPWT | 115 |
| 4A-326 | SYWIH | 108 | NINPTNGGTNYSQKFQG | 111 | AYYYGSLFAY | 112 | KASQNVGTAVA | 113 | SASYRHT | 114 | QQYSTYPWT | 115 |
| 4A-327 | SYWIH | 108 | NINPTNGGTNYSQKFQG | 111 | AYYYGSLFAY | 112 | KASQNVGTAVA | 113 | SASYRHT | 114 | QQYSTYPWT | 115 |
| 4A-328 | SYWIH | 108 | NINPTNGGTNYSQKFQG | 111 | AYYYGSLFAY | 112 | KASQNVGTAVA | 113 | SASYRHT | 114 | QQYSTYPWT | 115 |
| 4A-329 | SYWIH | 108 | NINPTNGGTNYSQKFQG | 111 | AYYYGSLFAY | 112 | KASQNVGTAVA | 113 | SASYRHT | 114 | QQYSTYPWT | 115 |
| 4A-330 | SYWIH | 108 | NINPTNGGTNYSQKFQG | 111 | AYYYGSLFAY | 112 | KASQNVGTAVA | 113 | SASYRHT | 114 | QQYSTYPWT | 115 |
| 4A-331 | SYWIH | 108 | NINPTNGGTNYSQKFQG | 111 | AYYYGSLFAY | 112 | KASQNVGTAVA | 113 | SASYRHT | 114 | QQYSTYPWT | 115 |

TABLE 7

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-21 | SYGLS | 116 | WINTYSGVPTYANDFKG | 117 | SLVDY | 123 | KSSQSLLYSDGKTYLS | 130 | LVSKLDS | 139 | WQGIDFHQT | 144 |
| 4A-332 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |

TABLE 7-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-333 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-334 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-335 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-336 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-337 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-338 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-339 | SYGLS | 116 | WINTYSGVPTYAQGFTG | 118 | SLVDY | 123 | KSSQSLLYSDGKTYLS | 130 | LVSKLDS | 139 | WQGIDFHQT | 144 |
| 4A-340 | SYGLS | 116 | WINTYSGVPTYSQKFQG | 119 | SLVDY | 123 | KSSQSLLYSDGKTYLS | 130 | LVSKLDS | 139 | WQGIDFHQT | 144 |
| 4A-341 | SYGLS | 116 | WINTYSGVPTYSQKFQG | 119 | SLVDY | 123 | KSSQSLLYSDGKTYLS | 130 | LVSKLDS | 139 | WQGIDFHQT | 144 |
| 4A-342 | SYGLS | 116 | INTYSGVPTYAQKFQG | 120 | SLVDY | 123 | KSSQSLLYSDGKTYLS | 130 | LVSKLDS | 139 | WQGIDFHQT | 144 |
| 4A-343 | SYGLS | 116 | WINTYSGVPTYAQKFQG | 121 | SLVDY | 123 | KSSQSLLYSDGKTYLS | 130 | LVSKLDS | 139 | WQGIDFHQT | 144 |
| 4A-344 | SYGLS | 116 | WINTYSGVPTYAQKFQG | 121 | SLVDY | 123 | KSSQSLLYSDGKTYLS | 130 | LVSKLDS | 139 | WQGIDFHQT | 144 |
| 4A-345 | SYGLS | 116 | WINTYSGVPTYSQKFQG | 119 | SLVDY | 123 | KSSQSLLYSDGKTYLS | 130 | LVSKLDS | 139 | WQGIDFHQT | 144 |
| 4A-346 | SYGLS | 116 | WINTYSGVPTYAQKFQG | 121 | SLVDY | 123 | KSSQSLLYSDGKTYLS | 130 | LVSKLDS | 139 | WQGIDFHQT | 144 |
| 4A-347 | SYGLS | 116 | WINTYSGVPTYSQKFQG | 119 | SLVDY | 123 | KSSQSLLYSDGKTYLS | 130 | LVSKLDS | 139 | WQGIDFHQT | 144 |
| 4A-348 | SYGLS | 116 | WINTYSGVPTYAQKFQG | 121 | SLVDY | 123 | KSSQSLLYSDGKTYLS | 130 | LVSKLDS | 139 | WQGIDFHQT | 144 |
| 4A-349 | SYGLS | 116 | WINTYSGVPTYAQKFQG | 121 | SLVDY | 123 | KSSQSLLYSDGKTYLS | 130 | LVSKLDS | 139 | WQGIDFHQT | 144 |
| 4A-350 | SYGLS | 116 | WINTYSGVPTYAQGFTG | 118 | TLADY | 124 | KSSQSLLYSDGKTYLS | 130 | LVSKLDS | 139 | WQGIDFHQT | 144 |
| 4A-351 | SYGLS | 116 | WINTYSGVPTYAQGFTG | 118 | TLADY | 124 | KSSRSLLYSDGKTYLS | 131 | LVSKLDS | 139 | WQGIDFHQT | 144 |

TABLE 7-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-352 | SYGLS | | WINTYSGVPTYAQGFTG | 116 | TLADY | 118 | KSSRSLLYSGGKTYLS | 124 | LVSKLDS | 132 | WQGIDFHQT | 139 | 144 |
| 4A-353 | SYGLS | | WINTYSGVPTYAQGFTG | 116 | TLADY | 118 | KSSRSLLYSEGKTYLS | 124 | LVSKLDS | 133 | WQGIDFHQT | 139 | 144 |
| 4A-354 | SYGLS | | WINTYSGVPTYAQGFTG | 116 | TLADY | 118 | KSSRSLLYSAGKTYLS | 124 | LVSKLDS | 134 | WQGIDFHQT | 139 | 144 |
| 4A-355 | SYGLS | | WINTYSGVPTYAQGFTG | 116 | TLADY | 118 | KSSRSLLYSSGKTYLS | 124 | LVSKLDS | 135 | WQGIDFHQT | 139 | 144 |
| 4A-356 | SYGLS | | WINTYSGVPTYAQGFTG | 116 | TLADY | 118 | KSSRSLLYSQGKTYLS | 124 | LVSKLDS | 136 | WQGIDFHQT | 139 | 144 |
| 4A-357 | SYGLS | | WINTYSGVPTYAQGFTG | 116 | TLADY | 118 | KSSQSLLYSDGKTYLS | 124 | EVSKLDS | 130 | WQGIDFHQT | 140 | 144 |
| 4A-358 | SYGLS | | WINTYSGVPTYAQGFTG | 116 | TLADY | 118 | KSSQSLLYSDGKTYLS | 124 | LVSKLDS | 130 | WQGIRFHQT | 139 | 145 |
| 4A-359 | SYGLS | | WINTYSGVPTYAQGFTG | 116 | TLADY | 118 | KASQSLLYSDGKTYLS | 124 | LVSKLDS | 137 | WQGIDFHQT | 139 | 144 |
| 4A-360 | SYGLS | | WINTYSGVPTYAQGFTG | 116 | TLADY | 118 | KSGQSLLYSDGKTYLS | 124 | LVSRLDS | 138 | WQGIDFHQT | 141 | 144 |
| 4A-361 | SYGLS | | WINTYSGVPTYAQGFTG | 116 | TLADY | 118 | KSSQSLLYSDGKTYLS | 124 | LVSKLES | 130 | WQGIDFHQT | 142 | 144 |
| 4A-362 | SYGLS | | WINTYSGVPTYAQGFTG | 116 | TLADY | 118 | KSSQSLLYSDGKTYLS | 124 | LVSRLDS | 130 | WQGIDFHQT | 141 | 144 |
| 4A-363 | SYGLS | | WINTYSGVPTYAQGFTG | 116 | TLADY | 118 | KSSQSLLYSDGKTYLS | 124 | LVSKLSS | 130 | WQGIDFHQT | 143 | 144 |
| 4A-364 | SYGLS | | WINTYSGVPTYAQGFTG | 116 | TMVDY | 118 | KASQSLLYSDGKTYLS | 125 | LVSKLDS | 137 | WQGIDFHQT | 139 | 144 |
| 4A-365 | SYGLS | | WINTYSGVPTYAQGFTG | 116 | TMVDY | 118 | KSSQSLLYSDGKTYLS | 125 | LVSKLSS | 130 | WQGIDFHQT | 143 | 144 |
| 4A-366 | SYGLS | | WINTYSGVPTYAQGFTG | 116 | TMVDY | 118 | KSSRSLLYSDGKTYLS | 125 | LVSKLDS | 131 | WQGIDFHQT | 139 | 144 |
| 4A-367 | SYGLS | | WINTYSGVPTYAQGFTG | 116 | TMVDY | 118 | KSSQSLLYSDGKTYLS | 125 | LVSKLDS | 130 | WQGIDFHQT | 139 | 144 |
| 4A-368 | SYGLS | | WINTYSGVPTYAQGFTG | 116 | TMVDY | 118 | KSSQSLLYSDGKTYLS | 125 | LVSKLES | 130 | WQGIDFHQT | 142 | 144 |
| 4A-369 | SYGLS | | WINTYSGVPTYAQGFTG | 116 | TMVDY | 118 | KSSQSLLYSDGKTYLS | 125 | LVSKLDS | 130 | WQGIRFHQT | 139 | 145 |
| 4A-370 | SYGLS | | WINTYSGVPTYAQGFTG | 116 | TLGDY | 118 | KSGQSLLYSDGKTYLS | 126 | LVSRLDS | 138 | WQGIDFHQT | 141 | 144 |

TABLE 7-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-371 | SYGLS | 116 | WINTYSGVPTYAQGFTG | 118 | TLGDY | 126 | KSSQSLLYSDGKTYLS | 130 | LVSKLDS | 139 | WQGIDFHQT | 144 |
| 4A-372 | SYGLS | 116 | WINTYSGVPTYAQGFTG | 118 | TLGDY | 126 | KSSQSLLYSDGKTYLS | 130 | LVSRLDS | 141 | WQGIDFHQT | 144 |
| 4A-373 | SYGLS | 116 | WINTYSGVPTYAQGFTG | 118 | TLVDY | 127 | KSSRSLLYSDGKTYLS | 131 | LVSKLDS | 139 | WQGIDFHQT | 144 |
| 4A-374 | SYGLS | 116 | WINTYSGVPTYAQGFAG | 122 | TLVDY | 127 | KSSRSLLYSDGKTYLS | 131 | LVSKLDS | 139 | WQGIDFHQT | 144 |
| 4A-375 | SYGLS | 116 | WINTYSGVPTYAQGFTG | 118 | SLADY | 128 | KSSRSLLYSDGKTYLS | 131 | LVSKLDS | 139 | WQGIDFHQT | 144 |
| 4A-376 | SYGLS | 116 | WINTYSGVPTYAQGFTG | 118 | SMADY | 129 | KSSRSLLYSDGKTYLS | 131 | LVSKLDS | 139 | WQGIDFHQT | 144 |
| 4A-377 | SYGLS | 116 | WINTYSGVPTYAQGFTG | 118 | SMADY | 129 | KSSRSLLYSGGKTYLS | 132 | LVSKLDS | 139 | WQGIDFHQT | 144 |
| 4A-378 | SYGLS | 116 | WINTYSGVPTYAQGFTG | 118 | SMADY | 129 | KSSRSLLYSEGKTYLS | 133 | LVSKLDS | 139 | WQGIDFHQT | 144 |
| 4A-379 | SYGLS | 116 | WINTYSGVPTYAQGFTG | 118 | SMADY | 129 | KSSRSLLYSAGKTYLS | 134 | LVSKLDS | 139 | WQGIDFHQT | 144 |
| 4A-380 | SYGLS | 116 | WINTYSGVPTYAQGFTG | 118 | SMADY | 129 | KSSRSLLYSSGKTYLS | 135 | LVSKLDS | 139 | WQGIDFHQT | 144 |
| 4A-381 | SYGLS | 116 | WINTYSGVPTYAQGFTG | 118 | SMADY | 129 | KSSRSLLYSQGKTYLS | 136 | LVSKLDS | 139 | WQGIDFHQT | 144 |

TABLE 8

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-25 | TSDMGVG | 146 | DIWWDDNKYYNPSLKS | 148 | RANYGNLFDY | 154 | KASQNVRSAVA | 155 | WASNRHT | 159 | QHWNYLT | 162 |
| 4A-382 | TSDMGVS | 147 | LIWWDDNKYYSTSLKT | 149 | RANYGNLFDY | 154 | RASQNVRSALA | 156 | WASNRHS | 160 | QQHWNYLT | 163 |
| 4A-383 | TSDMGVG | 146 | LIWWDDNKYYSPSLKS | 150 | RANYGNLFDY | 154 | RASQNVRSALA | 156 | WASNRHS | 160 | QQHWNYLT | 163 |
| 4A-384 | TSDMGVS | 147 | LIWWDDNKYYSTSLKT | 149 | RANYGNLFDY | 154 | QASQNVRSAVA | 157 | WASNRHT | 159 | QQHWNYLT | 163 |
| 4A-385 | TSDMGVG | 146 | LIWWDDNKYYSPSLKS | 150 | RANYGNLFDY | 154 | RASQNVRSALA | 156 | WASNRHS | 160 | QQHWNYLT | 163 |

TABLE 8-continued

| Antibody | CDR-H1 | SEQ ID NO: | CDR-H2 | SEQ ID NO: | CDR-H3 | SEQ ID NO: | CDR-L1 | SEQ ID NO: | CDR-L2 | SEQ ID NO: | CDR-L3 | SEQ ID NO: |
|---|---|---|---|---|---|---|---|---|---|---|---|---|
| 4A-386 | TSDMGVS | 147 | HIWWDDNKSYSTSLKS | 151 | RANYGNLFDY | 154 | RASQNVRSALA | 156 | WASNRHS | 160 | QQHWNYLT | 163 |
| 4A-387 | TSDMGVS | 147 | HIWWDDNKSYSTSLKS | 151 | RANYGNLFDY | 154 | QASQNVRSALN | 158 | WASNRHT | 159 | QQHWNYLT | 163 |
| 4A-388 | TSDMGVS | 147 | HIWWDDNKSYSTSLKS | 151 | RANYGNLFDY | 154 | QASQNVRSALN | 158 | WASNRHT | 159 | QQHWNYLT | 163 |
| 4A-389 | TSDMGVG | 146 | SIWWDDNKYYNPSLKS | 152 | RANYGNLFDY | 154 | RASQNVRSALA | 156 | WASSLQS | 161 | QQHWNYLT | 163 |
| 4A-390 | TSDMGVG | 146 | SIWYDDNKYYNPSLKS | 153 | RANYGNLFDY | 154 | QASQNVRSALN | 158 | WASNRHT | 159 | QQHWNYLT | 163 |

Example 2

Preparation of Recombinant MS4A4A Soluble Polypeptides

The primary amino acid sequence of human MS4A4A (SEQ ID NO:1) was analyzed to provide information about its secondary and tertiary structure. Human MS4A4A protein has four transmembrane domains (TMDs) and each TMD is composed of 21 amino acids. Predicted from the amino acid composition, residue numbers, and the thickness of the lipid bilayer, MS4A4A is predicted to comprise a four helix bundle (4HB) with two extra cellular loops (ECLs), connecting TMD1 and TMD2, and TMD3 and TMD4 from the N-terminus to the C-terminus, respectively (see FIG. 1). FIG. 1 shows the primary amino acid sequence of human MS4A4A; intracellular domains are italicized, transmembrane domains are underlined, and the two extracellular loops are bold-italicized.

Two template structures of soluble 4HB scaffold proteins (which are predicted to mimic the geometry and configuration of MS4A4A) were identified using the RC SB Protein Data Bank. The PDB ID of these protein scaffolds are 1P68 and 1M6T. FIG. 2A, FIG. 2B, and FIG. 2C show the structure and primary amino acid sequence of two soluble four-helix bundle scaffolds (PDB ID:1P68 and PDB ID:1M6T). In FIG. 2A, the transmembrane domains are rendered as helical in the structure; in FIG. 2B and FIG. 2C, the transmembrane domains are underlined in the corresponding amino acid sequences of 1P68 and 1M6T.

The amino acid sequences of the two ECLs of human MS4A4A were recombinantly placed into 1P68, resulting in polypeptide JS1 and polypeptide JS4 (negative control for polypeptide JS1) and into 1M6T, resulting in polypeptide JS5, polypeptide JS6; and polypeptide JS10 (which serve as negative controls for polypeptide JS5 and polypeptide JS6). (See FIG. 3.) FIG. 3A shows the amino acid sequences of polypeptide JS1, polypeptide JS5, and polypeptide JS6. FIG. 3B shows the amino acid sequences of negative control polypeptide JS4 and negative control polypeptide JS10. Nucleic acid encoding these protein/polypeptide scaffolds were inserted into pcDNA3.4 expression vector with a 3' his-tag and Avi-tag, respectively. The resulting clones were expressed in Expi293 cells and purified by Ni-NTA agarose (QIAGEN cat #30230) using the manufacturer's protocol. These recombinant MS4A4A soluble polypeptides (also referred to as loop grafted antigens) were produced in order to obtain soluble proteins that mimic the structure and function of the two ECLs of MS4A4A for use as soluble reagents for antibody binding characterizations.

Example 3

Epitope Determination of Anti-MS4A4A Antibodies by Peptide Binding

Epitope binding characteristics of anti-MS4A4A antibody 4A-21 were determined as follows. A panel of overlapping peptides derived from the extracellular loops (ECLs) of human MS4A4A (SEQ ID NO:1) were synthesized by JPT peptides (Berlin, Germany). These peptides were 15 amino acids in length, each offset by 2 amino acids. The peptides were biotinylated on the N-terminus. Peptides 4A.1 through 4A.4 were derived from human MS4A4A ECL1 and surrounding regions. Peptides 4A.5 through 4A.12 were derived from human MS4A4A ECL2 and surrounding regions.

The peptide library was printed onto a streptavidin-coated chip (Xantec SAD50M, Dusseldorf, Germany) using the Continuous Flow Microspotter (CFM). First, the chip was activated with 100 mM MES, pH 5.5, 100 μL EDC (133 mM final), 100 μL of S-NHS (33.3 mM final). The peptide library was immobilized onto the chip at 250 nM per peptide diluted into HBS-EP+ buffer (Teknova Cat #H8022) with 1 mg/ml BSA and 1 μg/ml mouse IgG-Biotin. Following immobilization, the chip surface was deactivated with 1M ethanolamine at pH 8.5 for 10 minutes. Hybridoma supernatants and purified anti-MS4A4A antibodies were diluted in HBS-EP+ buffer with 1 mg/ml BSA and injected onto the chip. Duplicate measurements for each anti-MS4A4A antibody were taken to ensure reproducibility. Binding characteristics were determined for each peptide-antibody combination, allowing the mapping of the linear peptide region each antibody interacts with.

Anti-MS4A4A antibody 4A-21 and commercially available anti-MS4A4A antibody 5C12 displayed robust binding to peptides corresponding to regions in human MS4A4A ECL2, as indicated in bold in Table 9 below. Anti-MS4A4A antibody 4A-21 binds peptides 4A.5 through 4A.9, spanning amino acid residues 155 to 177 of human MS4A4A. Anti-MS4A4A antibody 5C12 binds peptides 4A.6 through 4A.9, spanning amino acid residues 157 to 177 of human MS4A4A. The binding regions of these two antibodies are overlapping but not identical, indicating that they interact with different residues within ECL2 of human MS4A4A. Neither of these two antibodies showed binding to human MS4A4A ECL1 using the methodology described above.

TABLE 9

| Peptide | Sequence | 4A-21 | 5C12 |
|---|---|---|---|
| 4A.1 | ITMMCMASNTYGSNP (SEQ ID NO: 292) | -11.16 | -1.49 |
| 4A.2 | MMCMASNTYGSNPIS (SEQ ID NO: 293) | -11.53 | -0.19 |
| 4A.3 | CMASNTYGSNPISVY (SEQ ID NO: 294) | -10.55 | -1.54 |
| 4A.4 | ASNTYGSNPISVYIG (SEQ ID NO: 295) | -7.90 | -0.46 |
| 4A.5 | LAFYSFHHPYCNYYG (SEQ ID NO: 296) | 382.80 | 1.60 |
| 4A.6 | FYSFHHPYCNYYGNS (SEQ ID NO: 297) | 485.67 | 44.38 |
| 4A.7 | SFHHPYCNYYGNSNN (SEQ ID NO: 298) | 446.10 | 17.75 |
| 4A.8 | HHPYCNYYGNSNNCH (SEQ ID NO: 299) | 308.63 | 22.30 |
| 4A.9 | PYCNYYGNSNNCHGT (SEQ ID NO: 300) | 225.21 | 30.86 |
| 4A.10 | CNYYGNSNNCHGTMS (SEQ ID NO: 301) | -4.50 | 1.13 |
| 4A.11 | YYGNSNNCHGTMSIL (SEQ ID NO: 302) | -6.50 | -2.73 |
| 4A.12 | GNSNNCHGTMSILMG (SEQ ID NO: 303) | -5.20 | -4.08 |

Example 4

Anti-MS4A4A Antibody Binding to Peptides Corresponding to Human MS4A4A Extracellular Domains Anti-MS4A4A hybridoma supernatants (neat) or as purified mIgG (5 µg/ml) were tested for binding to human MS4A4A peptides corresponding to ECL1 (amino acid residues 86-98 of human MS4A4A of SEQ ID NO:1) and ECL2 (amino acid residues 159-179 of human MS4A4A of SEQ ID NO:1) using an enzyme-linked immunosorbent assay (ELISA). Briefly, 96-well polystyrene plates were coated with 2 or 10 µg/ml of synthetic free or BSA-conjugated peptides in coating buffer (0.05M carbonate buffer, pH9.6, Millipore Sigma Cat #C3041) overnight at 4° C. Coated plates were then blocked with ELISA diluent (PBS+0.5% BSA+0.05% Tween20) for 1-hour, washed 3×300 µL in PBST (PBS+0.05% Tween20, Thermo Cat #28352), and then the antibodies were added to the plate (50 l/well). After 30 mins incubation (room temperature, with shaking), the plates were washed 3×300 µL in PBST. A secondary anti-mouse HRP antibody (Jackson Immunoresearch Cat #115-035-003) was added at a 1:1000 dilution in ELISA diluent (50 µl/well) and incubated for 30 minutes at room temperature with shaking. After a final set of washes (3×300 µL in PBST), 50 µL of TMB substrate (BioFx Cat #TMBW-1000-01) was added and the reaction was then quenched after 5-10 mins with 50 µL of stop solution (BioFx Cat #BSTP-1000-01). The quenched reaction wells were detected for absorbance at 650 nm with a BioTek Synergy Microplate Reader using GENS 2.04 software.

Purified anti-MS4A4A murine antibodies and 3 commercially available murine anti-MS4A4A antibodies (5C12, 3F2, and 4H2) were tested. Murine anti-MS4A4A antibodies (4A-21, 4A-25, 4A-202, and 4A-214) displayed strong binding to the huMS4A4A-ELC2 free-peptide compared to that observed for BSA mouse DAP12, an irrelevant negative peptide control. The three commercially available anti-MS4A4A antibodies did not display binding to human MS4A4A ECL1 and ECL2 peptides.

Example 5

Epitope Determination of Anti-MS4A4A Antibodies

The primary amino acid sequence of MS4A4A provides important information about its secondary and tertiary structure. The MS4A4A protein has four transmembrane domains (TMDs) and each TMD is composed of 21 amino acids. A typical TMD is composed of a phosphodiester lipid bilayer with approximately 40 Å in thickness. The phosphate head moiety creates a hydrophilic layer that interacts with the hydrophilic environment either in the extracellular or cytosolic space and the lipid tail creates an internal lipid bilayer that interacts with the lipophilic residues of the TMDs. The thickness of the TMD lipid bilayer is approximately 32 to 34 Å. Predicted from the amino acid composition, residue numbers, and the thickness of the lipid bilayer, MS4A4A is predicted to comprise a four-helix bundle (4HB) with two extra cellular loops (ECLs), connecting TMD1 and TMD2, and TMD3 and TMD4 from the N-terminus to the C-terminus, respectively. The 4-helix bundle stabilizes the MS4A4A in the membrane by a significant enthalpy gain obtained from the helix-lipid bilayer interactions and helix-helix interactions.

The primary amino acid sequence and composition of the MS4A4A ECLs indicate important features associated with epitopes and dynamic properties. ECL1 is composed of 13 amino acids including one cysteine, one methionine, one alanine, three serine, one threonine, two asparagine, one tyrosine, one proline, one isoleucine, and only one glycine residue(s). ECL2 is composed of 21 amino acids including two cysteine residues which are separated by 8 amino acids, three serine, one threonine, one phenylalanine, three histidine, one proline, three tyrosine, four asparagine, one methionine, and only two glycine residues. Very few glycine residues but several large beta-branched amino acid residues and a proline residue are found in ECL1 and ECL2. Moreover, ECL2 contains two cysteine residues that are predicted to create an intra-loop disulfide bond, which further reduces conformational entropy. As a result, ECL1 and ECL2 tend to employ a significantly reduced number of conformational isomers interacting with each other in rigid-body type internal movements.

An expression plasmid encoding human MS4A4A (NM_024021) containing a C-terminal GFP tag was purchased from Origene (cat #RG223557) and used as template to generate single alanine scanning mutations in the coding region of extracellular loop 1 (ECL1) of human MS4A4A (4A.Ala1-Ala13 in Table 10 below; C67 to S79 of SEQ ID NO:1 corresponding to ECL1; CMASNTYGSNPIS; in the coding region of extracellular loop 2 (ECL2) of human MS4A4A (4A.Ala14-Ala34 in Table 10 below; S140 to S160 of SEQ ID NO:1 corresponding to ECL2; SFHHPYCNYYGNSNNCHGTMS; and ECL2 deletion mutations (4A.Ala35 (deletion of amino acid residues 150-152 of SEQ ID NO:1 within ECL2) and 4A.Ala36 (deletion of amino acid residues 148-152 of SEQ ID NO:1 within ECL2) in Table 11 below). The mutations were performed using overlap polymerase chain reaction techniques standard in the art. Each polymerase chain reaction polynucleic acid fragment was purified and subcloned back into the expression vector using MluI and AsiSI restriction sites.

Prior to performing epitope determination using alanine-scanning techniques, relative EC50s of the anti-MS4A4A antibodies were determined as follows using transient transfections of the above-described expression constructs in HEK293T cells. HEK293T cells were seeded in 6 well plates and grown overnight. The next day, cells were transfected with Fugene HD (Promega) or Lipofectamine 3000 (Thermo Fisher Scientific) with a 4:1 ratio of Fugene to DNA or a 3:1 ratio of Lipofectamine to DNA, following the manufacturer's protocols. Approximately 24 hours after transfection, cells were harvested using Trypsin-EDTA and processed for FACS staining.

For FACS staining, 150,000 cells were added to each well of 96 well plates and a titration of anti-MS4A4A antibodies was added in FACS buffer (PBS+2% FBS) and incubated on ice for 60 minutes. Plates were centrifuged (1,400 rpm, 3 minutes), supernatant decanted, and the cells were washed thrice with 200 µl FACS buffer, each followed by a spin and decant step. Antibodies were tested as msIgG1 or huIgG1 chimera and either goat anti-human PE (Southern Biotech, Cat #2040-09, 1:200) or goat anti-mouse APC (BD Biosciences, Cat #550826, 1:100) were added in FACS buffer on ice for 30 minutes. Cells were subsequently washed twice with 200 µl FACS buffer and imaged on an iQue cytometer. Median fluorescence intensity (MFI) was measured on the GFP positive population, representing cells expressing MS4A4A.

Six of the initially tested anti-MS4A4A antibodies bind to HEK293T cells expressing wild-type (WT) MS4A4A-GFP: these included anti-MS4A4A antibodies 4A-18, 4A-21, 4A-202, as well as published murine monoclonal anti-MS4A4A antibodies 4H2 (Kerafast), 5C12 (Biolegend), 3F2 (Millipore). Titration curves for each antibody were determined to establish the optimal anti-MS4A4A antibody concentrations for subsequent epitope mapping studies.

For epitope mapping experiments, HEK293T cells were transfected with the different human MS4A4A expression constructs (as described above; see Table 10 below), and antibody binding was determined using six different anti-MS4A4A antibodies: 4A-21, 4A-18, 4A-202, 4H2, 5C12, and 3F5. Anti-MS4A4A antibody binding was calculated as the % of the MFI from binding to cells transfected with wildtype human MS4A4A expression construct. If an amino acid mutation in the MS4A4A polypeptide resulted in decreased antibody binding to below 20% of that of binding to wildtype MS4A4A, the mutated amino acid was considered a critical amino acid necessary for anti-MS4A4A antibody binding to the MS4A4A protein. Some amino acid mutations in the MS4A4A protein resulted in a decrease in anti-MS4A4A antibody binding to below 51% but above 20% (compared to the binding to wildtype MS4A4A); such amino acids were defined as amino acids contributing to binding of the anti-MS4A4A antibody to the MS4A4A protein.

Some amino acids in MS4A4A affected binding of all tested antibodies, such as the two cysteines, C165 and C174, that are thought to form a cysteine bridge in MS4-type proteins. Such amino acids were considered structural amino acids.

The results of these experiments are provided in Table 10 below. As stated above, Ala.1 to Ala.13 refer to MS4A4A mutations in ECL1; Ala.14 to Ala.36 refer to MS4A4A mutations in ECL2. Data is shown as % binding of the anti-MS4A4A antibodies to the various alanine-scanning mutations compared to the binding of the anti-MS4A4A antibodies to wildtype MS4A4A protein. The mapping experiments were independently repeated twice with very similar results. One difference was that anti-MS4A4A antibodies 4A-21 and 4A-18 were tested once as huIgG1 and second as msIgG1 at two concentrations. Table 11 below shows results from the msIgG1 test for these antibodies. For all other antibodies, Table 10 shows average antibody binding across both experiments. Values showing anti-MS4A4A antibody binding to MS4A4A protein below 20% of that measured for binding to wildtype MS4A4A are in bold in Table 10 below.

All mutations showed equivalent transfection efficiencies of between approximately 22-33% (data not shown). No correlation between average antibody binding and GFP levels in the cells was observed, suggesting that GFP levels cannot be used as a predictor for MS4A4A cell surface expression.

TABLE 10

| Construct | Loop sequence | 4A-21 | 4A-18 | 4A-202* | 4H2 | 5C12 | 3F2 |
|---|---|---|---|---|---|---|---|
| WT ECL1 | CMASNTYGSNPIS (SEQ ID NO: 289) | | | | 100 | | |
| 4A.Ala.1 | SMASNTYGSNPIS (SEQ ID NO: 255) | 84.1 | 96.6 | 86.99 | 72.80 | 82.36 | 79.58 |
| 4A.Ala.2 | CAASNTYGSNPIS (SEQ ID NO: 256) | 12.5 | 19.1 | 9.93 | 7.42 | 11.04 | 7.33 |
| 4A.Ala.3 | CMSSNTYGSNPIS (SEQ ID NO: 257) | 90.7 | 116.6 | 99.12 | 87.76 | 94.47 | 87.46 |
| 4A.Ala.4 | CMAANTYGSNPIS (SEQ ID NO: 258) | 91.2 | 85.8 | 92.48 | 77.90 | 88.62 | 82.49 |

TABLE 10-continued

| Construct | Loop sequence | 4A-21 | 4A-18 | 4A-202* | 4H2 | 5C12 | 3F2 |
|---|---|---|---|---|---|---|---|
| 4A.Ala.5 | CMAS<u>A</u>TYGSNPIS (SEQ ID NO: 259) | 93.1 | 65.6 | 81.64 | 75.95 | 80.92 | 83.89 |
| 4A.Ala.6 | CMASN<u>A</u>YGSNPIS (SEQ ID NO: 260) | 100.4 | 87.5 | 83.22 | 77.29 | 78.57 | 78.38 |
| 4A.Ala.7 | CMASNT<u>A</u>GSNPIS (SEQ ID NO: 261) | 114.5 | 15.8 | 98.41 | 93.36 | 94.96 | 92.91 |
| 4A.Ala.8 | CMASNTY<u>A</u>SNPIS (SEQ ID NO: 262) | 94.6 | 70.4 | 83.82 | 74.41 | 17.39 | 84.41 |
| 4A.Ala.9 | CMASNTYG<u>A</u>NPIS (SEQ ID NO: 263) | 99.6 | 106.0 | 102.06 | 85.83 | 89.83 | 94.67 |
| 4A.Ala.10 | CMASNTYGS<u>A</u>PIS (SEQ ID NO: 264) | 102.3 | 103.2 | 124.27 | 91.27 | 93.95 | 89.57 |
| 4A.Ala.11 | CMASNTYGSN<u>A</u>IS (SEQ ID NO: 265) | 28.7 | 14.8 | 35.06 | 20.53 | 32.79 | 25.29 |
| 4A.Ala.12 | CMASNTYGSNP<u>A</u>S (SEQ ID NO: 266) | 66.4 | 91.4 | 57.21 | 48.93 | 56.33 | 49.19 |
| 4A.Ala.13 | CMASNTYGSNPI<u>A</u> (SEQ ID NO: 267) | 38.4 | 41.8 | 32.34 | 27.38 | 36.36 | 28.92 |
| WT ECL2 | SFHHPYCNYYGNSNNCHGTMS (SEQ ID NO: 290) | | | | 100 | | |
| 4A.Ala.14 | <u>A</u>FHHPYCNYYGNSNNCHGTMS (SEQ ID NO: 268) | 94.3 | 87.8 | 78.14 | 83.99 | 81.28 | 85.27 |
| 4A.Ala.15 | S<u>A</u>HHPYCNYYGNSNNCHGTMS (SEQ ID NO: 269) | 118.7 | 116.9 | 111.77 | 84.71 | 98.51 | 87.20 |
| 4A.Ala.16 | SF<u>A</u>HPYCNYYGNSNNCHGTMS (SEQ ID NO: 270) | 71.0 | 48.1 | 76.87 | 58.00 | 71.46 | 64.58 |
| 4A.Ala.17 | SFH<u>A</u>PYCNYYGNSNNCHGTMS (SEQ ID NO: 271) | 102.8 | 99.4 | 125.37 | 77.01 | 82.95 | 85.21 |
| 4A.Ala.18 | SFHH<u>A</u>YCNYYGNSNNCHGTMS (SEQ ID NO:) | 101.4 | 103.7 | 89.39 | 36.92 | 46.13 | 42.33 |
| 4A.Ala.19 | SFHHP<u>A</u>CNYYGNSNNCHGTMS (SEQ ID NO: 272) | 83.8 | 16.3 | 26.68 | 1.66 | 42.27 | 1.08 |
| 4A.Ala.20 | SFHHPY<u>S</u>NYYGNSNNCHGTMS (SEQ ID NO: 273) | 5.0 | 2.8 | 8.66 | 1.94 | 1.74 | 1.60 |
| 4A.Ala.21 | SFHHPYC<u>A</u>YYGNSNNCHGTMS (SEQ ID NO: 274) | 1.8 | 73.3 | 93.33 | 70.08 | 73.76 | 80.30 |
| 4A.Ala.22 | SFHHPYCN<u>A</u>YGNSNNCHGTMS (SEQ ID NO: 275) | 1.8 | 3.0 | 31.23 | 1.10 | 0.99 | 0.88 |
| 4A.Ala.23 | SFHHPYCNY<u>A</u>GNSNNCHGTMS (SEQ ID NO: 276) | 1.4 | 2.7 | 50.05 | 1.19 | 0.96 | 0.95 |
| 4A.Ala.24 | SFHHPYCNYY<u>A</u>NSNNCHGTMS (SEQ ID NO: 277) | 57.5 | 63.0 | 75.76 | 27.67 | 18.20 | 33.76 |
| 4A.Ala.25 | SFHHPYCNYYG<u>A</u>SNNCHGTMS (SEQ ID NO: 278) | 69.2 | 40.0 | 100.54 | 37.09 | 25.55 | 45.60 |
| 4A.Ala.26 | SFHHPYCNYYGN<u>A</u>NNCHGTMS (SEQ ID NO: 279) | 89.3 | 96.5 | 90.84 | 68.48 | 81.73 | 68.38 |
| 4A.Ala.27 | SFHHPYCNYYGNS<u>A</u>NCHGTMS (SEQ ID NO:) | 98.3 | 118.6 | 98.39 | 99.46 | 91.60 | 94.25 |
| 4A.Ala.28 | SFHHPYCNYYGNSN<u>A</u>CHGTMS (SEQ ID NO: 280) | 87.3 | 116.4 | 98.61 | 86.22 | 85.94 | 83.37 |
| 4A.Ala.29 | SFHHPYCNYYGNSNN<u>S</u>HGTMS (SEQ ID NO: 281) | 8.4 | 2.7 | 4.54 | 1.09 | 1.01 | 0.91 |

TABLE 10-continued

| Construct | Loop sequence | 4A-21 | 4A-18 | 4A-202* | 4H2 | 5C12 | 3F2 |
|---|---|---|---|---|---|---|---|
| 4A.Ala.30 | SFHHPYCNYYGNSNNCAGTMS (SEQ ID NO: 282) | 87.5 | 62.6 | 92.83 | 72.87 | 80.56 | 82.45 |
| 4A.Ala.31 | SFHHPYCNYYGNSNNCHATMS (SEQ ID NO: 283) | 147.8 | 158.6 | 142.81 | 123.13 | 124.19 | 135.58 |
| 4A.Ala.32 | SFHHPYCNYYGNSNNCHGAMS (SEQ ID NO: 284) | 61.6 | 42.9 | 63.28 | 44.61 | 56.19 | 45.14 |
| 4A.Ala.33 | SFHHPYCNYYGNSNNCHGTAS (SEQ ID NO: 285) | 81.8 | 36.1 | 73.09 | 62.83 | 59.85 | 60.45 |
| 4A.Ala.34 | SFHHPYCNYYGNSNNCHGTMA (SEQ ID NO: 286) | 113.4 | 91.0 | 117.02 | 102.44 | 99.15 | 103.80 |
| 4A.Ala.35 | SFHHPYCNYY---NNCHGTMS (SEQ ID NO: 287) | 107.3 | 2.7 | 73.14 | 1.08 | 1.00 | 0.88 |
| 4A.Ala.36 | SFHHPYCN-----NNCHGTMS (SEQ ID NO: 288) | 1.3 | 2.6 | 0.07 | 0.99 | 0.93 | 0.83 |

*antibody tested as huIgG1 chimera

Results shown above suggest that anti-MS4A4A antibodies of the present disclosure recognize distinct linear and/or 3D structural epitopes within MS4A4A.

Based on the anti-MS4A4A antibody binding data obtained from these experiments, the following loop amino acid residues within human MS4A4A were considered structural amino acids within the MS4A4A protein as mutating each of them affected binding of anti-MS4A4A antibodies tested: M87, C165, Y167, Y168, C174 (Based on human MS4A4A protein; SEQ ID NO:1). Amino acid residues C165 and C174 are predicted to establish a cysteine bridge forming a loop in ECL2. In the absence of this cysteine bridge, anti-MS4A4A antibodies did not bind MS4A4A protein, suggesting that the loop structure within ECL2 of MS4A4A is important for antibody binding More evidence for loop structure being important comes from the two loop deletion mutants (Ala.35 and Ala.36) which also strongly affect binding of the antibodies.

The results further showed that amino acid residues Y167 and Y168 strongly affected binding of anti-MS4A4A antibodies 4A-21, 4A-18, 4H2, 5C12, and 3F2. These amino acid residues also affected binding of anti-MS4A4A antibody 4A-202 to a lesser degree. Additionally, amino acid residues P96, I97, and S98 in ECL1 reduced binding to some degree of all anti-MS4A4A antibodies tested. These results suggested either that mutations in any of these five amino acid residues altered the structure of the extracellular domains important for antibody recognition and binding, or that these amino acid residues are important for the interaction and binding of each of the six anti-MS4A4A antibodies listed. Proline is the most restrained amino acid residue, which is critical to the secondary and tertiary structure of a polypeptide. For example, proline acts as a disrupter in the middle of regular secondary structure elements, including that of alpha helices and beta sheets; however, proline is commonly found as the first amino acid residue of an alpha helix and in the edge stands of beta sheets. Tyrosine, isoleucine, and serine residues provide multiple antigen-antibody interactions, including, for example, Van der Waals interaction(s), pi-pi stacking and pi-facial hydrogen bonding interactions, and/or hydrogen bonds. Accordingly, either tyrosine, proline, isoleucine, or serine residues can create well-defined structural epitopes. Any subtle changes in these four amino acid residues have the potential to significantly disrupt antibody binding affinity.

The mutation at amino acid residue M87A in MS4A4A greatly reduced or abolished binding of all anti-MS4A4A antibodies tested. Based on the prediction that ECL1 and ECL2 employ well-defined rigid body structures and may interact with each other, the M87A binding result shown indicated that the M87 amino acid residue is predicted to be one of the most critical residues in maintaining the rigid loop structure of MS4A4A, as the side chain of M87 can interact with one or more beta-branched amino acids in ECL1 and/or ECL2 by Van de Waals contacts and hydrogen bonds through backbone-side chain and/or backbone-backbone interactions.

Table 11 below lists the unique binding amino acid residues for anti-MS4A4A antibodies disclosed herein. Anti-MS4A4A antibody 4A-21 requires N166 in ECL2 for binding to human MS4A4A. The data showed that anti-MS4A4A antibodies 4A-18 and 5C12 bind ECL1 as well as ECL2 of human MS4A4A. Anti-MS4A4A antibody 4A-202 had some binding contribution by amino acid residue Y164.

All three commercial anti-MS4A4A antibodies bind P163, whereas none of the anti-MS4A4A antibodies disclosed herein and tested in this study did. This proline P163 of human MS4A4A is replaced by arginine in the cynomolgous MS4A4A protein. Such observation suggests that this proline to arginine change is important for determining cyno cross-reactivity, or the lack thereof, as displayed by the binding characteristics of the commercial MS4A4A antibodies. Proline is the most structurally restrained amino acid residue and arginine (in cyno MS4A4A) is a positively charged amino acid at physiological pH. The proline to arginine difference in human vs cyno MS4A4A may profoundly affect the conformation of the MS4A4A protein, therefore preventing the commercial MS4A4A antibodies from binding. Anti-MS4A4A antibodies 4A-18, 4A-21, and 4A-202 appeared not to be dependent on this amino acid for binding, and thus their binding to the cynomolgous protein was not affected.

In summary, anti-MS4A4A antibodies 4A-21, 4A-18, and 4A-202 bound epitopes on MS4A4A which are distinct from that of commercially available anti-MS4A4A antibodies (Table 11 below). The commercial anti-MS4A4A antibodies 4H2 and 3F2 exhibited identical epitopes, which overlapped significantly with that of anti-MS4A4A antibody 5C12. In contrast, anti-MS4A4A antibodies 4A-18, 4A-21, and 4A-202 each exhibited unique epitope binding characteristics distinct from each other and distinct from that of the commercial anti-MS4A4A antibodies. These differences in binding properties are shown in Table 10. Additionally, the results showed that no two anti-MS4A4A antibodies tested bound identical epitopes within human MS4A4A; however, there are shared amino acid binding residues across some or all antibodies (e.g., amino acid residues Y167 and Y168, Y164, N170, T177).

TABLE 11

| Antibody | ECL1 residues | ECL2 residues |
| --- | --- | --- |
| 4A-21 | | N166 (critical) |
| 4A-18 | Y92 (critical) | Y164 (critical) |
| | | H161, N170, T177, M178 (contribute) |
| 4A-202 | | Y164 (contributes) |
| 4H2 | | Y164 (critical) |
| | | P163, G169, N170, T177 (contribute) |
| 5C12 | G93 (critical) | G169 (critical) |
| | | P163, Y164, N170 (contribute) |
| 3F2 | | Y164 (critical) |
| | | P163, G169, N170, T177 (contribute) | with shaking for 1 hr, washed 3 times, then 1/2500 dilution of HRP conjugates goat anti human kappa antibodies added (SigmaAldrich cat #. A7164-1ML).

Figure 4:
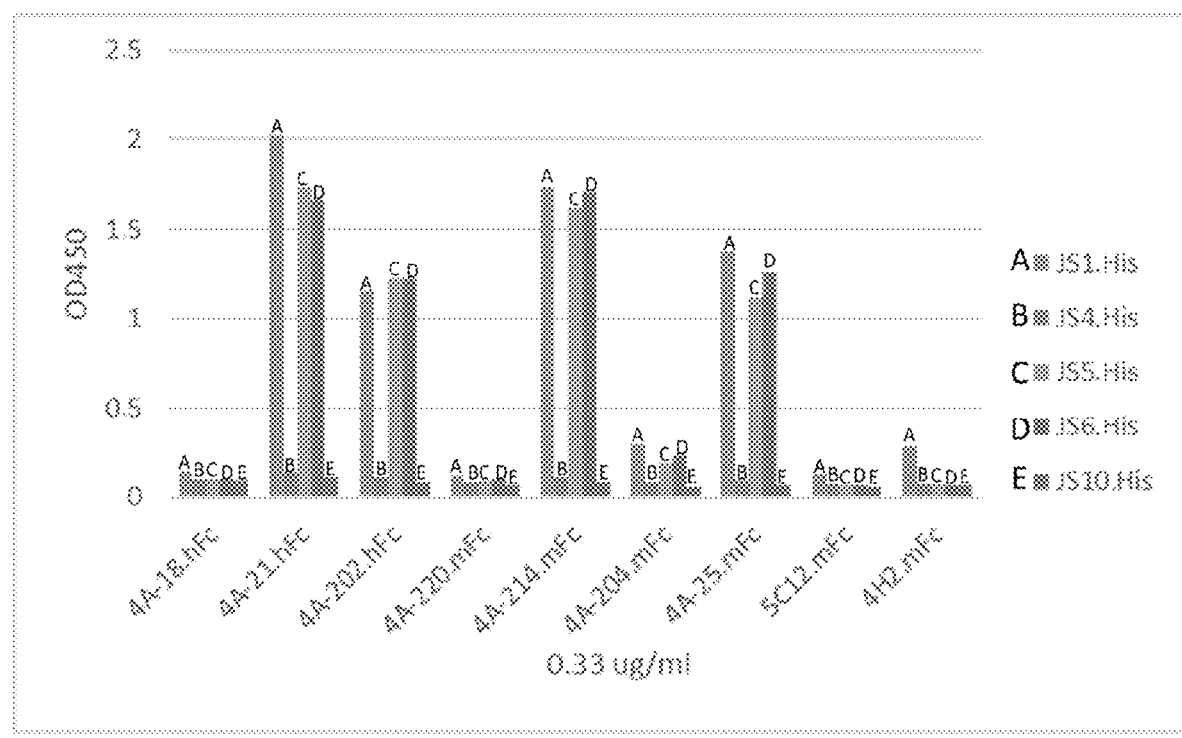
FIG. 4 shows certain anti-MS4A4A antibodies of the present disclosure binding to recombinant MS4A4A soluble looped grafted polypeptides JS1, JS4, JS5, JS6, and JS10 by ELISA.

FIG. 4 shows ELISA binding results of certain humanized anti-MS4A4A antibodies binding to recombinant MS4A4A soluble polypeptides JS1, JS4, JS5, JS6, and JS10. As shown in FIG. 4, certain anti-MS4A4A antibodies (4A-18.hFc, 4A-21.hFc, 4A-202.hFc, 4A-220.mFc, 4A-214.mFc, 4A-204.mFc' hFc refers to human Fc; mFc refers to murine Fc)) showed binding by ELISA to recombinant MS4A4A soluble polypeptides JS1, JS5, and JS6, which contain the two ECLs of human MS4A4A. Anti-MS4A4A antibodies of the present invention did not bind to recombinant soluble polypeptides JS4 and JS10, which are negative control polypeptides and do not contain MS4A4A ECL region sequence. Two commercially available anti-MS4A4A antibodies, 5C12 and 4H2, did not show binding to any of the recombinant MS4A4A soluble polypeptides (see FIG. 4). In FIG. 4, anti-MS4A4A antibody 4A-214 was previously disclosed in international patent application no PCT/US2019/016156, and has a heavy chain variable region amino acid sequence of
EVKLEESGG-GLVQPGRSMKLSCVASGFTFSNYWMNWVRQS-PEKGLEWVAEIRLKSNNYATHY AESVKGRFTISRDD-SKSSVYLQMNNLRAEDTGIYYCSSMIIVDYWGQG-TTVTVSS (SEQ ID NO:179) and a light chain variable region amino acid sequence of
DIVLTQSPASLTVSLGQRATISCRASQSVSSSTY-SYLHWYQQRPGQPPKLLIKYASNLESGVPARF SGSGSGTVFTLNIHPVEEEDTATYYCQHS-WEIPLTFGAGTKLEMK (SEQ ID NO:180).

Results presented in FIG. 4 were derived from data shown below in Table 12:

TABLE 12

| | 4A-18.hFc | 4A-21.hFc | 4A-202.hFc | 4A-220.mFc | 4A-214.mFc | 4A-204.mFc | 4A-25.mFc | 5C12.mFc | 4H2.mFc |
| --- | --- | --- | --- | --- | --- | --- | --- | --- | --- |
| JS1.His | 0.146 | 2.019 | 1.157 | 0.123 | 1.737 | 0.29 | 1.381 | 0.129 | 0.285 |
| JS4.His | 0.098 | 0.138 | 0.111 | 0.087 | 0.11 | 0.08 | 0.091 | 0.076 | 0.077 |
| JS5.His | 0.099 | 1.731 | 1.219 | 0.091 | 1.624 | 0.188 | 1.117 | 0.068 | 0.072 |
| JS6.His | 0.105 | 1.668 | 1.225 | 0.1 | 1.706 | 0.229 | 1.26 | 0.066 | 0.069 |
| JS10.His | 0.092 | 0.112 | 0.084 | 0.064 | 0.086 | 0.058 | 0.063 | 0.061 | 0.064 |

Example 6

Binding of Anti-MS4A4A Antibodies to Recombinant MS4A4A Soluble Polypeptides

Figure 5:
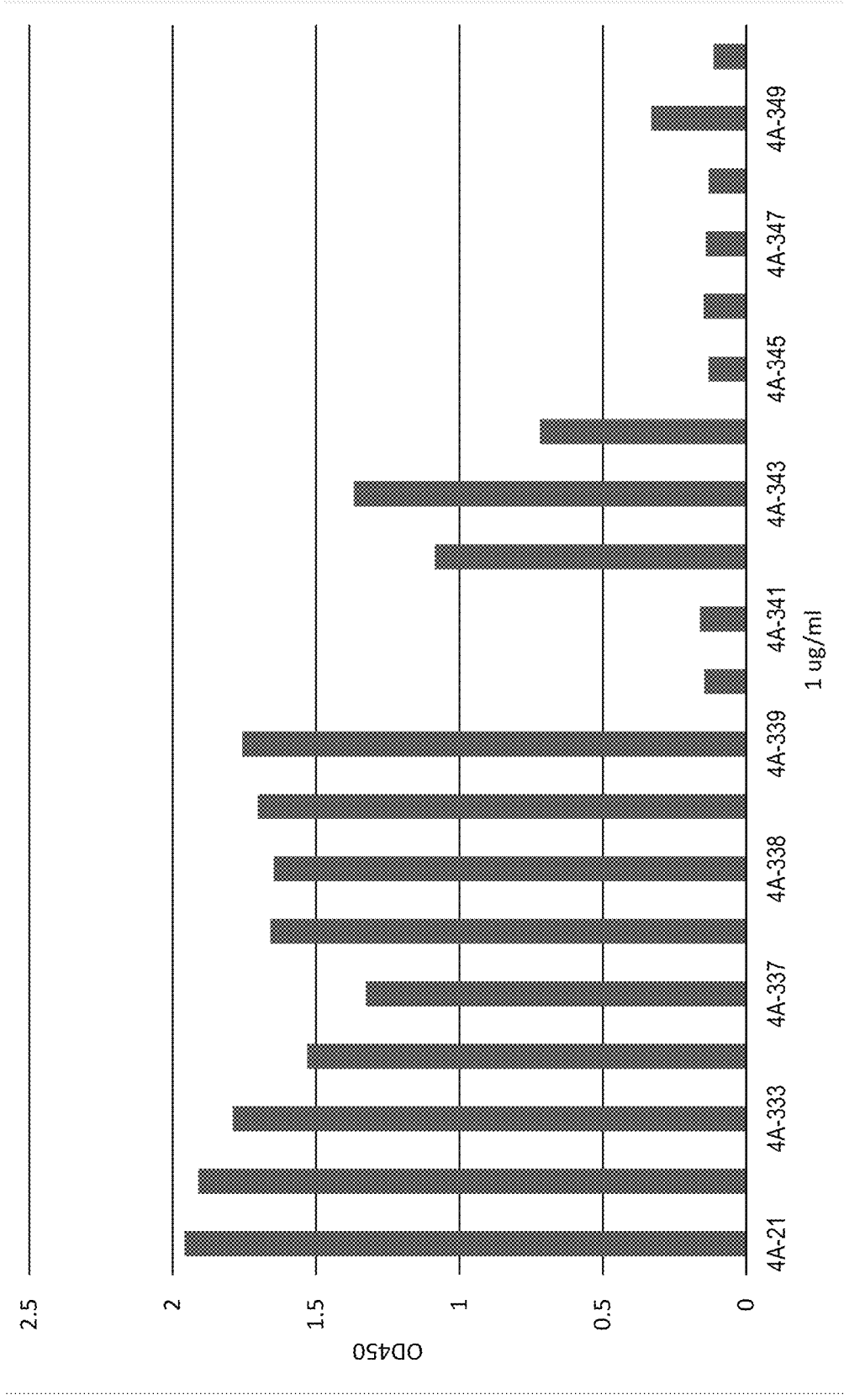
FIG. 5 shows certain humanized anti-MS4A4A antibody variants of murine anti-MS4A4A antibody 4A-21 binding to recombinant MS4A4A soluble looped grafted polypeptide JS1.

Anti-MS4A4A antibodies of the present disclosure were tested for their ability to bind to the different recombinant MS4A4A soluble polypeptides, as described in Example 2, as follows. Nucleic acid encoding the VH and VL domains of humanized anti-MS4A4A antibodies of the present disclosure were cloned into pcDNA3.4 vector which contains either the human IgG1 heavy chain constant domain or human kappa constant domain. The humanized anti-MS4A4A antibodies were expressed in Expi293 cells and were purified by Mab select antibody purification resin (GE Healthcare Life Science, cat #17519902) following the manufacture's protocol. ELISA was performed to measure binding of anti-MS4A4A antibodies of the present disclosure the recombinant MS4A4A soluble polypeptides. 1 µg/ml biotinylated antigens were preincubated on the streptavidin-coated ELISA plates (Thermo Scientific, cat #PI15120) for 1 hour. Plates were washed 3 times, followed by the addition of antibodies (1 µg/ml, 0.33 µg/ml, and 0.11 µg/ml antibodies. Plates were incubated at room temperature FIG. 5 shows ELISA binding results of humanized versions of murine anti-MS4A4A antibody 4A-21 to recombinant MS4A4A soluble polypeptide JS1. The antibodies were used at a concentration of 1 µg/ml. As shown in FIG. 5, many of the humanized versions of anti-MS4A4A antibody 4A-21 retained their ability to bind to this recombinant polypeptide. Certain humanized versions of anti-MS4A4A antibody 4A-21 showed reduced binding to recombinant MS4A4A soluble polypeptide JS1.

Results presented in FIG. 5 were derived from data shown below in Table 13:

TABLE 13

| Antibody | OD450 |
| --- | --- |
| 4A-21 | 1.958 |
| 4A-332 | 1.91 |
| 4A-333 | 1.79 |
| 4A-334 | 1.531 |
| 4A-337 | 1.326 |
| 4A-335 | 1.659 |
| 4A-338 | 1.647 |
| 4A-336 | 1.703 |
| 4A-339 | 1.757 |

TABLE 13-continued

| Antibody | OD450 |
| --- | --- |
| 4A-340 | 0.146 |
| 4A-341 | 0.162 |
| 4A-342 | 1.086 |
| 4A-343 | 1.368 |
| 4A-344 | 0.719 |
| 4A-345 | 0.132 |
| 4A-346 | 0.148 |
| 4A-347 | 0.141 |
| 4A-348 | 0.131 |
| 4A-349 | 0.331 |
| Isotype | 0.113 |

Figure 6:
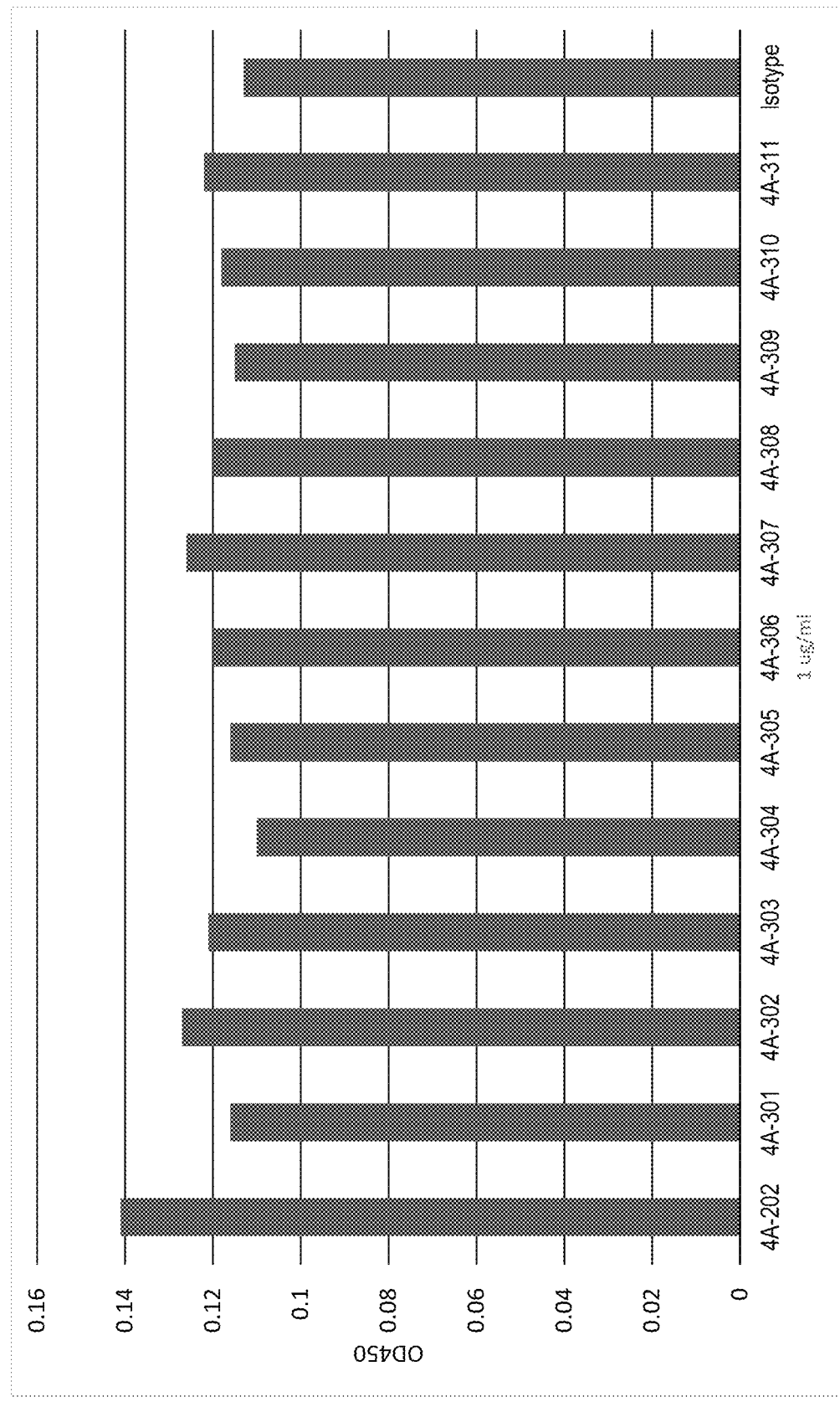
FIG. 6 shows certain humanized anti-MS4A4A antibody variants of murine anti-MS4A4A antibody 4A-202 binding to recombinant MS4A4A soluble looped grafted polypeptide JS1.

FIG. 6 shows ELISA binding results of humanized versions of murine anti-MS4A4A antibody 4A-202 to recombinant MS4A4A soluble polypeptide JS1. The antibodies were used at a concentration of 1 µg/ml. As shown in FIG. 6, humanized versions of anti-MS4A4A antibody 4A-202 were able to bind to this recombinant polypeptide.

Results presented in FIG. 6 were derived from data shown below in Table 14:

TABLE 14

| Antibody | OD450 |
| --- | --- |
| 4A-202 | 0.141 |
| 4A-301 | 0.116 |
| 4A-302 | 0.127 |
| 4A-303 | 0.121 |
| 4A-304 | 0.11 |
| 4A-305 | 0.116 |
| 4A-306 | 0.12 |
| 4A-307 | 0.126 |
| 4A-308 | 0.12 |
| 4A-309 | 0.115 |
| 4A-310 | 0.118 |
| 4A-311 | 0.122 |
| Isotype | 0.113 |

Various humanized versions of murine anti-MS4A4A antibody 4A-202 and murine anti-MS4A4A antibody 4A-21 were further tested for their ability to bind to recombinant MS4A4A soluble polypeptides. Humanized anti-MS4A4A antibody 4A-332 and humanized anti-MS4A4A antibody 4A-302 showed reasonable binding and were selected for further affinity improvement as follows. Random mutations in the 6 CDRs of anti-MS4A4A antibody 4A-322 and of anti-MS4A4A antibody 4A-302 were introduced using an overlapping PCR technique. Biotinylated recombinant MS4A4A soluble polypeptide JS5 was used for phage display panning of these antibody variants. After 3 rounds of panning, approximately 190 mutant anti-MS4A4A antibody variants were selected and expressed in TG1 cells, the lysates of which were screened by ELISA. Twenty-two humanized anti-MS4A4A antibody 4A-21 variants and fifteen humanized anti-MS4A4A antibody 4A-202 variants were selected, recombinantly converted to full human IgG, and expressed in Expi293 cells. The anti-MS4A4A antibodies were purified by MabSelect Antibody Purification Resin (GE Healthcare Life Science, cat #17519902) as indicated in the manufacturer's protocol. ELISA and Flow Cytometry experiments were subsequently repeated.

Humanized and affinity matured anti-MS4A4A antibodies 4A-312, 4A-313, and 4A-314 showed binding to recombinant MS4A4A soluble polypeptide JS5 by ELISA (see FIG. 7) at various antibody concentrations (1 µg/ml, 0.33 µg/ml, and 0.11 µg/ml), and were selected for further functional analysis.

Figure 7:
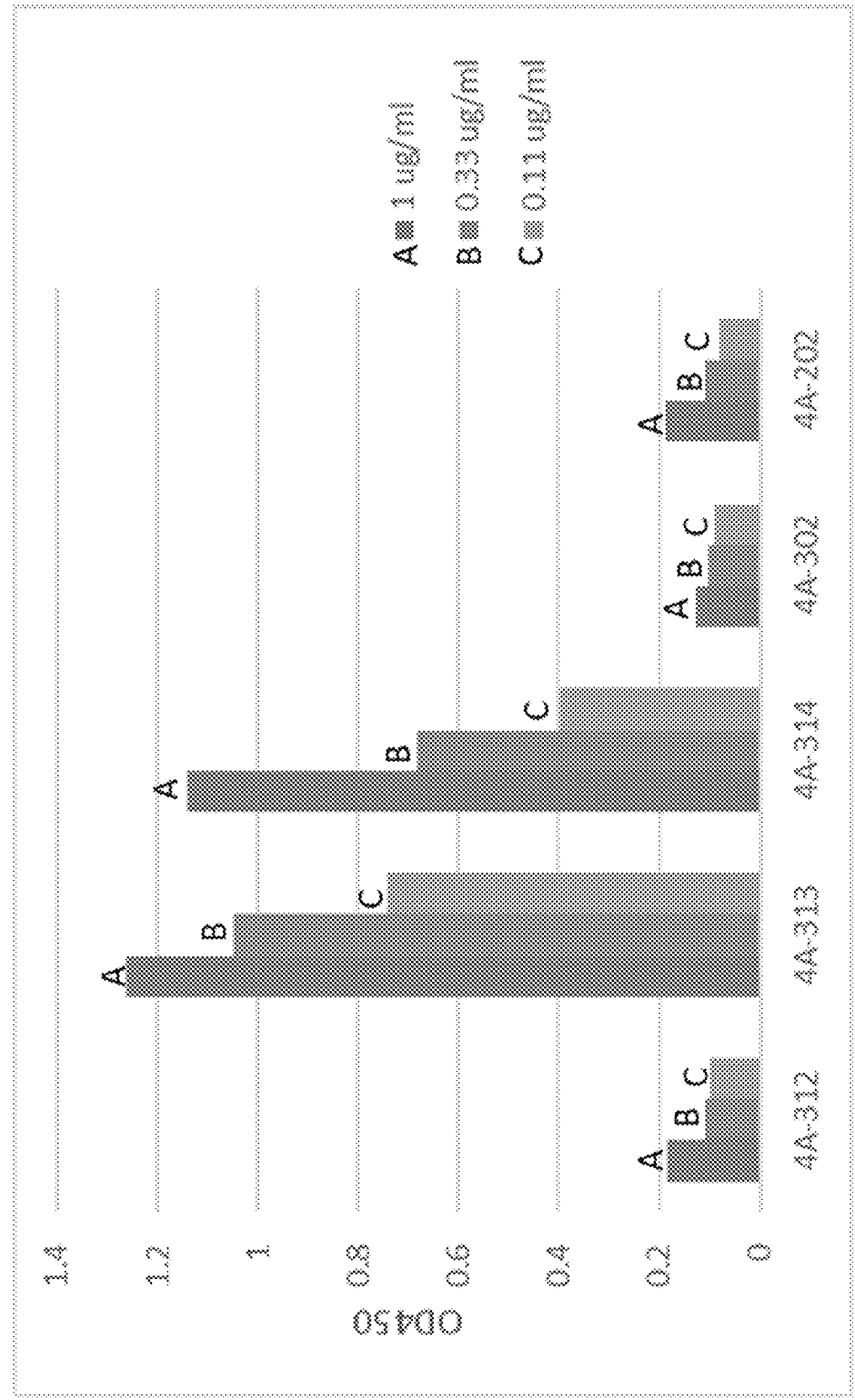
FIG. 7 shows certain humanized and affinity matured anti-MS4A4A antibody variants of murine anti-MS4A4A antibody 4A-202 binding to recombinant MS4A4A soluble looped grafted polypeptide JS5.

Results presented in FIG. 7 were derived from data shown below in Table 15:

TABLE 15

| Antibody | 1 ug/ml | 0.33 ug/ml | 0.11 ug/ml |
| --- | --- | --- | --- |
| 4A-312 | 0.184 | 0.11 | 0.097 |
| 4A-313 | 1.262 | 1.05 | 0.741 |
| 4A-314 | 1.142 | 0.682 | 0.399 |
| 4A-302 | 0.128 | 0.103 | 0.091 |
| 4A-202 | 0.188 | 0.111 | 0.079 |

Figure 8:
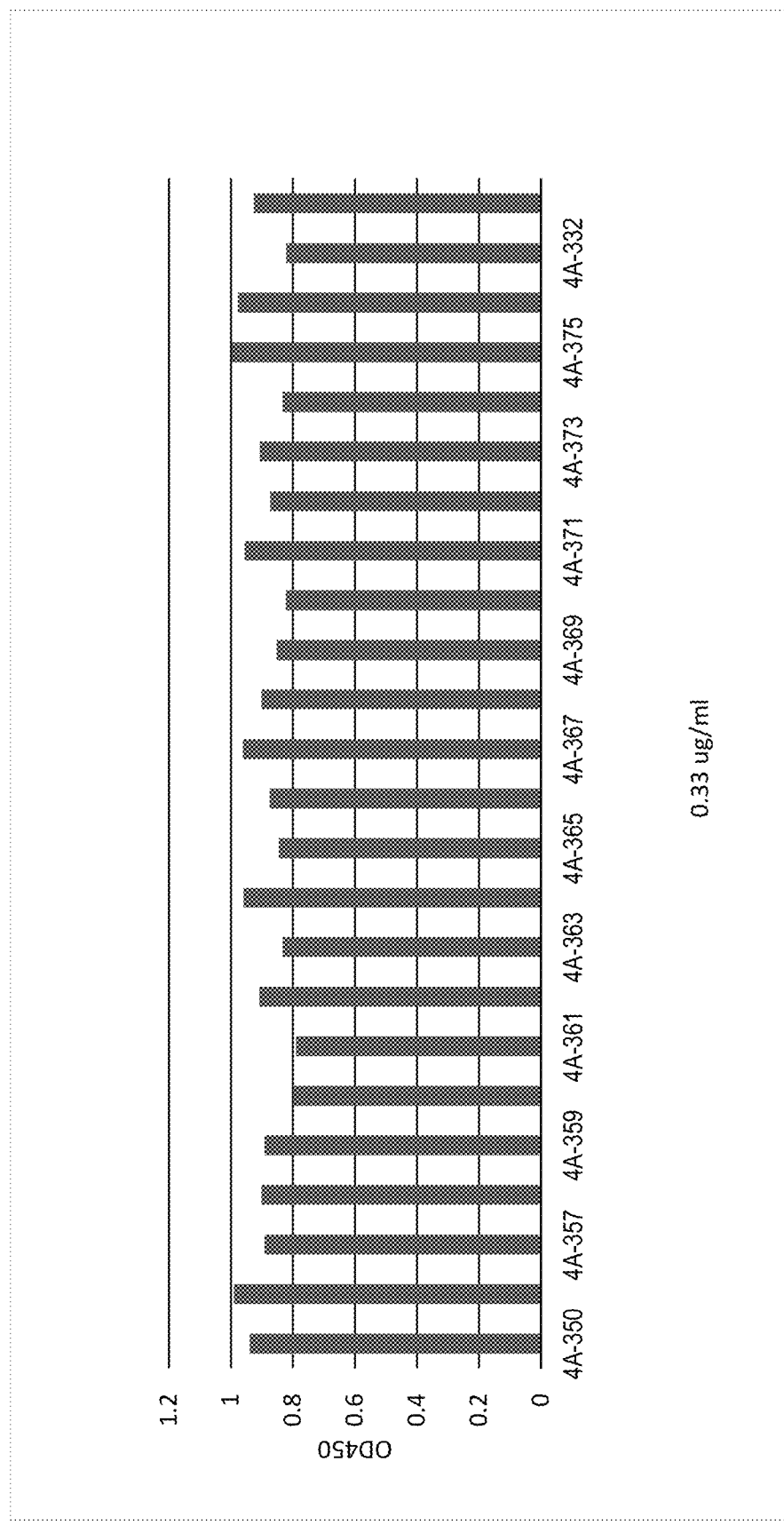
FIG. 8 shows certain humanized and affinity matured anti-MS4A4A antibody variants of murine anti-MS4A4A antibody 4A-21 binding to recombinant MS4A4A soluble looped grafted polypeptide JS5.

Humanized and affinity matured anti-MS4A4A antibodies 4A-351 and 4A-376 (0.4 µg/ml) showed good binding to recombinant MS4A4A soluble polypeptide JS5 by ELISA (see FIG. 8). These anti-MS4A4A antibodies were then selected for use as templates for which amino acid substitutions were made to amino acid D28 in CDR-L1; such amino acid substitutions included D28G, D28E, D28S, D28A, and D28Q.

Results presented in FIG. 8 were derived from data shown below in Table 16:

TABLE 16

| Antibody | OD450 |
| --- | --- |
| 4A-350 | 0.939 |
| 4A-351 | 0.99 |
| 4A-357 | 0.892 |
| 4A-358 | 0.901 |
| 4A-359 | 0.892 |
| 4A-360 | 0.797 |
| 4A-361 | 0.79 |
| 4A-362 | 0.908 |
| 4A-363 | 0.833 |
| 4A-364 | 0.959 |
| 4A-365 | 0.845 |
| 4A-366 | 0.875 |
| 4A-367 | 0.961 |
| 4A-368 | 0.901 |
| 4A-369 | 0.852 |
| 4A-370 | 0.822 |
| 4A-371 | 0.955 |
| 4A-372 | 0.873 |
| 4A-373 | 0.907 |
| 4A-374 | 0.833 |
| 4A-375 | 0.996 |
| 4A-376 | 0.977 |
| 4A-332 | 0.821 |
| 4A-21 | 0.925 |

Figure 9:
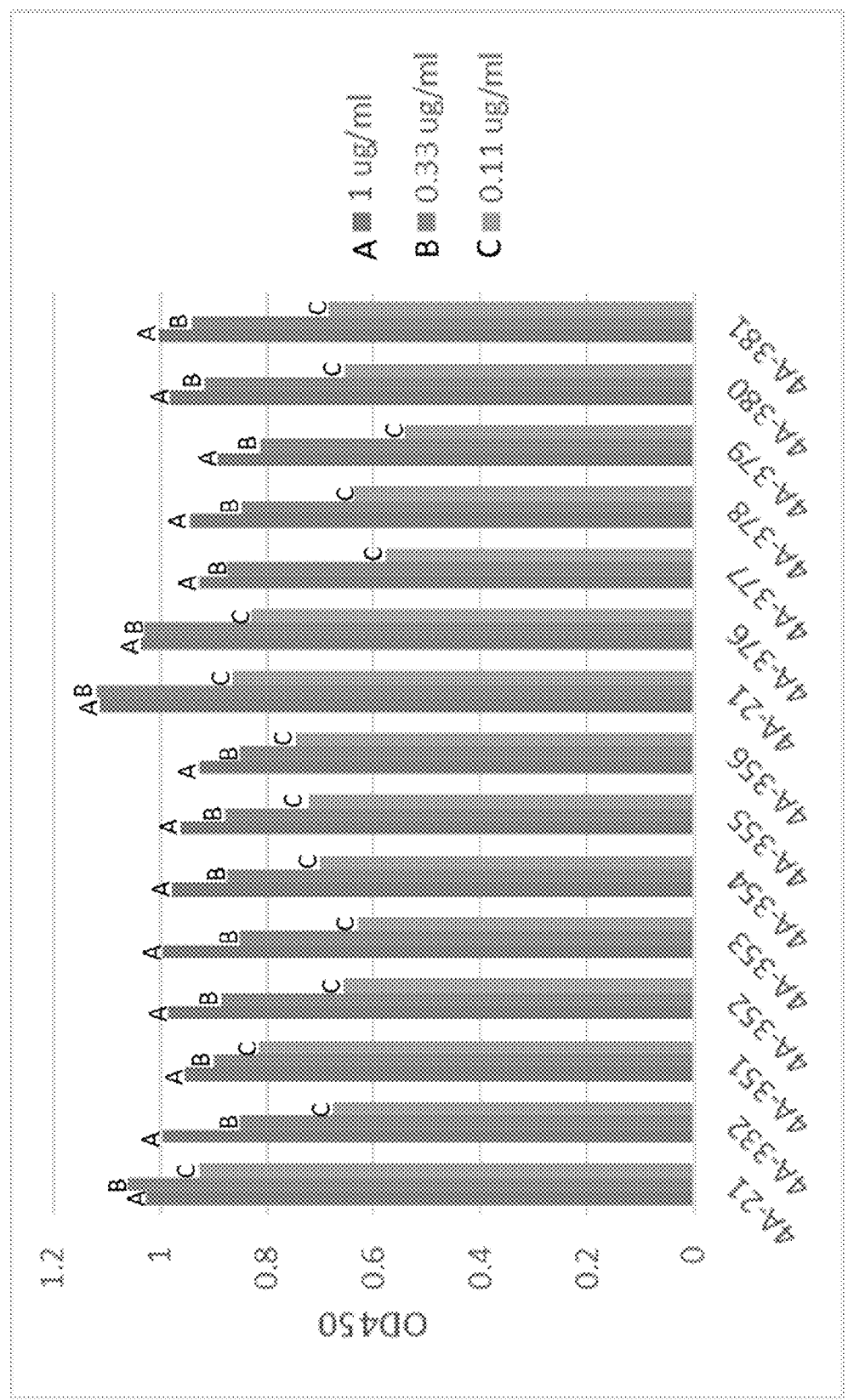
FIG. 9 shows certain humanized and affinity matured anti-MS4A4A antibody variants of murine anti-MS4A4A antibody 4A-21 binding to recombinant MS4A4A soluble looped grafted polypeptide JS5.

These additional anti-MS4A4A antibodies included anti-MS4A4A antibody 4A-352, 4A-353, 4A-354, 4A-355, 4A-356, 4A-377, 4A-378, 4A-379, 4A-380, and 4A-381, and were tested by ELISA for binding to recombinant MS4A4A soluble polypeptide JS5 at three different antibody concentrations (1 µg/ml, 0.33 µg/ml, and 0.11 µg/ml). The results of these studies are shown in FIG. 9. As shown in FIG. 9, these additional anti-MS4A4A antibodies showed binding to recombinant MS4A4A soluble polypeptide JS5.

Results presented in FIG. 9 were derived from data shown below in Table 17:

TABLE 17

| Antibody | 1 ug/ml | 0.33 ug/ml | 0.11 ug/ml |
| --- | --- | --- | --- |
| 4A-21 | 1.027 | 1.063 | 0.927 |
| 4A-332 | 0.997 | 0.851 | 0.677 |
| 4A-351 | 0.953 | 0.898 | 0.816 |
| 4A-352 | 0.985 | 0.885 | 0.655 |

TABLE 17-continued

| Antibody | 1 ug/ml | 0.33 ug/ml | 0.11 ug/ml |
|---|---|---|---|
| 4A-353 | 0.996 | 0.85 | 0.63 |
| 4A-354 | 0.98 | 0.874 | 0.701 |
| 4A-355 | 0.961 | 0.878 | 0.721 |
| 4A-356 | 0.927 | 0.85 | 0.746 |
| 4A-21 | 1.114 | 1.121 | 0.865 |
| 4A-376 | 1.037 | 1.031 | 0.83 |
| 4A-377 | 0.928 | 0.873 | 0.577 |
| 4A-378 | 0.944 | 0.848 | 0.636 |
| 4A-379 | 0.893 | 0.812 | 0.543 |
| 4A-380 | 0.981 | 0.916 | 0.654 |
| 4A-381 | 1.002 | 0.94 | 0.685 |

Example 7

Binding of Humanized and Affinity Matured Anti-MS4A4A Antibodies to U937 Cells Overexpressing Human MS4A4A Humanized and affinity matured versions of anti-MS4A4A antibodies of the present disclosure were evaluated for their binding to human MS4A4A-expressing U937 cells as follows.

Anti-MS4A4A antibodies tested were either mouse IgGs purified from hybridoma supernatant or human IgG1 Fc chimeras produced recombinantly in Expi293 cells. Affinity binding to cells was determined as follows. Briefly, cells were harvested, washed, and labeled with Aqua Live/Dead for viability discrimination. After a wash with PBS, 2×10^4 cells were aliquoted per well in 96-well U-bottom plates and incubated with 50 µL of purified anti-MS4A4A antibody at various concentrations (3× dilutions starting at 10 µg/mL) in FACS buffer (PBS+2% FBS+1 mM EDTA). After this primary incubation, the supernatant was removed via centrifugation, washed 2× with 150 µL of ice-cold FACS buffer, and incubated with the appropriate secondary antibody on ice for 15 minutes. Following the secondary antibody incubation, the cells were again washed 2× with ice-cold FACS buffer and resuspended in a final volume of 200 µL of FACS buffer. Flow cytometry analysis was performed on a FACSCanto system (BD Biosciences). Binding data was expressed as Median Fluorescent Intensity (MFI).

The results of these binding experiments are shown in Table 18 and Table 19 below. Table 18 shows binding of certain anti-MS4A4A antibodies of the present disclosure to U937 cells overexpressing recombinant human MS4A4A. These experiments were performed using anti-MS4A4A antibodies at a concentration of 5 µg/ml and were assayed for cell binding by flow cytometry.

TABLE 18

| Antibody | MFI |
|---|---|
| 4A-18 | 382 |
| 4A-202 | 216 |
| 4A-21 | 670 |
| 4A-25 | 648 |
| 4A-301 | 89.7 |
| 4A-302 | 113 |
| 4A-303 | 94.7 |
| 4A-304 | 112 |
| 4A-305 | 69.6 |
| 4A-306 | 71.3 |
| 4A-307 | 68.8 |
| 4A-308 | 97.2 |
| 4A-309 | 131 |

TABLE 18-continued

| Antibody | MFI |
|---|---|
| 4A-310 | 75.4 |
| 4A-311 | 68.8 |
| 4A-332 | 324 |
| 4A-333 | 350 |
| 4A-334 | 296 |
| 4A-335 | 286 |
| 4A-336 | 309 |
| 4A-337 | 218 |
| 4A-338 | 222 |
| 4A-339 | 284 |
| 4A-340 | 41.8 |
| 4A-341 | 65.3 |
| 4A-342 | 538 |
| 4A-343 | 513 |
| 4A-344 | 427 |
| 4A-345 | 54.4 |
| 4A-346 | 56.1 |
| 4A-347 | 50.2 |
| 4A-348 | 47.8 |
| 4A-349 | 142 |
| Isotype control | 33.4 |

Table 19 shows binding of certain anti-MS4A4A antibodies of the present disclosure to U937 cells over-expressing recombinant human MS4A4A. These experiments were performed using anti-MS4A4A antibodies at a concentration of 5 µg/ml and were assayed for cell binding by flow cytometry. In this assay, the MFI value of cells stained with secondary antibody alone was approximately 200.

TABLE 19

| Antibody | MFI |
|---|---|
| 4A-21 | 18779 |
| 4A-332 | 8821 |
| 4A-350 | 11581 |
| 4A-351 | 12175 |
| 4A-358 | 12107 |
| 4A-360 | 10277 |
| 4A-362 | 10023 |
| 4A-369 | 10079 |
| 4A-373 | 11874 |
| 4A-376 | 16664 |
| 4A-352 | 10955 |
| 4A-353 | 10363 |
| 4A-354 | 13682 |
| 4A-355 | 13418 |
| 4A-356 | 11974 |
| 4A-377 | 12243 |
| 4A-378 | 9913 |
| 4A-379 | 10567 |
| 4A-380 | 11809 |
| 4A-381 | 12588 |
| 4A-202 | 31745 |
| 4A-302 | 24450 |
| 4A-312 | 17715 |
| 4A-313 | 41794 |
| 4A-314 | 15289 |

Example 8

Anti-MS4A4A Antibodies Modulate TREM2 Protein in Primary Human Myeloid Cells

It has been reported that SNPs in the MS4A locus affect soluble TREM2 (sTREM2) levels in humans, the TREM2 pathway generally, and Alzheimer's disease susceptibility. Alzheimer's disease protective MS4A4A alleles are linked to increased sTREM2 levels in the cerebrospinal fluids. Together these pathways may play a role in the prevention of Alzheimer's Disease or other neurodegenerative diseases. Additionally, treatment of human macrophages in culture with commercially available anti-MS4A4A antibodies reduced sTREM2 levels (Piccio et.al. Acta Neuropathol 2016, 131:925-933). To examine the effect of anti-MS4A4A antibodies of the present disclosure modulating sTREM2 and plasma-membrane/cell surface TREM2 (mTREM2) levels in macrophages, the following studies were performed.

Primary human macrophages were plated in 96-well plates and treated with the panel of anti-MS4A4A antibodies (10 μg/ml) in complete RPMI. After 48 hours of incubation, supernatants were collected and sTREM2 levels determined using Meso Scale Discovery (MSD). Briefly, wells of an MSD plate (Cat #L15XA-3) were incubated with capture antibody at 1 μg/ml, overnight on orbital shaker at 500 RPM at 4° C. The wells were washed and then blocked in binding buffer (1% heat-inactivated high-grade BSA) in PBS for an hour on an orbital shaker at 500 RPM at 20° C. Standards (Recombinant Human Trem2 Fc 1828-T2 (R&D Systems)) and unknown samples at proper concentrations were prepared in binding buffer, added to the wells, then incubated for 1 hour on orbital shaker at 500 RPM at 20° C. The wells were washed and then incubated with secondary antibody (Biotinylated goat anti-human TREM2 (R&D Systems Cat #BAF1828)) at 100 ng/ml for 1 hour on an orbital shaker at 500 RPM at 20° C. The wells were washed and then incubated with a detection reagent (Sulfo Tag-Streptavidin; MSD Cat #R32AD) at 0.2 μg/ml in binding buffer. The wells were then washed, 150 μl read buffer (1×, MSD) was added to each well, and the plates read on a Sector Imager.

Separately, anti-MS4A4A antibody treated cells (above) were collected and subjected to flow cytometry to determine mTREM2 levels using an anti-TREM2 antibody (Alector) conjugated to allophycocyanin or similar fluorophores.

As shown in Table 20, anti-MS4A4A antibodies increased the level of sTREM2 in the supernatants of cultured human primary macrophages obtained from various donors. The results described herein showed that the anti-MS4A4A antibodies of the present disclosure increase or upregulate sTREM2 levels in the supernatants of human primary macrophages. Numbers reported in Table 20 are relative to those obtained using an isotype control antibody, which was set at 100.

TABLE 20

| Antibody | Donor | | |
|---|---|---|---|
| | 686 | 687 | 688 |
| 4A-202 | 249.7 | 208.9 | 431.2 |
| 4A-214 | 142.8 | 168.3 | 137.7 |
| 4A-18 | 151.2 | 152.4 | 181.0 |
| 4A-21 | 340.0 | 230.4 | 489.7 |
| huIgG1 | 100 | 100 | 100 |

As shown below in Table 21, anti-MS4A4A antibodies increased the level of plasma-membrane/cell surface TREM2 (mTREM2) on cultured human primary macrophages obtained from various donors. These results were consistent with the corresponding increase in sTREM2 observed in the supernatants of these cells, as shown above in Table 20. Numbers reported in Table 21 are relative to those obtained using an isotype control antibody, which was set at 100.

TABLE 21

| Antibody | Donor | | |
|---|---|---|---|
| | 695 | 696 | 697 |
| 4A-202 | 319.2 | 374.5 | 373.2 |
| 4A-214 | 178.3 | 124.6 | 65.7 |
| 4A-18 | 273.0 | 286.1 | 313.6 |
| 4A-21 | 209.1 | 356.4 | 546.1 |
| hIgG1 | 100.0 | 100.0 | 100.0 |

These data showed that treatment of human primary macrophages with anti-MS4A4A antibodies of the present invention increased both sTREM2 and mTREM2 levels in these cells of myeloid lineage. These results contrast with a prior report showing that the commercially available anti-MS4A4A antibody 5C12 reduced sTREM2 levels in supernatants of cultured human macrophages (Deming et al, supra).

The above experiments examining the effect of anti-MS4A4A antibodies on soluble and membrane TREM2 were repeated using anti-MS4A4A antibodies prepared to have low endotoxin levels. Levels of sTREM2 as measured in culture supernatants are shown in Table 22 below. Most of the anti-MS4A4A antibodies of the present disclosure, when highly purified and essentially free of endotoxin, induced increased sTREM2 levels to varying degrees. Commercially available anti-MS4A4A antibodies 3F2, 4H2, and 5C12 also increased sTREM2 levels, but to a lesser degree. These results are in contrast to previously published data, which showed that these commercially available anti-MS4A4A antibodies reduced sTREM2 levels in culture; this is likely due to contaminating endotoxin, impurities, and aggregates present in commercial preparations. Data in Table 22 shows levels of sTREM2 expressed in ng/ml and are normalized to that observed with isotype control antibody.

The increase in sTREM2 observed was paralleled by an increase in membrane bound TREM2 (mTREM2) levels after anti-MS4A4A antibody treatment (Table 23 below). Variation among donors' responsiveness notwithstanding, most of the anti-MS4A4A antibodies increased the level of mTREM2 in 2 or 3 of the three donors tested. When compared to commercially available anti-MS4A4A antibodies (3F2, 4H2 and 5C12), a number of antibodies in the present disclosure display equivalent or superior activity. Levels shown in Table 23 below are expressed as Mean Fluorescence Intensity as determined by flow cytometry and are normalized that observed using isotype control antibody.

TABLE 22

| Antibody | Donor | | |
|---|---|---|---|
| | 753 | 754 | 755 |
| 4A-202 | 50.5 | 15.1 | 16.1 |
| 4A-18 | 54.9 | −2.4 | −0.3 |
| 4A-21 | 108.3 | 36.5 | 65.5 |
| 4A-25 | 21.5 | 12.0 | 33.8 |
| 4A-214 | 43.9 | 15.1 | 28.5 |
| 3F2 | 14.1 | 5.0 | 17.4 |
| 4H2 | −1.0 | 7.5 | −5.1 |
| 5C12 | −0.4 | 5.5 | 35.2 |

TABLE 23

| Antibody | TREM2 MFI, delta over control | | |
|---|---|---|---|
| | Donor 753 | Donor 754 | Donor 755 |
| 4A-202 | 5258 | 1171 | 6591 |
| 4A-18 | 3531 | −76 | 4289 |
| 4A-21 | 5585 | 2097 | 6334 |
| 4A-25 | 687 | 888 | 2528 |
| 4A-214 | 6017 | 1774 | 6009 |
| 3F2 | 2176 | 103 | 2423 |
| 4H2 | 1625 | 207 | 2444 |
| 5C12 | 926 | 499 | 1803 |

As genetic studies have linked the Alzheimer's disease protective MS4A4A allele with increased levels of sTREM2 in Alzheimer's disease patients, these results suggested that anti-MS4A4A antibodies are an effective treatment for Alzheimer's disease and other neurodegenerative disorders by modulating (i.e., increasing) TREM2 activity and function.

The effect of humanized anti-MS4A4A antibodies of the present disclosure on sTREM2 and membrane bound TREM2 (mTREM2) were also determined. To examine this, human primary macrophages from two donors were treated with anti-MS4A4A antibodies of the present disclosure for 48 hours. Culture supernatants were collected and assayed for levels of soluble TREM2 using Mesoscale Discovery assays. Cell surface TREM2 was measured in separately treated cells by flow cytometry after staining with anti-TREM2 antibodies conjugated with fluorophores. Soluble TREM2 was measured in the culture supernatant of macrophages using the Mesoscale Discovery system (MSD, Rockville, Md., USA).

Table 24 below shows the results of the effect of anti-MS4A4A antibodies on changes in soluble TREM2 levels. In Table 24, soluble TREM2 levels are listed as ng/ml. As shown in Table 24, most of the anti-MS4A4A antibodies of the present disclosure increased soluble TREM2 levels in human primary macrophages. Commercially available anti-MS4A4A antibodies 5C12, 4H2, and 3F2 did not show an increase in soluble TREM2 levels to any significant degree compared to that observed with many of the anti-MS4A4A antibodies of the present disclosure, and the effects of 5C12, 4H2, and 3F2 were comparable to isotype control.

TABLE 24

| Antibody | Donor 888 | Donor 904 |
|---|---|---|
| hIgG1 isotype | 24.1 | 25.0 |
| 4A-202 | 46.5 | 38.4 |
| 4A-21 | 47.2 | 39.7 |
| 4A-25 | 41.3 | 41.2 |
| 4A-302 | 49.3 | 41.3 |
| 4A-312 | 41.4 | 36.2 |
| 4A-313 | 53.7 | 40.4 |
| 4A-314 | 47.9 | 37.2 |
| 4A-332 | 44.6 | 37.3 |
| 4A-350 | 51.4 | 44.0 |
| 4A-351 | 45.4 | 42.2 |
| 4A-352 | 41.2 | 41.0 |
| 4A-353 | 32.3 | 34.7 |
| 4A-354 | 41.4 | 38.0 |
| 4A-355 | 35.5 | 23.2 |
| 4A-356 | 40.4 | 38.0 |
| 4A-358 | 55.0 | 45.8 |
| 4A-360 | 45.3 | 38.4 |
| 4A-362 | 56.0 | 45.7 |
| 4A-369 | 54.4 | 41.6 |
| 4A-373 | 54.2 | 44.5 |
| 4A-376 | 54.2 | 51.1 |

TABLE 24-continued

| Antibody | Donor 888 | Donor 904 |
|---|---|---|
| 4A-377 | 34.4 | 37.0 |
| 4A-378 | 32.7 | 35.1 |
| 4A-379 | 31.9 | 31.2 |
| 4A-380 | 38.1 | 33.0 |
| 4A-381 | 33.7 | 33.1 |
| 4A-382 | 26.9 | 31.3 |
| 4A-383 | 29.0 | 30.5 |
| 4A-384 | 23.2 | 24.1 |
| 4A-385 | 27.4 | 27.2 |
| 4A-386 | 25.4 | 28.3 |
| 4A-387 | 26.0 | 30.6 |
| 4A-388 | 28.7 | 31.1 |
| 4A-390 | 26.8 | 31.5 |
| mIgG1 isotype | 25.9 | 28.8 |
| 5C12 | 29.7 | 30.0 |
| 4H2 | 28.9 | 30.6 |
| 3F2 | 29.4 | 28.8 |

Table 25 below shows the results of the effect of anti-MS4A4A antibodies on changes in cell surface (e.g., membrane) TREM2 levels. In Table 25, cell surface TREM2 levels are shown as mean fluorescence intensity (MFI) as measured in the flow cytometry procedure. As shown in Table 25, most of the anti-MS4A4A antibodies of the present invention increased cell surface TREM2 levels in human primary macrophages. Commercially available anti-MS4A4A antibodies 5C12, 4H2, and 3F2 did not show an increase in cell surface TREM2 levels to any significant degree compared to that observed with many of the anti-MS4A4A antibodies of the present disclosure, and the effects of 5C12, 4H2, and 3F2 were comparable to isotype control.

TABLE 25

| Antibody | Donor 888 | Donor 904 |
|---|---|---|
| hIgG1 isotype | 2566.5 | 2637.5 |
| 4A-202 | 4045.5 | 4100 |
| 4A-21 | 3329 | 3325 |
| 4A-25 | 2967.5 | 3191 |
| 4A-302 | 5336 | 4741.5 |
| 4A-312 | 5492 | 4672 |
| 4A-313 | 3645.5 | 3345.5 |
| 4A-314 | 4335 | 4070 |
| 4A-332 | 3257 | 3061 |
| 4A-350 | 3552 | 3192.5 |
| 4A-351 | 3464 | 3235.5 |
| 4A-352 | 3247.5 | 3227.5 |
| 4A-353 | 2835 | 3133 |
| 4A-354 | 2940 | 3092.5 |
| 4A-355 | 3319 | 3891.5 |
| 4A-356 | 2971.5 | 3328.5 |
| 4A-358 | 3659 | 3273.5 |
| 4A-360 | 3421.5 | 3154.5 |
| 4A-362 | 3759.5 | 3240 |
| 4A-369 | 3558.5 | 3256 |
| 4A-373 | 3430 | 3313 |
| 4A-376 | 3521 | 3398.5 |
| 4A-377 | 3376.5 | 3553.5 |
| 4A-378 | 3920.5 | 3804.5 |
| 4A-379 | 3847.5 | 3745 |
| 4A-380 | 4070 | 3754 |
| 4A-381 | 4070.5 | 3952.5 |
| 4A-382 | 2618.5 | 2621.5 |
| 4A-383 | 2611.5 | 2812.5 |
| 4A-384 | 2524.5 | 2601 |
| 4A-385 | 2576.5 | 2560.5 |

TABLE 25-continued

| Antibody | Donor 888 | Donor 904 |
| --- | --- | --- |
| 4A-386 | 2546 | 2614 |
| 4A-387 | 2534 | 2601 |
| 4A-388 | 2589.5 | 2624.5 |
| 4A-390 | 2561 | 2639.5 |
| mIgG1 isotype | 2459.5 | 2690.5 |
| 5C12 | 2596 | 2683.5 |
| 4H2 | 2611.5 | 2780 |
| 3F2 | 2629 | 2629.5 |

As shown in Table 24 and Table 25, both membrane TREM2 levels and soluble TREM2 levels were upregulated upon treatment with anti-MS4A4A antibodies of the present disclosure. Commercially available anti-MS4A4A antibodies 5C12, 4H2, and 3F2 did not induce TREM2 expression to any significant degree.

Example 9

Effect of Anti-MS4A4A Antibodies on Macrophage Cell Surface Markers

The effect of anti-MS4A4A antibodies on various M1 and M2 macrophage cell surface markers was examined as follows. Human primary macrophages were treated with various anti-MS4A4A antibodies (10 μg/ml) in complete RPMI1640 for 48 hours. The cells were then harvested and subjected to flow cytometry, using antibodies specific for M1 markers (CD16, MHC Class II, CD86), M2 markers (CD200R, Dectin-1, CD163), and a pan-macrophage marker CD14.

The results of these studies are shown in Table 26 below. Cell surface marker expression levels were assayed by flow cytometry and were normalized to that obtained in cells treated with an isotype control antibody, which was set at 100%. The cell surface expression of certain M1 markers, including CD86 and MHC-II, were unaltered or only modestly affected by anti-MS4A4A antibody treatment. By contrast, the cell surface expression of certain M2 markers, including CD200R, CD163, and Dectin-1 was significantly reduced by anti-MS4A4A antibody treatment.

TABLE 26

| Antibody | CD200R (M2) | CD14 (Pan) | Dectin-1 (M2) | CD16 (M1) | CD163 (M2) | MHC-II (M1) | CD86 (M1) |
| --- | --- | --- | --- | --- | --- | --- | --- |
| huIgG1 | 100.0 | 100.0 | 100.0 | 100.0 | 100.0 | 100.0 | 100.0 |
| 4A-202 | 35.2 | 60.2 | 47.3 | 171.0 | 39.1 | 73.6 | 121.8 |
| 4A-214 | 89.5 | 98.1 | 108.3 | 106.5 | 112.8 | 144.2 | 131.6 |
| 4A-18 | 29.0 | 56.6 | 46.6 | 239.3 | 33.6 | 45.6 | 112.3 |
| 4A-21 | 67.9 | 39.4 | 22.9 | 75.5 | 65.0 | 81.3 | 177.0 |

Together, these results indicated that anti-MS4A4A antibodies of the present disclosure affect macrophage polarization, affecting cells away from an M2 phenotype. These results suggested that within the CNS, anti-MS4A4A antibody treatment may provide a beneficial enhancement of microglial activity by potentiating, increasing, or restoring their neuroprotective function in the context of neurodegenerative diseases and disorders. As homeostatic microglia in healthy conditions express more M2 markers, such as CD200R, CD163 and CD115, these results suggested that anti-MS4A4A antibodies of the present disclosure are affective at altering the physiological state of microglial cells to that of a more protective phenotype, including to a more proinflammatory or activated state. As disease associated microglia (DAM) in Alzheimer's disease mouse models and in human Alzheimer's disease are in a proinflammatory or activated state, which is considered beneficial in Alzheimer's disease, anti-MS4A4A antibodies of the present disclosure are useful in treating Alzheimer's disease and other neurodegenerative disorders.

Example 10

Anti-MS4A4A Antibodies Increase Expression of Osteopontin and Gelsolin

Alzheimer's disease-associated genetic variants (SNPs) associated with the MS4A gene cluster have been identified. One of those variant alleles is rs1582763, which is associated with elevated CSF sTREM2 levels and with reduced Alzheimer's disease risk and delayed age-at-onset. (Deming et al, 2018, bioRxiv, doi: dx doi org/10.1101/352179). The rs1582763 allele decreases MS4A4A mRNA levels in blood. These findings suggest that the rs1582763 allele performs a protective role by reducing MS4A4A levels, potentially decreasing Alzheimer's disease risk or severity.

An RNA expression profile showing the effect of this protective allele in human macrophages was derived from published RNA expression data. The mRNA for SPP1 (osteopontin) and GSN (gelsolin) showed the most significant increase in expression, as indicated by fold change ("FC") and p-values (see columns under "rs1582763" in Table 27 and duplicated in Table 28 below), compared to other markers showing increased expression (not shown). The data indicated that SPP1 and GSN are pharmacodynamic markers for the protective biological activity associated with the rs158273 allele.

Parental MS4A4A antibodies were tested for their ability to phenocopy the protective allele. Human PBMC-derived macrophages were treated with anti-MS4A4A antibodies as indicated in Table 27 and Table 28 for 24 hours (up to three replicates). RNA was extracted and RNA libraries were prepared and sequenced, followed by genome mapping and quantification. The results indicated that all but one (4A-220) of the indicated parental anti-MS4A4A antibodies phenocopy the protective rs1582763 allele with respect to increasing expression of SPP1 and GSN (Table 27 and Table 28). These results suggested that MS4A4A antibodies of the present disclosure that are effective at increasing expression of SPP1 and GSN are biologically active in decreasing Alzheimer's disease risk and/or severity, similar to the protective allele.

TABLE 27

| | rs1582763 | | 4A-18 | | 4A-18+4A-21 | | 4A-25 | | 4A-214 | |
|---|---|---|---|---|---|---|---|---|---|---|
| Gene | FC | p | FC | p | FC | p | FC | p | FC | p |
| SPP1 | 0.82 | 4.E−06 | 0.73 | 1.E−08 | 0.25 | 4.E−02 | 0.37 | 3.E−03 | 0.29 | 1.E−02 |
| GSN | 0.34 | 6.E−06 | 1.28 | 1.E−17 | 0.85 | 2.E−09 | 0.65 | 3.E−06 | 0.56 | 8.E−06 |

TABLE 28

| | rs1582763 | | 4A-220 | | 4A-21 | | 4A-202 | |
|---|---|---|---|---|---|---|---|---|
| Gene | FC | p | FC | p | FC | p | FC | p |
| SPP1 | 0.82 | 4.E−06 | −0.13 | 3.E−01 | 0.56 | 7.E−06 | 0.49 | 2.E−03 |
| GSN | 0.34 | 6.E−06 | −0.11 | 4.E−01 | 0.94 | 5.E−11 | 0.82 | 2.E−06 |

Example 11

Derivation and Stimulation of iPSC-Derived Microglial Cells with Anti-MS4A4A Antibodies Adult cells of any tissue-origin can be converted into induced pluripotent stem cells (iPSCs) through the introduction of a mixture of transcriptional factors associated with stem cells. iPSCs can be maintained indefinitely, and when given appropriate growth factors, can be driven to differentiate into various mature cell types. Methods for deriving neurons from iPSC have long been established (Salimi et.al., Mol. Bio. Rep. 2014; 41: 1717-1721; Engle et.al., Neuron 2018; 100: 783-797). More recently, iPSCs have been used to derive astrocytes (*Julia* et.al., Stem Cell Report 2017; 9:600-614) and microglia (reviewed by Pocock and Piers, Nat. Rev. Neurosci. 2018; 19: 445-452). These culture systems allow investigation of the biology and function of these cell in controlled environments that may otherwise not be possible. Furthermore, iPSCs can be genetically manipulated by various methods, such as by CRISPR gene editing, to allow for further dissection of the functional relevance of genes of interest in these cell types.

After derivation from iPSCs, microglia are cultured alone in vitro, where they are subjected to stimulation with anti-MS4A4A antibodies in the present disclosure. After stimulation, cell viability is assessed by quantification of intracellular ATP levels. The effect on changes in cell surface TREM2 expression or on changes in soluble TREM2 levels is measured as described above. Supernatants from these cultures are analyzed for changes in expression or levels of various cytokines and chemokines as a result of anti-MS4A4A antibody treatment, using methods such as ELISA, Mesoscale Discovery assays (MSD, Rockville, Md., USA), Legendplex (BioLegend, San Diego, Calif., USA), or CBA (BD Biosciences, San Jose, Calif., USA). Changes in phagocytosis capacity, autophagy rate, surface marker expression, and gene expression profile in these iPSC-microglia resulting from anti-MS4A4A antibody treatment are measured and compared to that obtained from monocyte-derived macrophages treated with anti-MS4A4A antibodies, using various methods, including flow cytometry, western blotting, fixed- and real-time imaging, and RNAseq analysis.

Example 12

Effect of Anti-MS4A4A Antibodies on Macrophage Cell Surface Markers

Myeloid cells in both the CNS and in peripheral organs are inherently plastic in their phenotype and function. This can be modeled by macrophages in vitro, which can be divided into M1 and M2 type macrophages, showing differing phagocytic and inflammatory potentials, phenotypes, and activities. In peripheral organs, macrophages associated with the M1 phenotype are thought to be more pro-inflammatory and anti-microbial, while M2-like macrophages are more homeostatic and anti-inflammatory. Within the CNS, microglia in homeostatic conditions also express M2 markers such as CD200R, CD163, suggesting regulatory functions in this cell type. MS4A4A expression is elevated in M2 macrophages in vitro.

The effect of anti-MS4A4A antibodies on various M1 and M2 macrophage cell surface markers is examined as follows. Human primary macrophages are treated with various anti-MS4A4A antibodies (e.g., 10 µg/ml) in complete RPMI1640 for 48 hours. The cells are then harvested and subjected to flow cytometry, using antibodies specific for M1 markers (such as CD16, MHC Class II, CD86), M2 markers (such as CD200R, Dectin-1, CD163), and a pan-macrophage marker including CD14 and others.

Example 13

Kinetic Characterization of Anti-MS4A4A Antibodies

Binding kinetic characterization of the purified antibodies to MS4A4A ECL1 and ECL2 peptides is performed by Carterra (South San Francisco, Calif.) using a proprietary array Surface Plasmon Resonance (SPR) instrument (MX-96) as follows. Antibodies are printed onto a CMD500D chip (Xantec #SPMX CMD500D lot#SC CMD500D0117.a Exp. 31 Dec. 2018) using the Continous Flow Microspotter (CFM). First, the chip is activated with 100 mM MES pH 5.5, 100 µL EDC (133 mM final), 100 µL of S—NHS (33.3 mM final), for 7 minutes. A lawn of anti-mouse IgG-Fc (Jackson ImmunoResearch cat #115-005-071) is injected for 15 minutes to establish a surface density of 10000-12000 RU, after which the chip surface is deactivated with 1M ethanolamine at pH 8.5 for 10 minutes. Anti-MS4A4A antibodies in question are diluted 2:1 with HBS-EP+ buffer (Teknova Cat #H8022) and then printed as duplicates with a 20 minute and a 5-minute print from the same sample solution. Control antibodies are diluted to 20 µg/ml for printing.

To perform kinetic analysis, the peptides in question are prepared in HBS-EP+ buffer with 1 mg/ml BSA at final assay concentrations of 2000 nM, 400 nM, 80 nM, 16 nm, and 3.2 nM. These are then injected on the chip for five minutes, followed by a seven-minute dissociation period at 8 uL per second in a non-regenerative kinetic series. Duplicate measurements for each anti-MS4A4A antibody are taken to ensure reproducibility.

Example 14

Affinity Measurement of MS4A4A Antibodies to Transiently and Natively Expressing Cell Lines Purified anti-MS4A4A antibodies are evaluated for their binding affinity to various MS4A4A-expressing cell lines. These include transfected cells as described above in Example 8, as well as myeloid cell lines and primary cells that endogenously express MS4A4A. Anti-MS4A4A antibodies tested are either mouse IgGs purified from hybridoma supernatant or human IgG1 Fc chimeras produced recombinantly in Expi293 cells. Affinity binding to cells is determined as follows. Briefly, cells are harvested, washed and labeled with Aqua Live/Dead for viability discrimination. After a wash with PBS, 2×10^5 cells are aliquoted per well in 96-well U-bottom plates and incubated with 50 µL of purified anti-MS4A4A antibody at various concentrations (3× dilutions starting at 10 µg/mL) in FACS buffer (PBS+2% FBS+1 mM EDTA). After primary incubation, the supernatant was removed via centrifugation, washed 2× with 150 µL of ice-cold FACS buffer and incubated with the appropriate secondary antibody on ice for 30 minutes. Following the secondary incubation, the cells are again washed 2× with ice-cold FACS buffer and resuspended in a final volume of 200 µL of FACS buffer. Flow cytometry analysis is performed on a FACSCanto system (BD Biosciences). Binding data was analyzed using Median fluorescent intensity and curves were fit in Prism (nonlinear regression: log inhibitor vs. dose response with four parameters) to determine EC50 values.

Example 15

Downregulation of MS4A4A Protein

The ability of anti-MS4A4A antibodies to reduce cell surface and total cellular protein levels of MS4A4A in various cell lines and primary cells is evaluated. Reduction in MS4A4A protein in either compartment indicates a reduction in MS4A4A activity in the cells.

Cells are incubated with anti-MS4A4A antibodies of the present disclosure for various time periods and then the levels of MS4A4A protein remaining associated with the cells is assayed by either FACS (cell surface) or western blot (total cell protein level). For FACS assays, detection of the remaining MS4A4A is carried out with direct-allophycocyanin (APC) conjugated, non-competing antibodies. For Western blot detection, cells are lysed by the addition of 50 µL lysis buffer (RIPA lysis buffer (ThermoFischerScientific Cat #89900)+1:100 HALT protease inhibitor cocktail (ThermoFischerScientific Cat #87786), and cleared for insoluble debris by centrifugation at 14,000×g for 15 minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies, washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577) and recorded digitally with iBright FL1000 (ThermoFisher Scientific A32752) or other compatible systems.

Down-regulation of MS4A4A protein levels may also be accomplished by down-regulation of MS4A4A nucleic acid expression or levels, by, e.g., use of antisense methodologies, gene therapy, etc, using methods known and available to one of skill in the art.

Example 16

Characterization of the Activity of Anti-MS4A4A Antibodies Utilizing Animal Models for Aging, Seizures, Spinal Cord Injury, Retinal Dystrophy, Frontotemporal Dementia, and Alzheimer's Disease The therapeutic utility of anti-MS4A4A antibodies can also be tested in animal models for aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 17

Characterization of the Effects of Anti-MS4A4A Antibodies Utilizing Animal Models for Oncology Myeloid cells represent a major component of the immune cells present in most solid tumors. Their role in tumor biology is context-dependent—while such cells have the potential to play a key role in the eradication of tumors, they are most often co-opted by the host tumor to assist in providing a pro-tumor phenotype. This is achieved mostly through the polarization of myeloid cells towards an M2-phenotype, which is typically immunosuppressive and thus blocks the immune system from eradicating the tumor.

Anti-MS4A4A antibodies, through repolarization of myeloid cells, can reverse this immunosuppressive phenotype and promote an anti-tumor immune response.

Numerous animal tumor models exist. Examples of relevant animal models include humanized mouse models, where the mouse immune system is genetically deleted, as typified by the NSG mice (Jackson Laboratory, Bar Harbor, Me.). These mice act as receptive hosts for human immune cells, leading to the engraftment of human adaptive and innate immune cells. These animals are then inoculated with tumor cells, usually under the skin on the flanks. Tumor size over time represents the balance between the growth of tumor cells and their eradication by the host immune system. Throughout the time course the animals are treated with anti-MS4A4A antibodies, which modifies tumor progression when compared to isotype-treated animals. At the end of treatment period tumors are extracted and subjected to various analyses to determine the effect of anti-MS4A4A antibodies on the tumor cells and infiltrating immune cells. Tumors can be sectioned, mounted onto slides and analyzed under the microscope for histological changes. mRNA can be analyzed by RT-PCR, RNASeq or microarray to determine changes in gene expression. Single cell suspensions of tumor and infiltrating immune cells can be prepared, stained with antibodies against various cell surface markers and analyzed by flow cytometry, to delineate changes in cell surface phenotype, especially in immune cells such as macrophages and T cells. Changes observed as a result of anti-MS4A4A treatment in any of these analyses will indicate an immune-modulatory function for these antibodies.

Example 18

Effect of Anti-MS4A4A Antibodies on TREM2 Transcription and mRNA

The effect of anti-MS4A4A antibodies on TREM2 transcriptional level and mRNA is evaluated as follows. Cultured cells are treated with various concentration of an anti-MS4A4A antibody of the present disclosure for various periods of time. Afterward, changes in TREM2 mRNA levels within the cells are then determined using standard methodologies for measuring and/or quantitating mRNA levels known to one of skill in the art.

Example 19

Effect of Anti-MS4A4A Antibodies on TREM2 Recycling and Degradation

In order to better understand the effect of anti-MS4A4A antibodies on increased levels of sTREM2 and mTREM2, the following studies to examine TREM2 recycling and/or degradation are performed. In these studies, cycloheximide treatment of cells is used in order to prevent further new TREM2 synthesis in association with anti-MS4A4A antibody treatment. Various methods known in the art are available to examine the recycling and degradation of TREM2 in control cells compared to cells treated with anti-MS4A4A antibodies.

Example 20

Additional Anti-MS4A4A Antibodies

Two additional anti-MS4A4A antibodies were humanized and affinity matured from the parental antibody 4A-21, as described above in Example 1, resulting in anti-MS4A4A antibody 4A-450 and anti-MS4A4A antibody 4A-419. The variable heavy chain and variable light chain sequences of each of these antibodies are shown below in Table 29, with their corresponding CDRs (according to Kabat) underlined. The heavy chain CDR sequences are shown in Table 30; the light chain CDR sequences are shown in Table 31.

TABLE 29

| Antibody | Heavy Chain Variable | SEQ ID NO: | Light Chain Variable | SEQ ID NO: |
|---|---|---|---|---|
| 4A-450 | QVQLVQSGSELKKPGASVK VSCKASGYAFT<u>SYGLS</u>WVR QAPGQGLEWMG<u>WINTYSG VPTYAQGFTG</u>RFVFSLDTS VSTAYLQISSLKAEDTAVY YCAR<u>TMADY</u>WGQGTLVTV SS | 304 | DVVMTQSPLSLPVTLGQ PASISC<u>KSSRSLLYSAG KTYLS</u>WFQQRPGQSPRR LIY<u>LVSKLDS</u>GVPDRFS GSGSGTDFTLKISRVEA EDVGVYYC<u>WQGIDFHQT</u> FGGGTKVEIK | 305 |
| 4A-419 | QVQLVQSGSELKKPGASVK VSCKASGYRFT<u>SYGLS</u>WVR QAPGQGLEWMG<u>WINTYSG VPTYAQGFKG</u>RFVFSLDTS VSTAYLQISSLKAEDTAVY YCAR<u>TMADY</u>WGQGTLVTV SS | 306 | DVVMTQSPLSLPVTLGQ PASISC<u>KSSRSLLYSAG KTYLS</u>WFQQRPGQSPRR LIY<u>LVSKLDS</u>GVPDRFS GSGSGTDFTLKISRVEA EDVGVYYC<u>WQGIDFHQT</u> FGGGTKVEIK | 307 |

TABLE 30

| Antibody | CDR-H1 | SEQ ID NO: | CDR-H2 | SEQ ID NO: | CDR-H3 | SEQ ID NO: |
|---|---|---|---|---|---|---|
| 4A-450 | SYGLS | 308 | WINTYSGVP TYAQGFTG | 309 | TMADY | 310 |
| 4A-419 | SYGLS | 311 | WINTYSGVP TYAQGFKG | 312 | TMADY | 313 |

TABLE 31

| Antibody | CDR-L1 | SEQ ID NO: | CDR-L2 | SEQ ID NO: | CDR-L3 | SEQ ID NO: |
|---|---|---|---|---|---|---|
| 4A-450 | KSSRSLLY SAGKTYLS | 314 | LVSKLDS | 315 | WQGIDFHQT | 316 |
| 4A-419 | KSSRSLLY SAGKTYLS | 317 | LVSKLDS | 318 | WQGIDFHQT | 319 |

Example 21

Effect of Anti-MS4A4A Antibodies on sTREM Levels In Vivo

To examine the effect of anti-MS4A4A antibodies of the present disclosure on sTREM levels in serum and cerebrospinal fluid (CSF) in vivo, the following studies were performed.

Cynomolgus monkeys were administered anti-MS4A4A antibody 4A-202 or isotype control (huIgG1) at a single dose of 80 mg/ml by intravenous infusion. Serum samples were collected from the animals at pre-dose, 0.5, 4, 10, 24, 48, 96, 192, 312, 480, and 648 hours post administration of antibody; CSF samples were collected from the animals at pre-dose, 48, 96, 192, and 336 hours post administration of antibody.

sTREM levels in serum and CSF were measured as follows. Single spot Meso Scale Discovery (MSD) plates (Rockville, Md.) were coated with a capture antibody in PBS at 4° C. overnight. Monkey serum and CSF samples (as well as monkey TREM2-Fc standards) were diluted in binding buffer and added to the wells for 1 hour at room temperature. Biotinylated goat anti-human TREM2 polyclonal antibody (R&D Systems) was added at a 1:2,000 dilution in binding buffer and incubated for 1 hour at room temperature, followed by detection with sulfo tag streptavidin (MSD). 150 µl of 1× Read Buffer was added to the plates, and the plates were then analyzed on a Sector Imager (MSD).

Figure 10A:
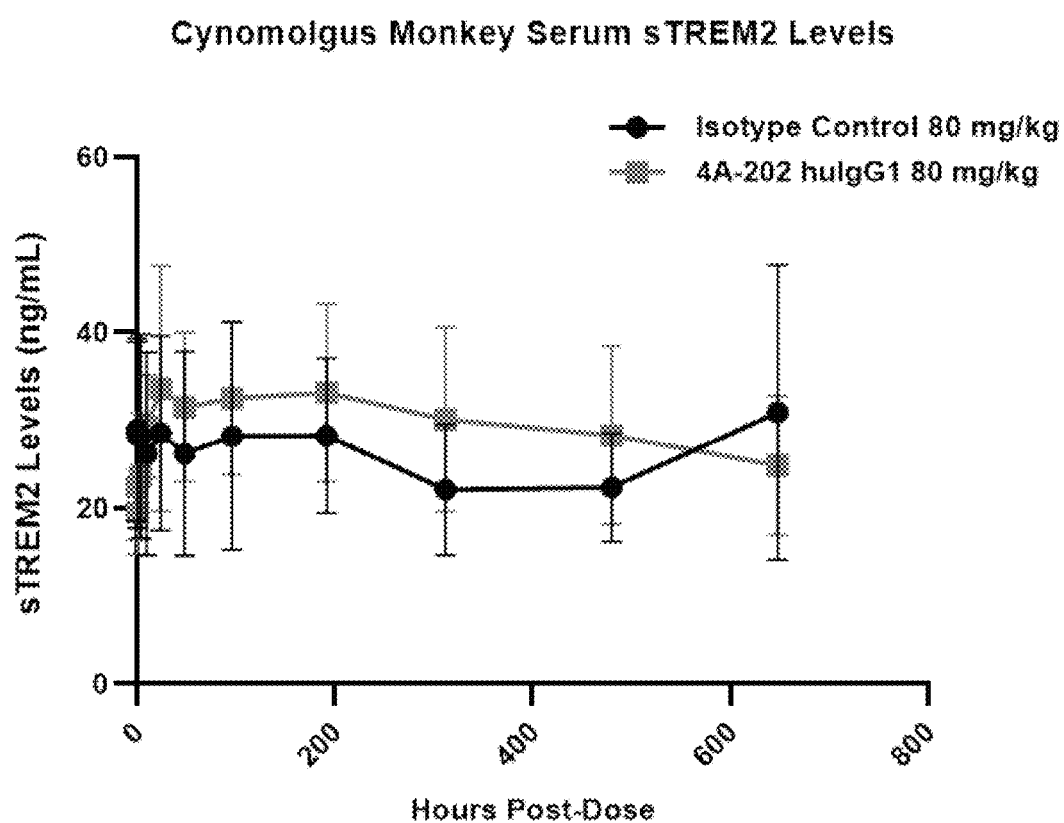
FIGS. 10A-10B show the effect of anti-MS4A4A antibody 4A-202 on the levels of sTREM2 in the serum of cynomolgus monkeys.
Figure 10B:
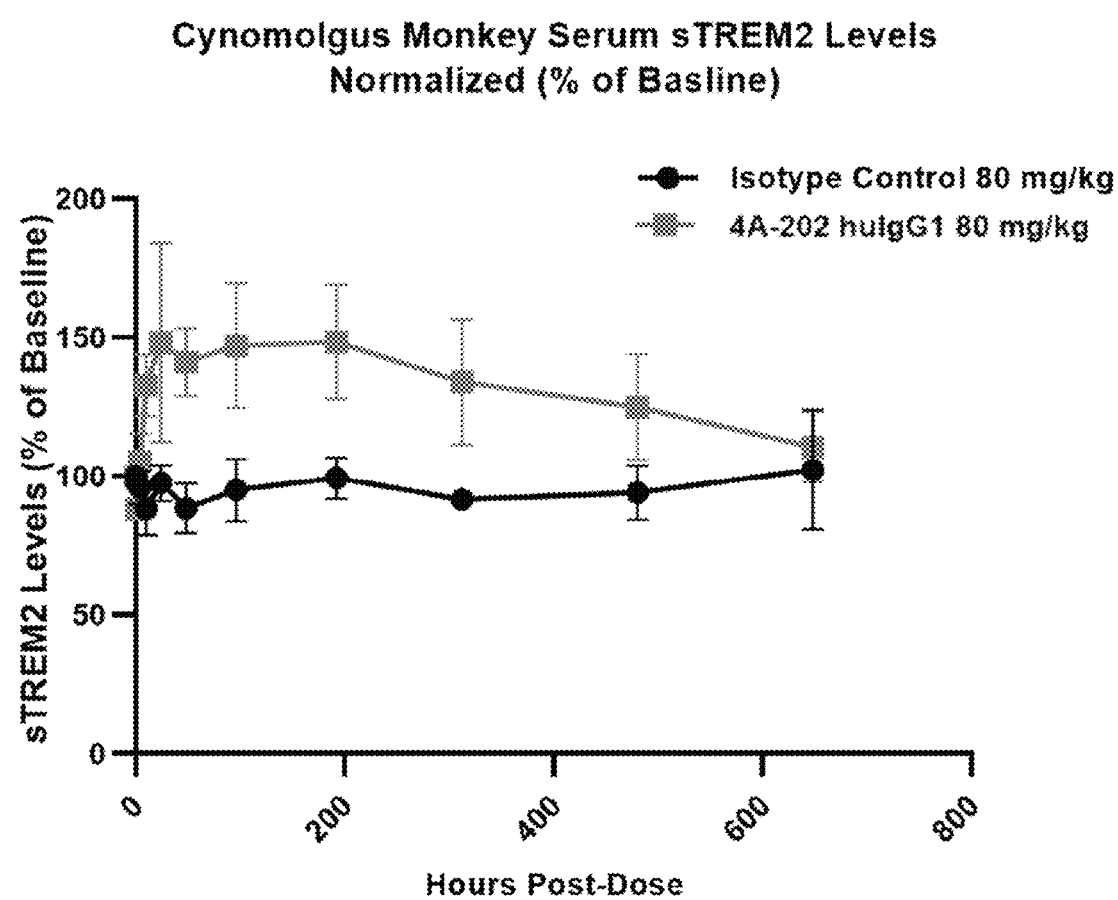

In serum, sTREM2 levels increased approximately 1.5-fold from baseline (approximately 50% increase from baseline) following administration of anti-MS4A4A antibody 4A-202 (FIGS. 10A-10B). Serum sTREM2 levels remained elevated (above baseline levels) for at least 480 hours (20 days) following a single dose of anti-MS4A4A antibody 4A-202 in cynomolgus monkeys.

Figure 11A:
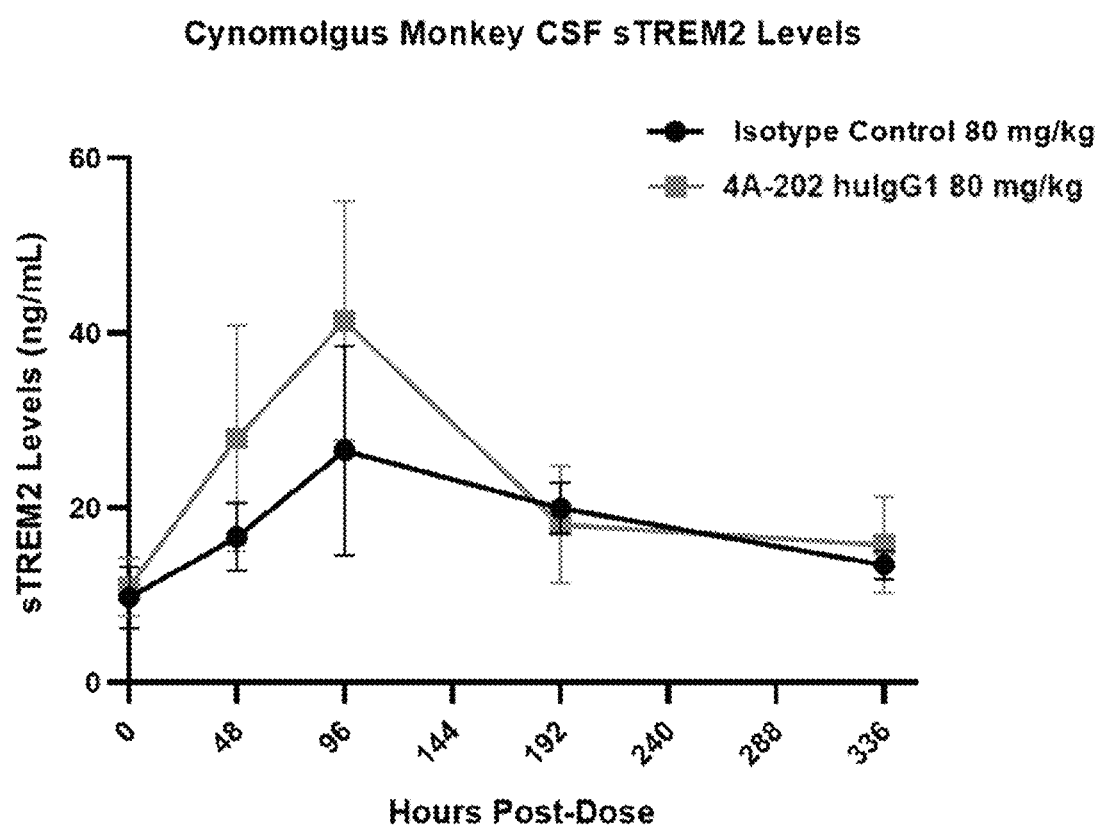
FIGS. 11A-11B show the effect of anti-MS4A4A antibody 4A-202 on the levels of sTREM2 in the cerebrospinal fluid (CSF) of cynomolgus monkeys.
Figure 11B:
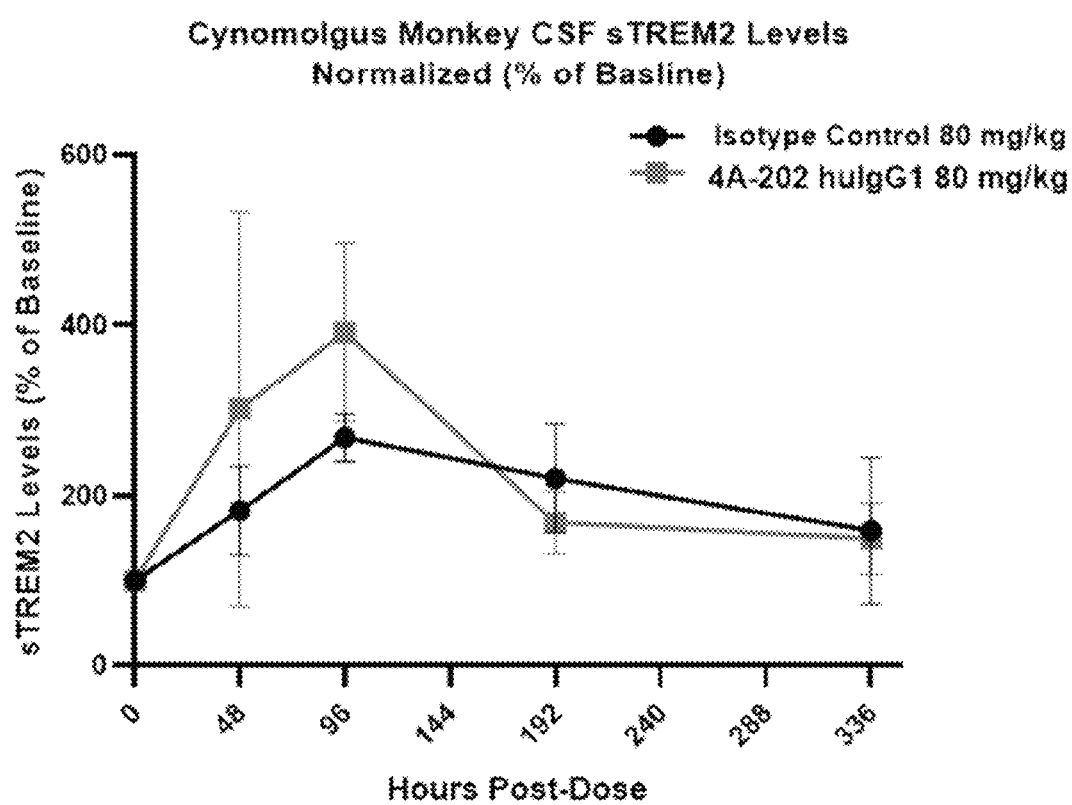

In CSF, sTREM2 levels increased approximately 2- to 4-fold above baseline (approximately 300% increase from baseline) following administration of anti-MS4A4A antibody 4A-202 (FIGS. 11A-11B). CSF sTREM2 levels remained elevated (above baseline levels) for at least 96 hours (4 days) following a single dose of anti-MS4A4A antibody 4A-202 in cynomolgus monkeys.

These results showed that anti-MS4A4A antibodies of the present disclosure are effective at increasing sTREM2 levels in serum and in CSF in vivo.

Example 22

Binding of Anti-MS4A4A Antibodies to U937 Cells Overexpressing Recombinant MS4A4A Anti-MS4A4A antibodies of the present disclosure were evaluated for their binding affinity to human recombinant MS4A4A-expressing U937 cells (the generation of these cells is described above). Binding affinity of anti-MS4A4A antibodies to the cells was determined as follows. Briefly, U937 cells expressing recombinant human MS4A4A were harvested, washed, and labeled with Aqua Live/Dead for viability discrimination. After washing the cells with PBS, 2×10^4 cells were aliquoted per well in 96-well U-bottom plates and incubated with 50 µL of purified anti-MS4A4A antibody at various concentrations in FACS buffer (PBS+2% FBS+1 mM EDTA). After this primary incubation, the supernatant was removed via centrifugation, the cells washed 2× with 150 µL of ice-cold FACS buffer, and then incubated with the appropriate secondary antibody on ice for 15 minutes. Following the secondary antibody incubation, the cells were again washed 2× with ice-cold FACS buffer and resuspended in a final volume of 200 µL of FACS buffer. Flow cytometry analysis was then performed using the FACSCanto system (BD Biosciences). Binding data was expressed as Mean Fluorescent Intensity (MFI). MFI values measured by the flow cytometer were analyzed on Prism (Graphpad) software, using the following equation (or one could use a similar 4-parameter fit) based on Kuek, et al, 2016, Immunology and Cell Biology. 94:11-23:

$$Y=((F_{max}-B)/(n^*((C/6.02e23)/(V^*1e-6)))^*[[(aptKD+X+n^*((C/6.02e23)/(V^*1e-6)))\text{-SQRT}\{((aptKD+X+n^*((C/6.02e23)/(V^*1e-6)))^\hat{}2)-4^*(n^*((C/6.02e23)/(V^*1e-6))^*X)\}]/2]+B)$$

In these analyses, the following values were constrained according to experimental conditions: C=number of cells per well (20,000); V=total volume of staining in microliters; n=number of receptors on cell surface, estimated to be 100,000 receptors per cell. The results of these binding studies are shown in FIG. 12.

Figure 12:
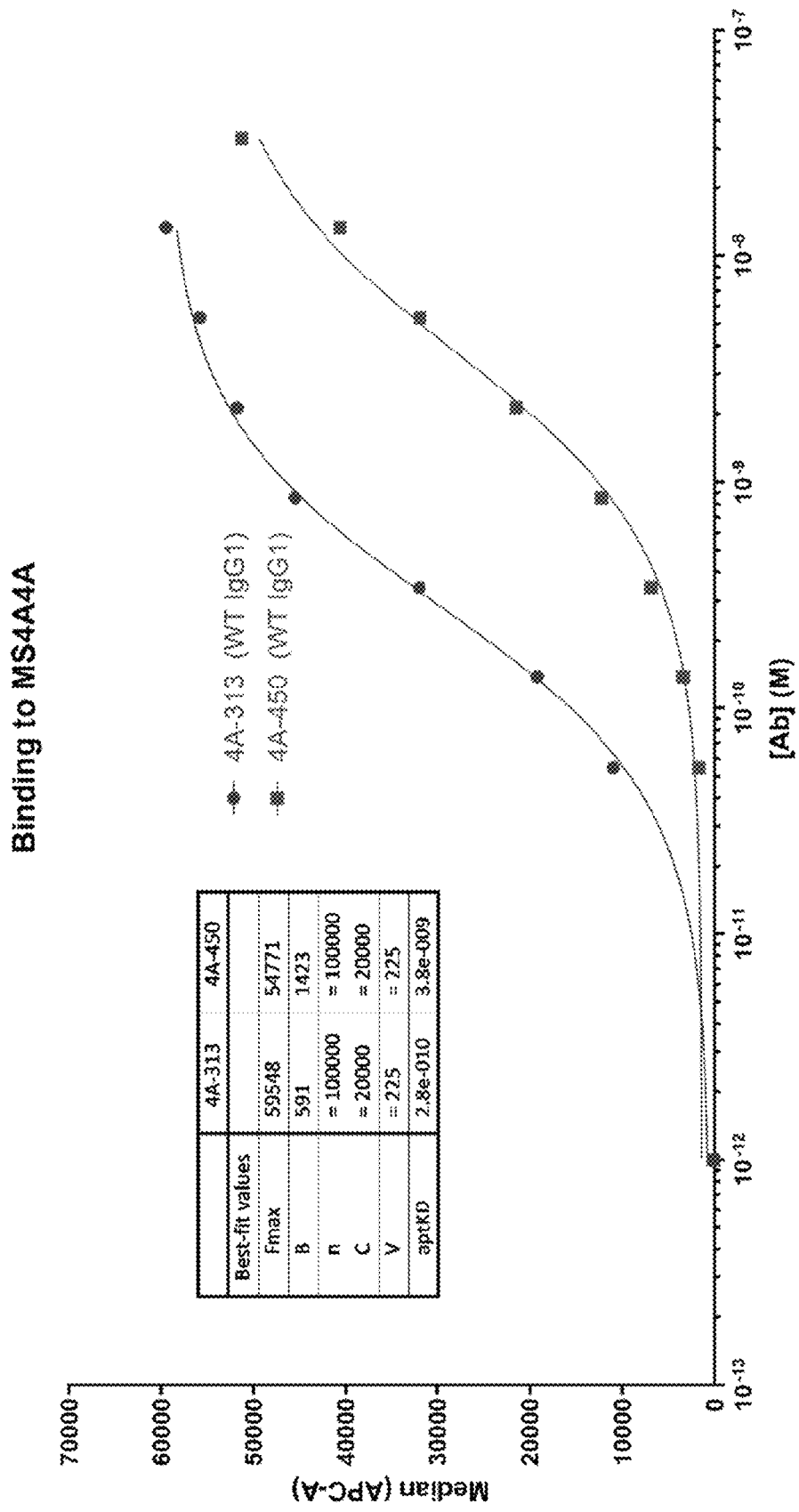
FIG. 12 sets forth data showing binding curves of anti-MS4A4A antibodies 4A-313 wildtype (WT) huIgG1 and 4A-450 WT huIgG1 to U937 cells expressing recombinant human MS4A4A.

As shown in FIG. 12, anti-MS4A4A antibody 4A-313 WT huIgG1 displayed a binding affinity to recombinant human MS4A4A expressed on U937 cells of approximately 2.8e-10, while anti-MS4A4A antibody 4A-450 WT huIgG1 displayed a binding affinity of 3.8e-09 in this assay.

Example 23

Generation of MS4A4A Overexpressing Cell Line

Given the difficulty for generating stably transfected HEK293 cell lines expressing recombinant human MS4A4A, other DNA vectors and cell lines were examined to determine if they would be more compatible for expression of recombinant human MS4A4A. For stable transfection, MS4A4A coding sequence was introduced into expression vectors pD2533-G418 or pD3539-puro (Atum, Newark, Calif., USA).

MS4A4A is expressed natively in myeloid cells in vivo. Therefore, to overcome the toxicity observed using cells described above, several myeloid-derived cell lines were tested for their ability to express recombinant human MS4A4A with minimal or no observed toxicity. The panel of myeloid-derived cell lines used in these studies included THP-1 cells (ATCC TIB202), U937 cells (ATCC CRL-1593.2), K562 cells (ATCC CCL243), HL60 cells (ATCC CCL240), and Kasumi-1 cells (ATCC CRL-2724). 300.19 cells (Tufts University T000710), a mouse pre-B cell line, were also tested as these cells are commonly used for recombinant protein expression purposes. Each of these cell lines was screened for antibiotic susceptibility in order to determine a suitable dose of G418 or puromycin for selection and transfection efficiency. Transfectants from U937 cells, K562 cells, and 300.19 cells were found to be viable after recombinant human encoding MS4A4A expression plasmid transfection and antibiotic selection. After cloning these cells by limiting-dilution, individual clones were generated and subsequently screened for human MS4A4A protein cell surface expression using flow cytometry.

Example 24

Humanized and Affinity Matured Anti-MS4A4A Antibodies Modulate TREM2 Protein in Primary Human Myeloid Cells Data from human genetics studies have identified links between MS4A4A, the TREM2 pathway, and Alzheimer's disease (AD) susceptibility (Piccio et al., 2016, Acta Neuropathol, 131:925-933; doi: https://dx.doi.org/10.1101/352179). For example, AD-protective MS4A4A alleles are linked to increased sTREM2 levels in cerebrospinal fluid. To gain insight into these protective pathways, the following studies were performed. Human primary macrophages were treated with various concentrations of anti-MS4A4A antibodies of the present disclosure for 48 hours. In these studies, the following anti-MS4A4A antibodies were tested: 4A-450 with wildtype huIgG1 Fc (WT), 4A-450 with huIgG1 Fc N325S and L328F (NSLF), 4A-450 with huIgG1 Fc K322A, 4A-313 WT huIgG1, 4A-313 NSLF huIgG1, and 4A-313 K322A huIgG1. Cell surface (membrane bound) expression of TREM2 was then measured by flow cytometry after the cells were subsequently stained with an anti- TREM2 antibody conjugated with fluorophores. Soluble TREM2 levels were measured in the culture supernatant of the cells using Mesoscale Discovery system (MSD, Rockville, Md., USA).

Figure 13:
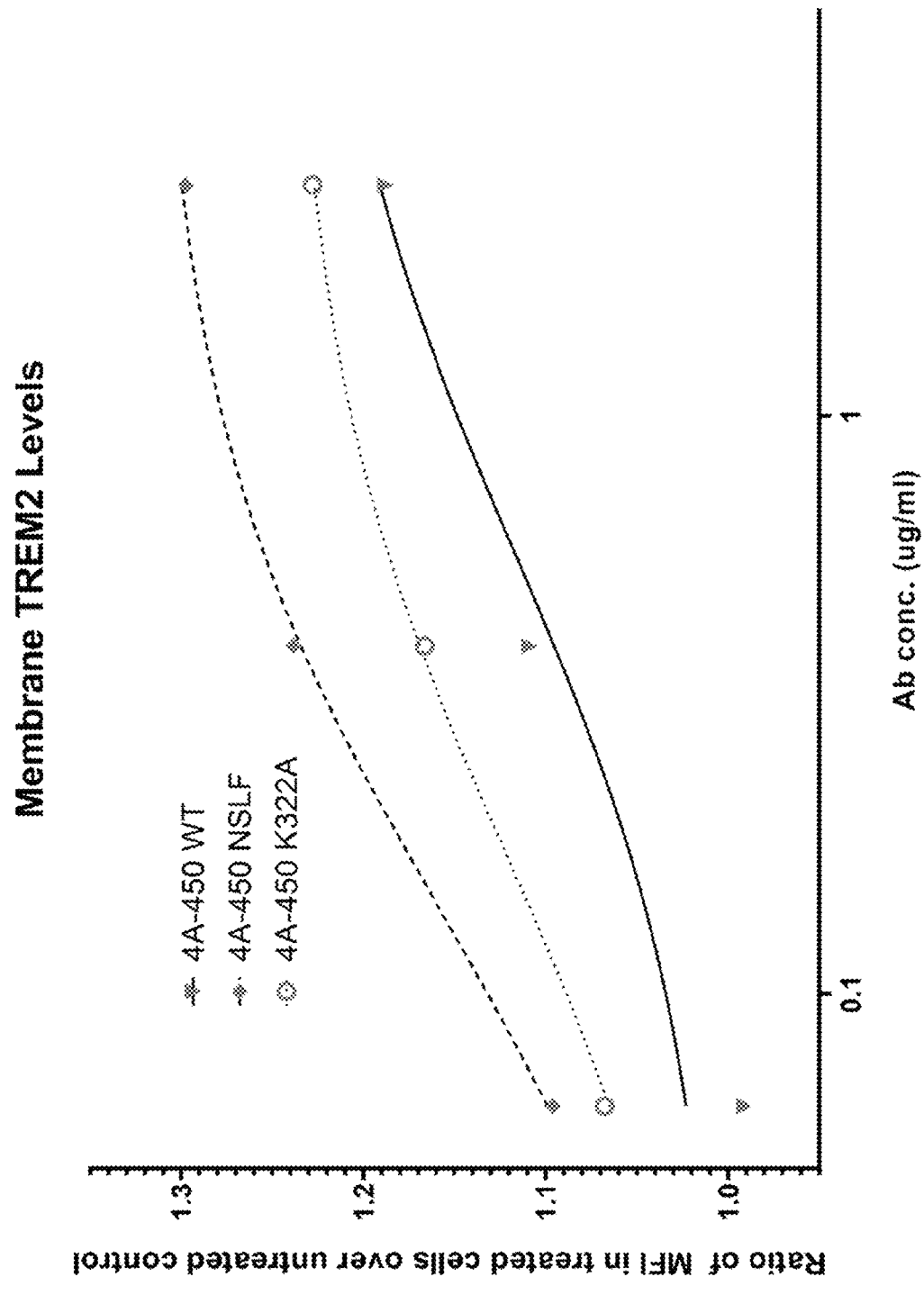
FIG. 13 sets forth data showing membrane TREM2 levels in primary human macrophages treated with anti-MS4A4A antibodies 4A-450 WT huIgG1, 4A-450 NSLF huIgG1, and 4A-450 K322A huIgG1.
Figure 14:
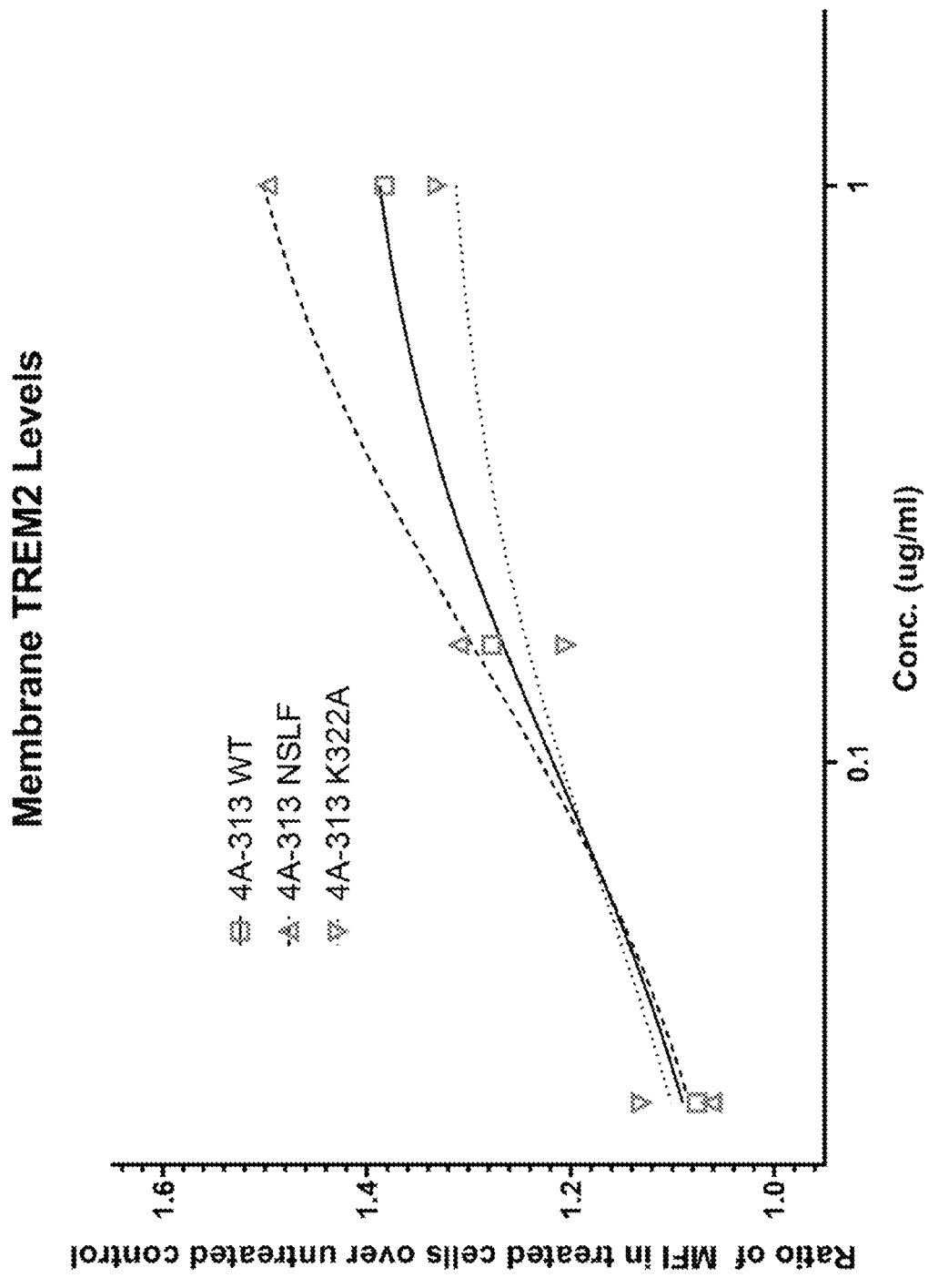
FIG. 14 sets forth data showing membrane TREM2 levels in primary human macrophages treated with anti-MS4A4A antibodies 4A-313 WT huIgG1, 4A-313 NSLF huIgG1, and 4A-313 K322A huIgG1.

As shown in FIGS. 13 and 14, membrane TREM2 levels were increased in human primary macrophages following addition to the cells of anti-MS4A4A antibodies in a dose-dependent manner. Anti-MS4A4A antibodies on different huIgG1 Fc sequences—wildtype huIgG1, N325S/L328F amino acid substitutions in huIgG1, and K322A amino acid substitution in huIgG1 were all capable of increasing membrane TREM2 expression levels. Tables 32 and 33 below present the numeric values for the ratio of MFI observed in anti-MS4A4A treated cells for changes in membrane bound TREM2 levels compared to that observed in untreated control cells obtained from FIGS. 13 and 14, respectively.

Figure 15:
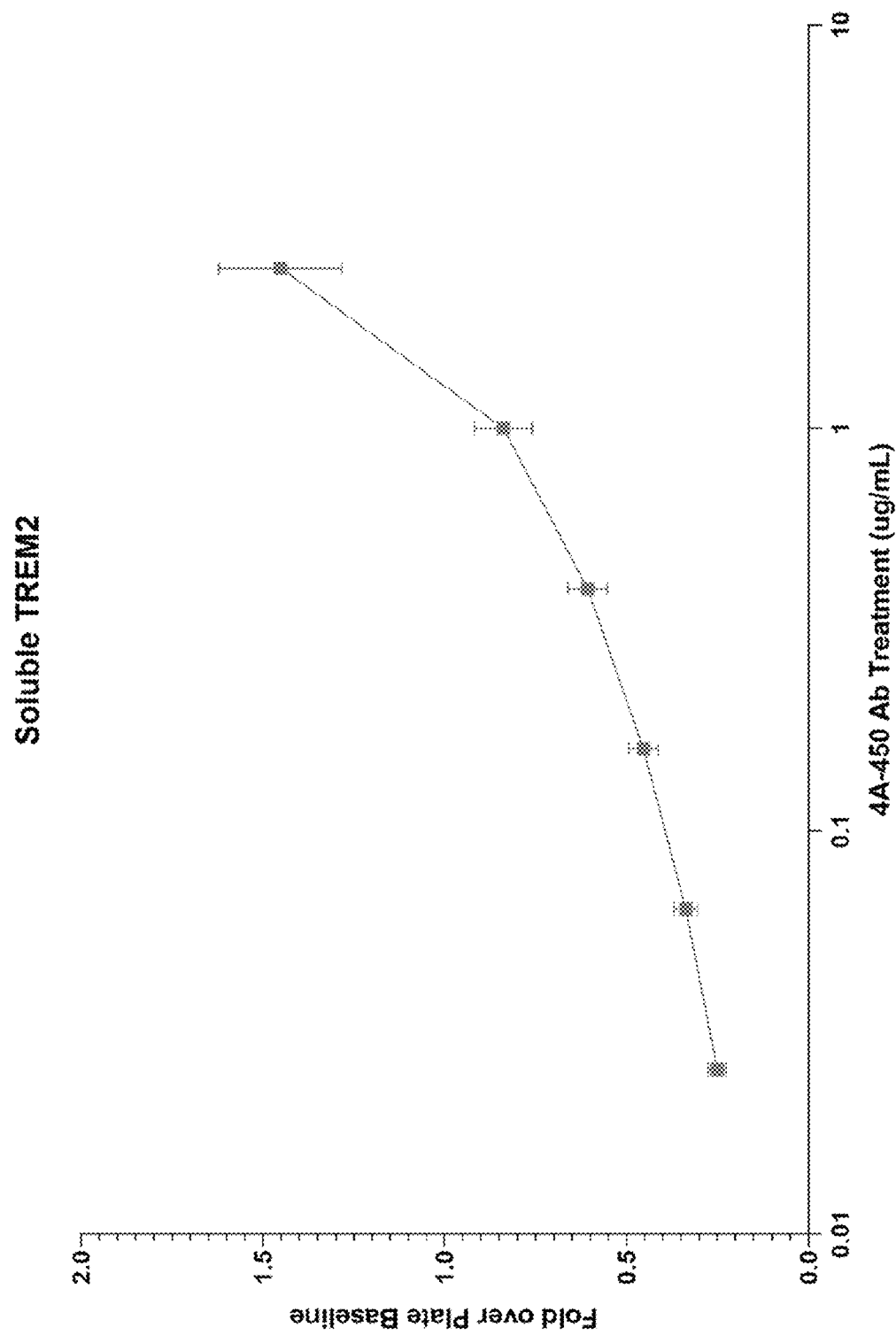
FIG. 15 sets forth data showing increased soluble TREM2 levels in the supernatant of primary human macrophages treated with anti-MS4A4A antibody 4A-450 huIgG1.
Figure 16:
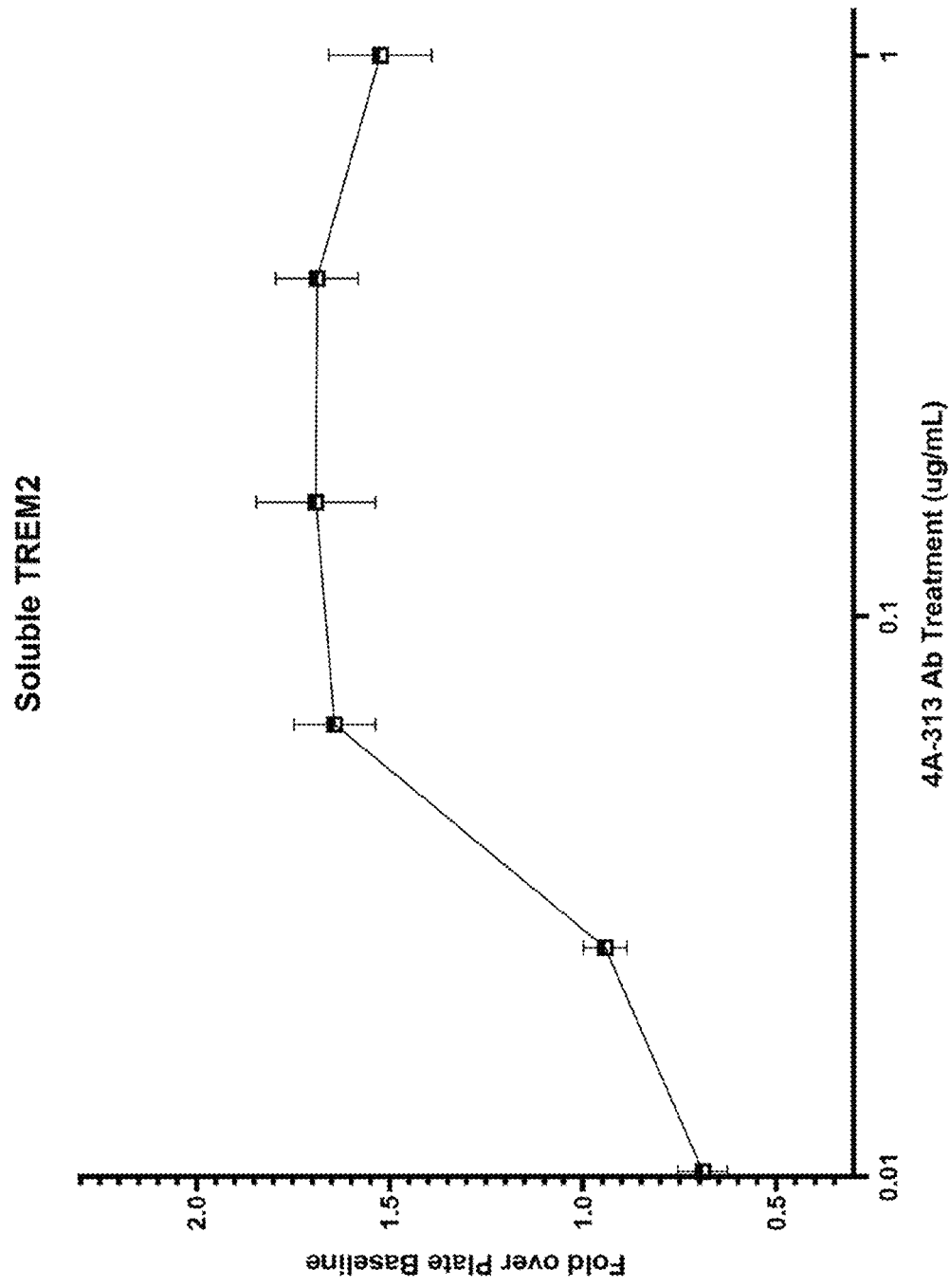
FIG. 16 sets forth data showing increased soluble TREM2 levels in the supernatant of primary human macrophages treated with anti-MS4A4A antibody 4A-313 huIgG1.

FIGS. 15 and 16 show anti-MS4A4A antibodies 4A-450 and 4A-313 on a wildtype huIgG1 Fc backbone (respectively) increased soluble TREM2 levels in the supernatants of primary human macrophages in a dose-dependent manner. Tables 34 and 35 below present the numeric values of the fold increase in soluble TREM2 observed in anti-MS4A4A treated cells over that measured as plate baseline levels obtained from FIGS. 15 and 16, respectively.

human macrophages by about 1.4-fold compared to untreated cells. These results also showed that anti-MS4A4A antibody 4A-313 WT huIgG1 increased sTREM levels in primary human macrophages by about 1.5-fold to about 1.7-fold compared to untreated cells. These results indicated that anti-MS4A4A antibodies of the present disclosure are effective at increasing sTREM levels in vitro and thus may provide an effective means of increasing sTREM levels in plasma and CSF in vivo, mimicking the effect of MS4A4A alleles protective to developing Alzheimer's disease.

Example 25

Effect of Anti-MS4A4A Antibodies on Cellular ATP Levels

Human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate). To obtain macro-

TABLE 32

| Antibody (µg/ml) | 4A-450 WT | | | 4A-450 NSLF | | | 4A-450 K322A | | |
|---|---|---|---|---|---|---|---|---|---|
| 2.5 | 1.184 | 1.174 | 1.205 | 1.297 | 1.176 | 1.418 | 1.176 | 1.180 | 1.327 |
| 0.4 | 1.236 | 1.063 | 1.028 | 1.276 | 1.270 | 1.168 | 1.163 | 1.173 | 1.163 |
| 0.064 | 1.043 | 1.033 | 0.897 | 1.169 | 1.026 | 1.093 | 1.002 | 1.178 | 1.023 |

TABLE 33

| Antibody (µg/ml) | 4A-313 WT | | | 4A-313 NSLF | | | 4A-313 K322A | | |
|---|---|---|---|---|---|---|---|---|---|
| 1 | 1.431 | 1.242 | 1.475 | 1.570 | 1.380 | 1.542 | 1.348 | 1.240 | 1.405 |
| 0.16 | 1.388 | 1.210 | 1.235 | 1.392 | 1.262 | 1.274 | 1.290 | 1.155 | 1.170 |
| 0.0256 | 1.194 | 1.056 | 0.978 | 1.106 | 1.103 | 0.974 | 1.163 | 1.161 | 1.068 |

TABLE 34

| 4A-450 WT IgG1 (µg/ml) | sTREM2 (fold over plate background) |
|---|---|
| 0.0256 | 0.250851509 |
| 0.064 | 0.337610359 |
| 0.16 | 0.453324666 |
| 0.4 | 0.60750507 |
| 1 | 0.838142928 |
| 2.5 | 1.452549482 |

TABLE 35

| 4A-313 WT IgG1 (µg/ml) | sTREM2 (fold over plate background) |
|---|---|
| 0.0256 | 0.690304672 |
| 0.064 | 0.942481014 |
| 0.16 | 1.64173901 |
| 0.4 | 1.690748748 |
| 1 | 1.687668894 |
| 2.5 | 1.52381547 |

These results showed that anti-MS4A4A antibody 4A-450 WT huIgG1 (2.5 µg/ml) increased sTREM levels in primary phages from these isolated monocytes, 100 ng/ml human M-CSF and 8% v/v human serum were added to the cells for 5-7 days. Cells were then plated at 50,000 cells/well in complete RPMI-1640 and cultured for 2 days in the presence or absence of various concentrations of anti-MS4A4A antibodies (4A-313 NSLF, 4A-313 PS, 4A-450 NSLF, and 4A-450 PS) or isotype control antibody at various concentrations in solution for 48 hours. ATP content within the cells was then quantified using the CellTiter-Glo Luminescent cell viability kit (Promega, Cat #G7571) following the manufacturer's protocol.

Figure 17:
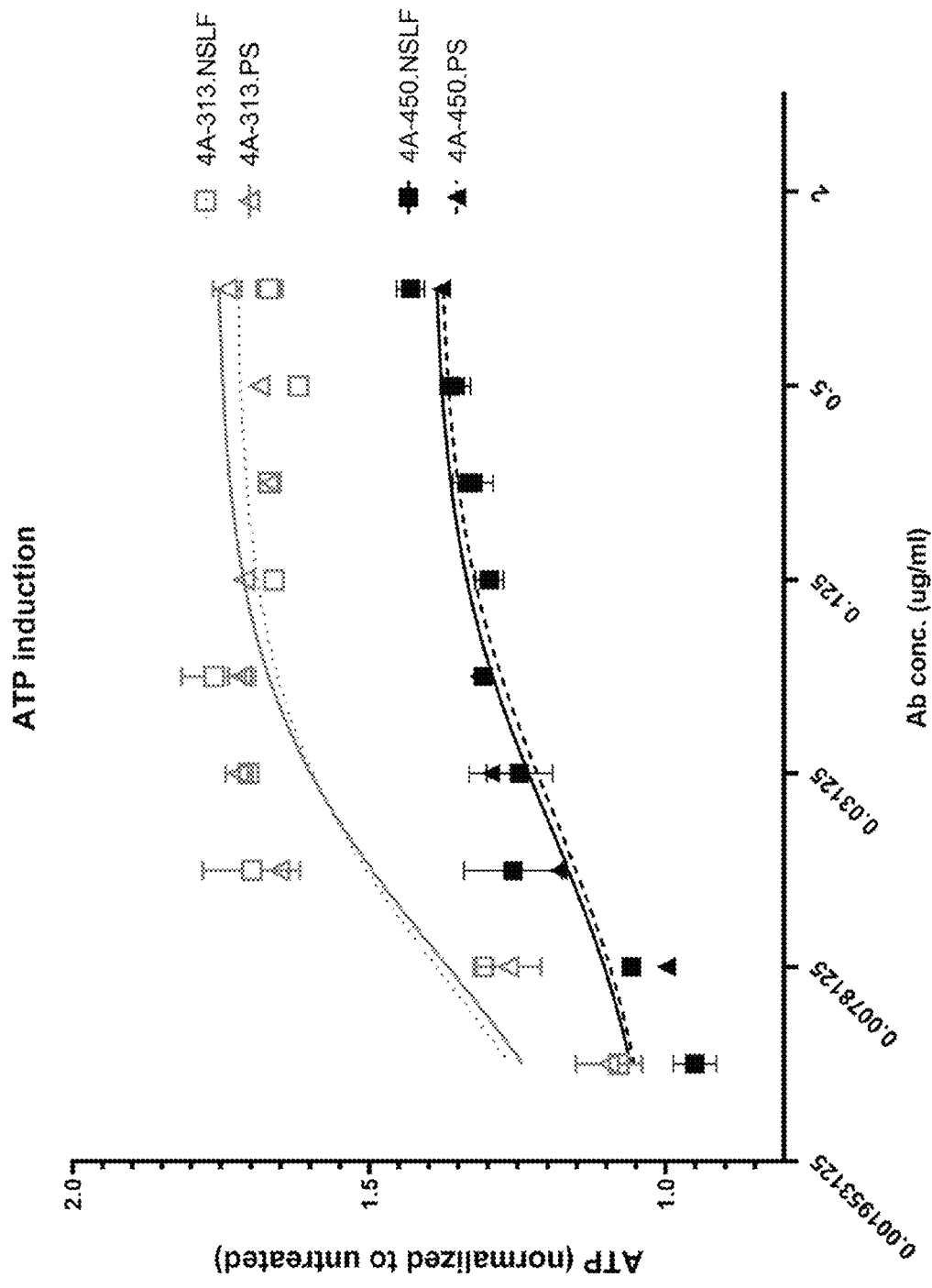
FIG. 17 sets forth data showing increased ATP levels in primary human macrophages treated with anti-MS4A4A antibodies 4S-313 NSLF huIgG1, 4A-313 PS huIgG1, 4A-450.NSLF huIgG1, and 4A-450.PS hu IgG1.

As shown in FIG. 17, anti-MS4A4A antibodies 4A-313 NSLF huIgG1, 4A-313 PS huIgG1, 4A-450 NSLF huIgG1, and 4A-450 PS huIgG1 increased ATP levels in primary human macrophages in a dose-dependent manner. Anti-MS4A4A antibodies having huIgG1 Fc containing N325S/L328F amino acid substitutions, which abolish FcγRIIIa binding (Journal of Biological Chemistry 2014, 289: 15309-15318), or having huIgG1 Fc containing P331S amino acid substitution, which abolishes C1q binding (Journal of Immunology 2000, 164: 4178-4184), were both effective at increasing ATP levels in human macrophages. The increase in ATP levels indicates increased viability of the human macrophages.

Table 36 below presents the numeric values of ATP levels determined in these studies (associated with FIG. 17), which were normalized to that observed in untreated macrophages. These results showed that anti-MS4A4A antibodies of the present disclosure were effective at increasing ATP levels in human macrophages in a dose-dependent manner. ATP levels increased by about 1.2-fold (with 0.016 µg/ml anti-MS4A4A antibody) to about 1.4-fold (with 1.0 µg/ml anti-MS4A4A antibody) above that observed in non-treated cells using anti-MS4A4A antibody 4A-450. ATP levels increased by about 1.3-fold (with 0.008 µg/ml anti-MS4A4A antibody) to about 1.7-fold (with 1.0 µg/ml anti-MS4A4A antibody) above that observed in non-treated ells using anti-MS4A4A antibody 4A-313.

TABLE 36

| Antibody (µg/ml) | 4A-450.NSLF | 4A-450.PS | 4A-313.NSLF | 4A-313.PS |
|---|---|---|---|---|
| 1.000 | 1.431 | 1.378 | 1.669 | 1.739 |
| 0.500 | 1.362 | 1.355 | 1.620 | 1.685 |
| 0.250 | 1.332 | 1.325 | 1.670 | 1.667 |
| 0.125 | 1.298 | 1.303 | 1.661 | 1.711 |
| 0.063 | 1.308 | 1.317 | 1.762 | 1.715 |
| 0.031 | 1.247 | 1.296 | 1.704 | 1.720 |
| 0.016 | 1.258 | 1.182 | 1.698 | 1.652 |
| 0.008 | 1.058 | 1.000 | 1.308 | 1.266 |
| 0.004 | 0.952 | 0.957 | 1.079 | 1.096 |

Example 26

Effect of Anti-MS4A4A Antibodies on Macrophage Cell Surface Markers

Myeloid cells in both the CNS and peripheral organs are inherently plastic in their phenotype and function. In peripheral organs, macrophages having an M1-like phenotype are more pro-inflammatory and anti-microbial, while macrophages having an M2-like phenotype are more homeostatic and anti-inflammatory. Within the CNS, microglia in homeostatic conditions also express M2-like markers, such as, for example, CD200R and CD163. MS4A4A expression is elevated in M2-like macrophages in vitro, and it has been suggested that MS4A4A is a novel cell surface marker for M2-like macrophages (Immunology and Cell Biology 2017, 95: 611-619).

The effect of anti-MS4A4A antibodies of the present disclosure on various macrophage cell surface markers was examined as follows. Human primary macrophages were treated with various concentrations (10 µg/ml, 1.0 µg/ml, 0.1 µg/ml) of anti-MS4A4A antibodies 4A-313 NSLF huIgG1 or 4A-419 wildtype (WT) huIgG1 in complete RPMI1640 for 48 hours. The cells were then harvested and subjected to flow cytometry, using antibodies specific for Ml-like markers (e.g., CD16, MHC Class II, CD86), M2-like markers (e.g., CD200R, Dectin-1, CD163), and a pan-macrophage marker CD14.

Figure 18A:
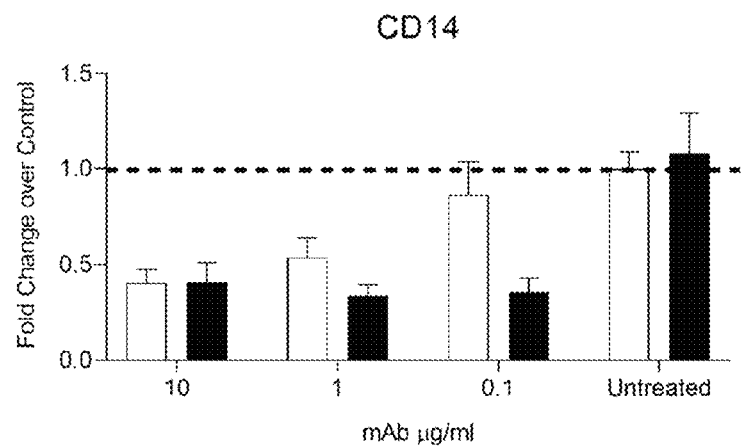
FIGS. 18A, 18B, and 18C set forth data showing changes in the levels of CD14, CD163, and CD200R (respectively) in primary human macrophages treated with anti-MS4A4A antibodies 4A-313 NSLF huIgG1 and 4A-419 WT huIgG1.
Figure 18B:
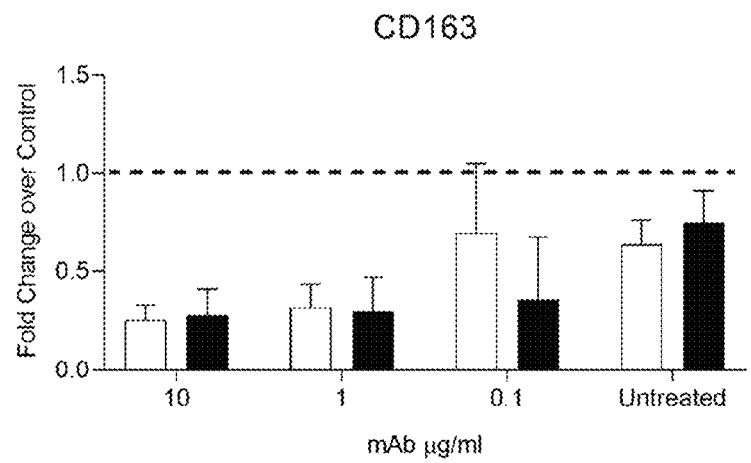
Figure 18C:
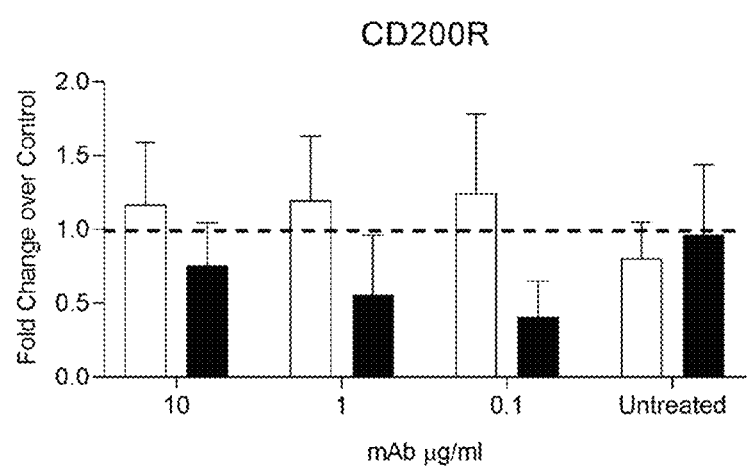

As shown in FIGS. 18A, 18B, and 18C, addition of anti-MS4A4A antibodies to primary human macrophages resulted in a decrease in CD14 and in CD163 cell surface markers in a dose-dependent manner compared to that observed in untreated cells (anti-MS4A4A antibody 4A-313 NSLF huIgG1 Fc (bars on the right in each pair), anti-MS4A4A antibody 4A-419 wildtype huIgG1 Fc (WT) (bars on the left in each pair). Addition of anti-MS4A4A antibody 4A-313 NSLF to primary human macrophages resulted in levels of CD200R cell surface marker that were below that observed in untreated cells. In contrast, addition of anti-MS4A4A antibody 4A-419 to primary human macrophages resulted in an increase in CD200R cell surface marker compared to that observed in untreated cells. This result is considered an anomaly to this specific experiment in view of the results obtained with anti-MS4A4A antibody 4A-313 NSLF, above, and in view of the results obtained with other anti-MS4A4A antibodies of the present disclosure, which reduced M2-like cell surface markers such as CD200R (see Example 9 and Table 26 above). Table 37 below presents numeric values for the fold change (above untreated cells) in the cell surface makers obtained from the graphs in FIGS. 18A, 18B, and 18C. Data is averaged over triplicate wells from two donors.

TABLE 37

| Antibody (µg/ml) | 4A-419.WT | 4A-313.NSLF |
|---|---|---|
| CD14 | | |
| 10 | 0.40 | 0.41 |
| 1 | 0.54 | 0.34 |
| 0.1 | 0.86 | 0.36 |
| Untreated | 1.00 | 1.08 |
| CD163 | | |
| 10 | 0.25 | 0.28 |
| 1 | 0.32 | 0.30 |
| 0.1 | 0.70 | 0.36 |
| Untreated | 0.63 | 0.75 |
| CD200R | | |
| 10 | 1.17 | 0.75 |
| 1 | 1.20 | 0.56 |
| 0.1 | 1.24 | 0.41 |
| Untreated | 0.80 | 0.96 |

These results showed that anti-MS4A4A antibodies of the present disclosure are effective at decreasing M2-like macrophage cell surface makers.

Example 27

Human IgG1 Fc Variants in Complement Dependent Cytotoxicity (CDC) Assay

The Fc domain of a human IgG1 antibody affects effector functions by its interaction with multiple downstream effector molecules, such as for example, C1q, Fc gamma receptors, and neonatal Fc receptors. The ability of anti-MS4A4A antibodies of the present disclosure having variant huIgG1 Fc regions to affect complement deposition was measured using a C3b deposition/cell killing assay as follows.

U937 cells overexpressing recombinant human MS4A4A, generated as described above, were used as target cells in these studies. Cells were harvested, washed 1× in PBS, and diluted to $2 \times 10^6$ cells/mL in RPMI 1640 media. 50 µL of target cells were aliquoted per well ($1 \times 10^5$ cells per well) in round-bottom 96 well plates (Falcon #351177). To these cells was added 25 µL of anti-MS4A4A antibodies prepared in the same media at four times predetermined concentrations. Cell-antibody mixture was incubated at 37° C. for 15 min, then 25 µL of pooled complement human serum (Innovative Research, IPLA-CSER) was added per well as a complement source and the plates incubated for a further 2 h at 37° C. Afterwards, cells were washed 2× with FACS buffer (PBS+2% FBS+1 mM EDTA) and 100 µL of 1:50 diluted anti-C3b-APC antibody (Biolegend 846106) was added per well and incubated on ice for 30 minutes. Cells were washed 2× with FACS buffer and resuspended in 80 μL of FACS buffer+0.25 μL/well of propidium iodide (Fischer Scientific, BD 556463) prior to analysis on an iQue flow cytometer (IntelliCyt). Complement activity was measured in two ways, either by percentage of PI-high cells to identify the extent of CDC-mediated cell killing, or MFI of cells in the APC channel to measure C3b deposition.

Figure 19:
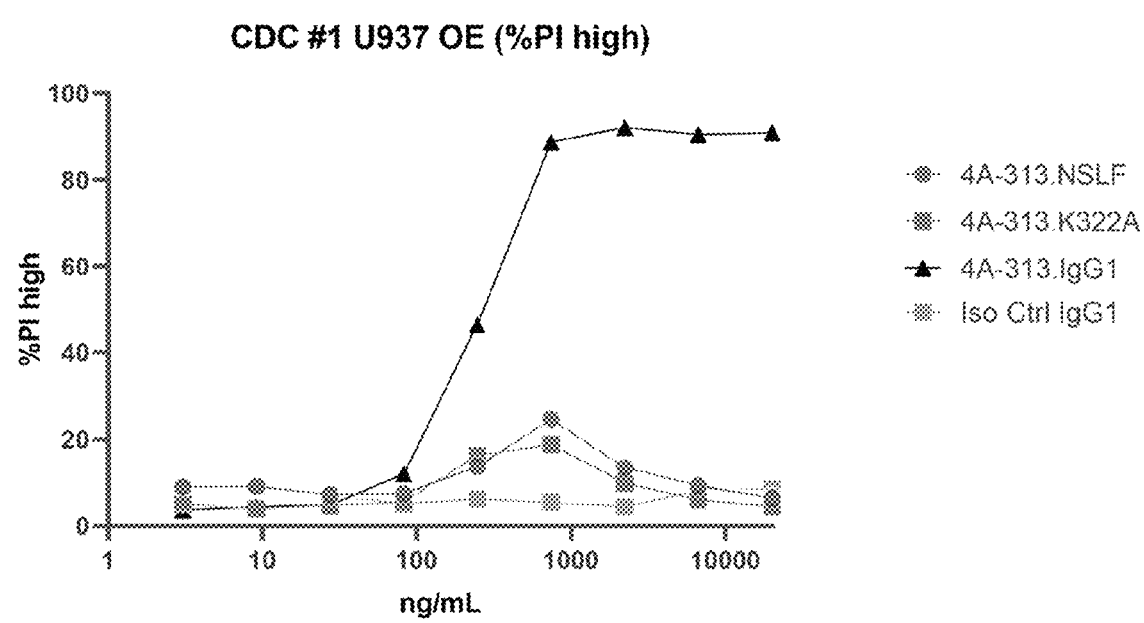
FIG. 19 sets forth data showing complement dependent cytotoxicity (CDC) activity of anti-MS4A4A antibodies 4A-313 NSLF huIgG1, 4A-313 K322A huIgG1 and 4A-313 WT huIgG1 in U937 cells expressing recombinant human MS4A4A as measured by propidium iodide uptake.

FIG. 19 shows the % PI (propidium iodide) uptake in U937 cells expressing recombinant human MS4A4A treated with anti-MS4A4A antibody 4A-313 with various huIgG1 Fc variants. As shown in FIG. 19, anti-MS4A4A antibody 4A-313 with a wildtype huIgG1 is highly capable of driving complement deposition and killing of target-expressing cells, observed as an increase in PI uptake by the cells. This effect was dose dependent. Anti-MS4A4A antibody 4A-313 with huIgG1 N325S/L328F amino acid substitutions in the Fc region (which significantly reduces C1q binding), CDC was almost completely abolished in this assay. Additionally, anti-MS4A4A antibody 4A-313 with huIgG1 K322A amino acid substitution in the Fc region had a similar effect of no CDC activity in this assay.

Table 38 below shows the numeric values associated with the graphs shown in FIG. 19.

TABLE 38

| Antibody (ng/mL) | 4A-313.NSLF | 4A-313.K322A | 4A-313.IgG1 | Isotype Ctrl IgG1 |
|---|---|---|---|---|
| 20,000.0 | 6.35 | 4.42 | 90.93 | 8.51 |
| 6,666.7 | 9.27 | 5.96 | 90.53 | 8.08 |
| 2,222.2 | 13.48 | 9.82 | 92.19 | 4.38 |
| 740.7 | 24.70 | 18.79 | 88.78 | 5.36 |
| 246.9 | 13.64 | 16.27 | 46.49 | 6.15 |
| 82.3 | 7.39 | 5.43 | 11.95 | 5.08 |
| 27.4 | 7.15 | 4.72 | 4.72 | 7.14 |
| 9.1 | 9.04 | 3.89 | 4.38 | 9.01 |
| 3.0 | 8.96 | 4.95 | 3.63 | 9.13 |
| 0.0 | 7.58 | 5.49 | 7.09 | 9.29 |

These results showed that anti-MS4A4A antibodies having a wildtype human IgG1 Fc region are effective at complement dependent cytotoxicity while anti-MS4A4A antibodies having a human IgG1 Fc variant of either N325S/L328F amino acid substitutions or K322A amino acid substitutions are not effective at complement dependent cytotoxicity.

Example 28

Human IgG1 Fc Variants in Antibody Dependent Cellular Phagocytosis (ADCP)

The ability of anti-MS4A4A antibodies of the present disclosure to mediate antibody-dependent cellular phagocytosis (ADCP) was evaluated using the ADCH Reporter Bioassay system (Promega #G9901). This system utilizes an engineered Jurkat T cell line stably expressing FcγRIIa receptor (H131 variant) and an NFAT response element driving expression of firefly luciferase. Activity in this assay correlates with ADCP activity by effector cells (in this case, myeloid cells). Target cells used here were either U937 cells over-expressing recombinant human MS4A4A or primary human macrophages derived from monocytes and polarized with hIL-4 (20 ng/ml) and dexamethasone (20 nM).

Cells were diluted in assay buffer (RPMI+4% low IgG Serum) at a concentration of 1.2×10$^6$ per mL, and 25 μL of cells (30,000 per well) were aliquoted to inner wells of a 96-well white assay plate (Costar 3922). The outer wells of the plate were filled with 75 μL of assay buffer with no cells or antibody. To wells containing cells, 25 μL of anti-MS4A4A antibody at a concentration 3 times the desired final concentration, also diluted in assay buffer, were added. Following addition of antibody to the target cells, the effector cells provided in the assay system (frozen at 2×10$^7$ per mL) were thawed at 37° C., and 630 μL added to 3.6 mL of prewarmed (37° C.) assay buffer and gently mixed. Twenty-five μL of effector cells (75,000 per well, for an E:T ratio of 2.5) were immediately added to the wells containing target cells and antibody. The plate was then incubated at 37° C. and 5% CO$_2$ for six hours to allow for receptor cell activation and luciferase expression. After this incubation, the plate was equilibrated to room temperature (15 min), after which 75 μL of the Luciferase Assay Reagent were added to each well. The plate was then incubated for 20 min on a plate shaker and luminescence was measured on a BioTek plate reader.

Figure 20:
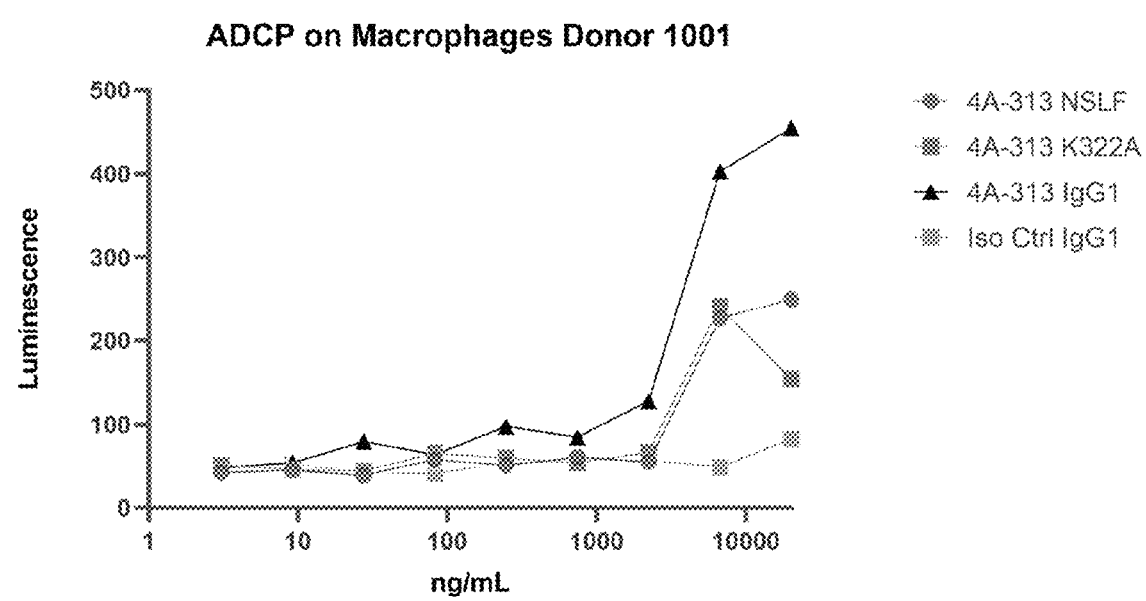
FIG. 20 sets forth data showing ADCP activity of anti-MS4A4A antibodies 4A-313 NSLF huIgG1, 4A-313 K322A huIgG1, and 4A-313 WT huIgG1 in primary human macrophages as measured by FcγRIIIa activation.

As shown in FIG. 20, wildtype huIgG1 (Iso Ctrl IgG1) was robust at driving luciferase activity in this assay, which is an indication of FcγRIIa-H131 activation. Anti-MS4A4A antibody 4A-313 having a huIgG1 Fc with N325S/L328F amino acid substitutions displayed a substantial loss of FcγRIIa-H131 activation compared to that observed with Iso Ctlr IgG1; anti-MS4A4A antibody 4A-313 having a huIgG1 Fc with K322A amino acid substitution had a similar effect in this assay.

Table 39 below provides the numeric values associated with the graphs presented in FIG. 20.

TABLE 39

| Antibody (ng/mL) | 4A-313.NSLF | 4A-313.K322A | 4A-313.IgG1 | Isotype Ctrl IgG1 |
|---|---|---|---|---|
| 20,000 | 250 | 154 | 455 | 83 |
| 6,666.667 | 227 | 242 | 403 | 49 |
| 2,222.222 | 55 | 67 | 128 | 57 |
| 740.7407 | 61 | 54 | 85 | 60 |
| 246.9136 | 51 | 60 | 98 | 54 |
| 82.30453 | 58 | 66 | 64 | 41 |
| 27.43484 | 39 | 44 | 80 | 42 |
| 9.144947 | 45 | 46 | 54 | 52 |
| 3.048316 | 42 | 51 | 48 | 45 |
| 0 | 50 | 50 | 49 | 64 |

These results showed that anti-MS4A4A antibodies having a wildtype human IgG1 Fc region are effective at antibody dependent cellular phagocytosis. Additionally, these results showed that anti-MS4A4A antibodies having a human IgG1 Fc variant of either N325S/L328F amino acid substitutions or K322A amino acid substitutions are also effective at antibody dependent cellular phagocytosis, albeit to a lesser degree.

Example 29

Human IgG1 Fc Variants in Antibody Dependent Cellular Cytotoxicity (ADCC)

Antibodies bound to their target cells can mediate ADCC, an activity thought to be primarily driven by FcγRIIIa activation on natural killer cells. The ability of anti-MS4A4A antibodies of the present disclosure to cause antibody-dependent cellular cytotoxicity (ADCC) was evaluated using an ADCC Reporter Bioassay system (Promega #G7010). This assay system utilizes an engineered Jurkat T cell line stably expressing the FcγRIIIa receptor (V158 variant) and an NFAT response element driving expression of firefly luciferase. Target cells used here were either U937 cells over-expressing recombinant human MS4A4A or primary human macrophages derived from monocytes and polarized with hIL-4 (20 ng/ml) and dexamethasone (20 nM). Target cells were diluted in assay buffer (RPMI+4% low IgG Serum) at a concentration of $1.2 \times 10^6$ per mL and 25 μL of cells (30,000 per well) were aliquoted to inner wells of a 96-well white assay plate (Costar 3922). The outer wells of the plate were filled with 75 μL of assay buffer without cells or antibody. To wells containing cells, 25 μL of antibody at a concentration of 3 times the desired final concentrations, also diluted in assay buffer, were added. Following addition of antibody to target cells, the provided effector cells (frozen at $2 \times 10^7$ per mL) were thawed at 37° C., and 630 μL added to 3.6 mL of warmed (37° C.) assay buffer, gently mixed, and 25 μL of effector cells (75,000 per well, for an E:T ratio of 2.5) immediately added to the wells containing target cells and antibody. The plate was then incubated at 37° C. and 5% $CO_2$ for six hours to allow for receptor cell activation and luciferase expression. After this incubation, the plate was equilibrated to room temperature (15 min), after which 75 μL of the Luciferase Assay Reagent were added to each well. The plate then incubated for 20 min on a plate shaker and luminescence was measured on a BioTek plate reader.

Figure 21:
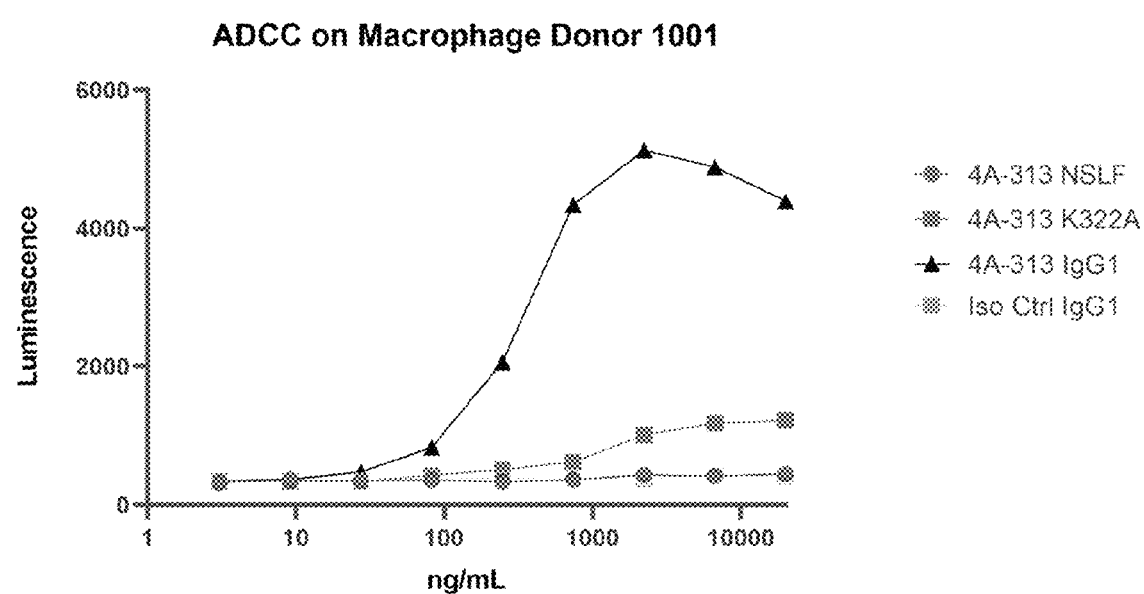
FIG. 21 sets forth data showing ADCC activity of anti-MS4A4A antibodies 4A-313 NSLF huIgG1, 4A-313 K322A huIgG1, and 4A-313 WT huIgG1 in primary human macrophages as measured by FcγRIIIa activation.

As shown in FIG. 21, wildtype hu IgG1 (Iso Ctrl IgG1) was robust at driving luciferase activity in this assay, an indication of FcγRIIIa-V158 activation. Anti-MS4A4A antibody 4A-313 having a huIgG1 Fc with N325S/L328F amino acid substitutions displayed a substantial loss of FcγRIIa-H131 activation compared to that observed with Iso Ctrl IgG1; anti-MS4A4A antibody 4A-313 having a huIgG1 Fc with K322A amino acid substitution had a similar effect in this assay.

Table 40 below provides the numeric values associated with the graphs presented in FIG. 21.

TABLE 40

| Antibody (ng/mL) | 4A-313.NSLF | 4A-313.K322A | 4A-313.IgG1 | Isotype Ctrl IgG1 |
|---|---|---|---|---|
| 20,000 | 442 | 1222 | 4397 | 399 |
| 6,666.667 | 415 | 1182 | 4891 | 431 |
| 2,222.222 | 431 | 1017 | 5133 | 373 |
| 740.7407 | 363 | 623 | 4346 | 379 |
| 246.9136 | 332 | 508 | 2063 | 381 |
| 82.30453 | 360 | 426 | 839 | 377 |
| 27.43484 | 347 | 341 | 473 | 340 |
| 9.144947 | 356 | 338 | 367 | 329 |
| 3.048316 | 324 | 338 | 346 | 314 |
| 0 | 328 | 343 | 348 | 368 |

These results showed that anti-MS4A4A antibodies having a wildtype hu IgG1 Fc region are effective at antibody dependent cellular cytotoxicity while anti-MS4A4A antibodies having a human IgG1 Fc variant of either N325S/L328F amino acid substitutions or K322A amino acid substitutions are not effective at antibody dependent cellular cytotoxicity.

Example 30

Effect of MS4A4A Knockout on Membrane and Soluble TREM2 Levels in Primary Human Macrophages The effect of MS4A4A knockout on membrane and soluble TREM2 levels in macrophages was examined as follows. CRISPR technology was used to knockout expression of MS4A4A in primary human macrophages. In brief, knockout macrophages were generated by electroporation with Cas9 protein (IDT), which was complexed with non-targeting (NT) or MS4A4A-specific gRNAs consisting of locus-specific crRNAs (IDT; NT1, IDT negative control crRNA #1 and #2; NT2, GTAGGCGCGCCGCTCTCTAC (SEQ ID NO:345) and AACCCCTGATTGTATCCGCA (SEQ ID NO:346); MS4A4A #1, AATTGTGTACCCGA-TATACA (SEQ ID NO:347); MS4A4A #2, AAC-CATGCAAGGAATGGAAC (SEQ ID NO:348); MS4A4A #3, TATTCATTCCTAGACTACCT (SEQ ID NO:349); MS4A4A #4, GCTCTGTACTGGCTGCATCA (SEQ ID NO:350)) annealed to a tracrRNA (IDT). MS4A4A knockout efficiency was evaluated by flow cytometric analysis and was greater than 90% (data not shown).

Figure 22A:
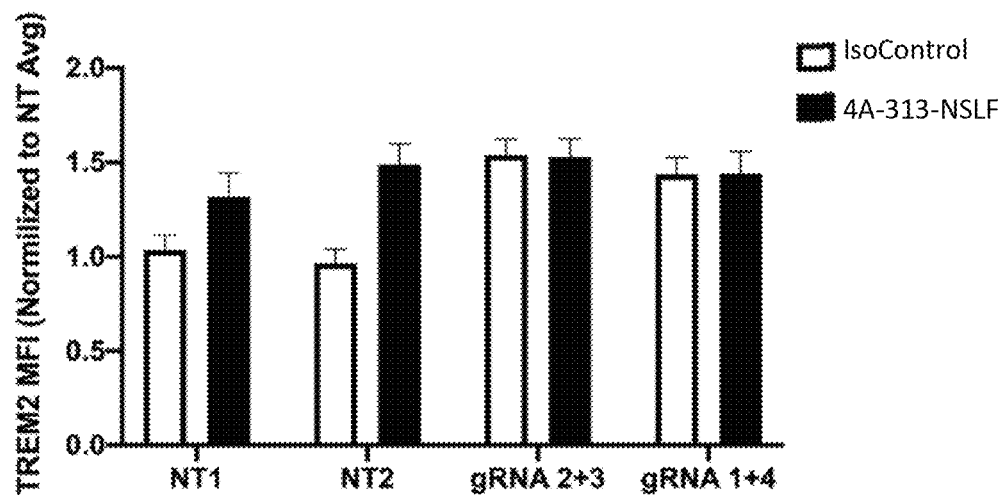
FIGS. 22A and 22B set forth data showing the effect of MS4A4A knockout on membrane TREM2 (FIG. 22A) and soluble TREM2 (FIG. 22B) in primary human macrophages.
Figure 22B:
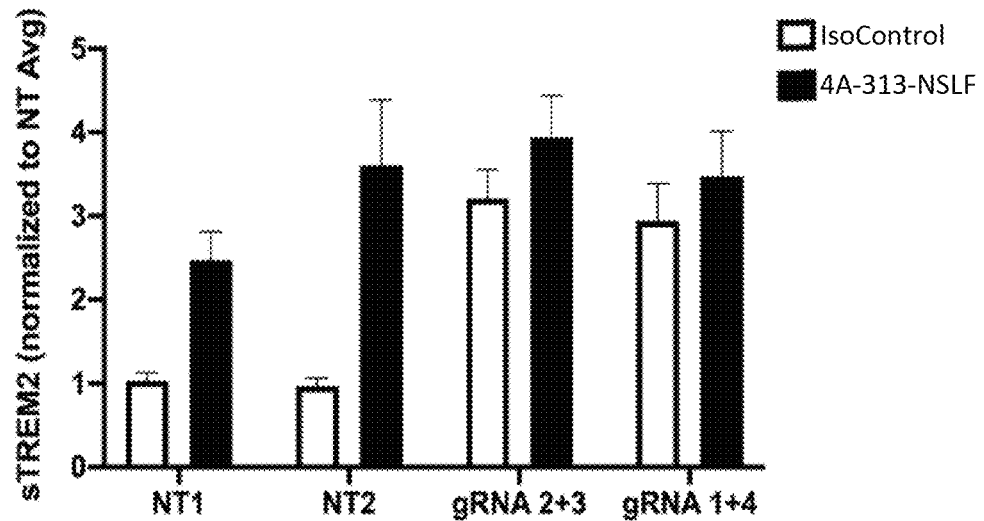

FIGS. 22A and 22B show the effect of MS4A4A knockout on membrane TREM2 (mTREM2) levels and soluble TREM2 (sTREM2) levels. In FIGS. 22A and 22B, NT1 and NT2 are non-targeting CRISPR controls; gRNA 2+3 and gRNA 1+4 refer to different guides used for knocking out MS4A4A.

As shown in FIGS. 22A and 22B, knockout of MS4A4A in primary human macrophages resulted in an increase in mTREM2 and sTREM2 levels. The increased levels of mTREM2 and sTREM2 observed upon MS4A4A knockout were comparable to the increase in mTREM2 and sTREM2 levels upon addition of anti-MS4A4A antibody 4A-313 to the NT1 and NT2 control cells. Upon anti-MS4A4A antibody treatment of the MS4A4A knockout primary human macrophages, no further increase in mTREM2 or sTREM2 levels was observed, suggesting that the increase in mTREM2 and sTREM2 levels observed upon addition of anti-MS4A4A antibody of the present disclosure to human macrophages is a result of anti-MS4A4A antibody binding to MS4A4A on the cells.

Example 31

Kinetics of Membrane and Soluble TREM2 Modulation by Anti-MS4A4A Antibodies

Cell surface expression of TREM2 protein is regulated by endocytosis/exocytosis of TREM2 to and from the plasma membrane and by regulated cleavage of TREM2 by membrane bound proteases (Thornton et al., 2017, EMBO Mol. Med. 9: 1366-1378; doi: 10.15252/emmm.201707673). As described in Examples above, treatment of human macrophages with anti-MS4A4A antibodies of the present disclosure increased both membrane and soluble TREM2 levels. The following studies were performed to further understand the kinetics of the changes in levels of membrane and soluble TREM2.

To assess changes in soluble TREM2 (sTREM2) levels, primary human macrophages were plated in either 24-well or 96-well plates followed by the addition of anti-MS4A4A antibodies 4A-313.NSLF, 4A-450.NSLF, or isotype control antibody (all at 1 μg/ml). After 0.5, 1, 4, 24, and 48 hours of cell culture in the presence of the antibodies, supernatants were collected and sTREM2 levels determined using Meso Scale Discovery.

The kinetics of the increase in membrane TREM2 (mTREM2) levels in primary human macrophages following addition of anti-MS4A4A antibodies of the present disclosure were assessed as follows. Primary human macrophages were plated at 100,000 cells/well in 96-well U-bottom plates 3 days before analysis (T minus 72 hrs). At various time points (T minus 48 hrs, T minus 24 hrs, T minus 4 hrs, T minus 1 hr), antibodies were added to the plated cells, which included an isotype control antibody (IsoControl.NSLF) and anti-MS4A4A antibody 4A-313.NSLF. 72-hrs post-plating, cell surface (membrane bound) expression levels of TREM2 was measured by flow cytometry after staining the cells with a fluorophore-conjugated anti-TREM2 antibody.

Figure 23A:
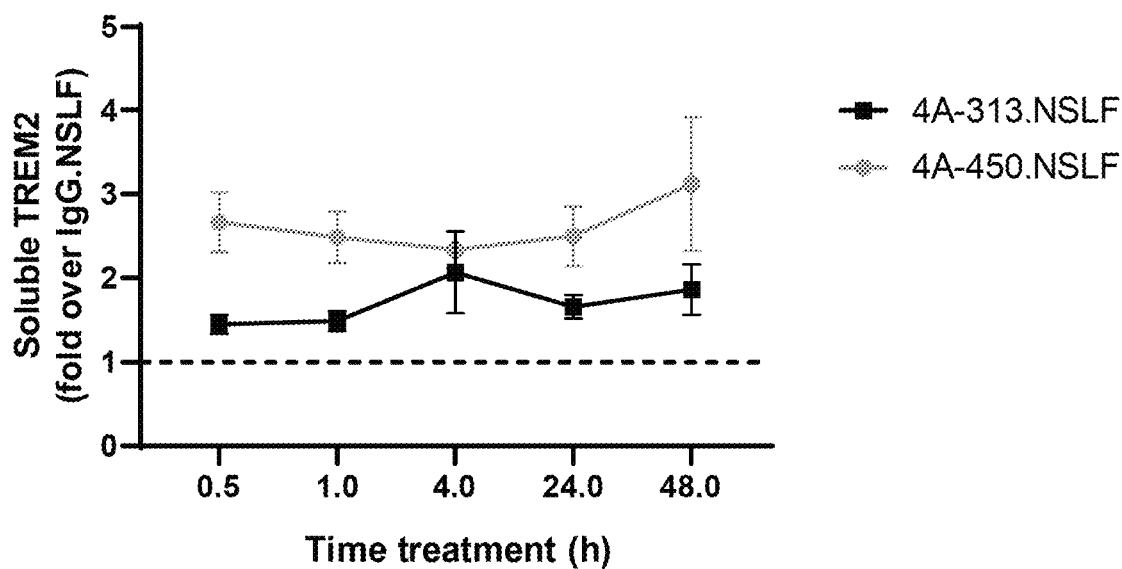
FIGS. 23A, 23B, and 23C set forth data showing the kinetics of changes in soluble TREM2 protein levels, membrane TREM2 protein levels, and TREM2 mRNA levels, respectively, in human macrophages treated with anti-MS4A4A antibodies of the present disclosure.

As shown in FIG. 23A, anti-MS4A4A antibodies of the present disclosure rapidly increased the levels of sTREM2 in the supernatants of cultured primary human macrophages obtained from various donors. Anti-MS4A4A antibody 4A-313.NSLF increased sTREM2 levels approximately 0.5-fold above that observed in cells treated with isotype control antibody (approximately 50% increase). Anti-MS4A4A antibody 4A-450.NSLF increased sTREM2 levels approximately 2.5-fold above that observed in cells treated with isotype control antibody (approximately 250% increase).

Figure 23B:
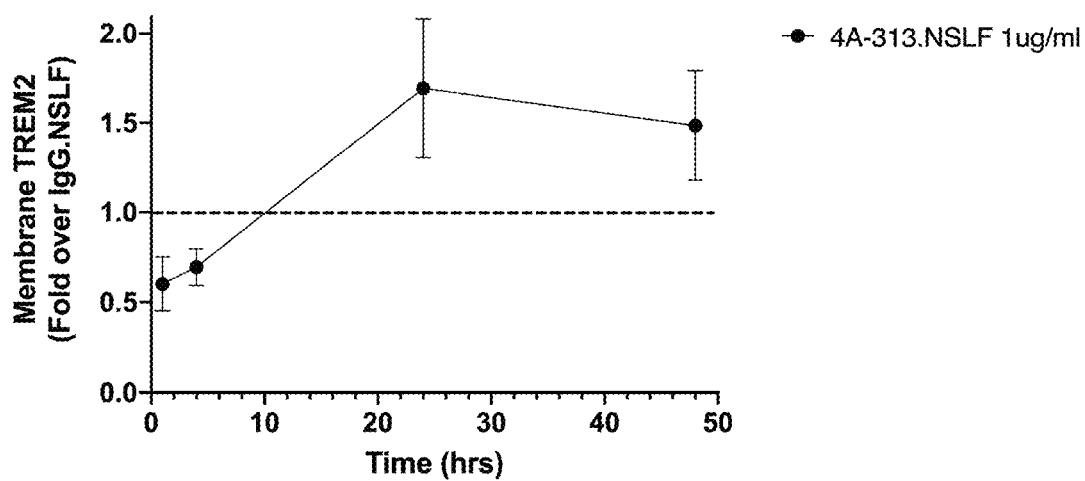

As shown in FIG. 23B, at 1 hour and 4 hours following addition of anti-MS4A4A antibody 4A-313.NSLF to primary human macrophages, membrane TREM2 levels decreased compared to that observed following the addition of an isotype control antibody. In FIG. 23B, the dotted line represents the level of mTREM2 in isotype control antibody treated cells. At 24-hour and 48-hour timepoints following addition of anti-MS4A4A antibody 4A-313.NSLF, levels of mTREM2 increased above that observed in cells treated with isotype control antibody. The early decrease in membrane TREM2 is consistent with increases in TREM2 shedding at all time points examined, as shown in FIG. 23A.

As anti-MS4A4A antibodies of the present disclosure increased TREM2 protein levels in primary human macrophages, the following experiments were performed to examine the effects on TREM2 mRNA levels following anti-MS4A4A antibody addition. Primary human macrophages were plated either in 24 or in 96-well plates and treated with anti-MS4A4A antibody 4A-313.NSLF and isotype (1 µg/ml) in complete RPMI. After 0.5, 1, 4, 24, and 48 hours of incubation, cell pellets were collected, and TREM2 mRNA levels determined using quantitative PCR analysis (qPCR). Briefly, RNA was extracted using the RNeasy Mini Kit (Qiagen), cDNA was prepared from the total RNA using QuantiNova Reverse Transcription Kit (Qiagen). Gene expression levels were analyzed by real-time PCR using TaqMan assays for TREM2 (Hs00219132_m1) and GAPDH (Hs027886624_g1). CT values for each sample were normalized to CT values for the housekeeping gene GAPDH.

Figure 23C:
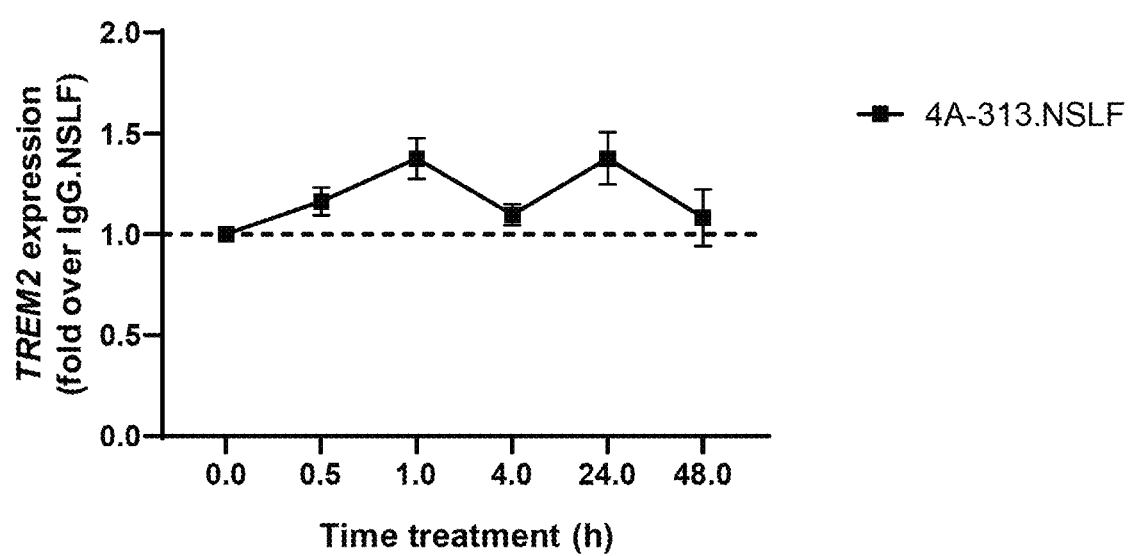

As shown in FIG. 23C, anti-MS4A4A antibody 4A-313.NSLF did not affect TREM2 mRNA levels in cultured human primary macrophages obtained from various donors; some minor fluctuations in mRNA levels were observed (less than 0.5-fold above that observed in isotype control). These results indicated that anti-MS4A4A antibodies of the present disclosure increased TREM2 protein levels without affecting TREM2 mRNA levels in cultured human primary macrophages.

Example 32

Anti-MS4A4A Antibodies Increase SPP1 and IL1RN Secretion in Primary Human Macrophages The effect of anti-MS4A4A antibodies of the present disclosure on secreted levels of osteopontin (SSP1) and interleukin-1 receptor antagonist (IL1RN) in primary human macrophages was examined and compared to that observed in primary human macrophages genetically modified to knockout MS4A4A expression as follows.

MS4A4A genetic knockout in primary human macrophages was generated by electroporation with Cas9 protein, which was complexed with guide RNAs (gRNAs) in the form of either single gRNA molecules or gRNA duplexes consisting of crRNAs annealed to a tracrRNA: non-targeting NT1 (IDT negative control RNA #1 and #2); NT2 (GTAGGCGCGCCGCTCTCTAC [SEQ ID NO:345] and AACCCCTGATTGTATCCGCA [SEQ ID NO:346]); MS4A4A #1 (AATTGTGTACCCGATATACA [SEQ ID NO:347]); MS4A4A #2 (AACCATGCAAGGAATGGAAC [SEQ ID NO:348]); MS4A4A #3 (TATTCATTCCTAGAC-TACCT [SEQ ID NO:349]); MS4A4A #4, GCTCTGTACTGGCTGCATCA [SEQ ID NO:350]) (all from IDT, Coralville, Iowa, USA) using standard procedures. Cells were then plated at 50,000 cells/well in complete RPMI-1640 and cultured for 48 hours in the presence of anti-MS4A4A antibody 4A-313.NSLF (0.1 µg/ml), anti-MS4A4A antibody 4A-450.NSLF (0.1 µg/ml), or isotype control antibody. Supernatants from the cells were collected, and levels of IL1RN and SPP1 were analyzed using R&D DuoSet ELISA kits (IL1RN Cat #DY280, SPP1 Cat #DY1433).

Treatment of NT control cells with either anti-MS4A4A antibody 4A-313.NSLF or 4A-450.NSLF resulted in an increase in the level of secreted SPP1. Genetic knockout of MS4A4A in these cells also resulted in an increase in secreted SPP1 levels comparable to that seen with MS4A4A antibody treatment. Levels of SPP1 in these studies were: approximately 100 ng/ml following addition of isotype control antibody in NT control cells; approximately 200 ng/ml following addition of anti-MS4A4A antibody 4A-313.NSLF in NT control cells; approximately 275 ng/ml following addition of anti-MS4A4A antibody 4A-450.NSLF in NT control cells; and approximately 225 ng/ml in MS4A4A knockout cells. The increase in secreted SPP1 levels following addition of either anti-MS4A4A antibody of the present disclosure was comparable to that observed in cells in which MS4A4A expression was genetically knocked-out.

Treatment of NT control cells with either anti-MS4A4A antibody 4A-313.NSLF or 4A-450.NSLF resulted in an increase in the level of secreted IL1RN. Genetic knockout of MS4A4A in these cells also resulted in an increase in secreted IL1RN levels comparable to that seen with MS4A4A antibody treatment. Levels of IL1RN in these studies were: approximately 8 ng/ml following addition of isotype control antibody in NT control cells; approximately 12 ng/ml following addition of anti-MS4A4A antibody 4A-313.NSLF in NT control cells; approximately 16 ng/ml following addition of anti-MS4A4A antibody 4A-450.NSLF in NT control cells; and approximately 14 ng/ml in MS4A4A knockout cells. The increase in secreted IL1RN levels following addition of either anti-MS4A4A antibody of the present disclosure was comparable to that observed in cells in which MS4A4A expression was genetically knocked-out.

Taken together, these results indicated that anti-MS4A4A antibodies of the present disclosure are effective at increasing secreted levels of SPP1 and of IL1RN in primary human macrophages. Additionally, these results showed that the effect of anti-MS4A4A antibodies of the present disclosure on increasing the level of secreted SPP1 and IL1RN was similar to that observed when expression of MS4A4A was genetically knocked-out, suggesting that anti-MS4A4A antibodies of the present disclosure reduced or blocked the activity of MS4A4A in these cells, resulting in the observed increases in SPP1 and IL1RN levels.

Example 33

Anti-MS4A4A Antibody-Induced Viability in Human Macrophages is TREM2-Independent As shown above, anti-MS4A4A antibodies of the present disclosure were effective at increasing the viability of primary human macrophages (as measured by increases in total cellular ATP) following anti-MS4A4A antibody addition. Additionally, as shown above, anti-MS4A4A antibodies of the present disclosure increased membrane TREM2 levels in cells. As anti-MS4A4A antibodies of the present disclosure increased membrane TREM2 levels, and as anti-MS4A4A antibodies increased cell viability, a series of experiments were performed to examine whether the increase in cell viability observed in response to anti-MS4A4A antibody addition was, at least in part, TREM2-dependent. To explore this, TREM2 was genetically knocked-out in human primary macrophages using CRISPR technology to examine the effects of anti-MS4A4A antibodies of the present disclosure on cell viability in primary human macrophages genetically lacking TREM2 expression.

TREM2 knockout macrophages were generated by electroporation with Cas9 protein, which was complexed with guide RNAs (gRNAs) in the form of either single gRNA molecules or gRNA duplexes consisting of crRNAs annealed to tracrRNA: non-targeting 1 (NT1) (IDT negative control crRNA #1 and #2); NT2 (GTAGGCGCGCCGCTCTCTAC [SEQ ID NO:345] and AACCCCTGATTGTATCCGCA [SEQ ID NO:346]); TREM2 #1 (GCCATCACAGACGATACCCT [SEQ ID NO:351]); TREM2 #2 (ATAGGGGCAAGACACCTGCA [SEQ ID NO:352]); TREM2 #3 (CAGCATCCCGGTGATCCAGG [SEQ ID NO:353]); TREM2 #4, TGGAGATCTCTGGTTCCCCG [SEQ ID NO:354]) (all from IDT, Coralville, Iowa, USA).

The cells were then plated at 50,000 cells/well in complete RPMI-1640 and cultured in the presence of anti-MS4A4A antibodies (4A-313 NSLF, 4A-450 NSLF), or isotype control antibody (all at 0.1 µg/ml) in solution for 48 hours. ATP content within the cells was then quantified using the CellTiter-Glo Luminescent cell viability kit (Promega, Cat #G7571) following the manufacturer's protocol.

Addition of anti-MS4A4A antibody 4A-313.NSLF or anti-MS4A4A antibody 4A-450.NSLF increased ATP levels in NT control cells by approximately 20% compared to that observed with the isotype control antibody. Additionally, anti-MS4A4A antibody addition to the TREM2 knockout cells resulted in increased ATP levels by approximately 15%-20% above that observed with the isotype control antibody. Taken together, these results showed that anti-MS4A4A antibodies of the present disclosure increase cellular ATP levels (and thus cell viability), at least in part, in a TREM2-independent manner.

Example 34 siRNA Knockdown of MS4A4A Increases Membrane and Soluble TREM2 Levels in Primary Human Macrophages As shown above, genetic ablation of MS4A4A expression using CRISPR technology resulted in increased membrane and soluble TREM2 levels in human macrophages. To further support these findings, the effect of loss of expression of MS4A4A on TREM2 levels was assessed using an independent experimental approach. In these studies, siRNA knockdown of MS4A4A in primary human macrophages was performed and its effect on membrane and soluble TREM2 levels measured.

MS4A4A knock-down macrophages were generated by transfecting control (Millipore Sigma, SIC001) and MS4A4A-targeting siRNAs (Millipore Sigma, SASI_Hs01_00150955) using the N-TER Nanoparticle siRNA Transfection System (Millipore Sigma). MS4A4A knockout efficiency was evaluated by flow cytometric analysis (data not shown). Cell surface (membrane bound) expression of TREM2 was measured by flow cytometry after staining the cells with a fluorophore-conjugated anti-TREM2 antibody.

Figure 24A:
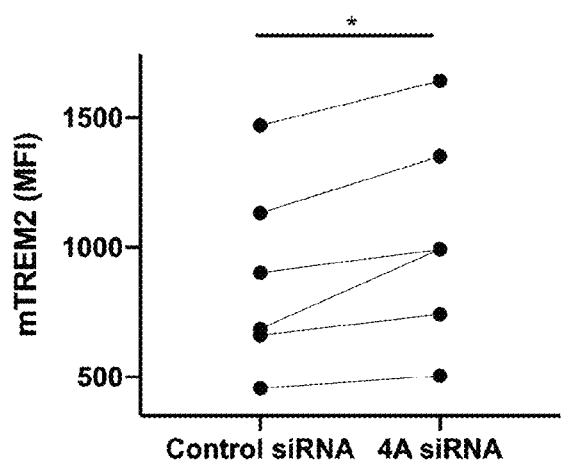
FIGS. 24A and 24B set forth data showing siRNA knockdown of MS4A4A increased membrane TREM2 and soluble TREM2 levels in human macrophages.
Figure 24B:
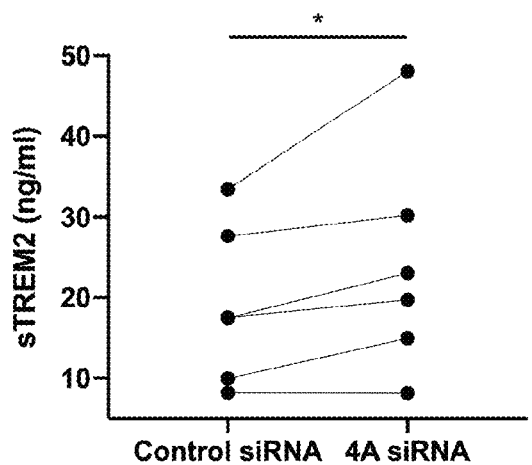

As shown in FIG. 24A and FIG. 24B, siRNA knockdown of MS4A4A expression led to an increase in membrane TREM2 levels and in soluble TREM2 levels, respectively. In FIG. 24A and FIG. 24B, each set of connected dots represents the average result from one individual donor (for a total of 6 donors) with and without siRNA knockdown. These data are in alignment with similar results showing increased mTREM2 and sTREM2 levels in genetically engineered MS4A4A knockout cells described above. Taken together, these results indicated that loss of MS4A4A expression or activity increased both soluble TREM2 levels and membrane TREM2 levels in primary human macrophages.

Example 35

Anti-MS4A4A Antibody Potency at Increasing mTREM2, sTREM2, and ATP Levels In Vitro The effect of anti-MS4A4A antibodies of the present disclosure at increasing mTREM2, sTREM2, and ATP levels (as previously described above in Examples 24 and 25) was further examined in primary human macrophages obtained from three separate donors. Primary human macrophages were treated with various concentrations of anti-MS4A4A antibodies 4A-313.NSLF and 4A-450.NSLF for 48 hours. Changes in the levels of mTREM2, sTREM2, and ATP were then measured.

Figure 25A:
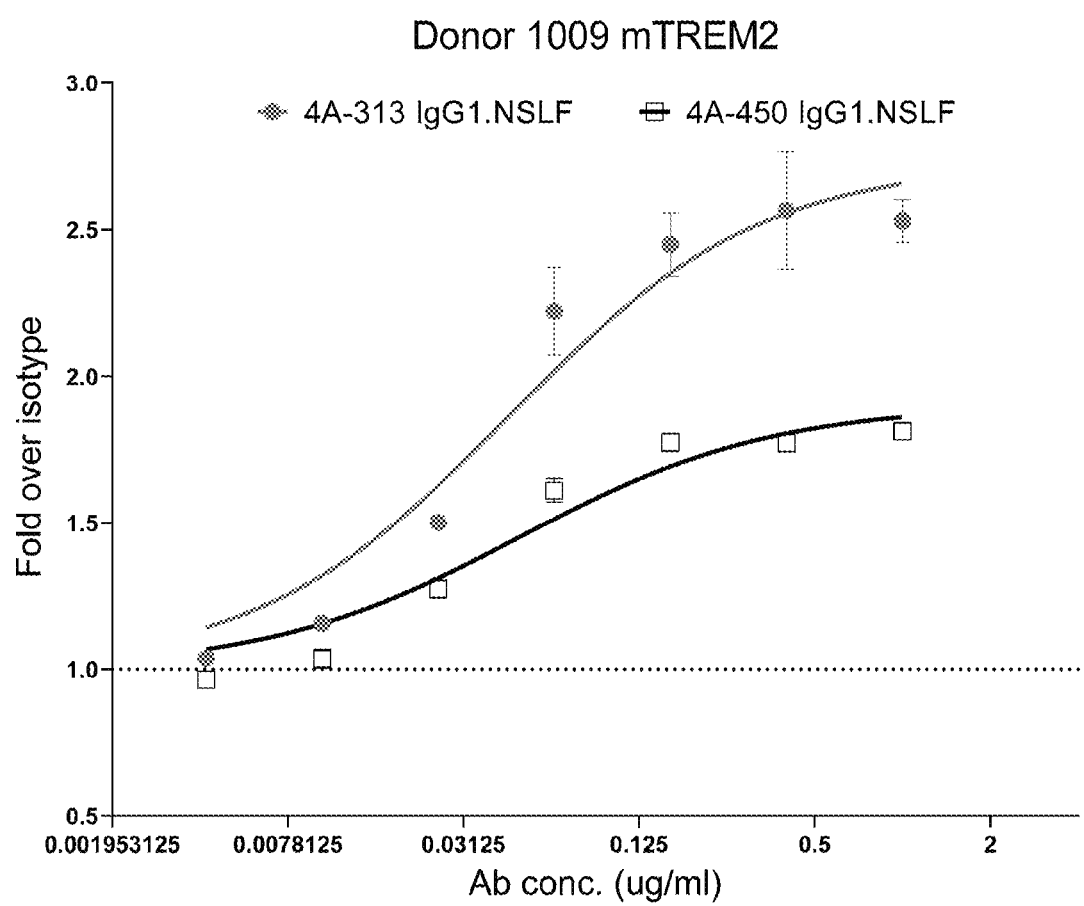
FIGS. 25A, 25B, and 25C set forth data showing a dose-dependent increase in membrane TREM2 levels in primary human macrophages from three different donors following addition of anti-MS4A4A antibodies of the present disclosure.
Figure 25B:
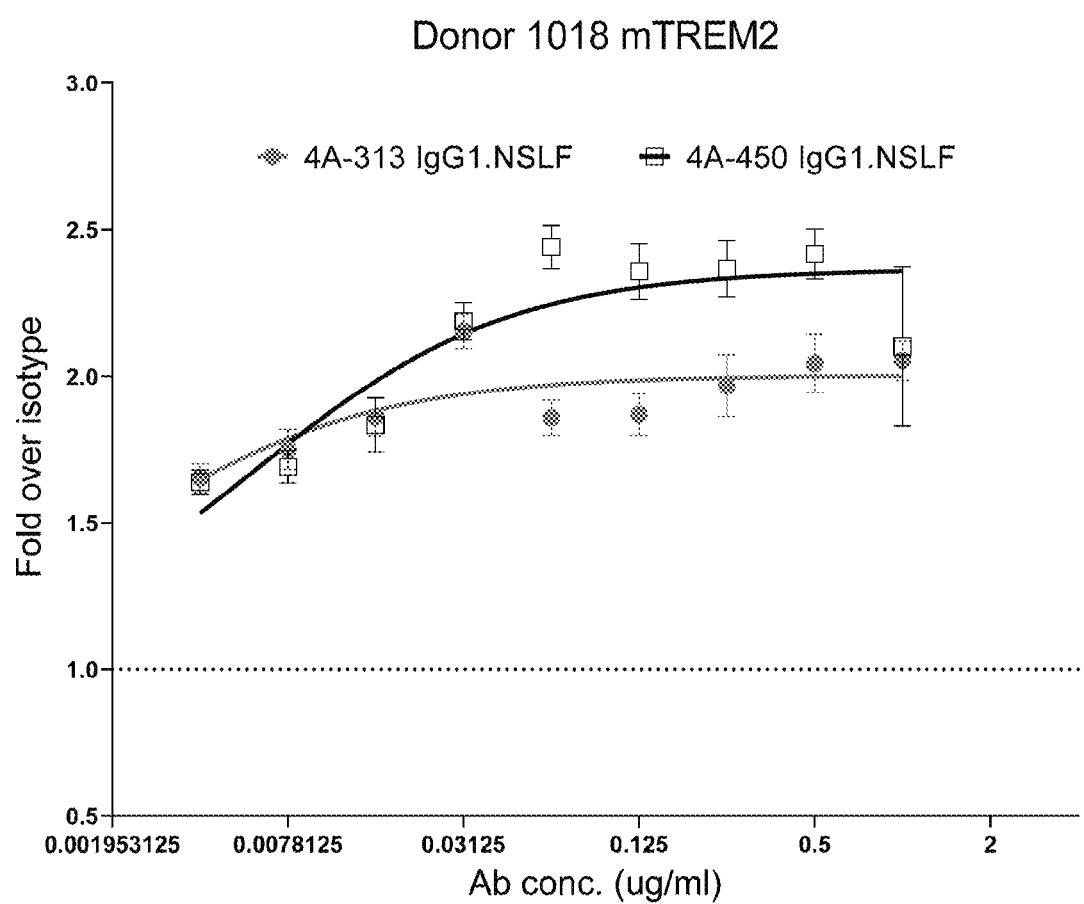
Figure 25C:
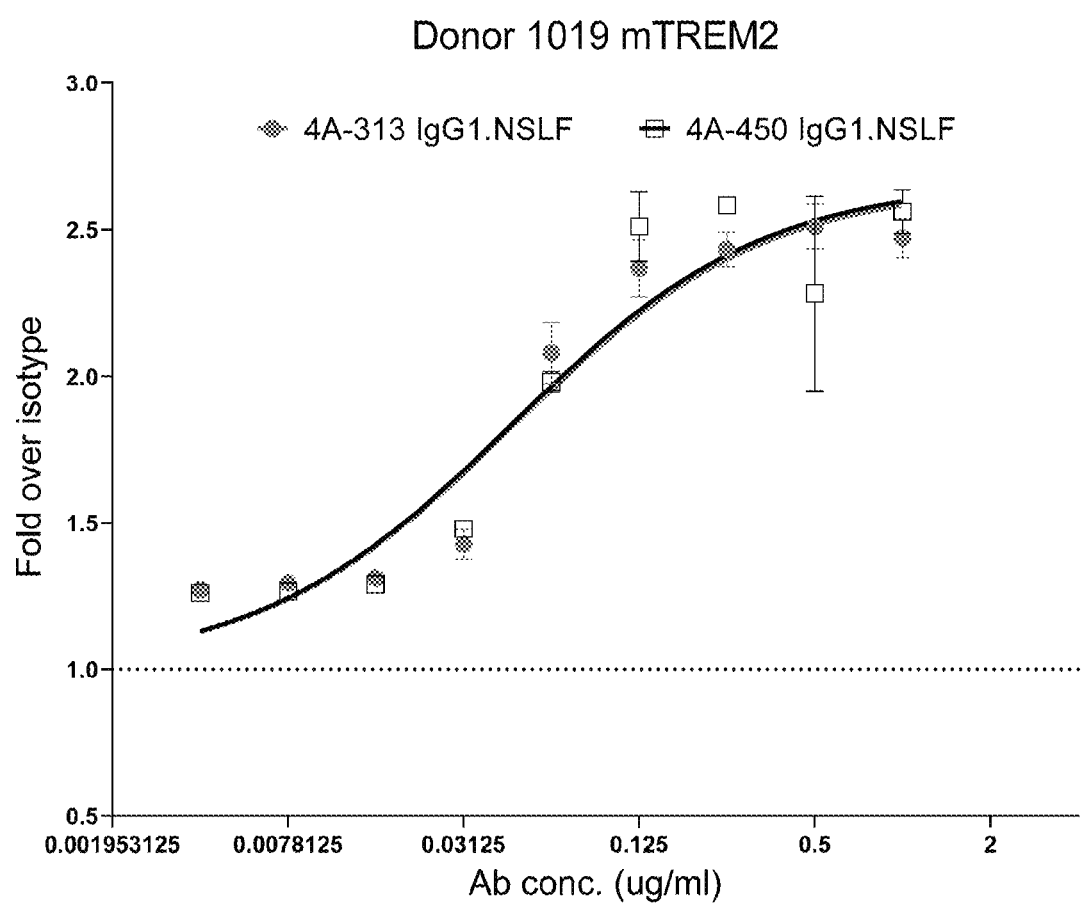

As shown in FIG. 25A, FIG. 25B, and FIG. 25C, anti-MS4A4A antibody 4A-313.NSLF and anti-MS4A4A antibody 4A-450.NSLF increased levels of mTREM2 in a dose-dependent manner in primary human macrophages obtained from three different donors, respectively. Data in FIG. 25A, FIG. 25B, and FIG. 25C is presented as fold-increase in the levels of mTREM2 over that observed using an isotype control antibody (the x-axis shows antibody concentrations (µg/ml) and the y-axis shows fold-increase above control, which was set at 1.0). Data from these graphs were analyzed to determine EC50 values and maximum response; these results are shown below in Table 41 (shown as mean+/−SEM).

TABLE 41

| Antibody | EC50 (µg/ml) | Max mTREM2 Response (fold increase over isotype control) |
|---|---|---|
| 4A-313.NSLF | 0.028 +/− 0.013 | 2.45 +/− 0.23 |
| 4A-450.NSLF | 0.039 +/− 0.014 | 2.36 +/− 0.27 |

Figure 26A:
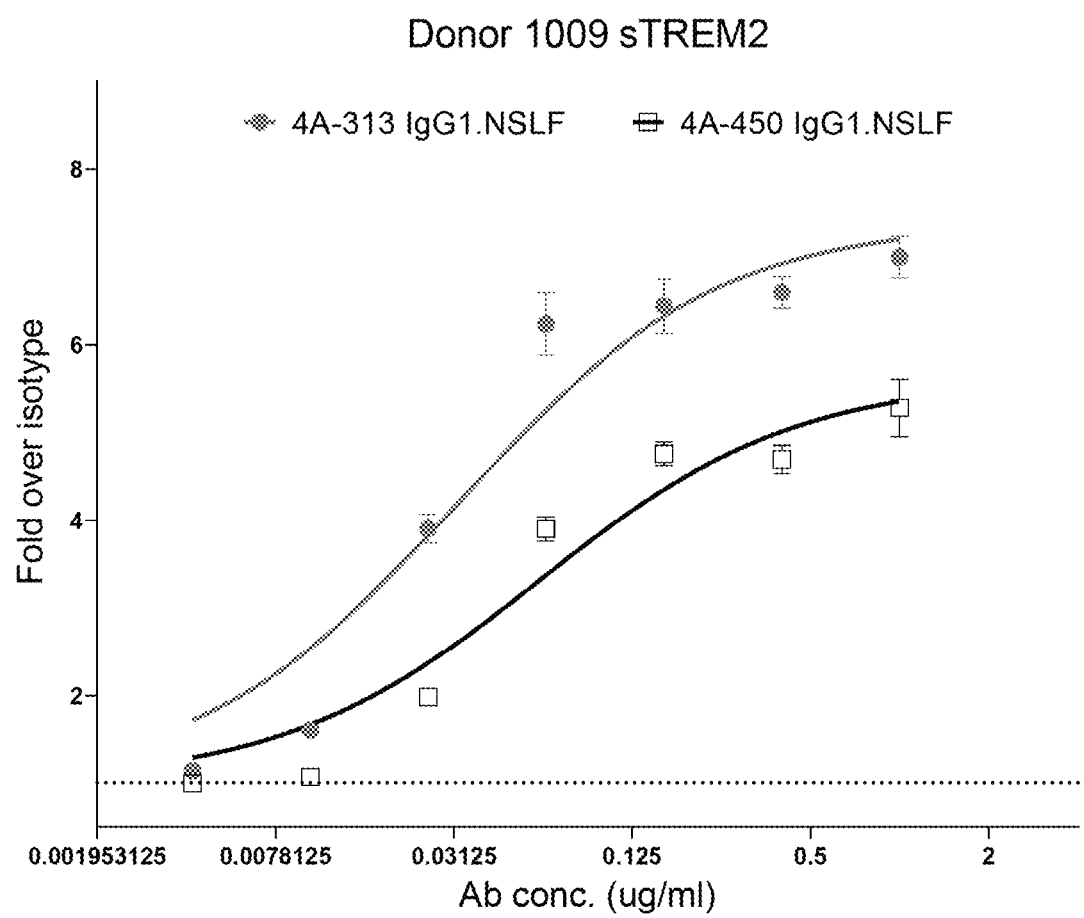
FIGS. 26A, 26B, and 26C set forth data showing a dose-dependent increase in soluble TREM2 levels in primary human macrophages from three different donors following addition of anti-MS4A4A antibodies of the present disclosure.
Figure 26B:
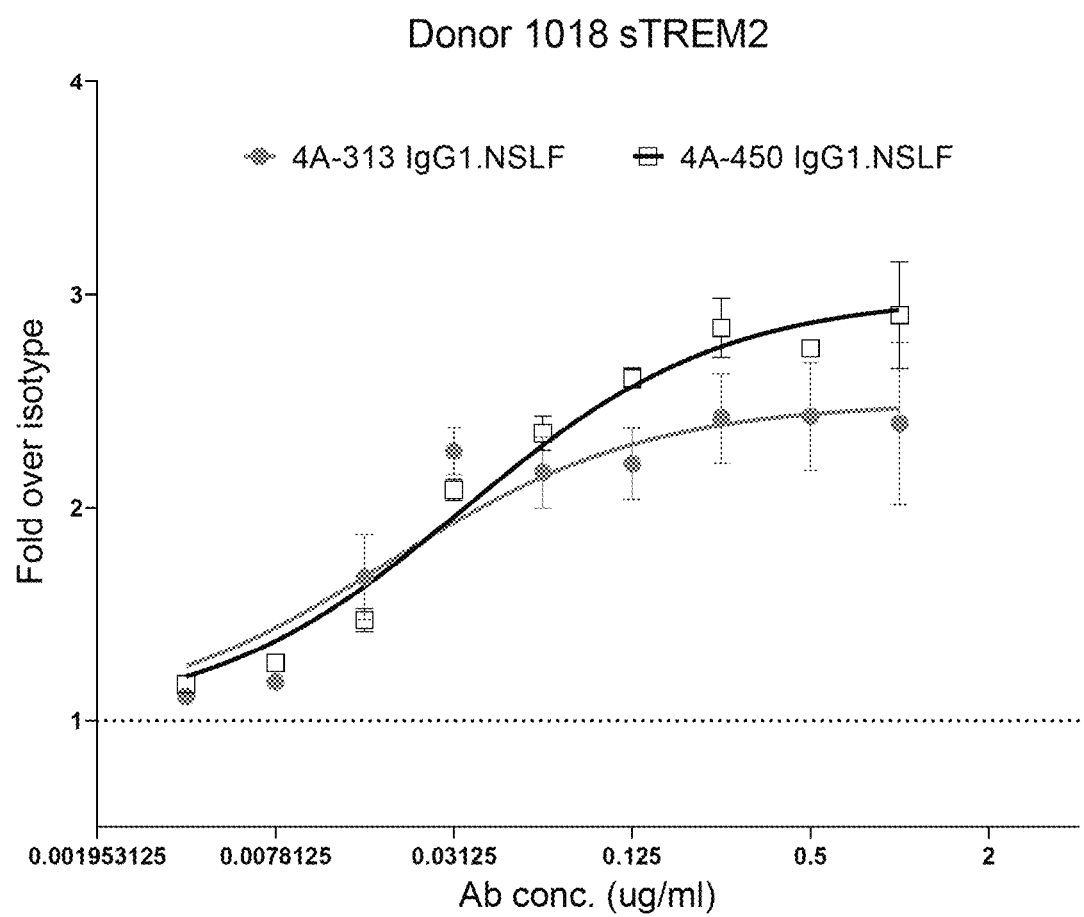
Figure 26C:
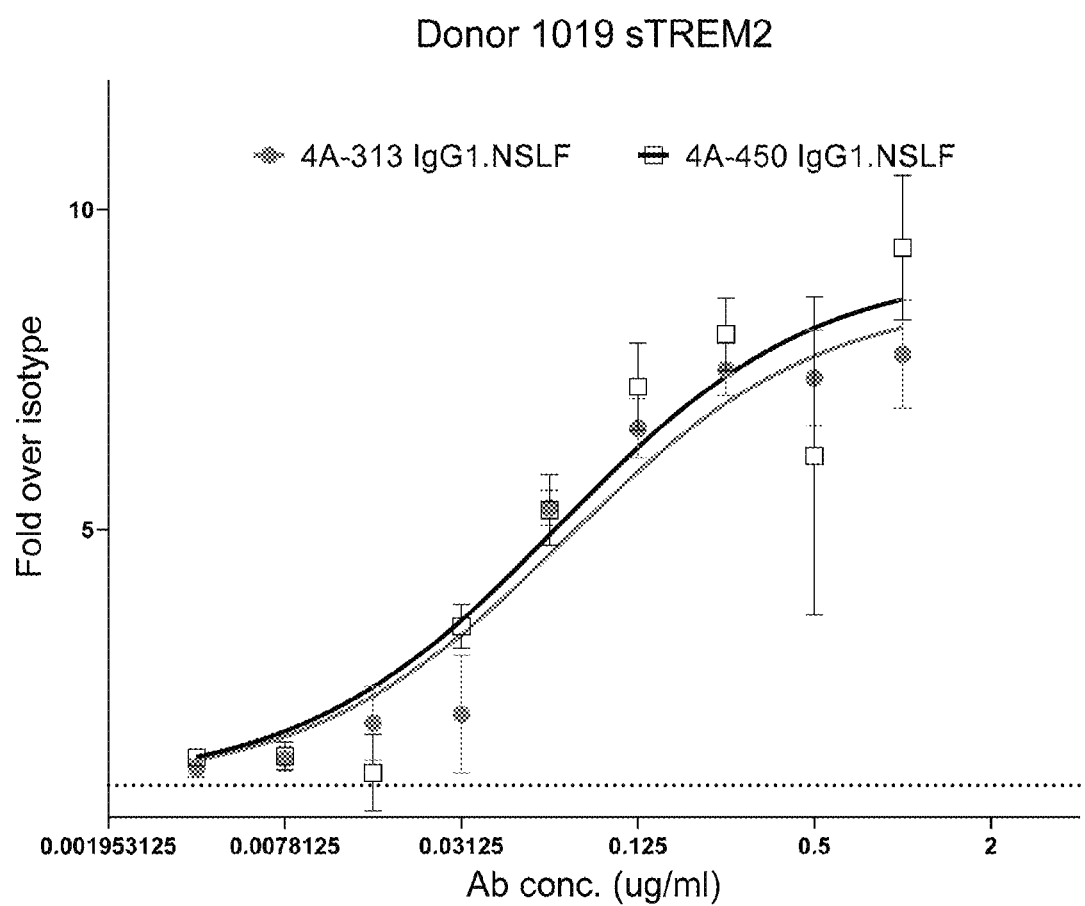

As shown in FIG. 26A, FIG. 26B, and FIG. 26C, anti-MS4A4A antibody 4A-313.NSLF and anti-MS4A4A antibody 4A-450.NSLF increased levels of sTREM2 in a dose-dependent manner in primary human macrophages obtained from three different donors, respectively. Data in FIG. 26A, FIG. 26B, and FIG. 26C is presented as fold-increase in the levels of sTREM2 over that observed using an isotype control antibody (the x-axis shows antibody concentrations (μg/ml) and the y-axis shows fold-increase above control, which was set at 1.0). Data from these graphs were analyzed to determine EC50 values and maximum response; these results are shown below in Table 42 (shown as mean+/−SEM).

TABLE 42

| Antibody | EC50 (μg/ml) | Max sTREM2 Response (fold increase over isotype control) |
|---|---|---|
| 4A-313.NSLF | 0.025 +/− 0.007 | 6.17 +/− 1.90 |
| 4A-450.NSLF | 0.069 +/− 0.006 | 5.74 +/− 1.65 |

Figure 27A:
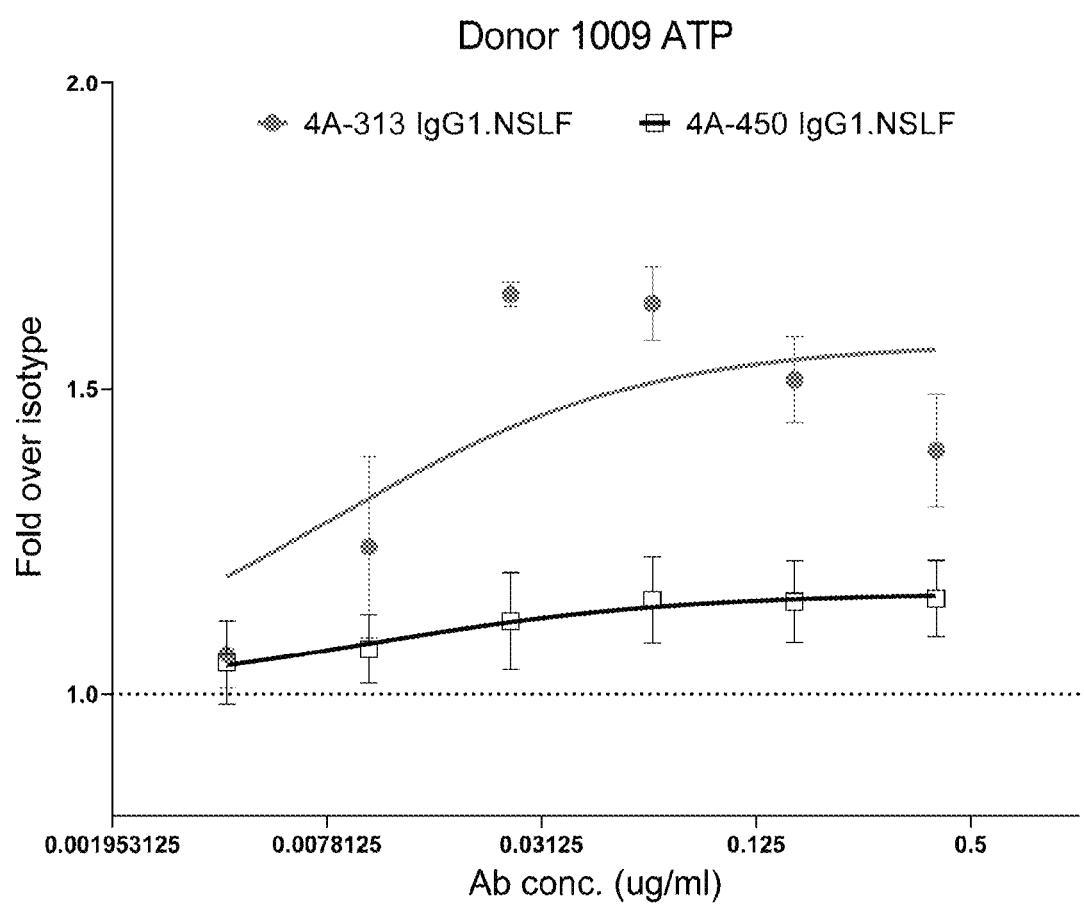
FIGS. 27A, 27B, and 27C set forth data showing a dose-dependent increase in ATP levels in primary human macrophages from three different donors following addition of anti-MS4A4A antibodies of the present disclosure.
Figure 27B:
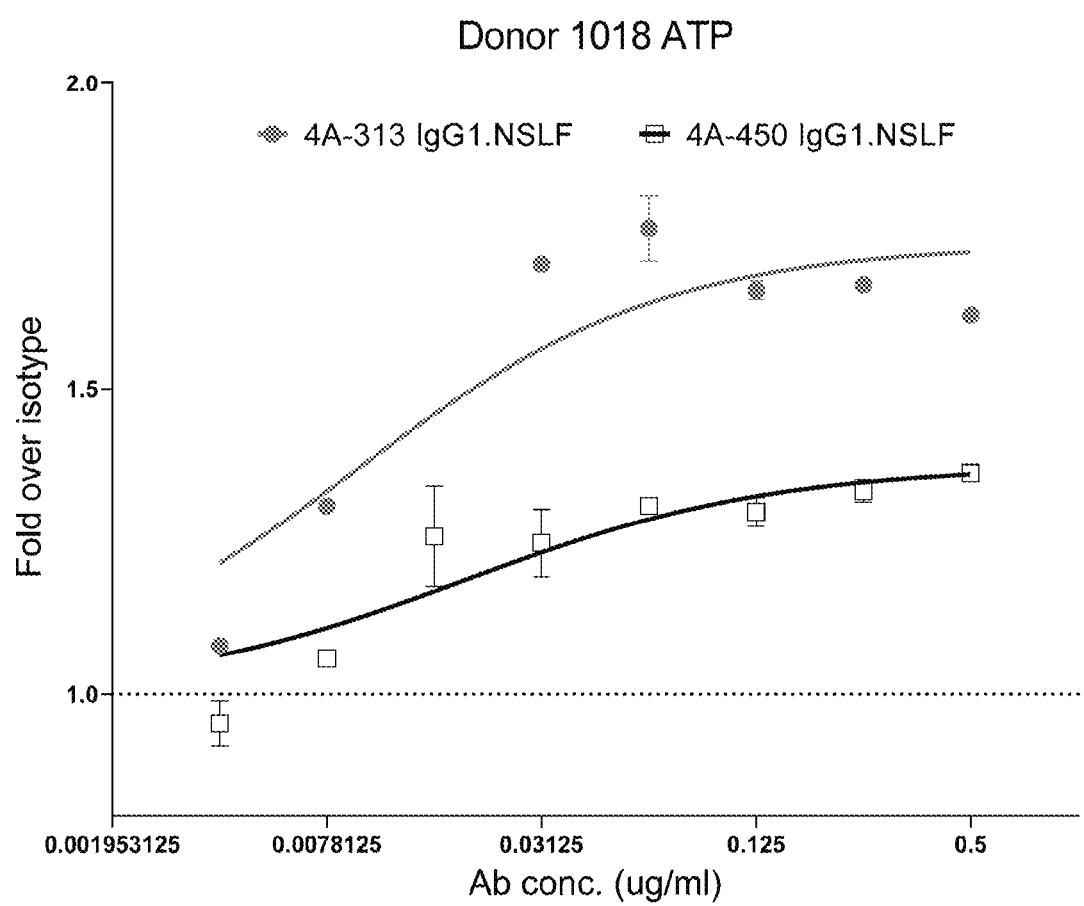
Figure 27C:
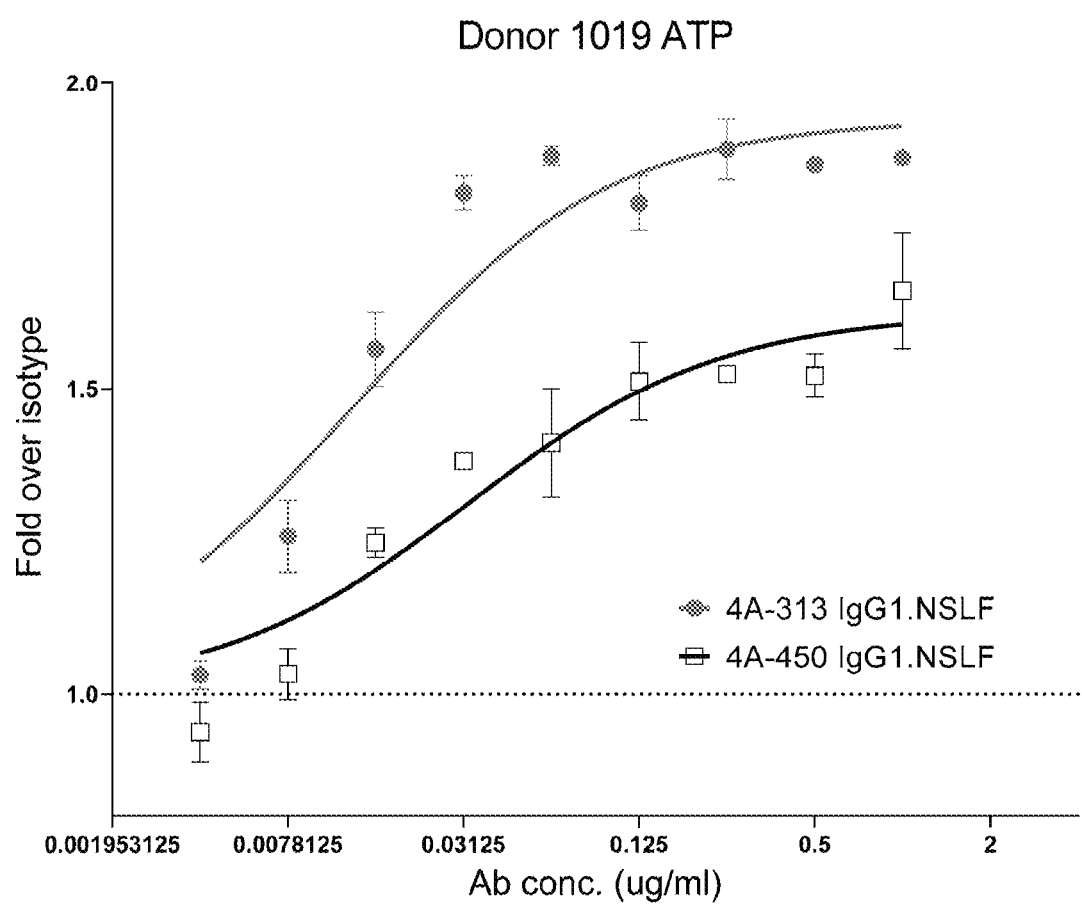

As shown in FIG. 27A, FIG. 27B, and FIG. 27C, anti-MS4A4A antibody 4A-313.NSLF and anti-MS4A4A antibody 4A-450.NSLF increased levels of cellular ATP in a dose-dependent manner in primary human macrophages obtained from three different donors, respectively. Data in FIG. 27A, FIG. 27B, and FIG. 27C is presented as fold-increase in the levels of cellular ATP over that observed using an isotype control antibody (the x-axis shows antibody concentrations (μg/ml) and the y-axis shows fold-increase above control, which was set at 1.0). Data from these graphs were analyzed to determine EC50 values and maximum response; these results are shown below in Table 43 (shown as mean+/−SEM).

TABLE 43

| Antibody | EC50 (μg/ml) | Max Cellular ATP Response (fold increase over isotype control) |
|---|---|---|
| 4A-313.NSLF | 0.010 +/− 0.001 | 1.76 +/− 0.10 |
| 4A-450.NSLF | 0.021 +/− 0.006 | 1.43 +/− 0.10 |

Taken together, these results showed that anti-MS4A4A antibodies of the present disclosure induced functional changes in primary human macrophages as evidenced by increased levels of mTREM2, sTREM2, and cellular ATP following antibody addition.

Example 36

Anti-MS4A4A Antibodies Rescue CSF1R Inhibition Induced Cell Death

To evaluate the ability of MS4A4A to sustain survival of human macrophages after CSF1R inhibition, anti-MS4A4A antibodies of the present disclosure were studied for their ability to enhance cell survival in the presence of a CSF1R inhibitor, PLX3397 (See DeNardo et al., Cancer Discov (2011) 1(1):54-67. 22039576); Peng, et al., J. of Exp Canc Res (2019) 38(1):372. PMID: 31438996).

Human monocytes were isolated from whole blood using RosetteSep Human Monocyte Enrichment Protocol (Stem Cell Technologies). To prepare human monocyte derived macrophages, monocytes were counted and plated in complete RPMI media (RPMI supplemented with Glutamax, penicillin/streptomycin, non-essential amino acids, sodium-pyruvate, and 10% heat inactivated fetal bovine serum) and 50 ng/ml MCSF (Peprotech). After 6 days, differentiated monocytes (macrophages) were harvested and plated onto 96-well plates at a density of $0.1 \times 10^6$ cells/well in complete RPMI media with 50 ng/ml M-CSF. Macrophages were allowed to recover overnight. On Day 7, anti-MS4A4A antibodies 4A-313.NSLF and 4A-450.NSLF were added to the cultured macrophages with and without PLX3397 (1 μM). All antibodies were added at a final concentration of 1 μg/ml. Cell viability was determined using cytotox red reagent, a DNA dye that labels dying cells (Essen Bioscience). The level of cytotox red reagent was determined by measuring fluorescence signal over several days using the IncuCyte Live Cell imaging system (Essen Bioscience).

Figure 28A:
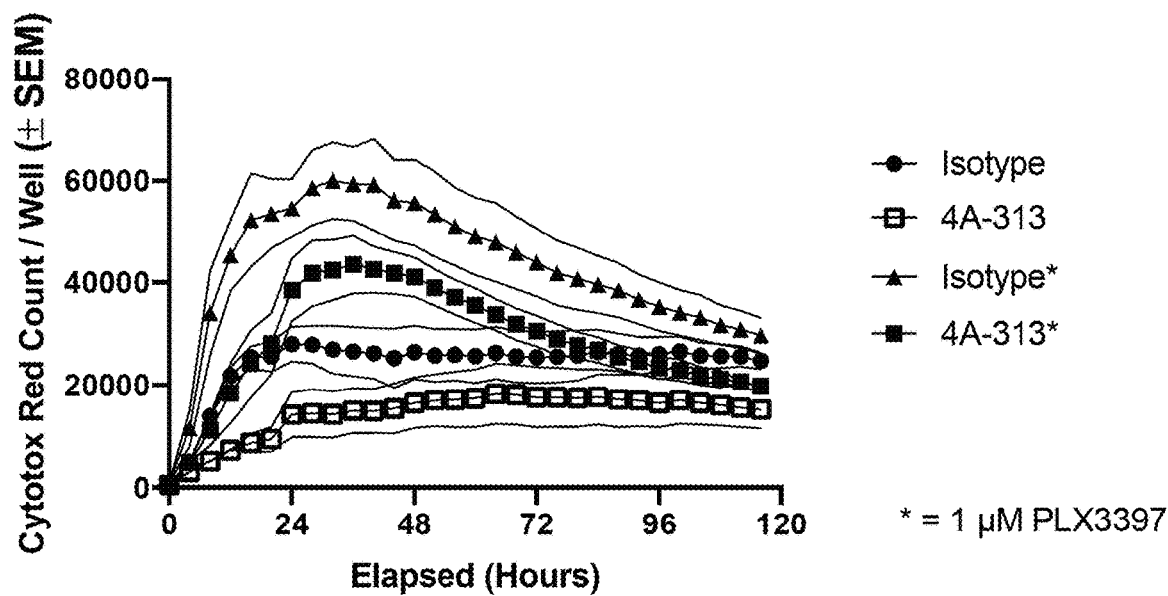
FIGS. 28A and 28B set forth data showing anti-MS4A4A antibodies of the present disclosure are effective at rescuing CSF1R inhibition-induced cell death.

As shown in FIG. 28A, human macrophages treated with PLX3397 and anti-MS4A4A antibody 4A-313.NSLF showed a decrease in cytotox red count compared to that observed in cells treated with PLX3397 plus isotype control antibody. Data in FIG. 28A are graphed as mean±SEM; N=3 from three human donors.

Figure 28B:
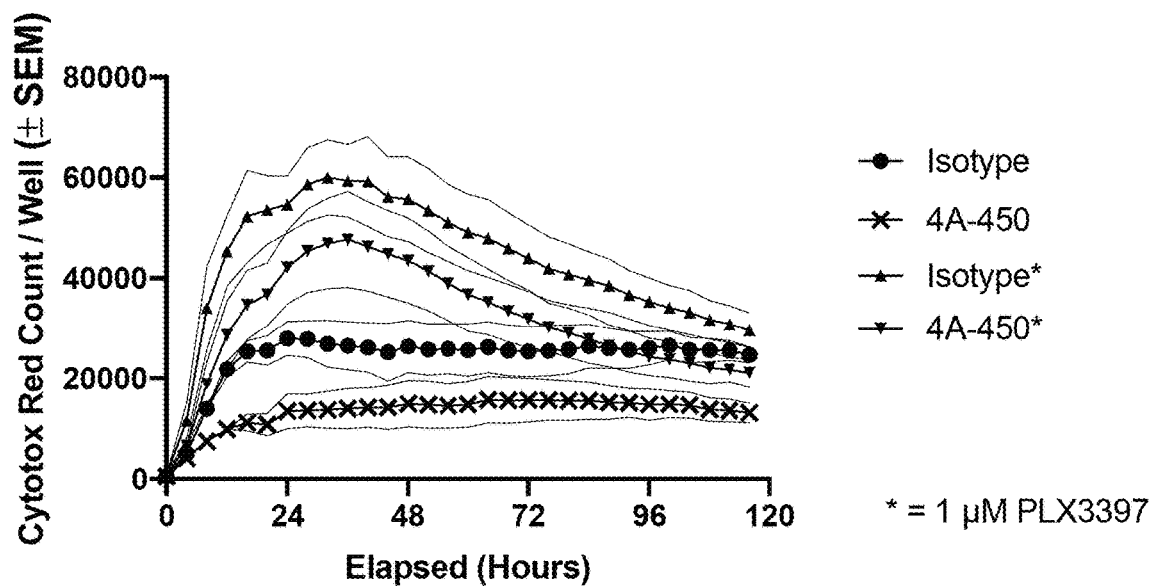

As shown in FIG. 28B, human macrophages treated with PLX3397 and anti-MS4A4A antibody 4A-450.NSLF showed a decrease in cytotox red count compared to that observed in cells treated with PLX3397 plus isotype control antibody. Data in FIG. 28B are graphed as mean±SEM; N=3 from three human donors.

Taken together, these results showed that anti-MS4A4A antibodies of the present disclosure reduced cell death and sustained survival of human macrophages following CSF1R inhibition. Accordingly, the anti-MS4A4A antibodies of the present disclosure are useful for treating an individual having a CSF1R-deficient disease or disorder, such as ALSP or HDLS.

Example 37

Pharmacokinetics of Anti-MS4A4A Antibodies in Cynomolgus Monkey Serum

To examine the pharmacokinetics (PK) of anti-MS4A4A antibodies of the present disclosure in serum in vivo, the following studies were performed.

Cynomolgus monkeys (cyno) were administered anti-MS4A4A antibodies 4A-21.WT, 4A-25.WT, 4A-18.WT, or isotype control (huIgG1) at doses of 80 mg/kg by intravenous bolus injection. Each animal group was administered a total of five doses; the first and second doses separated by an interval of 28 days and the remaining four doses were separated by an interval of 7 days between each dose.

Serum samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

Levels of anti-MS4A4A antibodies 4A-21.WT, 4A-25.WT, and 4A-18.WT in cynomolgus monkey serum were measured using a custom Gyrolab assay based on a stepwise sandwich format with a biotin labeled Goat anti-human IgG (Cat no. NBPI-74983; Novus Biologicals) as the capturing reagent and an Alexa fluor® 647 labeled anti-human IgG (Cat no. 2049-31 Southern Biotech) as the detection reagent. Standards, quality controls, and samples were diluted in Rexxip HN buffer (Cat no. P0004996, Gyrolab). Anti-MS4A4A antibodies present in samples were captured by the biotinviated anti-human IgG bound to the streptavidin coated affinity column of the gyrolab bioaffy 200 CD. Captured anti-MS4A4A antibodies were detected by the fluorescently labelled anti-human IgG antibody. The intensity of the fluorescent signals produced were proportional to the amount of anti-MS4A4A antibodies present in the sample. Data was analyzed using Gyrolab xP and Excel.

Following administration of an 80 mg/kg dose to the animals, anti-MS4A4A antibody concentrations in the serum steadily declined after reaching mean maximum observed concentration ($C_{max}$), with an average half-life ($t_{1/2}$) value (mean±SD) of 140±54.5 hours for anti-MS4A4A antibody 4A-21.WT, 269±114 hours for anti-MS4A4A antibody 4A-25.WT, and 193±26.8 hours for anti-MS4A4A antibody 4A-18.WT after day 1 (day of first dose) administration. The clearance (CL) was inversely proportional to $t_{1/2}$ with an average CL (mean±SD) of 0.625±0.107 mL/hr/kg for antibody 4A-21.WT, 0.124±0.025 mL/hr/kg for antibody 4A-25.WT, and 0.402±0.09 mL/hr/kg for antibody 4A-18.WT on Day 1. The steady state volume of distribution (Vss) values on day 1 ranged from 30.8 to 51.4 mL/kg, 22.6 to 41.7 mL/kg, and 24.9 to 41.3 mL/kg for antibody 4A-21.WT, 4A-25.WT, 4A-18.WT groups, respectively.

Exposure was assessed by $C_{max}$ and area under the concentration-time curve from 0 to 168 hours post dose ($AUC_{0-168}$). On day 1, antibody 4A-25.WT had the highest mean $C_{max}$ (6.26×10$^6$ ng/mL), followed by antibody 4A-18.WT (4.81×10$^6$ ng/mL). Anti-MS4A4A antibody 4A-21.WT (3.53×10$^6$ ng/mL) had the lowest $C_{max}$ amongst the test articles.

Anti-MS4A4A antibodies 4A-25.WT and 4A-18.WT had similar $AUC_{0-168}$ (3.47×10$^8$ ng*hr/mL and 3.35×10$^8$ ng*hr/mL, respectively), that was significantly higher than that of antibody 4A-21 (1.15×10$^8$ ng*hr/mL).

Example 38

Anti-MS4A4A Antibodies Increase Serum and CSF sTREM2 Levels In Vivo

To examine the effect of anti-MS4A4A antibodies of the present disclosure on sTREM2 levels in serum and cerebrospinal fluid (CSF) in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/kg by intravenous bolus injection. Each group was administered a total of five doses; the first and second doses separated by an interval of 28 days and the remaining four doses were separated by an interval of 7 days between each dose.

Serum samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody. CSF samples were also collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

In serum, following the administration of anti-MS4A4A antibodies 4A-25.WT, 4A-18.WT, and 4A-21.WT, sTREM2 levels increased greater than 2-fold from baseline, with peak levels of 232%, 261%, and 287%, respectively, of their pre-dose baseline levels, 48 to 96 hours after administration of the first antibody dose. Furthermore, the levels of sTREM2 in the serum remained elevated with repeated weekly dosing of anti-MS4A4A antibodies on days 29, 36, 43, and 50 with average sTREM2 levels approximately 2-fold (214%, 4A-25.WT; 226%, 4A-18.WT; 199%, 4A-21.WT) above that observed at pre dose baseline levels. The isotype control remained close to predose levels (107% of baseline) throughout the dosing period.

In the CSF, sTREM2 levels significantly increased at 24 and 96 hours following the administration of anti-MS4A4A antibodies 4A.21.WT (p=0.0008, 2-way ANOVA) and 4A-25.WT (p=0.004, 2-way ANOVA), respectively, compared to that observed in isotype control treated animals. The sTREM2 levels in the 4A-18.WT treated group remained similar to that observed in the isotype control group.

Taken together, these results showed that anti-MS4A4A antibodies of the present disclosure are effective at increasing sTREM2 levels in both serum and CSF in vivo.

Example 39

Anti-MS4A4A Antibodies Increase CSF Osteopontin Levels In Vivo

To examine the effect of anti-MS4A4A antibodies of the present disclosure on osteopontin levels in CSF in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/kg by intravenous bolus injection. Each group was administered a total of five doses; the first and second doses separated by an interval of 28 days and the remaining four doses were separated by an interval of 7 days between each dose. CSF samples were collected from the animals at pre-dose, 0.5, 4, 6, 10, 12, 24, 48, 96, 168, 192, 264, 312, 336, 480, 504, 648, 672, 672.5, 684, 720, 840, 840.5, 852, 888, 1008, 1008.5, 1014, 1020, 1032, 1056, 1104, 1176, 1188, and 1224 hours post administration of antibody.

Anti-MS4A4A antibodies 4A-25.WT, 4A-18.WT, and 4A-21.WT significantly increased osteopontin levels in the CSF compared to that observed with isotype control antibody. Repeat administration of anti-MS4A4A antibody 4A-21.WT resulted in significantly increased CSF osteopontin levels that peaked at 12 hours post first dose to approximately 280 ng/ml (p<0.0001, 2-way ANOVA) compared to the isotype control and continued to show peak levels at 12 to 24 hours post subsequent doses. Repeat administration of anti-MS4A4A antibody 4A-25.WT and antibody 4A-18.WT showed a trend in increased CSF osteopontin levels 12 to 24 hours (to levels of approximately 50-80 ng/ml) after each dose compared to the isotype control.

These results showed that anti-MS4A4A antibodies of the present disclosure are effective at increasing osteopontin levels in CSF in vivo.

Example 40

Anti-MS4A4A Antibodies Increase Osteopontin Levels In Various Brain Regions In Vivo To examine the effect of anti-MS4A4A antibodies of the present disclosure on osteopontin levels in the frontal cortex and hippocampus of cynomolgus monkeys in vivo, the following studies were performed.

Cynomolgus monkeys were administered anti-MS4A4A antibodies 4A-21.WT, 4A-25.WT, 4A-18.WT, or isotype control (huIgG1) at doses of 80 mg/ml by intravenous bolus injection. Each group was administered a total of five doses; the first and second doses were separated by an interval of 28 days between each dose, and the remaining four doses were separated by an interval of 7 days between each dose. The animals were euthanized 48 hours after the fifth dose and the frontal cortex and hippocampus were removed and frozen.

Osteopontin levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Osteopontin levels in the brain tissue of cynomolgus monkeys increased after treatment with anti-MS4A4A antibody 4A-21.WT. Repeat administration of anti-MS4A4A antibody 4A-21.WT to cynomolgus monkeys resulted in significantly increased (p<0.035 and p=0.0003, respectively; 1-way ANOVA) osteopontin levels in the frontal cortex of cynomolgus monkeys when compared to that observed with isotype control antibody. In particular, mean osteopontin levels measured in the frontal cortex following antibody administration were as follows: approximately 0.6 ng/mg (isotype control antibody); approximately 1.2 ng/mg (4A-21.WT); approximately 0.7 ng/mg (4A-25.WT and 4A-18.WT). Repeat administration of anti-MS4A4A antibodies resulted in a trend in increased osteopontin levels in the hippocampus of cynomolgus monkeys when compared to that observed with isotype control antibody. In particular, mean osteopontin levels measured in the hipposcampus following antibody administration were as follows: approximately 1.3 ng/mg (isotype control antibody); approximately 1.8 ng/mg (4A-21.WT and 4A-18.WT); and approximately 2.4 ng/mg (4A-25.WT). These results showed that anti-MS4A4A antibodies of the present disclosure are effective at increasing osteopontin levels in the frontal cortex and hippocampus in non-human primates.

Example 41

Effect of Anti-MS4A4A Antibodies on CSF Protein Biomarkers

Cerebral spinal fluid obtained from cynomolgus monkeys administered a peripheral injection of anti-MS4A4A antibody 4A-21.WT (80 mg/kg) was further analysed for changes in protein biomarker expression in vivo. In these studies, changes in protein expression levels in CSF were measured using Somalogic Somascan 1.3 k assay performed on CSF samples obtained from the animals 24-hours following injection of the antibody.

Figure 29:
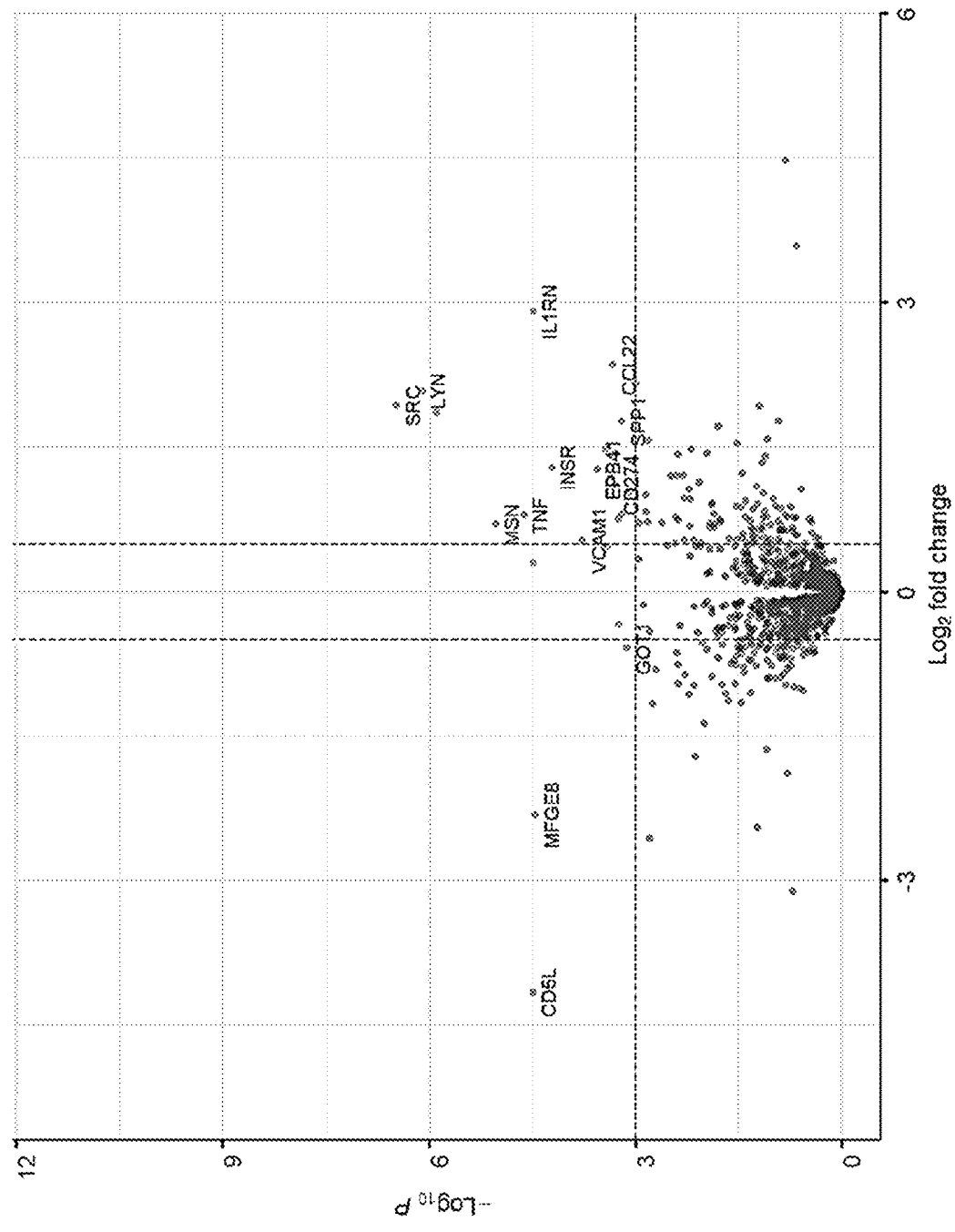
FIG. 29 shows a volcano plot of proteome-wide effects in cynomolgus monkey CSF following administration of an anti-MS4A4A antibody of the present disclosure.

Protein changes in CSF were observed following administration of anti-MS4A4A antibody 4A-21.WT to cynomolgus monkeys. FIG. 29 is a volcano plot presenting the proteome-wide effects from three CSF samples taken from cynomolgus monkeys after peripheral injection of anti-MS4A4A antibody 4A-21.WT (80 mg/kg). Each dot in the volcano plot represents 1 protein. For each measured protein, values on the x-axis represent the fold-change difference in a protein's levels in CSF between antibody treated animals and control animals; values on the y-axis represents the significance of these observed differences, expressed as the minus log 10 of the p-value for differential expression, assessed by ANOVA. Protein symbols in FIG. 29 are presented for proteins differentially expressed in antibody-treated vs control animals with a p-value of <1E-3.

As shown in FIG. 29, an increase in CSF levels of osteopontin (SSP1) and IL1RN (2 microglial markers) was observed in animals administered anti-MS4A4A antibody. Taken together, these results showed that anti-MS4A4A antibodies of the present disclosure increased IL1RN and osteopontin protein levels in both CSF and serum of non-human primates.

Example 42

Anti-MS4A4A Antibodies Increase Serum sTREM2 Levels In Vivo

The effect of anti-MS4A4A antibodies of the present disclosure on sTREM2 levels in serum and cerebrospinal fluid (CSF) in vivo was examined further in another series of experiments performed in non-human primates.

Cynomolgus monkeys were administered anti-MS4A4A antibodies 4A-313.NSLF, 4A-313.WT, and 4A-450.NSLF at doses of 80 mg/ml; anti-MS4A4A antibody 4A-313.NSLF at doses of 250 mg/ml, or vehicle control by intravenous bolus injection. Each group was administered a total of four doses; the first and second doses separated by an interval of 7 days, the second and third doses separated by an interval of 14 days, and the third and fourth doses separated by an interval of 28 days.

Serum samples were collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody; CSF samples were also collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody.

sTREM levels in serum were measured as follows. Single spot Meso Scale Discovery (MSD) plates (Rockville, Md.) were coated with a capture antibody in PBS at 4° C. overnight. Monkey serum samples (as well as monkey TREM2-Fc standards) were diluted in binding buffer and added to the wells for 1 hour at room temperature. Biotinylated goat anti-human TREM2 polyclonal antibody (R&D Systems) was added at a 1:2,000 dilution in binding buffer and incubated for 1 hour at room temperature, followed by detection with sulfo tag streptavidin (MSD). 150 μl of 1× Read Buffer was added to the plates, and the plates were then analyzed.

Figure 30:
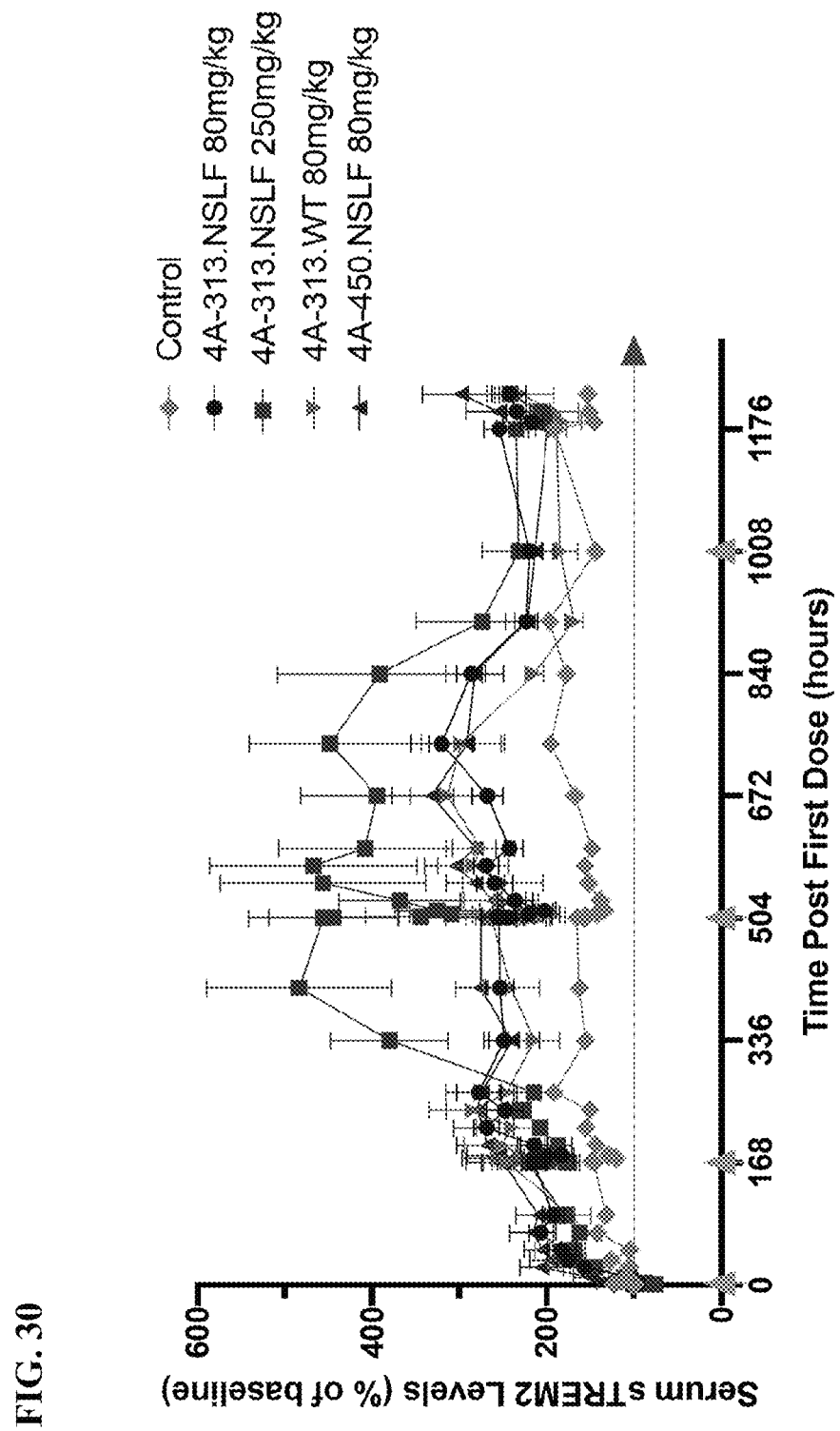
FIG. 30 sets forth data showing increased sTREM2 levels in cynomolgus monkey serum following administration of anti-MS4A4A antibodies of the present disclosure.

Results of these studies are shown in FIG. 30. In serum, sTREM2 levels increased approximately 1.5-fold above that observed at baseline (~150% of predose baseline levels) following administration of anti-MS4A4A antibody 4A-313.NSLF at 80 mg/kg, at 24 hours post dose. Levels of sTREM2 continued increasing over time, reaching maximum levels of 3-fold above that observed at baseline (~300% of predose baseline levels) after multiple doses at 80 mg/kg.

At doses of 250 mg/kg of anti-MS4A4A antibody 4A-313.NSLF, serum sTREM2 levels increased approximately 1.5-fold from that observed at baseline at 24 hours post dose and continued increasing with time, reaching maximum levels of 4.8-fold from that observed at baseline after multiple doses at 250 mg/kg.

Following administration of anti-MS4A4A antibody 4A-313.WT at 80 mg/kg, serum sTREM2 levels increased approximately 1.5-fold from that observed at baseline starting 24 hours post dose. With repeated doses of 4A-313.WT at 80 mg/kg, serum sTREM2 levels increased up to a maximum of 3-fold from that observed at baseline.

Following administration of anti-MS4A4A antibody 4A-450.NSLF at 80 mg/kg, serum sTREM2 levels increased approximately 2-fold from that observed at baseline at 24 hours post dose and continued increasing with time, reaching maximum levels of 3-fold from that obserbed at baseline after multiple doses of 4A-450.NSLF at 80 mg/kg.

Taken together, these results showed that anti-MS4A4A antibodies of the present invention were effective at increasing sTREM2 levels in serum in non-human primates.

Example 43

Anti-MS4A4A Antibodies Increase CSF Osteopontin Levels In Vivo

To examine the effect of anti-MS4A4A antibodies of the present disclosure on osteopontin levels in cerebrospinal fluid (CSF) in vivo, the following studies were performed.

Cynomolgus monkeys were administered anti-MS4A4A antibodies 4A-313.NSLF, 4A-313.WT, 4A-450.NSLF at doses of 80 mg/ml, 4A-313.NSLF at doses of 250 mg/ml, or vehicle control by intravenous bolus injection. Each group was administered a total of four doses; the first and second doses separated by an interval of 7 days, the second and third doses separated by an interval of 14 days, and the third and fourth doses separated by an interval of 28 days.

CSF samples were collected from the animals at pre-dose, 0.5, 2, 6, 10, 24, 34, 48, 72, 96, 168, 168.5, 170, 174, 178, 192, 216, 240, 264, 336, 408, 504, 504.5, 506, 510, 514, 528, 552, 576, 600, 672, 744, 840, 912, 1008, 1176, 1186, 1200, and 1224 hours post administration of antibody.

Osteopontin levels in CSF were measured as follows. Single spot Meso Scale Discovery (MSD) plates (Rockville, Md.) were coated with a capture antibody in PBS at 4° C. overnight. Monkey CSF samples were diluted in binding buffer and added to the wells for 1 hour at room temperature. Biotinylated goat anti-human Osteopontin polyclonal antibody (R&D Systems) was added at a 1:2,000 dilution in binding buffer and incubated for 1 hour at room temperature, followed by detection with sulfo tag streptavidin (MSD). 150 µl of 1× Read Buffer was added to the plates, and the plates were then analyzed on a Sector Imager (MSD).

Figure 31A:
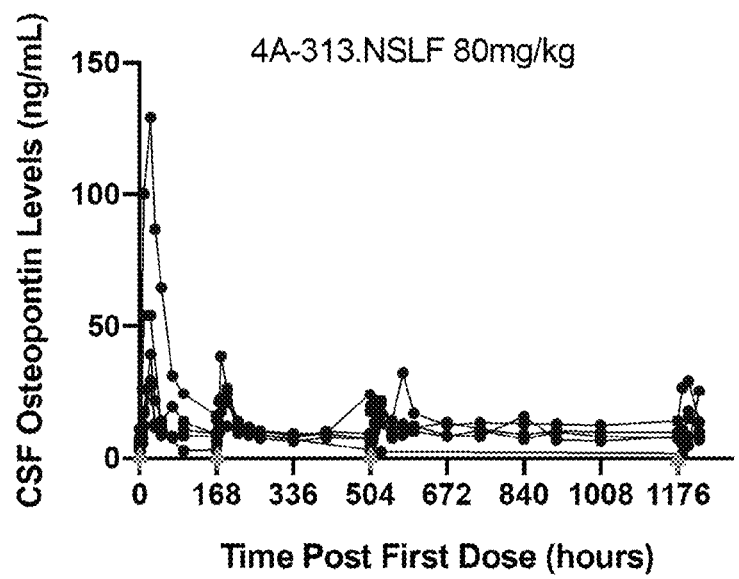
FIGS. 31A, 31B, 31C, and 31D set forth data showing increased osteopontin levels in cynomolgus monkey CSF following administration of anti-MS4A4A antibodies of the present disclosure.
Figure 31B:
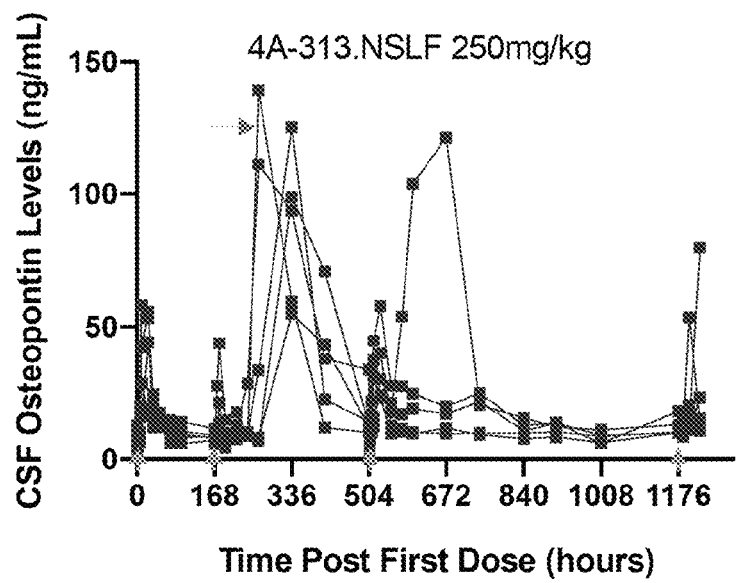

Osteopontin levels in the CSF of cynomolgus monkeys increased after administration of anti-MS4A4A antibodies of the present disclosure. Following administration of anti-MS4A4A antibody 4A-313.NSLF at doses 80 mg/kg and 250 mg/kg, CSF osteopontin levels peaked on average approximately 13-fold and 6-fold from that observed at baseline, respectively, 24 hours post first dose followed by a decline to 1.5-fold of baseline levels (FIGS. 31A and 31B). With repeated dosing of anti-MS4A4A antibody 4A-313.NSLF at 80 mg/kg, CSF osteopontin levels peaked at 10 to 24 hours after each dose, reaching peak levels of 3-fold to 5-fold of that observed at baseline levels (FIG. 31A). With repeated dosing at 250 mg/kg of anti-MS4A4A antibody 4A-313.NSLF, CSF osteopontin levels increased, and reached peak levels of 14-fold from that observed at baseline 168 hours post second dose (FIG. 31B) and peak levels of 4-fold to 5-fold from that observed at baseline 24 to 48 hours post subsequent doses (FIG. 31B).

Figure 31C:
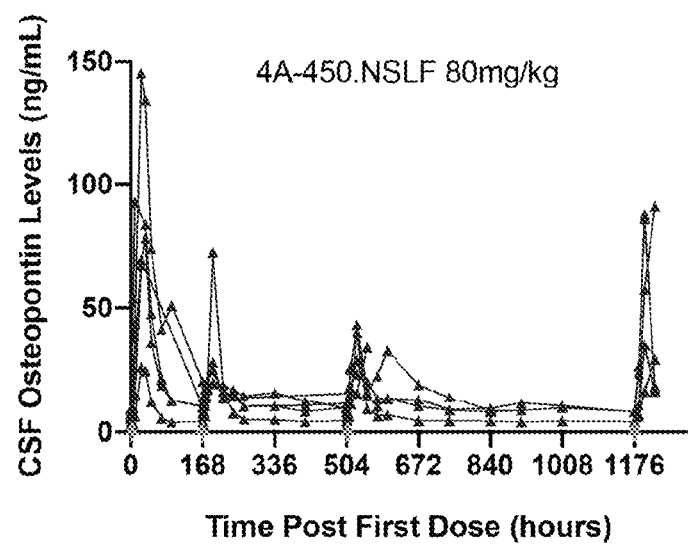
Figure 31D:
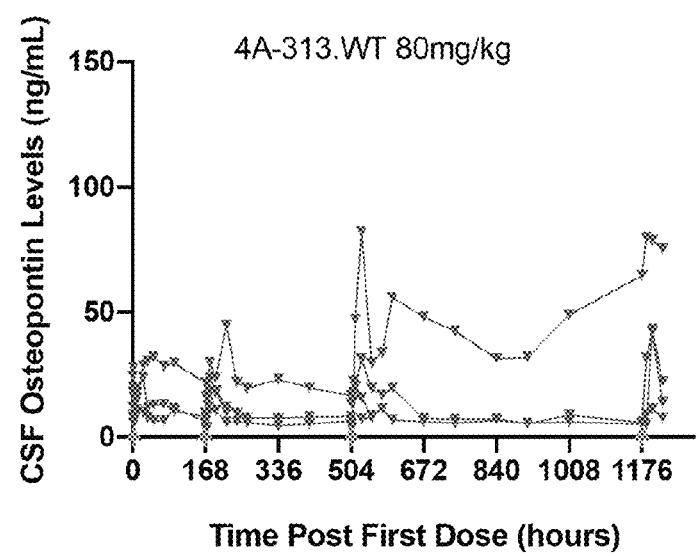

Following administration of anti-MS4A4A antibody 4A-450.NSLF at 80 mg/kg, CSF osteopontin levels peaked approximately 13-fold from that observed at baseline, 24 hours post first dose followed by a decline to baseline levels (FIGS. 31C and 31D). With repeated dosing of 4A-450.NSLF at 80 mg/kg, CSF osteopontin levels peaked at 24 hours after each dose, reaching peak levels of 6-fold to 9-fold from that observed at baseline levels (FIG. 31C).

Following repeated administration of anti-MS4A4A antibody 4A-313.WT at 80 mg/kg, CSF osteopontin levels peaked approximately 1.5-fold from that observed at baseline, 24 hours after each dose followed by a decline to baseline levels (FIG. 31D).

Taken together, these results showed that anti-MS4A4A antibodies of the present disclosure are effective at increasing osteopontin levels in CSF in non-human primates.

Example 44

Anti-MS4A4A Antibodies Increase Osteopontin Levels in Various Brain Regions In Vivo To examine the effect of anti-MS4A4A antibodies of the present disclosure on osteopontin levels in frontal cortex and hippocampus in vivo, the following studies were performed.

Cynomolgus monkeys were administered anti-MS4A4A antibodies 4A-313.NSLF, 4A-313.WT, and 4A-450.NSLF at doses of 80 mg/kg, and anti-MS4A4A antibody 4A-313.NSLF at doses of 250 mg/kg, or vehicle control by intravenous bolus injection. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen.

Osteopontin levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Figure 32A:
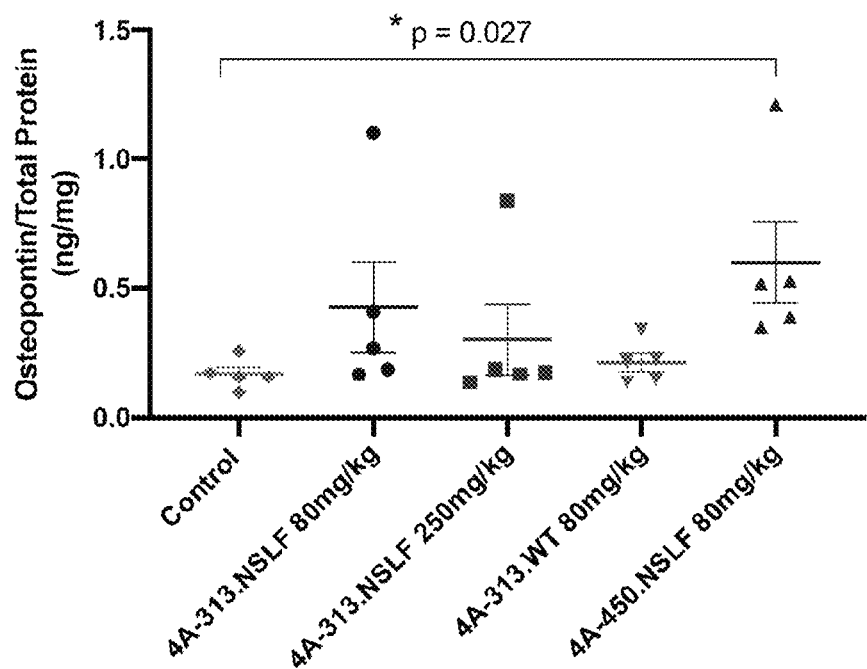
FIGS. 32A and 32B set forth data showing increased osteopontin levels in frontal cortex and hippocampus, respectively, in cynomolgus monkey brains following administration of anti-MS4A4A antibodies of the present disclosure.
Figure 32B:
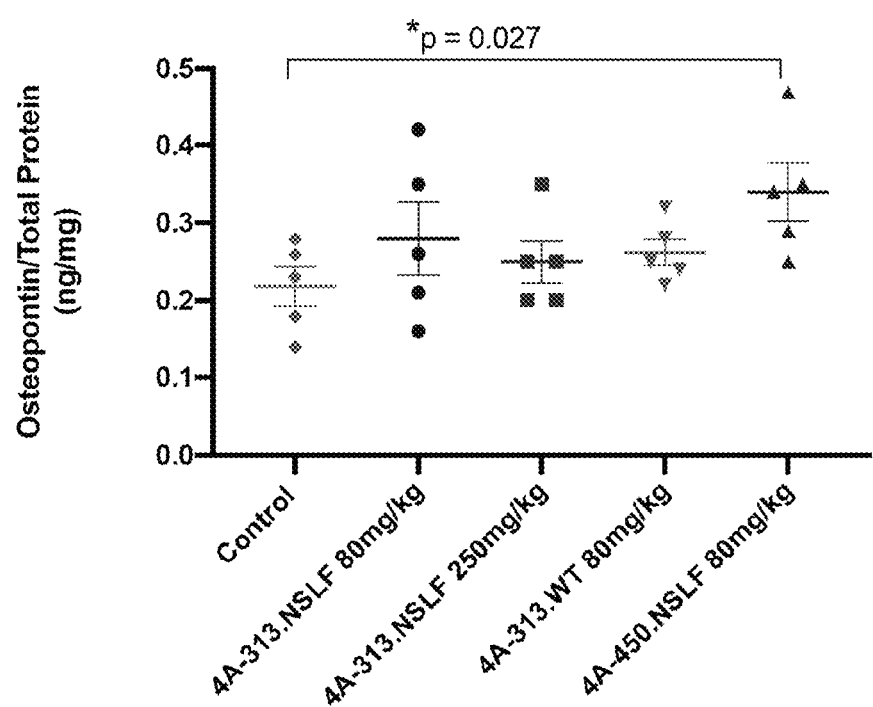

Osteopontin levels in the brain tissue of cynomolgus monkeys increased after administration of anti-MS4A4A antibody 4A-450.NSLF. Repeat administration of antibody 4A-450.NSLF at 80 mg/kg, resulted in significantly increased (p=0.027, t-test) osteopontin levels in the frontal cortex of cynomolgus monkeys when compared to that observed in control animals (FIG. 32A). Similarly, repeat administration of anti-MS4A4A antibody 4A-450.NSLF at 80 mg/kg resulted in significantly increased (p=0.027, t-test) osteopontin levels in the hippocampus of cynomolgus monkeys when compared to that observed in control treated animals (FIG. 32B).

Taken together, these results showed that anti-MS4A4A antibodies of the present disclosure are effectinve at increasing osteopontin levels in brain tissue (e.g., frontal cortex and hippocampus) in non-human primates.

Example 45

Anti-MS4A4A Antibodies Increase CSF1R Levels in Various Brain Regions In Vivo To examine the effect of anti-MS4A4A antibodies of the present disclosure on Colony stimulating factor 1 receptor (CSF1R) levels in the frontal cortex and hippocampus in vivo, the following studies were performed.

Cynomolgus monkeys were administered anti-MS4A4A antibodies 4A-313.NSLF, 4A-313.WT, and 4A-450.NSLF at doses of 80 mg/kg, anti-MS4A4A antibody 4A-313.NSLF at doses of 250 mg/kg, or vehicle control by intravenous infusion. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen.

CSF1R levels in brain tissue were measured as follows. Frozen brain samples were lysed with N-Per Neuronal Protein Extraction Reagent (cat #87792, Thermo Scientific) and Halt Protease inhibitor (cat #1861278) on ice for 20 minutes according to manufacturer instructions. Samples were centrifuged and supernatants were transferred to a new tube and stored at −80° C. until further analysis. The total protein concentration in each sample was measured by BCA protein analysis kit (cat #23225, Thermo Scientific) according to manufacturer instructions. The protein concentration values were used to normalize analyte concentrations measured in brain tissues.

Figure 33A:
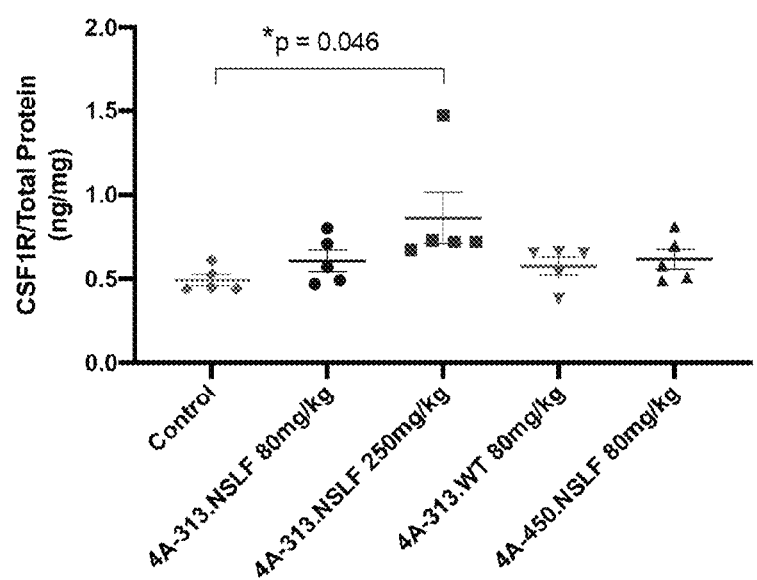
FIGS. 33A and 33B set forth data showing increased CSF1R levels in frontal cortex and hippocampus, respectively, in cynomolgus monkey brains following administration of anti-MS4A4A antibodies of the present disclosure.
Figure 33B:
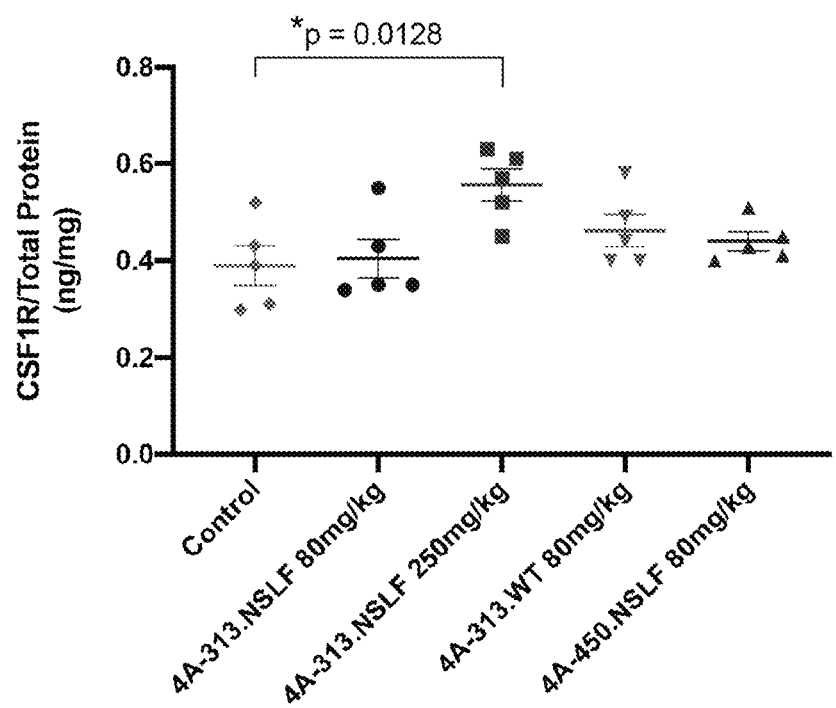

CSF1R levels in the brain tissue of cynomolgus monkeys increased after administration with anti-MS4A4A antibody 4A-313.NSLF. Repeat administration of antibody 4A-313.NSLF at 250 mg/kg resulted in significantly increased ($p=0.046$, t-test) CSF1R levels in the frontal cortex of cynomolgus monkeys when compared to that observed in control treated animals (FIG. 33A). Similarly, repeat administration of anti-MS4A4A antibody 4A-450.NSLF at 80 mg/kg resulted in significantly increased ($p=0.013$, t-test) CSF1R levels in the hippocampus of cynomolgus monkeys when compared to that observed in control animals (FIG. 33B).

Taken together, these results showed that anti-MS4A4A antibodies of the present disclosure are effective at increasing CSF1R levels in brain tissue (e.g., frontal cortex and hippocampus) in non-human primates.

Example 46

Anti-MS4A4A Antibodies Increase Total TREM2 Levels in Various Brain Regions In Vivo To examine the effect of anti-MS4A4A antibodies of the present disclosure on soluble TREM2 and membrane TREM2 (total TREM2) levels in frontal cortex and hippocampus in vivo, the following studies were performed.

Cynomolgus monkeys were administered anti-MS4A4A antibodies, 4A-313.NSLF, 4A-313.WT, 4A-450.NSLF at doses of 80 mg/kg, 4A-313.NSLF at doses of 250 mg/kg, or vehicle control by intravenous bolus injection. Each group was administered a total of four doses; the first and second doses separated by an interval of 7 days, the second and third doses separated by an interval of 14 days, and the third and fourth doses separated by an interval of 28 days. The animals were euthanized 48 hours after the fourth dose and the frontal cortex and hippocampus were removed and frozen. The total TREM2 levels were measured in these brain regions.

Figure 34A:
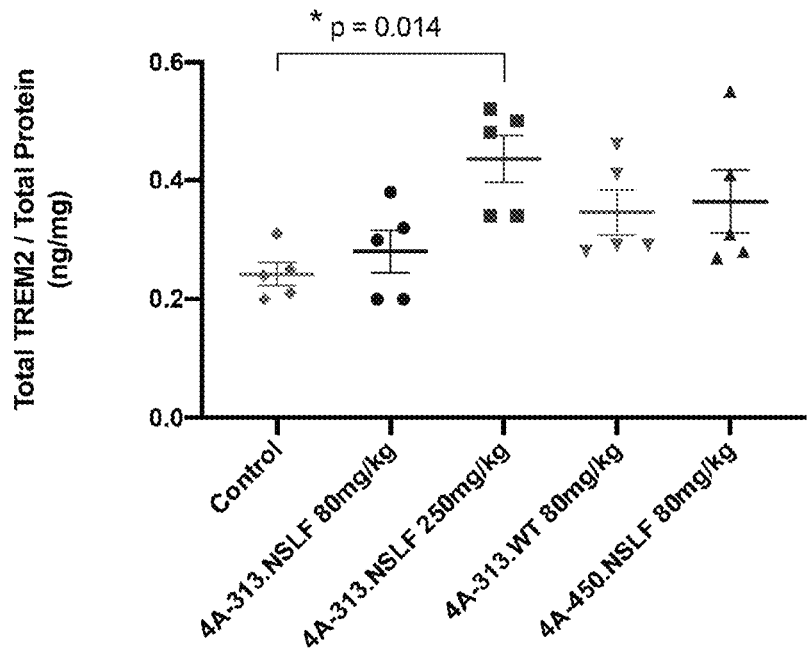
FIGS. 34A and 34B set forth data showing increased total TREM2 protein levels in frontal cortex and hippocampus, respectively, in cynomolgus monkey brains following administration of anti-MS4A4A antibodies of the present disclosure.
Figure 34B:
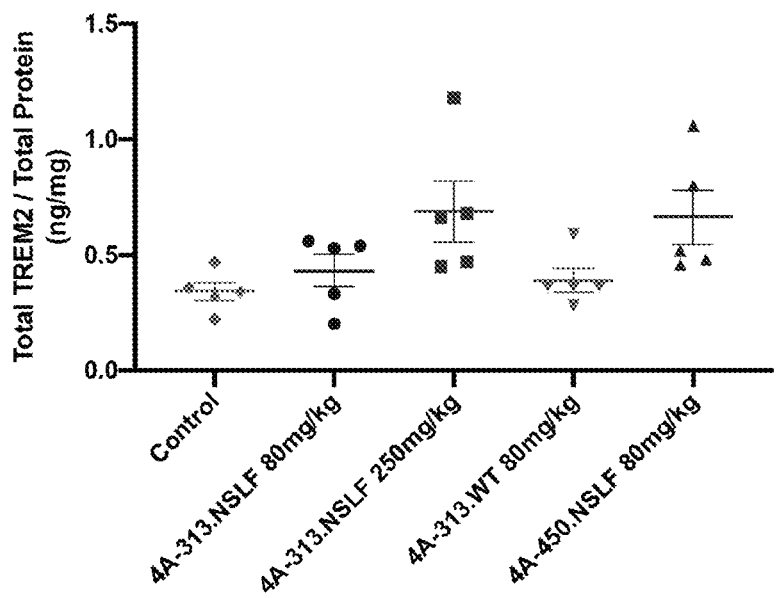

Total TREM2 levels in the brain tissue of cynomolgus monkeys increased after treatment with anti-MS4A4A antibodies, 4A-313.NSLF, 4A-313.WT, and 4A-450.NSLF. Repeat administration of antibody 4A-313.NSLF at 250 mg/kg resulted in a statistically significant increase ($p=0.014$, 1-way ANOVA) in total TREM2 levels in the hippocampus of cynomolgus monkyes compared to that observed in control treated animals (FIG. 34A). Repeat administration of antibody 4A-313.NSLF at 250 mg/kg and antibody 4A-313.WT at 80 mg/kg resulted in a trend in increased TREM2 levels in the frontal cortex of cynomolgus monkeys when compared to that observed in control treated animals (FIG. 34B).

Taken together, these results showed that anti-MS4A4A antibodies of the present disclosure are effective at increasing TREM2 levels in brain tissue (e.g., frontal cortex and hippocampus) in non-human primates.

Example 47

Effect of Anti-MS4A4A Antibodies on Gene Expression Profile in Microglia In Vivo Changes in gene expression as measured by microglia RNAseq analysis following administration of anti-MS4A4A antibodies of the present disclosure to cynomolgus monkeys as described above was performed as follows. The anti-MS4A4A antibodies included antibody 4A-313.WT (80 mg/kg), 4A-313.NSLF (80 mg/kg and 250 mg/kg), and 4A-450.NSLF (80 mg/kg). After terminal take down of the animals, frontal cortex samples were dissociated using a gentle manual dissociation protocol followed by Percoll gradient separation to remove debris. Cell pellet was stained with Cd11b antibodies for 20 minutes, washed, labeled with DAPI and processed for FACS isolation of microglia. DAPI$^-$:CD11b$^+$ cells were sorted directly into 350 ul or RLT plus buffer (Qiagen) and cells were processed immediately for RNA isolation. RNA quality was determined using tape station and libraries were generated using the low input protocol for Lexogen QuantSeq with mild modifications. Libraries were quantitated using tape station and sequenced using Next Seq. Sequenced data was demultiplexed using Lexogen multiple error correction tool and analyzed.

Figure 35A:
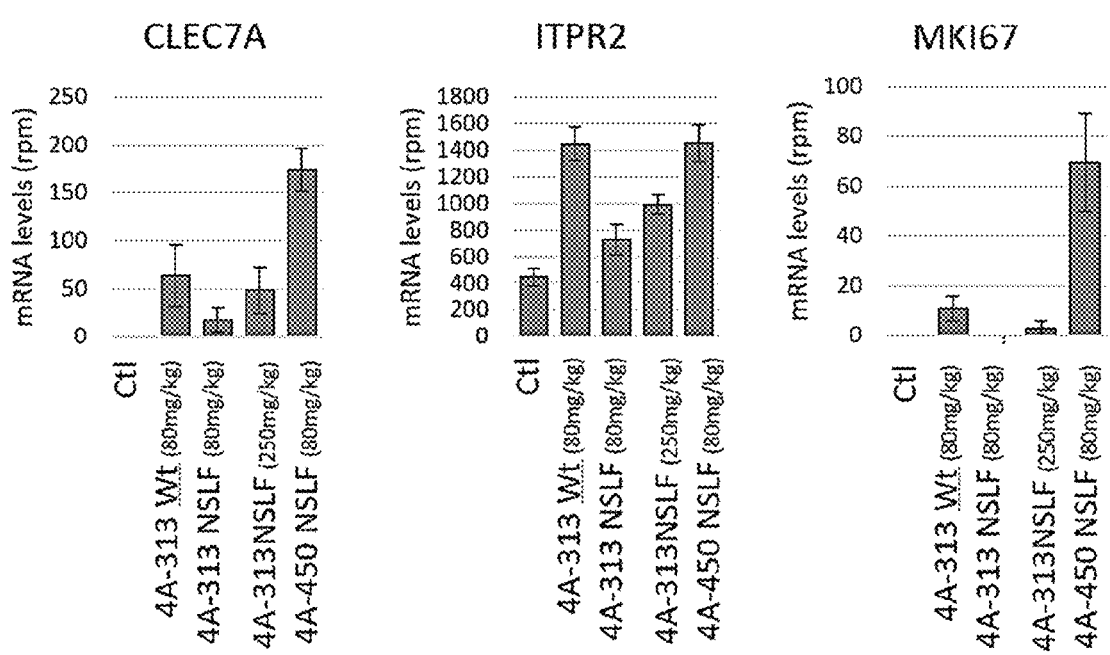
FIGS. 35A, 35B, and 35C set forth data showing changes in mRNA levels in markers of microglia activation, migration, and proliferation in microglia isolated from the brains of cynomolgus monkeys administered anti-MS4A4A antibodies of the present disclosure.
Figure 35B:
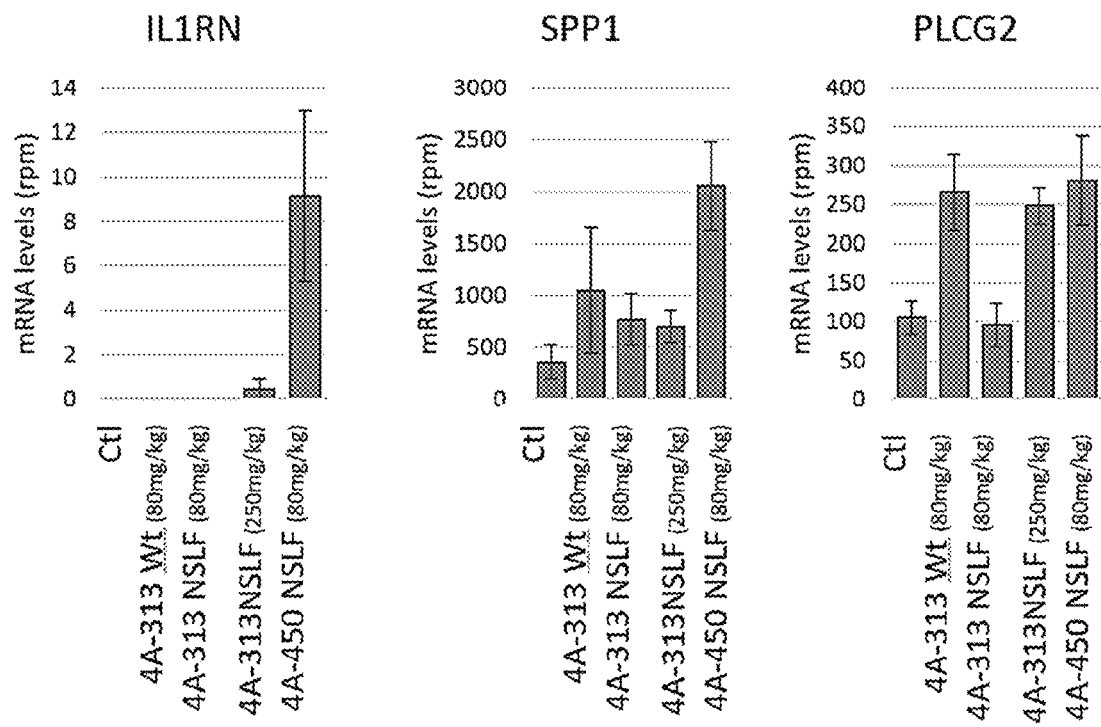
Figure 35C:
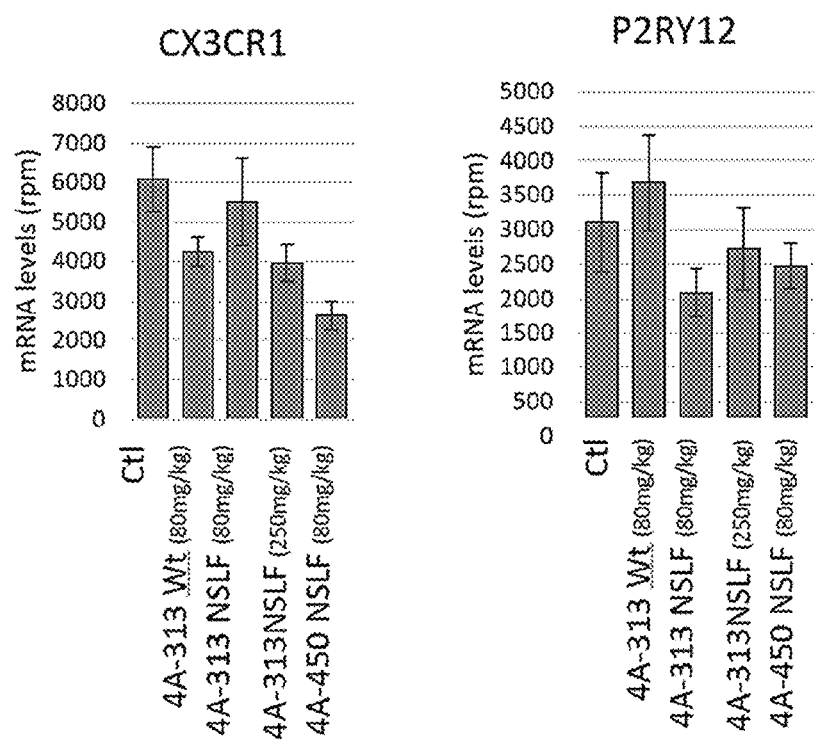

As shown in FIGS. 35A, 35B, and 35C, peripheral injection of anti-MS4A4A antibodies of the present disclosure in cynomolgus monkeys resulted in gene expression changes in microglia as measured by RNAseq analysis in FACS-sorted microglia isolated from the frontal cortex of these non-human primates. Among the genes showing a strong induction by anti-MS4A4A antibody treatment in microglia are markers of microglia activation (C-type lectin domain family 7 member A, CLEC7A), microglia migration (inositol 1,4,5-triphosphate receptor 2, ITPR2), and microglia proliferation (antigen KI-67 (MKI67)) (FIG. 35A). Changes in additional markers of microglia activation were also observed, and included microglia activation markers IL1RN, SPP1, and 1-phosphatidylinositol-4,5-bisphosphate phosphodiesterase gamma-2 (PLCG2) as shown in FIG. 35B. FIG. 35C. The effect of anti-MS4A4A antibodies of the present disclosure on two homeostatic microglia markers (purinergic receptor P2RY12 and CX3C chemokine receptor 1 (CX3CR1)) is shown in FIG. 35C, where the expression levels of these two homeostatic microglia makers decreased following anti-MS4A4A antibody treatment. Data in FIGS.

35A, 35B, and 35C are presented as means on log 2 scale, error bars are SEM, and N=5 per experimental group and per timepoint.

Taken together, these results showed that anti-MS4A4A antibodies of the present disclosure are effective at activating microglia in vivo as evidenced by increases in various mRNA levels of proteins associated with microglia activation, migration, and proliferation; and by decreases in various mRNA levels of proteins associated with microglia homeostasis.

Example 48

Anti-MS4A4A Antibodies Decrease Surface Expression of HA-Snorkel-Tagged MS4A4A on U937 Cells U937 cells (ATCC CRL-1593.2) were transfected with an expression plasmid encoding for human MS4A4A tagged with a snorkel tag (a transmembrane domain followed by a HA-tag was attached to the cytoplasmic C-terminus of the human MS4A4A). In this way the tag is displayed extracellularly, but structurally separate from the membrane protein. Transfected U937 cells were viable after plasmid transfection and antibiotic selection. The cells were then screened for human MS4A4A protein cell surface expression using flow cytometry, and only the 5% most positive cells were collected for use in the following studies.

U937 cells overexpressing recombinant human MS4A4A-snorkel, generated as described above, were used as target cells in these studies. Cells were pretreated for 24 hours with PMA (25 ng/ml), then harvested and seeded at 100,000 cells/well in round-bottom 96 well plates, in RPMI 1640 media complete, with PMA and anti-MS4A4A antibodies and isotype control antibody at the final concentrations of 0.01, 0.1, and 1 ug/ml. Cells were incubated for 48 hours. Cells were washed with cold FACS buffer (PBS+2% FBS) and 50 µL of 1:200 diluted anti-HA Tag Monoclonal Antibody (ThermoFisher, A-21287) was added per well and incubated on ice for 30 minutes, cells were also labeled with Aqua Live/Dead for viability discrimination. Cells were washed 2× with cold FACS buffer and resuspended in 200 µL of FACS buffer. Flow cytometry analysis was performed on a FACSCanto system (BD Biosciences). Binding data was analyzed using Median fluorescent intensity.

Figure 36:
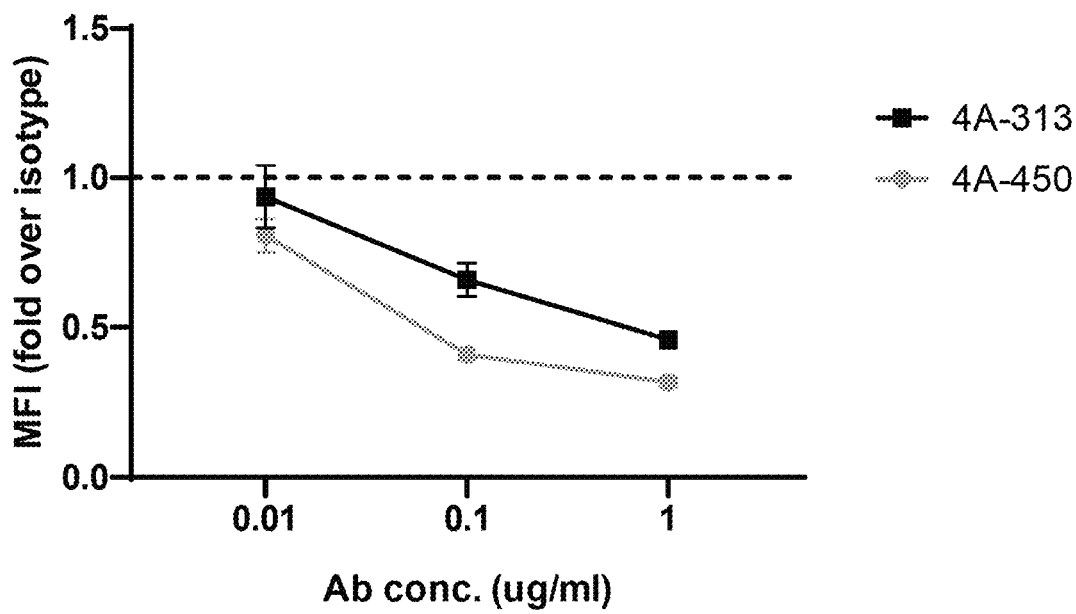
FIG. 36 sets forth data showing anti-MS4A4A antibodies of the present disclosure decrease cell surface expression of HA-Snorkel-tagged MS4A4A protein recombinantly expressed in U937 cells.

As shown in FIG. 36, anti-MS4A4A antibodies 4A-313.NSLF an d4A-450.NSLF decreased the level of plasma membrane MS4A4A in U937 cells expressing human MS4A4A-snorkel-tagged protein in a dose related fashion. At the highest anti-MS4A4A antibody concentration of 1 µg/ml, anti-MS4A4A antibodies 4A-313.NSLF and 4A-450.NSLF decreased surface MS4A4A levels by approximately 50% compared to that observed in cells treated with isotype control antibody. These results showed that the anti-MS4A4A antibodies of the present disclosure decreased or downregulated cell surface MS4A4A levels in U937 cells expressing recombinant human MS4A4A-snorkel.

Example 49

Anti-MS4A4A Antibodies Modulate Glycoprotein Nonmetastatic Melanoma Protein B (GPNMB) Protein Levels in Primary Human Myeloid Cells GPNMB is a surface glycoprotein expressed in multiple cell types including tissue macrophages and microglia. Several genetic variants have been associated with Parkinson's disease (PD) risk. GPNMB protein levels are elevated in the substantia nigra of PD patients and GPNMB levels are increased following lysosomal stress (Moloney et.al., 2018, Neurobio Dis. 120: 1-11). Additionally, increased expression of GPNMB was linked to SNP rs199347, this risk SNP being located withing the GPNMB gene (Murthy et al, 2017, 18:121-133). To determine whether MS4A4A may modulate the expression levels of GPNMB, human primary macrophages from two donors (donor #1117 and #1118) were treated with various concentrations of anti-MS4A4A antibody 4A-313.NSLF for 48 hours. Cell surface (membrane bound) GPNMB was measured by flow cytometry after cells were stained with an anti-GPNMB antibody conjugated with fluorophores.

Figure 37:
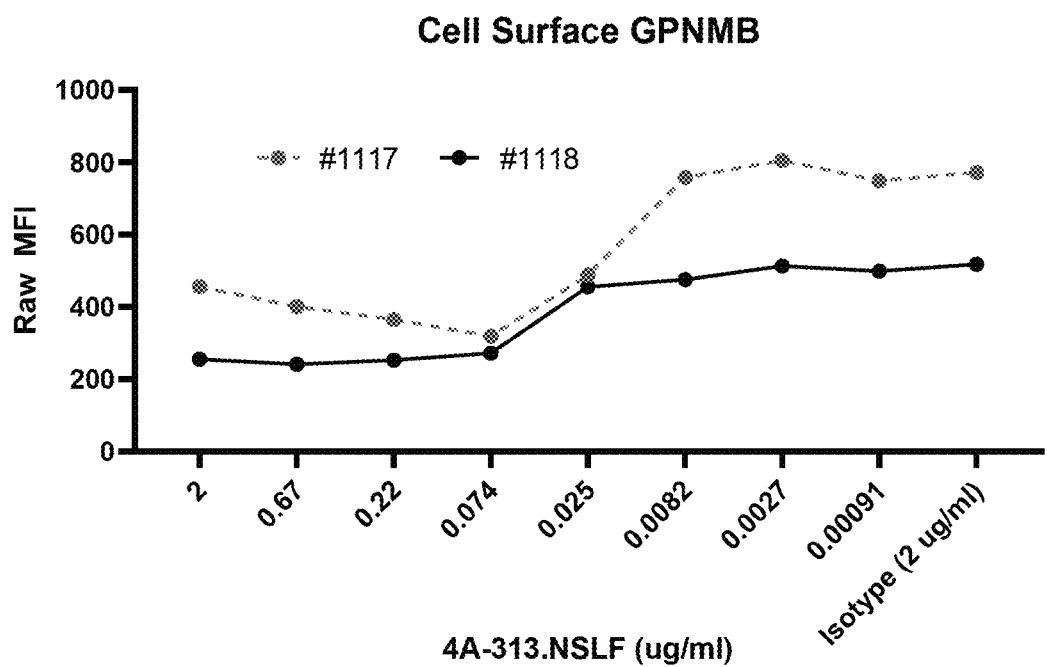
FIG. 37 sets forth data showing anti-MS4A4A antibody of the present disclosure reduced GPNMB cell surface expression in primary human macrophages.

As shown in FIG. 37, membrane GPNMB levels decreased in human primary macrophages following addition to the cells of anti-MS4A4A antibody 4A.313.NSLF. The decrease in GPNMB levels in response to anti-MS4A4A antibody treatment was dose-dependent manner. These results showed that anti-MS4A4A antibodies of the present disclosure are effective at decreasing cell surface expression levels of GPNMB in myeloid cells, e.g., macrophages.

Exemplary anti-MS4A4A antibody heavy chain amino acid sequences having wildtype huIgG1 or Fc variants of wildtype huIgG1:

```
4A-450 (huIgG1 heavy chain)
                                                          (SEQ ID NO: 320)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-450 (huIgG1 heavy chain without C-terminal K)
                                                          (SEQ ID NO: 321)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG
```

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-450 (hIgG1 heavy chain; P331S)
(SEQ ID NO: 322)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-450 (hIgG1 heavy chain P331S without C-terminal K)
(SEQ ID NO: 323)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-450 (huIgG1 heavy chain N325S/L328F)
(SEQ ID NO: 324)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-450 (hIgG1 heavy chain N325S/L328F without C-terminal K)
(SEQ ID NO: 325)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-450 (huIgG1 heavy chain K322A)
(SEQ ID NO: 326)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-450 (huIgG1 heavy chain K322A without C-terminal K)
(SEQ ID NO: 327)
QVQLVQSGSELKKPGASVKVSCKASGYAFTSYGLSWVRQAPGQGLEWMGWINTYSGVPTYAQGFTGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG

\*\*\*\*\*\*\*\*

4A-419 (huIgG1 heavy chain)
(SEQ ID NO: 328)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (huIgG1 heavy chain without C-terminal K)
(SEQ ID NO: 329)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (hIgG1 heavy chain P331S)
(SEQ ID NO: 330)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (hIgG1 heavy chain P331S without C-terminal K)
(SEQ ID NO: 331)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPASIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (huIgG1 heavy chain N325S/L328F)
(SEQ ID NO: 332)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (hIgG1 heavy chain N325S/L328F without C-terminal K)
(SEQ ID NO: 333)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSSKAFPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPG 4A-419 (huIgG1 heavy chain K322A)
(SEQ ID NO: 334)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSV

MHEALHNHYTQKSLSLSPGK 4A-419 (huIgG1 heavy chain K322A without C-terminal K)
(SEQ ID NO: 335)
QVQLVQSGSELKKPGASVKVSCKASGYRFTSYGLSWVRQAPGQGLEWMGWINTYSGVPTYAQGFKGRFV

FSLDTSVSTAYLQISSLKAEDTAVYYCARTMADYWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVKFNWYVDGVEVH

NAKTKPREEQYNSTYRVVSVLTVLHQDWLNGKEYKCAVSNKALPAPIEKTISKAKGQPREPQVYTLPPSRD

-continued

ELTKNQVSLTCLVKGFYPSDIAVEWESNGQPENNYKTTPPVLDSDGSFFLYSKLTVDKSRWQQGNVFSCSV

MHEALHNHYTQKSLSLSPG

\*\*\*\*\*\*\*\*

4A-313 (huIgG1 heavy chain constant region)
(SEQ ID NO: 336)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (huIgG1 heavy chain constant region without C-terminal K)
(SEQ ID NO: 337)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG 4A-313 (hIgG1 heavy chain constant region P331S)
(SEQ ID NO: 338)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

SIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (hIgG1 heavy chain constant region P331S without C-terminal K)
(SEQ ID NO: 339)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPA

SIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG 4A-313 (huIgG1 heavy chain constant region N325S/L328F)
(SEQ ID NO: 340)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSSKAFPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (hIgG1 heavy chain constant region N325S/L328F without
C-terminal K)
(SEQ ID NO: 341)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSSKAFPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

-continued 4A-313 (huIgG1 heavy chain constant region K322A)
(SEQ ID NO: 342)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCAVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK 4A-313 (huIgG1 heavy chain constant region K322A without C-terminal K)
(SEQ ID NO: 343)
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCAVSNKALPA

PIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

********

Human IgG1 Light Chain Constant Region
(SEQ ID NO: 344)
RTVAAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

********

4A-313 (huIgG1 heavy chain)
(SEQ ID NO: 355)
QVQLVQSGAEVKKPGASVKVSCKASGYTFT<u>NYWMQ</u>WVRQAPGQGLEWMG<u>ATHPGHGDTRYAQKFQG</u>R VTMTRDTSTSTVYMELSSLRSEDTAVYYCAR<u>EEVYYGFRSYWYFDL</u>WGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (huIgG1 heavy chain without C-terminal K)
(SEQ ID NO: 356)
QVQLVQSGAEVKKPGASVKVSCKASGYTFT<u>NYWMQ</u>WVRQAPGQGLEWMG<u>ATHPGHGDTRYAQKFQG</u>R VTMTRDTSTSTVYMELSSLRSEDTAVYYCAR<u>EEVYYGFRSYWYFDL</u>WGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (hIgG1 heavy chain P331S)
(SEQ ID NO: 357)
QVQLVQSGAEVKKPGASVKVSCKASGYTFT<u>NYWMQ</u>WVRQAPGQGLEWMG<u>ATHPGHGDTRYAQKFQG</u>R VTMTRDTSTSTVYMELSSLRSEDTAVYYCAR<u>EEVYYGFRSYWYFDL</u>WGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPASIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

-continued 4A-313 (hIgG1 heavy chain P331S without C-terminal K)
(SEQ ID NO: 358)
QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPASIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (huIgG1 heavy chain N325S/L328F)
(SEQ ID NO: 359)
QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSSKAFPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (hIgG1 heavy chain N325S/L328F without C-terminal K)
(SEQ ID NO: 360)
QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSSKAFPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG 4A-313 (huIgG1 heavy chain K322A)
(SEQ ID NO: 361)
QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCAVSNKALPAPIEKTISKAKGQP

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK 4A-313 (huIgG1 heavy chain K322A without C-terminal K)
(SEQ ID NO: 362)
QVQLVQSGAEVKKPGASVKVSCKASGYTFTNYWMQWVRQAPGQGLEWMGATHPGHGDTRYAQKFQGR

VTMTRDTSTSTVYMELSSLRSEDTAVYYCAREEVYYGFRSYWYFDLWGRGTLVTVSSASTKGPSVFPLAP

SSKSTSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCAVSNKALPAPIEKTISKAKGQP

-continued

REPQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPG

\*\*\*\*\*\*\*\*

4A-450 - full length light chain
(SEQ ID NO: 363)

DVVMTQSPLSLPVTLGQPASISC<u>KSSRSLLYSAGKTYLS</u>WFQQRPGQSPRRLIY<u>LVSKLDS</u>GVPDR

FSGSGSGTDFTLKISRVEAEDVGVYYC<u>WQGIDFHQT</u>FGGGTKVEIKRTVAAPSVFIFPPSDEQLKS

GTASVVCLLNNFYPREAKVQWKVDNALQSGNSQESVTEQDSKDSTYSLSSTLTLSKADYEKHK

VYACEVTHQGLSSPVTKSFNRGEC 4A-419 - full length light chain
(SEQ ID NO: 364)

DVVMTQSPLSLPVTLGQPASISC<u>KSSRSLLYSAGKTYLS</u>WFQQRPGQSPRRLIY<u>LVSKLDS</u>GVPDR

FSGSGSGTDFTLKISRVEAEDVGVYYC<u>WQGIDFHQT</u>FGGGTKVEIKRTVAAPSVFIFPPSDEQLKS

GTASVVCLLNNFYPREAKVQWKVDNALQSGNSQESVTEQDSKDSTYSLSSTLTLSKADYEKHK

VYACEVTHQGLSSPVTKSFNRGEC 4A-313 - full length light chain
(SEQ ID NO: 365)

EIVLTQSPATLSLSPGERATLSC<u>RASESVDNYGVSRMN</u>WYQQKPGQAPRLLIY<u>GASNQGS</u>GIPAR

FSGSGSGTDFTLTISSLEPEDFAVYYC<u>QQSKEVPPT</u>FGGGTKVEIKRTVAAPSVFIFPPSDEQLKSG

TASVVCLLNNFYPREAKVQWKVDNALQSGNSQESVTEQDSKDSTYSLSSTLTLSKADYEKHKV

YACEVTHQGLSSPVTKSFNRGEC

---

What is claimed is:

1. An isolated antibody that binds to a MS4A4A protein, wherein the antibody comprises a heavy chain variable region and a light chain variable region, wherein the heavy chain variable region comprises: an HVR-H1 comprising an amino acid sequence of SEQ ID NO:308; an HVR-H2 comprising an amino acid sequence of SEQ ID NO:309; and an HVR-H3 comprising an amino acid sequence of SEQ ID NO:310; and the light chain variable region comprises: an HVR-L1 comprising an amino acid sequence of SEQ ID NO:314; an HVR-L2 comprising an amino acid sequence of SEQ ID NO:315; and an HVR-L3 comprising an amino acid sequence of SEQ ID NO:316.

2. The antibody of claim 1, wherein the antibody is humanized.

3. The antibody of claim 1, wherein the antibody (a) decreases cell surface levels of MS4A4A or decreases intracellular levels of MS4A4A, (b) increases soluble TREM2 levels, increases membrane TREM2 levels, or increases soluble TREM2 and increases membrane TREM2 levels in myeloid cells, (c) reduces expression of M2 cell surface markers on myeloid cells and/or (d) increases mRNA and/or protein expression of gelsolin and/or osteopontin on myeloid cells.

4. The antibody of claim 1, wherein the antibody increases mRNA and/or protein expression of gelsolin and/or osteopontin on myeloid cells.

5. The antibody of claim 1, wherein the antibody is a monoclonal antibody.

6. The antibody of claim 1, wherein the antibody further binds to cynomolgus monkey MS4A4A of SEQ ID NO:3.

7. A pharmaceutical composition comprising the antibody of claim 1 and a pharmaceutically acceptable carrier.

8. A method of treating an individual having a disease, disorder, or injury selected from the group consisting of Alzheimer's disease and late onset Alzheimer's disease, the method comprising administering to an individual in need thereof a therapeutically effective amount of the antibody of claim 1.

9. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 1.

10. The antibody of claim 1, wherein the antibody has an IgG1 isotype.

11. The antibody of claim 1, wherein the antibody comprises a heavy chain variable region, wherein the heavy chain variable region comprises an amino acid sequence of SEQ ID NO: 304.

12. A pharmaceutical composition comprising the antibody of claim 11 and a pharmaceutically acceptable carrier.

13. The antibody of claim 1, wherein the antibody comprises a light chain variable region, wherein the light chain variable region comprises an amino acid sequence of SEQ ID NO:305.

14. A pharmaceutical composition comprising the antibody of claim 13 and a pharmaceutically acceptable carrier.

15. The antibody of claim 1, wherein the antibody comprises a heavy chain and a light chain, wherein the heavy chain comprises an amino acid sequence selected from the group consisting of SEQ ID NOs: 320-327 and the light chain comprises an amino acid sequence of SEQ ID NO:363.

16. The antibody of claim 15, wherein the antibody comprises a heavy chain and a light chain, wherein the heavy chain comprises an amino acid sequence of SEQ ID NO: 327 and the light chain comprises an amino acid sequence of SEQ ID NO:363.

17. The antibody of claim 15, wherein the antibody comprises a heavy chain and a light chain, wherein the heavy chain comprises an amino acid sequence of SEQ ID NO: 323 and the light chain comprises an amino acid sequence of SEQ ID NO:363.

18. The antibody of claim 1, wherein the antibody is an antibody fragment.

19. The antibody of claim 18, wherein the antibody fragment is a Fab, Fab', Fab'-SH, F(ab')2, Fv or scFv fragment.

20. The antibody of claim 1, wherein the antibody is a bispecific antibody recognizing a first antigen and a second antigen.

21. The antibody of claim 20, wherein the first antigen is MS4A4A and the second antigen is
an antigen facilitating transport across the blood-brain-barrier.

22. The antibody of claim 20, wherein the first antigen is MS4A4A and the second antigen is an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, basigin, Glutl, CD98hc, and ANG1005.

23. The antibody of claim 20, wherein the first antigen is MS4A4A and the second antigen is:
(a) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides (b) a ligand and/or a protein expressed on immune cells, wherein the ligand and/or protein is selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; or (c) a protein, lipid, polysaccharide, or glycolipid expressed on one or more tumor cells.

24. An isolated nucleic acid comprising a nucleic acid sequence encoding the antibody of claim 1.

25. An isolated host cell comprising the nucleic acid of claim 24.

26. A method of producing an antibody that binds to human MS4A4A, comprising culturing the cell of claim 25 so that the antibody is produced.

27. The antibody of claim 1, wherein the antibody is of the IgG class and has an IgG1, IgG2, or IgG4 isotype.

28. The antibody of claim 27, wherein the antibody has an IgG1 isotype and comprises a modified Fc comprising the K332A mutation according to EU numbering.

29. The antibody of claim 27, wherein the antibody has an IgG1 isotype and comprises a modified Fc comprising the N325S and L328F mutations according to EU numbering.

30. A method of treating an individual having a disease, disorder, or injury selected from the group consisting of Alzheimer's disease and late onset Alzheimer's disease, the method comprising administering to an individual in need thereof a therapeutically effective amount of the antibody of claim 29.

31. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 29.

32. The antibody of claim 1, wherein the antibody comprises a heavy chain variable region and a light chain variable region, wherein the heavy chain variable region comprises an amino acid sequence of SEQ ID NO:304, and the light chain variable region comprises an amino acid sequence of SEQ ID NO:305.

33. A pharmaceutical composition comprising the antibody of claim 32 and a pharmaceutically acceptable carrier.

34. A method of treating an individual having a disease, disorder, or injury selected from the group consisting of Alzheimer's disease and late onset Alzheimer's disease, the method comprising administering to an individual in need thereof a therapeutically effective amount of the antibody of claim 32.

35. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 32.

36. The antibody of claim 32, wherein the antibody has an IgG1 isotype and comprises a modified Fc comprising the K332A mutation according to EU numbering.

37. The antibody of claim 32, wherein the antibody is of the IgG class and has an IgG1, IgG2, or IgG4 isotype.

38. The antibody of claim 37, wherein the antibody has an IgG1 isotype and comprises a modified Fc comprising the N325S and L328F mutations according to EU numbering.

39. A method of treating an individual having a disease, disorder, or injury selected from the group consisting of Alzheimer's disease and late onset Alzheimer's disease, the method comprising administering to an individual in need thereof a therapeutically effective amount of the antibody of claim 38.

40. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 38.

41. The antibody of claim 32, wherein the antibody is a bispecific antibody recognizing a first antigen and a second antigen.

42. The antibody of claim 41, wherein the first antigen is MS4A4A and the second antigen is an antigen facilitating transport across the blood-brain-barrier.

43. The antibody of claim 41, wherein the first antigen is MS4A4A and the second antigen is an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, basigin, Glutl, CD98hc, and ANG1005.

44. The antibody of claim 41, wherein the first antigen is MS4A4A and the second antigen is a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides.

45. The antibody of claim 41, wherein the first antigen is MS4A4A and the second antigen is a ligand and/or a protein expressed on immune cells, wherein the ligand and/or protein is selected from the group consisting of CD40, OX40, ICOS, CD28, CD137/4-1BB, CD27, GITR, PD-L1, CTLA- 4, PD-L2, PD-1, B7-H3, B7-H4, HVEM, BTLA, KIR, GALS, TIM3, A2AR, LAG-3, and phosphatidylserine.

46. The antibody of claim 41, wherein the first antigen is MS4A4A and the second antigen is a protein, lipid, polysaccharide, or glycolipid expressed on one or more tumor cells.

47. The antibody of claim 32, wherein the antibody has an IgG1 isotype.

48. An isolated nucleic acid comprising a nucleic acid sequence encoding the antibody of claim 32.

49. An isolated host cell comprising the nucleic acid of claim 48.

50. A method of producing an antibody that binds to human MS4A4A, comprising culturing the cell of claim 49 so that the antibody is produced.

51. The antibody of claim 32, wherein the antibody is an antibody fragment.

52. The antibody of claim 51, wherein the antibody fragment is a Fab, Fab', Fab'-SH, F(ab')2, Fv or scFv fragment.

53. An isolated antibody that binds to a MS4A4A protein, wherein the antibody comprises a heavy chain variable region and a light chain variable region, wherein the heavy chain variable region comprises: an HVR-H1 comprising the amino acid sequence of SEQ ID NO:94; an HVR-H2 comprising the amino acid sequence of SEQ ID NO:96; and an HVR-H3 comprising the amino acid sequence of SEQ ID NO:102; and the light chain variable region comprises: an HVR-L1 comprising the amino acid sequence of SEQ ID NO:104; an HVR-L2 comprising the amino acid sequence of SEQ ID NO:105; and an HVR-L3 comprising the amino acid sequence of SEQ ID NO:107.

54. A method of treating an individual having a disease, disorder, or injury selected from the group consisting of Alzheimer's disease and late onset Alzheimer's disease, the method comprising administering to an individual in need thereof a therapeutically effective amount of the antibody of claim 53.

55. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 53.

56. A pharmaceutical composition comprising the antibody of claim 53 and a pharmaceutically acceptable carrier.

57. The antibody of claim 53, wherein the antibody is humanized.

58. The antibody of claim 53, wherein the antibody is a monoclonal antibody.

59. The antibody of claim 53, wherein the antibody (a) decreases cell surface levels of MS4A4A or decreases intracellular levels of MS4A4A, (b) increases soluble TREM2 levels, increases membrane TREM2 levels, or increases soluble TREM2 and increases membrane TREM2 levels in myeloid cells, (c) reduces expression of M2 cell surface markers on myeloid cells and/or (d) increases mRNA and/or protein expression of gelsolin and/or osteopontin on myeloid cells.

60. The isolated antibody of claim 53, wherein the antibody increases mRNA and/or protein expression of gelsolin and/or osteopontin on myeloid cells.

61. The antibody of claim 53, wherein the antibody further binds to cynomolgus monkey MS4A4A of SEQ ID NO:3.

62. The antibody of claim 53, wherein the antibody comprises a heavy chain variable region and a light chain variable region, wherein the heavy chain variable region comprises the amino acid sequence of SEQ ID NO:14, and the light chain variable region comprises the amino acid sequence of SEQ ID NO:22.

63. A pharmaceutical composition comprising the antibody of claim 62 and a pharmaceutically acceptable carrier.

64. A method of treating an individual having a disease, disorder, or injury selected from the group consisting of Alzheimer's disease and late onset Alzheimer's disease, the method comprising administering to an individual in need thereof a therapeutically effective amount of the antibody of claim 62.

65. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 62.

66. An isolated nucleic acid comprising a nucleic acid sequence encoding the antibody of claim 53.

67. An isolated host cell comprising the nucleic acid of claim 66.

68. A method of producing an antibody that binds to human MS4A4A, comprising culturing the cell of claim 67 so that the antibody is produced.

69. The antibody of claim 53, wherein the antibody is of the IgG class and has an IgG1, IgG2, or IgG4 isotype.

70. The antibody of claim 69, wherein the antibody has an IgG1 isotype and comprises a modified Fc comprising the N325S and L328F mutations according to EU numbering.

71. The antibody of claim 69, wherein the antibody has an IgG1 isotype and comprises a modified Fc comprising the K332A mutation according to EU numbering.

72. The antibody of claim 53, wherein the antibody is an antibody fragment.

73. The antibody of claim 72, wherein the antibody fragment is a Fab, Fab', Fab'-SH, F(ab')2, Fv or scFv fragment.

74. The antibody of claim 53, wherein the antibody is a bispecific antibody recognizing a first antigen and a second antigen.

75. The antibody of claim 74, wherein the first antigen is MS4A4A and the second antigen is:
(a) an antigen facilitating transport across the blood-brain-barrier;
(b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, basigin, Glutl, CD98hc, and ANG1005;
(c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;

(d) a ligand and/or a protein expressed on immune cells, wherein the ligand and/or protein is selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; or (e) a protein, lipid, polysaccharide, or glycolipid expressed on one or more tumor cells.

76. The antibody of claim 1, wherein the antibody comprises a heavy chain and a light chain, wherein the heavy chain comprises an amino acid sequence of SEQ ID NOs: 324 or 325 and the light chain comprises an amino acid sequence of SEQ ID NO:363.

77. A pharmaceutical composition comprising the antibody of claim 76 and a pharmaceutically acceptable carrier.

78. A method of treating an individual having a disease, disorder, or injury selected from the group consisting of Alzheimer's disease and late onset Alzheimer's disease, the method comprising administering to an individual in need thereof a therapeutically effective amount of the antibody of claim 76.

79. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 76.

80. An isolated nucleic acid comprising a nucleic acid sequence encoding the antibody of claim 76.

81. An isolated host cell comprising the nucleic acid of claim 80.

82. A method of producing an antibody that binds to human MS4A4A, comprising culturing the cell of claim 81 so that the antibody is produced.

83. The antibody of claim 53, wherein the antibody comprises a heavy chain and a light chain, wherein the heavy chain comprises an amino acid sequence selected from the group consisting of SEQ ID NOs: 355-362 and the light chain comprises an amino acid sequence of SEQ ID NO:365.

84. The antibody of claim 83, wherein the antibody comprises a heavy chain and a light chain, wherein the heavy chain comprises an amino acid sequence of SEQ ID NO: 360 and the light chain comprises an amino acid sequence of SEQ ID NO:365.

85. The antibody of claim 83, wherein the antibody comprises a heavy chain and a light chain, wherein the heavy chain comprises an amino acid sequence of SEQ ID NO: 362 and the light chain comprises an amino acid sequence of SEQ ID NO:365.

86. The antibody of claim 83, wherein the antibody comprises a heavy chain and a light chain, wherein the heavy chain comprises an amino acid sequence of SEQ ID NO: 358 and the light chain comprises an amino acid sequence of SEQ ID NO:365.

87. A pharmaceutical composition comprising the antibody of claim 84 and a pharmaceutically acceptable carrier.

88. A method of treating an individual having a disease, disorder, or injury selected from the group consisting of Alzheimer's disease and late onset Alzheimer's disease, the method comprising administering to an individual in need thereof a therapeutically effective amount of the antibody of claim 84.

89. A method of treating an individual having a CSF1R-deficient disease or disorder, wherein the CSF1R-deficient disease or disorder is adult-onset leukoencephalopathy with axonal spheroids and pigmented glia (ALSP) or hereditary diffuse leukoencephalopathy with spheroids (HDLS), the method comprising administering to an individual in need thereof a therapeutically effective amount of the antibody of claim 84.

90. An antibody that binds to a MS4A4A protein, wherein the antibody comprises a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of SEQ ID NOs: 94, 98, 100, 103, 105, and 107, respectively; SEQ ID NOs: 94, 96, 101, 103, 106, and 107, respectively; SEQ ID NOs: 94, 99, 100, 104, 105, and 107, respectively; SEQ ID NOs: 116, 118, 124, 130, 139, and 144, respectively; SEQ ID NOs: 116, 118, 124, 132, 139, and 144, respectively;

SEQ ID NOs: 116, 118, 124, 133, 139, and 144, respectively; SEQ ID NOs: 116, 118, 124, 136, 139, and 144, respectively; SEQ ID NOs: 116, 118, 124, 130, 139, and 145, respectively; SEQ ID NOs: 116, 118, 124, 138, 141, and 144, respectively; SEQ ID NOs: 116, 118, 124, 130, 141, and 144, respectively; SEQ ID NOs: 116, 118, 125, 130, 139, and 145, respectively; SEQ ID NOs: 116, 118, 127, 131, 139, and 144, respectively; SEQ ID NOs: 116, 118, 129, 131, 139, and 144, respectively; SEQ ID NOs: 116, 118, 129, 132, 139, and 144, respectively; SEQ ID NOs: 116, 118, 129, 133, 139, and 144, respectively; SEQ ID NOs: 116, 118, 129, 134, 139, and 144, respectively;

SEQ ID NOs: 116, 118, 129, 135, 139, and 144, respectively; SEQ ID NOs: 116, 118, 129, 136, 139, and 144, respectively; SEQ ID NOs: 147, 149, 154, 156, 160, and 163, respectively; SEQ ID NOs: 146, 150, 154, 156, 160, and 163, respectively; SEQ ID NOs: 147, 149, 154, 157, 159, and 163, respectively; SEQ ID NOs: 146, 150, 154, 156, 160, and 163, respectively; SEQ ID NOs: 147, 151, 154, 156, 160, and 163, respectively; SEQ ID NOs: 147, 151, 154, 158, 159, and 163, respectively; SEQ ID NOs: 147, 151, 154, 158, 159, and 163, respectively; SEQ ID NOs: 146, 152, 154, 156, 161, and 163, respectively; SEQ ID NOs: 146, 153, 154, 158, 159, and 163, respectively; or SEQ ID NOs: 311, 312, 313, 317, 318, and 319, respectively.

91. The antibody of claim 90, wherein the antibody comprises a heavy chain variable region and a light chain variable region, wherein the heavy chain variable region and the light chain variable region comprise the amino acid sequences of SEQ ID NOs:12 and 17, respectively; SEQ ID NOs:13 and 21, respectively; SEQ ID NOs:15 and 22, respectively;

SEQ ID NOs:47 and 55, respectively; SEQ ID NOs:47 and 63, respectively; SEQ ID NOs:47 and 64, respectively; SEQ ID NOs:47 and 67, respectively; SEQ ID NOs:47 and 69, respectively; SEQ ID NOs:47 and 71, respectively; SEQ ID NOs:47 and 73, respectively; SEQ ID NOs:48 and 69, respectively; SEQ ID NOs:50 and 62, respectively; SEQ ID NOs:53 and 62, respectively; SEQ ID NOs: 53 and 63, respectively; SEQ ID NOs: 53 and 64, respectively; SEQ ID NOs: 53 and 65, respectively; SEQ ID NOs: 53 and 66, respectively; SEQ ID NOs: 53 and 67, respectively; SEQ ID NOs: 76 and 86, respectively; SEQ ID NOs: 77 and 87, respectively; SEQ ID NOs: 78 and 88, respectively; SEQ ID NOs: 79 and 89, respectively; SEQ ID NOs: 80 and 90, respectively; SEQ ID NOs: 81 and 91, respectively; SEQ ID NOs: 82 and 91, respectively; SEQ ID NOs: 83 and 92, respectively; SEQ ID NOs: 84 and 93, respectively; or SEQ ID NOs:306 and 307, respectively.

92. An antibody that binds to a MS4A4A protein, wherein the antibody comprises a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of SEQ ID NOs: 94, 96, 100, 103, 105, and 107 respectively; SEQ ID NOs: 116, 118, 123, 130, 139, and 144 respectively; SEQ ID NOs: 116, 118, 124, 131, 139, and 144 respectively; SEQ ID NOs: 116, 118, 124, 134, 139, and 144 respectively; or SEQ ID NOs: 116, 118, 124, 135, 139, and 144 respectively.

93. The antibody of claim 92, wherein the antibody comprises a heavy chain variable region and a light chain variable region, wherein the heavy chain variable region and the light chain variable region comprises the amino acid sequences of SEQ ID NOs:5 and 18, respectively; SEQ ID NOs:40 and 55, respectively; SEQ ID NOs:47 and 62, respectively; SEQ ID NOs:47 and 65, respectively; or SEQ ID NOs:47 and 66, respectively.

* * * * *

UNITED STATES PATENT AND TRADEMARK OFFICE
CERTIFICATE OF CORRECTION

PATENT NO. : 11,667,699 B2
APPLICATION NO. : 16/943123
DATED : June 6, 2023
INVENTOR(S) : Jeonghoon Sun et al.

It is certified that error appears in the above-identified patent and that said Letters Patent is hereby corrected as shown below:

In the Specification

In Column 8, Line 14, Change "SFFI" to "SFH"

In Column 30, Line 55, Change "dislsoure" to "disclosure"

In Column 33, Line 50, Change "demonstates" to "demonstrates"

In Column 35, Line 60, Change "Alzhemier's" to "Alzheimer's"

In Column 36, Line 60, Change "withing" to "within"

In Column 36, Line 66, Change "myeoid" to "myeloid"

In Column 61, Line 41, Change "SFFI" to "SFH"

In Column 69, Line 56, Change "GALS" to "GAL9"

In Column 73, Line 24, Change "N-aceylgalactosamine" to "N-acetylgalactosamine"

In Column 83, Line 62, Change "tyloxapal);" to "tyloxapol);"

In Column 85, Line 60, Change "taupathy" to "tauopathy"

In Column 86, Line 29, Change "taupathy" to "tauopathy"

In Column 86, Line 37, Change "granulomartous" to "granulomatous"

In Column 87, Line 3, Change "taupathy" to "tauopathy"

Signed and Sealed this
Nineteenth Day of December, 2023

Katherine Kelly Vidal
*Director of the United States Patent and Trademark Office*

In Column 87, Line 11, Change "granulomartous" to "granulomatous"

In Column 89, Line 67, Change "taupathy" to "tauopathy"

In Column 132, Lines 53-54, Change "cynomolgous" to "cynomolgus"

In Column 132, Line 66, Change "cynomolgous" to "cynomolgus"

In Column 146, Line 60, Change "Continous" to "Continuous"

In Column 162, Line 37, Change "secreated" to "secreted"

In Column 166, Line 65, Change "biotinviated" to "biotinylated"

In Column 169, Line 34, Change "hipposcampus" to "hippocampus"

In Column 171, Line 11, Change "obserbed" to "observed"

In Column 172, Line 65, Change "effectinve" to "effective"

In Column 174, Line 10, Change "monkyes" to "monkeys"

In Column 176, Line 27, Change "withing" to "within"

In the Claims

In Claim 23, Column 427, Line 12, Change "GALS" to "GAL9"

In Claim 28, Column 427, Line 28, Change "K332A" to "K322A"

In Claim 36, Column 428, Line 3, Change "K332A" to "K322A"

In Claim 45, Column 429, Line 2, Change "GALS" to "GAL9"

In Claim 71, Column 430, Line 37, Change "K332A" to "K322A"

In Claim 75, Column 431, Line 21, Change "GALS" to "GAL9"

In Claim 90, Column 432, Lines 54-55, Delete "SEQ ID NOs: 146, 150, 154, 156, 160, and 163, respectively;"

In Claim 90, Column 432, Lines 58-59, Delete "SEQ ID NOs: 147, 151, 154, 158, 159, and 163, respectively;"

In Claim 92, Column 434, Line 7, Change "107" to "107,"

CERTIFICATE OF CORRECTION (continued)
U.S. Pat. No. 11,667,699 B2

In Claim 92, Column 434, Line 8, Change "144" to "144,"

In Claim 92, Column 434, Line 9, Change "144" to "144,"

In Claim 92, Column 434, Line 10, Change "144" to "144,"

In Claim 92, Column 434, Line 12, Change "144" to "144,"

SEQUENCE LISTING

<160> NUMBER OF SEQ ID NOS: 365

<210> SEQ ID NO 1
<211> LENGTH: 239
<212> TYPE: PRT
<213> ORGANISM: Homo sapiens

<400> SEQUENCE: 1

```
Met His Gln Thr Tyr Ser Arg His Cys Arg Pro Glu Glu Ser Thr Phe
1               5                   10                  15

Ser Ala Ala Met Thr Thr Met Gln Gly Met Glu Gln Ala Met Pro Gly
            20                  25                  30

Ala Gly Pro Gly Val Pro Gln Leu Gly Asn Met Ala Val Ile His Ser
        35                  40                  45

His Leu Trp Lys Gly Leu Gln Glu Lys Phe Leu Lys Gly Glu Pro Lys
    50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
            100                 105                 110

Ile Ser Gly Ser Leu Ser Ile Ala Ala Gly Ile Arg Thr Thr Lys Gly
        115                 120                 125

Leu Val Arg Gly Ser Leu Gly Met Asn Ile Thr Ser Ser Val Leu Ala
    130                 135                 140

Ala Ser Gly Ile Leu Ile Asn Thr Phe Ser Leu Ala Phe Tyr Ser Phe
145                 150                 155                 160
```

His His Pro Tyr Cys Asn Tyr Tyr Gly Asn Ser Asn Cys His Gly
            165                 170                 175

Thr Met Ser Ile Leu Met Gly Leu Asp Gly Met Val Leu Leu Leu Ser
        180                 185                 190

Val Leu Glu Phe Cys Ile Ala Val Ser Leu Ser Ala Phe Gly Cys Lys
            195                 200                 205

Val Leu Cys Cys Thr Pro Gly Gly Val Val Leu Ile Leu Pro Ser His
        210                 215                 220

Ser His Met Ala Glu Thr Ala Ser Pro Thr Pro Leu Asn Glu Val
225                 230                 235

<210> SEQ ID NO 2
<211> LENGTH: 236
<212> TYPE: PRT
<213> ORGANISM: Mus musculus

<400> SEQUENCE: 2

Met Leu Val Ile Gln Gly Thr Glu Gln Ser Ala Leu Glu Ala Gly Tyr
1               5                   10                  15

Gly Ala Gln Gln Asn Gly Gln Pro Leu Tyr Val Asn Ser His Ser Trp
            20                  25                  30

Lys Arg Met Thr Glu Lys Phe Leu Lys Gly Glu Pro Lys Ile Leu Gly
        35                  40                  45

Ile Val Gln Ile Val Ile Ala Ile Met Asn Leu Ser Ile Gly Ile Met
    50                  55                  60

Met Ile Ile Ala Thr Val Ser Thr Gly Glu Ile Pro Pro Ser Ser Val
65                  70                  75                  80

Tyr Ile Gly Tyr Pro Ile Trp Gly Ser Leu Met Phe Ile Ile Ser Gly
                85                  90                  95

Ser Phe Ser Ile Val Ala Gly Arg Arg Thr Thr Lys Gly Leu Val Arg
            100                 105                 110

Ser Ser Leu Gly Leu Asn Ile Thr Ser Ser Val Phe Ala Phe Ser Gly
        115                 120                 125

Ile Val Ile Ser Ser Leu Ser Pro Gly Ile Tyr Ser Phe His Val Tyr
    130                 135                 140

Tyr Cys Thr Tyr Arg Gly Ser Ser Glu Gly Cys His Met Thr Leu Ser
145                 150                 155                 160

Ile Leu Met Gly Leu Asp Ile Val Val Val Leu Ser Val Leu Glu
                165                 170                 175

Phe Cys Ile Gly Val Ser Leu Ser Ala Phe Gly Cys Arg Val Met Cys
            180                 185                 190

Cys Asn Pro Gly Gly Val Met Ile Ile Met Pro Ser Asn Pro Thr Lys
        195                 200                 205

Ala Glu Thr Ala Asn Pro Val Thr Leu Gln Ser Gly Leu Met Pro Pro
    210                 215                 220

Glu His Gln Glu Arg Asn Val Pro Glu Asn Met His
225                 230                 235

<210> SEQ ID NO 3
<211> LENGTH: 238
<212> TYPE: PRT
<213> ORGANISM: Macaca fascicularis

<400> SEQUENCE: 3

His Gln Thr Tyr Arg Arg His Cys Arg Pro Glu Glu Thr Phe Ser
1               5                   10                  15

-continued

Ala Ala Met Thr Thr Met Gln Gly Met Glu Gln Ala Thr Pro Gly Ala
            20                  25                  30

Gly Pro Gly Val Pro Gln Leu Gly Asn Met Ala Val Val His Ser His
        35                  40                  45

Leu Trp Lys Gly Leu Gln Glu Lys Phe Leu Lys Gly Glu Pro Lys Val
50                  55                  60

Leu Gly Val Val Gln Ile Leu Ala Leu Met Ser Leu Ser Met Gly
65                  70                  75                  80

Ile Thr Met Met Cys Val Ala Phe Ser Ala Tyr Gly His Tyr Pro Ile
                85                  90                  95

Ser Val Tyr Ile Gly Tyr Thr Ile Trp Gly Ser Val Met Phe Ile Ile
            100                 105                 110

Ser Gly Ser Leu Ser Ile Ala Ala Gly Ile Arg Thr Thr Lys Gly Leu
            115                 120                 125

Val Arg Gly Ser Leu Gly Met Asn Ile Thr Ser Ser Val Leu Ala Val
        130                 135                 140

Ser Ala Ile Leu Ile Asn Thr Ile Ser Leu Thr Ile Tyr Ser Phe Tyr
145                 150                 155                 160

His Arg Tyr Cys Asn Tyr Tyr Gly Asn Pro Asn Asn Cys His Gly Thr
                165                 170                 175

Val Ser Ile Leu Met Gly Met Asp Gly Met Val Leu Leu Leu Ser Val
            180                 185                 190

Leu Glu Phe Cys Ile Ala Val Ser Leu Ser Ala Phe Gly Cys Lys Ala
        195                 200                 205

Ile Cys Cys Thr Pro Gly Gly Val Val Leu Ile Ile Pro Ser Asn Ser
210                 215                 220

His Met Ala Glu Ala Ala Pro Leu Thr Pro Leu Asn Glu Val
225                 230                 235

<210> SEQ ID NO 4
<211> LENGTH: 124
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45

Gly Ala Thr His Pro Gly His Gly Asp Thr Arg Tyr Thr Gln Lys Phe
    50                  55                  60

Lys Gly Lys Ala Thr Leu Ser Ala Asp Lys Ser Ser Ser Thr Ala Tyr
65                  70                  75                  80

Met Gln Leu Ser Asn Leu Ala Ser Glu Asp Ser Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 5
<211> LENGTH: 124

```
<212> TYPE: PRT
<213> ORGANISM: Artificial Sequence
<220> FEATURE:
<223> OTHER INFORMATION: Synthetic Construct

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met Gln Trp Val Arg Gln Ala Pro Gly Gln Gly Leu Glu Trp Met
            35                  40                  45

Gly Ala Thr His Pro Gly His Gly Asp Thr Arg Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
                100                 105                 110

Val Trp Gly Arg Gly Thr Leu Val Thr Val Ser Ser
            115                 120

<210> SEQ ID NO 6
<211> LENGTH: 124
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
                20                  25                  30

Trp Met Gln Trp Val Arg Gln Met Pro Gly Lys Gly Leu Glu Trp Met
            35                  40                  45

Gly Ala Thr His Pro Gly His Gly Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Glu Val Tyr Tyr Gly Phe Arg Ser Tyr Trp Tyr Phe Asp
                100                 105                 110

Val Trp Gly Arg Gly Thr Leu Val Thr Val Ser Ser
            115                 120

<210> SEQ ID NO 7
<211> LENGTH: 124
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
```

```
                    20                  25                  30

Trp Met Gln Trp Val Gln Gln Ala Pro Gly Lys Gly Leu Glu Trp Met
            35                  40                  45

Gly Ala Thr His Pro Gly His Gly Asp Thr Arg Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 8
<211> LENGTH: 124
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
            35                  40                  45

Gly Ala Thr His Pro Gly His Gly Asp Thr Arg Tyr Ala Gln Lys Phe
        50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 9
<211> LENGTH: 124
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
            35                  40                  45

Gly Ala Thr His Pro Gly His Gly Asp Thr Arg Tyr Ala Gln Lys Phe
        50                  55                  60

Gln Gly Arg Val Thr Met Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Leu Thr Ala Asp Lys Ser Ile Ser Thr Ala Tyr
65                  70                  75                  80

Met Glu Leu Ser Arg Leu Arg Ser Asp Thr Val Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Met Gln Trp Val Arg Gln Met Pro Gly Lys Gly Leu Glu Trp Met
        35                  40                  45

Gly Ala Thr His Pro Gly His Gly Asp Thr Arg Tyr Ser Pro Ser Phe
    50                  55                  60

Gln Gly Gln Val Thr Ile Ser Ala Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 12
```

```
<211> LENGTH: 124
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
            20                  25                  30

Trp Met Gln Trp Val Gln Gln Ala Pro Gly Lys Gly Leu Glu Trp Met
        35                  40                  45

Gly Ala Thr His Pro Gly His Gly Asp Thr Arg Tyr Ala Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 13
<211> LENGTH: 124
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Asp Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser
        115                 120
```

<210> SEQ ID NO 15
<211> LENGTH: 124
<212> TYPE: PRT
<213> ORGANISM: Artificial Sequence
<220> FEATURE:
<223> OTHER INFORMATION: Synthetic Construct

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Thr Thr Leu Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120
```

<210> SEQ ID NO 16
<211> LENGTH: 111
<212> TYPE: PRT
<213> ORGANISM: Artificial Sequence
<220> FEATURE:
<223> OTHER INFORMATION: Synthetic Construct

<400> SEQUENCE: 16

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Val Ser Phe Met Asn Trp Phe Gln Gln Lys Pro Gly Gln Pro Pro
        35                  40                  45

Lys Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80
```

Pro Met Glu Glu Asp Asp Thr Ala Met Tyr Phe Cys Gln Gln Ser Lys
            85                  90                  95

Glu Val Pro Pro Thr Phe Gly Gly Gly Thr Lys Leu Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Synthetic Construct

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Val Ser Phe Met Asn Trp Tyr Gln Gln Lys Pro Gly Gln Pro Pro
        35                  40                  45

Lys Leu Leu Ile Tyr Gly Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
            85                  90                  95

Glu Val Pro Pro Thr Phe Gly Gly Gly Thr Lys Val Glu Ile Lys
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: Synthetic Construct

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Gly Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
            85                  90                  95

Glu Val Pro Pro Thr Phe Gly Gly Gly Thr Lys Val Glu Ile Lys
            100                 105                 110

<210> SEQ ID NO 19
<211> LENGTH: 111
<212> TYPE: PRT
<213> ORGANISM: Artificial Sequence
<220> FEATURE:
<223> OTHER INFORMATION: Synthetic Construct

<400> SEQUENCE: 19

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Gly Ala Ser Asn Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Pro Thr Phe Gly Gly Gly Thr Lys Val Glu Ile Lys
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Synthetic Construct

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Val Ser Phe Met Asn Trp Tyr Gln Gln Lys Pro Gly Lys Ala Pro
        35                  40                  45

Lys Leu Leu Ile Tyr Gly Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Val Pro Pro Thr Phe Gly Gly Gly Thr Lys Val Glu Ile Lys
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Synthetic Construct

<400> SEQUENCE: 21

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Gly Ala Ser Asn Gln Gln Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95
```

-continued

Glu Val Pro Pro Thr Phe Gly Gly Gly Thr Lys Val Glu Ile Lys
              100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Arg Met Asn Trp Tyr Gln Gln Lys Pro Gly Gln Ala Pro
        35                  40                  45

Arg Leu Leu Ile Tyr Gly Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Pro Thr Phe Gly Gly Gly Thr Lys Val Glu Ile Lys
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Asn Ile Asn Pro Thr Asn Gly Gly Thr Asn Tyr Asn Glu Arg Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Asn Ile Asn Pro Thr Asn Gly Gly Thr Asn Tyr Ala Gln Lys Phe
    50                  55                  60

Gln Gly Arg Val Thr Met Thr Arg Asp Thr Ser Thr Thr Val Tyr
65              70                  75                  80

Met Glu Leu Ser Ser Leu Arg Ser Glu Asp Thr Ala Val Tyr Tyr Cys
            85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
            115                 120

<210> SEQ ID NO 25
<211> LENGTH: 120
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Asn Ile Asn Pro Thr Asn Gly Gly Thr Asn Tyr Ala Gln Lys Phe
    50                  55                  60

Gln Gly Arg Val Thr Met Thr Val Asp Lys Ser Thr Ser Thr Val Tyr
65              70                  75                  80

Met Glu Leu Ser Ser Leu Arg Ser Glu Asp Thr Ala Val Tyr Tyr Cys
            85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
            115                 120

<210> SEQ ID NO 26
<211> LENGTH: 120
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Asn Ile Asn Pro Thr Asn Gly Gly Thr Asn Tyr Ala Gln Lys Phe
    50                  55                  60

Gln Gly Arg Val Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Asn Ile Asn Pro Thr Asn Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Asn Ile Asn Pro Thr Asn Gly Gly Thr Asn Tyr Ala Gln Lys Phe
    50                  55                  60

Gln Gly Arg Val Thr Ser Thr Val Asp Lys Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser

-continued

```
<210> SEQ ID NO 29
<211> LENGTH: 120
<212> TYPE: PRT
<213> ORGANISM: Artificial Sequence
<220> FEATURE:
<223> OTHER INFORMATION: Synthetic Construct

<400> SEQUENCE: 29
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Arg Leu Glu Trp Met
        35                  40                  45

Gly Asn Ile Asn Pro Thr Asn Gly Gly Thr Asn Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

```
<210> SEQ ID NO 30
<211> LENGTH: 120
<212> TYPE: PRT
<213> ORGANISM: Artificial Sequence
<220> FEATURE:
<223> OTHER INFORMATION: Synthetic Construct

<400> SEQUENCE: 30
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Arg Leu Glu Trp Met
        35                  40                  45

Gly Asn Ile Asn Pro Thr Asn Gly Gly Thr Asn Tyr Ser Gln Lys Phe
    50                  55                  60

Gln Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

```
<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31
```

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Ser Gln Gln Lys Pro Gly Gln Ser Pro Lys Leu Leu Ile
            35                  40                  45

Tyr Ser Ala Ser Tyr Arg His Thr Gly Val Pro Asp Arg Phe Thr Gly
50                      55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Tyr Pro Trp
                85                  90                  95

Thr Phe Gly Gly Gly Thr Lys Leu Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
            35                  40                  45

Tyr Ser Ala Ser Tyr Arg His Thr Gly Val Pro Ser Arg Phe Ser Gly
50                      55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
            100                 105

<210> SEQ ID NO 33
<211> LENGTH: 108
<212> TYPE: PRT
<213> ORGANISM: Artificial Sequence
<220> FEATURE:
<223> OTHER INFORMATION: Synthetic Construct

<400> SEQUENCE: 33

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
            35                  40                  45

Tyr Ser Ala Ser Tyr Arg His Thr Gly Val Pro Ser Arg Phe Ser Gly
50                      55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp

-continued

```
                    85                  90                  95
Thr Phe Gly Gly Gly Thr Lys Val Glu Ile Lys Arg
                100                 105
```

<210> SEQ ID NO 34
<211> LENGTH: 107
<212> TYPE: PRT
<213> ORGANISM: Artificial Sequence
<220> FEATURE:
<223> OTHER INFORMATION: Synthetic Construct

<400> SEQUENCE: 34

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
                20                  25                  30

Val Ala Trp Tyr Gln Gln Lys Pro Glu Lys Ala Pro Lys Ser Leu Ile
            35                  40                  45

Tyr Ser Ala Ser Tyr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
                100                 105
```

<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
                20                  25                  30

Val Ala Trp Tyr Gln Gln Lys Pro Glu Lys Ala Pro Lys Ser Leu Ile
            35                  40                  45

Tyr Ser Ala Ser Tyr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
                100                 105
```

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

```
Ala Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
                100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
                100                 105

<210> SEQ ID NO 38
<211> LENGTH: 107
<212> TYPE: PRT
<213> ORGANISM: Artificial Sequence
<220> FEATURE:
<223> OTHER INFORMATION: Synthetic Construct

<400> SEQUENCE: 38

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Trp
                85                  90                  95

Thr Phe Gly Gly Gly Thr Lys Val Glu Ile Lys
```

```
<210> SEQ ID NO 39
<211> LENGTH: 114
<212> TYPE: PRT
<213> ORGANISM: Artificial Sequence
<220> FEATURE:
<223> OTHER INFORMATION: Synthetic Construct

<400> SEQUENCE: 39

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Ile Phe Thr Ser Tyr
            20                  25                  30
Gly Leu Ser Trp Val Lys Gln Thr Pro Gly Lys Gly Leu Lys Trp Met
        35                  40                  45
Gly Trp Ile Asn Thr Tyr Ser Gly Val Pro Thr Tyr Ala Asn Asp Phe
    50                  55                  60
Lys Gly Arg Phe Ala Phe Ser Leu Glu Thr Ser Ala Ser Thr Thr Tyr
65                  70                  75                  80
Leu Arg Ile Asn Asn Leu Lys Asn Asp Asp Thr Ala Thr Tyr Phe Cys
                85                  90                  95
Ala Arg Ser Leu Val Asp Tyr Trp Gly Gln Gly Thr Pro Leu Thr Val
            100                 105                 110
Ser Ser

<210> SEQ ID NO 40
<211> LENGTH: 114
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Ile Phe Thr Ser Tyr
            20                  25                  30
Gly Leu Ser Trp Val Arg Gln Ala Pro Gly Gln Gly Leu Glu Trp Met
        35                  40                  45
Gly Trp Ile Asn Thr Tyr Ser Gly Val Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Ser Leu Val Asp Tyr Trp Gly Gln Gly Thr Leu Val Thr Val
            100                 105                 110
Ser Ser

<210> SEQ ID NO 41
<211> LENGTH: 114
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ser Glu Leu Lys Lys Pro Gly Ala
```

```
                1               5                  10                   15
Ser Val Lys Val Ser Cys Lys Ala Ser Gly Tyr Ile Phe Thr Ser Tyr
                20                  25                  30

Gly Leu Ser Trp Val Arg Gln Ala Pro Gly Gln Gly Leu Glu Trp Met
                35                  40                  45

Gly Trp Ile Asn Thr Tyr Ser Gly Val Pro Thr Tyr Ala Gln Gly Phe
     50                  55                  60

Thr Gly Arg Phe Val Phe Ser Leu Asp Thr Ser Val Ser Thr Thr Tyr
65                  70                  75                  80

Leu Gln Ile Ser Ser Leu Lys Ala Glu Asp Thr Ala Val Tyr Tyr Cys
                85                  90                  95

Ala Arg Ser Leu Val Asp Tyr Trp Gly Gln Gly Thr Leu Val Thr Val
                100                 105                 110

Ser Ser

<210> SEQ ID NO 42
<211> LENGTH: 114
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Gly Leu Ser Trp Val Arg Gln Ala Pro Gly Gln Arg Leu Glu Trp Met
                35                  40                  45

Gly Trp Ile Asn Thr Tyr Ser Gly Val Pro Thr Tyr Ser Gln Lys Phe
     50                  55                  60

Gln Gly Arg Val Thr Ile Thr Leu Asp Thr Ser Ala Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Ser Leu Val Asp Tyr Trp Gly Gln Gly Thr Leu Val Thr Val
                100                 105                 110

Ser Ser

<210> SEQ ID NO 43
<211> LENGTH: 114
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Gly Leu Ser Trp Val Arg Gln Ala Pro Gly Gln Arg Leu Glu Trp Met
                35                  40                  45

Gly Trp Ile Asn Thr Tyr Ser Gly Val Pro Thr Tyr Ser Gln Lys Phe
     50                  55                  60

Gln Gly Arg Val Thr Ile Thr Arg Asp Thr Ser Ala Ser Thr Ala Tyr
65                  70                  75                  80
```

Met Glu Leu Ser Ser Leu Arg Ser Glu Asp Thr Ala Val Tyr Tyr Cys
            85                  90                  95

Ala Arg Ser Leu Val Asp Tyr Trp Gly Gln Gly Thr Leu Val Thr Val
            100                 105                 110

Ser Ser

<210> SEQ ID NO 44
<211> LENGTH: 114
<212> TYPE: PRT
<213> ORGANISM: Artificial Sequence
<220> FEATURE:
<223> OTHER INFORMATION: Synthetic Construct

<400> SEQUENCE: 44

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Leu Val Asp Tyr Trp Gly Gln Gly Thr Leu Val Thr Val
            100                 105                 110

Ser Ser

<210> SEQ ID NO 45
<211> LENGTH: 114
<212> TYPE: PRT
<213> ORGANISM: Artificial Sequence
<220> FEATURE:
<223> OTHER INFORMATION: Synthetic Construct

<400> SEQUENCE: 45

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Lys Phe
50                  55                  60

Gln Gly Arg Val Thr Met Thr Leu Asp Thr Ser Thr Ser Thr Thr Tyr
65                  70                  75                  80

Met Glu Leu Ser Ser Leu Arg Ser Glu Asp Thr Ala Val Tyr Tyr Cys
            85                  90                  95

Ala Arg Ser Leu Val Asp Tyr Trp Gly Gln Gly Thr Leu Val Thr Val
            100                 105                 110

Ser Ser

<210> SEQ ID NO 46
<211> LENGTH: 114
<212> TYPE: PRT

```
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Leu Val Asp Tyr Trp Gly Gln Gly Thr Leu Val Thr Val
            100                 105                 110

Ser Ser

<210> SEQ ID NO 47
<211> LENGTH: 114
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Leu Ala Asp Tyr Trp Gly Gln Gly Thr Leu Val Thr Val
            100                 105                 110

Ser Ser

<210> SEQ ID NO 48
<211> LENGTH: 114
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Ile Arg Gln Ala Pro Gly Gln Gly Leu Glu Trp Met
```

```
                35                  40                  45
Gly Trp Ile Asn Thr Tyr Ser Gly Val Pro Thr Tyr Ala Gln Gly Phe
 50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Thr Met Val Asp Tyr Trp Gly Gln Gly Thr Leu Val Thr Val
                100                 105                 110
Ser Ser

<210> SEQ ID NO 49
<211> LENGTH: 114
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Val Gln Ser Gly Ser Glu Leu Lys Lys Pro Gly Ala
  1               5                  10                  15
Ser Val Lys Val Ser Cys Lys Ala Ser Gly Tyr Ile Phe Thr Ser Tyr
                 20                  25                  30
Gly Leu Ser Trp Val Arg Gln Ala Pro Gly Gln Gly Leu Glu Trp Met
                 35                  40                  45
Gly Trp Ile Asn Thr Tyr Ser Gly Val Pro Thr Tyr Ala Gln Gly Phe
 50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Thr Leu Gly Asp Tyr Trp Gly Gln Gly Thr Leu Val Thr Val
                100                 105                 110
Ser Ser

<210> SEQ ID NO 50
<211> LENGTH: 114
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Val Gln Ser Gly Ser Glu Leu Lys Lys Pro Gly Ala
  1               5                  10                  15
Ser Val Lys Val Ser Cys Lys Ala Ser Gly Tyr Ile Phe Thr Ser Tyr
                 20                  25                  30
Gly Leu Ser Trp Val Arg Gln Ala Pro Gly Gln Gly Leu Glu Trp Met
                 35                  40                  45
Gly Trp Ile Asn Thr Tyr Ser Gly Val Pro Thr Tyr Ala Gln Gly Phe
 50                  55                  60
Thr Gly Arg Phe Val Phe Ser Leu Asp Thr Ser Val Ser Thr Ala Tyr
 65                  70                  75                  80
Leu Gln Ile Ser Ser Leu Lys Ala Glu Asp Thr Ala Val Tyr Tyr Cys
                 85                  90                  95
Ala Arg Thr Leu Val Asp Tyr Trp Gly Gln Gly Thr Leu Val Thr Val
                100                 105                 110
```

-continued

Ser Ser

<210> SEQ ID NO 51
<211> LENGTH: 114
<212> TYPE: PRT
<213> ORGANISM: Artificial Sequence
<220> FEATURE:
<223> OTHER INFORMATION: Synthetic Construct

<400> SEQUENCE: 51

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Ala Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Leu Val Asp Tyr Trp Gly Gln Gly Thr Leu Val Thr Val
            100                 105                 110

Ser Ser
```

<210> SEQ ID NO 52
<211> LENGTH: 114
<212> TYPE: PRT
<213> ORGANISM: Artificial Sequence
<220> FEATURE:
<223> OTHER INFORMATION: Synthetic Construct

<400> SEQUENCE: 52

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Leu Ala Asp Tyr Trp Gly Gln Gly Thr Leu Val Thr Val
            100                 105                 110

Ser Ser
```

<210> SEQ ID NO 53
<211> LENGTH: 114
<212> TYPE: PRT
<213> ORGANISM: Artificial Sequence
<220> FEATURE:
<223> OTHER INFORMATION: Synthetic Construct

<400> SEQUENCE: 53

-continued

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Met Ala Asp Tyr Trp Gly Gln Gly Thr Leu Val Thr Val
            100                 105                 110

Ser Ser
```

<210> SEQ ID NO 54
<211> LENGTH: 112
<212> TYPE: PRT
<213> ORGANISM: Artificial Sequence
<220> FEATURE:
<223> OTHER INFORMATION: Synthetic Construct

<400> SEQUENCE: 54

```
Asp Val Val Met Thr Gln Thr Pro Phe Thr Leu Ser Val Thr Ile Gly
1               5                   10                  15

Gln Ser Ala Ser Ile Ser Cys Lys Ser Ser Gln Ser Leu Leu Tyr Ser
            20                  25                  30

Asp Gly Lys Thr Tyr Leu Ser Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ile Asp Phe His Gln Thr Phe Gly Gly Gly Thr Lys Leu Glu Ile Lys
            100                 105                 110
```

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Trp Gln Gly
             85                  90                  95

Ile Asp Phe His Gln Thr Phe Gly Gly Gly Thr Lys Val Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Synthetic Construct

<400> SEQUENCE: 56

Asp Ile Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Leu Gln Gln Arg Pro Gly Gln Pro
        35                  40                  45

Pro Arg Leu Leu Ile Tyr Leu Val Ser Lys Leu Asp Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Trp Gln Gly
             85                  90                  95

Ile Asp Phe His Gln Thr Phe Gly Gly Gly Thr Lys Val Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: Synthetic Construct

<400> SEQUENCE: 57

Asp Val Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Leu Gln Gln Arg Pro Gly Gln Pro
        35                  40                  45

Pro Arg Leu Leu Ile Tyr Leu Val Ser Lys Leu Asp Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Trp Gln Gly
             85                  90                  95

Ile Asp Phe His Gln Thr Phe Gly Gly Gly Thr Lys Val Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: Synthetic Construct

<400> SEQUENCE: 58

Asp Val Val Met Thr Gln Thr Pro Leu Ser Ser Pro Val Thr Leu Gly
```

Gln Pro Ala Ser Ile Ser Cys Lys Ser Gln Ser Leu Leu Tyr Ser
            20                  25                  30

Asp Gly Lys Thr Tyr Leu Ser Trp Leu Gln Gln Arg Pro Gly Gln Pro
        35                  40                  45

Pro Arg Leu Ile Tyr Leu Val Ser Lys Leu Asp Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
                100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Asp Val Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Tyr Ser
            20                  25                  30

Asp Gly Lys Thr Tyr Leu Ser Trp Tyr Leu Gln Lys Pro Gly Gln Pro
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
                100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Asp Val Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Tyr Ser
            20                  25                  30

Asp Gly Lys Thr Tyr Leu Ser Trp Tyr Leu Gln Lys Pro Gly Gln Pro
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Tyr Leu Gln Lys Pro Gly Gln Pro
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser

```
                20                  25                  30

Gly Gly Lys Thr Tyr Leu Ser Trp Phe Gln Gln Arg Pro Gly Gln Ser
            35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Asp Phe His Gln Thr Phe Gly Gly Gly Thr Lys Val Glu Ile Lys
                100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Arg Ser Leu Leu Tyr Ser
             20                  25                  30

Glu Gly Lys Thr Tyr Leu Ser Trp Phe Gln Gln Arg Pro Gly Gln Ser
            35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Asp Phe His Gln Thr Phe Gly Gly Gly Thr Lys Val Glu Ile Lys
                100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: Synthetic Construct

<400> SEQUENCE: 65

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Arg Ser Leu Leu Tyr Ser
             20                  25                  30

Ala Gly Lys Thr Tyr Leu Ser Trp Phe Gln Gln Arg Pro Gly Gln Ser
            35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Asp Phe His Gln Thr Phe Gly Gly Gly Thr Lys Val Glu Ile Lys
                100                 105                 110
```

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

```
Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Ser Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110
```

<210> SEQ ID NO 67
<211> LENGTH: 112
<212> TYPE: PRT
<213> ORGANISM: Artificial Sequence
<220> FEATURE:
<223> OTHER INFORMATION: Synthetic Construct

<400> SEQUENCE: 67

```
Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Gln Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110
```

<210> SEQ ID NO 68
<211> LENGTH: 112
<212> TYPE: PRT
<213> ORGANISM: Artificial Sequence
<220> FEATURE:
<223> OTHER INFORMATION: Synthetic Construct

<400> SEQUENCE: 68

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Phe Gln Gln Arg Pro Gly Gln Ser
```

```
            35                  40                  45

Pro Arg Arg Leu Ile Tyr Glu Val Ser Lys Leu Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Asp Phe His Gln Thr Phe Gly Gly Gly Thr Lys Val Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Synthetic Construct

<400> SEQUENCE: 69

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Arg Phe His Gln Thr Phe Gly Gly Gly Thr Lys Val Glu Ile Lys
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthetic Construct

<400> SEQUENCE: 70

Asp Val Val Met Thr Gln Ser Pro Leu Ser Leu Pro Val Thr Leu Gly
 1               5                  10                  15

Gln Pro Ala Ser Ile Ser Cys Lys Ala Ser Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Ala Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ile Asp Phe His Gln Thr Phe Gly Gly Gly Thr Lys Val Glu Ile Lys
            100                 105                 110

<210> SEQ ID NO 71
<211> LENGTH: 112
```

```
<212> TYPE: PRT
<213> ORGANISM: Artificial Sequence
<220> FEATURE:
<223> OTHER INFORMATION: Synthetic Construct

<400> SEQUENCE: 71
```

Asp Val Val Met Thr Gln Ser Pro Leu Ser Leu Pro Val Thr Leu Gly
1               5                   10                  15

Gln Pro Ala Ser Ile Ser Cys Lys Ser Gly Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Arg Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

```
<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72
```

Asp Val Val Met Thr Gln Ser Pro Leu Ser Leu Pro Val Thr Leu Gly
1               5                   10                  15

Gln Pro Ala Ser Ile Ser Cys Lys Ser Gly Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

```
<210> SEQ ID NO 73
<211> LENGTH: 112
<212> TYPE: PRT
<213> ORGANISM: Artificial Sequence
<220> FEATURE:
<223> OTHER INFORMATION: Synthetic Construct

<400> SEQUENCE: 73
```

Asp Val Val Met Thr Gln Ser Pro Leu Ser Leu Pro Val Thr Leu Gly
1               5                   10                  15

Gln Pro Ala Ser Ile Ser Cys Lys Ser Gly Gln Ser Leu Leu Tyr Ser
            20                  25                  30

Asp Gly Lys Thr Tyr Leu Ser Trp Phe Gln Gln Arg Pro Gly Gln Ser
        35                  40                  45

Pro Arg Arg Leu Ile Tyr Leu Val Ser Arg Leu Asp Ser Gly Val Pro

```
                50              55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                    85                  90                  95

Ile Asp Phe His Gln Thr Phe Gly Gly Gly Thr Lys Val Glu Ile Lys
               100                 105                 110

<210> SEQ ID NO 74
<211> LENGTH: 112
<212> TYPE: PRT
<213> ORGANISM: Artificial Sequence
<220> FEATURE:
<223> OTHER INFORMATION: Synthetic Construct

<400> SEQUENCE: 74

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Tyr Ser
                20                  25                  30

Asp Gly Lys Thr Tyr Leu Ser Trp Phe Gln Gln Arg Pro Gly Gln Ser
            35                  40                  45

Pro Arg Arg Leu Ile Tyr Leu Val Ser Lys Leu Ser Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                    85                  90                  95

Ile Asp Phe His Gln Thr Phe Gly Gly Gly Thr Lys Val Glu Ile Lys
               100                 105                 110

<210> SEQ ID NO 75
<211> LENGTH: 120
<212> TYPE: PRT
<213> ORGANISM: Artificial Sequence
<220> FEATURE:
<223> OTHER INFORMATION: Synthetic Construct

<400> SEQUENCE: 75

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Arg Thr Ser
                20                  25                  30

Asp Met Gly Val Gly Trp Val Arg Gln Pro Ser Gly Glu Gly Leu Glu
            35                  40                  45

Trp Leu Ala Asp Ile Trp Trp Asp Asp Lys Tyr Tyr Asn Pro Ser
 50                  55                  60

Leu Lys Ser Arg Leu Thr Ile Ser Lys Asp Thr Ser Asn Gln Val
 65                  70                  75                  80

Phe Leu Lys Ile Thr Ser Val Asp Thr Ala Asp Thr Ala Thr Tyr Tyr
                85                  90                  95

Cys Ala Arg Arg Ala Asn Tyr Gly Asn Leu Phe Asp Tyr Trp Gly Gln
               100                 105                 110

Gly Thr Ala Val Thr Val Ser Ser
           115                 120

<210> SEQ ID NO 76
<211> LENGTH: 120
```

```
<212> TYPE: PRT
<213> ORGANISM: Artificial Sequence
<220> FEATURE:
<223> OTHER INFORMATION: Synthetic Construct

<400> SEQUENCE: 76

Gln Val Thr Leu Lys Glu Ser Gly Pro Ala Leu Val Gln Pro Thr Gln
1               5                   10                  15

Thr Leu Thr Leu Thr Cys Thr Phe Ser Gly Phe Ser Leu Arg Thr Ser
            20                  25                  30

Asp Met Gly Val Ser Trp Ile Arg Gln Pro Pro Gly Glu Ala Leu Glu
        35                  40                  45

Trp Leu Ala Leu Ile Trp Trp Asp Asp Asn Lys Tyr Tyr Ser Thr Ser
    50                  55                  60

Leu Lys Thr Arg Leu Thr Ile Ser Lys Asp Thr Ser Ser Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Asn Tyr Gly Asn Leu Phe Asp Tyr Trp Gly Gln
            100                 105                 110

Gly Thr Ala Val Thr Val Ser Ser
        115                 120

<210> SEQ ID NO 77
<211> LENGTH: 120
<212> TYPE: PRT
<213> ORGANISM: Artificial Sequence
<220> FEATURE:
<223> OTHER INFORMATION: Synthetic Construct

<400> SEQUENCE: 77

Gln Val Thr Leu Lys Glu Ser Gly Pro Thr Leu Val Gln Pro Thr Gln
1               5                   10                  15

Thr Leu Thr Leu Thr Cys Thr Phe Ser Gly Phe Ser Leu Arg Thr Ser
            20                  25                  30

Asp Met Gly Val Gly Trp Ile Arg Gln Pro Pro Gly Lys Ala Leu Glu
        35                  40                  45

Trp Leu Ala Leu Ile Trp Trp Asp Asp Asn Lys Tyr Tyr Ser Pro Ser
    50                  55                  60

Leu Lys Ser Arg Leu Thr Ile Ser Lys Asp Thr Ser Ser Asn Gln Val
65                  70                  75                  80

Val Leu Thr Met Thr Asn Met Asp Pro Val Asp Thr Ala Thr Tyr Tyr
                85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Synthetic Construct

<400> SEQUENCE: 78

Gln Val Thr Leu Arg Glu Ser Gly Pro Ala Leu Val Gln Pro Thr Gln
1               5                   10                  15

Thr Leu Thr Leu Thr Cys Thr Phe Ser Gly Phe Ser Leu Arg Thr Ser
```

```
            20                  25                  30
Asp Met Gly Val Ser Trp Ile Arg Gln Pro Pro Gly Glu Ala Leu Glu
            35                  40                  45

Trp Leu Ala Leu Ile Trp Trp Asp Asp Asn Lys Tyr Tyr Ser Thr Ser
 50                  55                  60

Leu Lys Thr Arg Leu Thr Ile Ser Lys Asp Thr Ser Ser Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Ala Asn Tyr Gly Asn Leu Phe Asp Tyr Trp Gly Gln
                100                 105                 110

Gly Thr Leu Val Thr Val Ser Ser
            115                 120

<210> SEQ ID NO 79
<211> LENGTH: 120
<212> TYPE: PRT
<213> ORGANISM: Artificial Sequence
<220> FEATURE:
<223> OTHER INFORMATION: Synthetic Construct

<400> SEQUENCE: 79

Gln Val Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Arg Thr Ser
            20                  25                  30

Asp Met Gly Val Gly Trp Ile Arg Gln Pro Pro Gly Lys Ala Leu Glu
            35                  40                  45

Trp Leu Ala Leu Ile Trp Trp Asp Asp Asn Lys Tyr Tyr Ser Pro Ser
 50                  55                  60

Leu Lys Ser Arg Leu Thr Ile Thr Lys Asp Thr Ser Ser Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Ala Asn Tyr Gly Asn Leu Phe Asp Tyr Trp Gly Gln
                100                 105                 110

Gly Thr Leu Val Thr Val Ser Ser
            115                 120

<210> SEQ ID NO 80
<211> LENGTH: 120
<212> TYPE: PRT
<213> ORGANISM: Artificial Sequence
<220> FEATURE:
<223> OTHER INFORMATION: Synthetic Construct

<400> SEQUENCE: 80

Gln Val Thr Leu Lys Glu Ser Gly Pro Gly Leu Val Gln Pro Thr Glu
 1               5                  10                  15

Thr Leu Thr Leu Thr Cys Thr Phe Ser Gly Phe Ser Leu Arg Thr Ser
            20                  25                  30

Asp Met Gly Val Ser Trp Ile Arg Gln Pro Pro Gly Lys Ala Leu Glu
            35                  40                  45

Trp Leu Ala His Ile Trp Trp Asp Asp Asn Lys Ser Tyr Ser Thr Ser
 50                  55                  60

Leu Lys Ser Arg Leu Thr Ile Ser Lys Asp Thr Ser Ser Asn Gln Val
 65                  70                  75                  80
```

-continued

Val Leu Thr Met Thr Asn Met Asp Pro Val Asp Ala Thr Tyr Tyr
            85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 81
<211> LENGTH: 120
<212> TYPE: PRT
<213> ORGANISM: Artificial Sequence
<220> FEATURE:
<223> OTHER INFORMATION: Synthetic Construct

<400> SEQUENCE: 81

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Arg Thr Ser
            20                  25                  30

Asp Met Gly Val Ser Trp Ile Arg Gln Pro Ser Gly Lys Ala Leu Glu
        35                  40                  45

Trp Leu Ala His Ile Trp Trp Asp Asp Asn Lys Ser Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 82
<211> LENGTH: 120
<212> TYPE: PRT
<213> ORGANISM: Artificial Sequence
<220> FEATURE:
<223> OTHER INFORMATION: Synthetic Construct

<400> SEQUENCE: 82

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Arg Thr Ser
            20                  25                  30

Asp Met Gly Val Ser Trp Ile Arg Gln Pro Ser Gly Glu Gly Leu Glu
        35                  40                  45

Trp Leu Ala His Ile Trp Trp Asp Asp Asn Lys Ser Tyr Ser Thr Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 83

<211> LENGTH: 120
<212> TYPE: PRT
<213> ORGANISM: Artificial Sequence
<220> FEATURE:
<223> OTHER INFORMATION: Synthetic Construct

<400> SEQUENCE: 83

Gln Val Thr Leu Gln Glu Ser Gly Pro Gly Leu Val Lys Pro Ser Glu
1               5                   10                  15

Thr Leu Ser Leu Thr Cys Ala Val Ser Gly Phe Ser Leu Arg Thr Ser
            20                  25                  30

Asp Met Gly Val Gly Trp Ile Arg Gln Pro Pro Gly Glu Gly Leu Glu
        35                  40                  45

Trp Ile Gly Ser Ile Trp Trp Asp Asp Asn Lys Tyr Tyr Asn Pro Ser
    50                  55                  60

Leu Lys Ser Arg Val Thr Ile Ser Lys Asp Thr Ser Lys Asn Gln Val
65                  70                  75                  80

Ser Leu Lys Leu Ser Ser Val Asp Ala Ala Asp Thr Ala Val Tyr Tyr
                85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 84
<211> LENGTH: 120
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Gln Glu Ser Gly Pro Gly Leu Val Gln Pro Ser Glu
1               5                   10                  15

Thr Leu Ser Leu Thr Cys Ala Val Ser Gly Phe Ser Leu Arg Thr Ser
            20                  25                  30

Asp Met Gly Val Gly Trp Ile Arg Gln Pro Pro Gly Lys Gly Leu Glu
        35                  40                  45

Trp Ile Gly Ser Ile Trp Tyr Asp Asp Asn Lys Tyr Tyr Asn Pro Ser
    50                  55                  60

Leu Lys Ser Arg Val Thr Ile Ser Lys Asp Thr Ser Ser Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Ala Asn Tyr Gly Asn Leu Phe Asp Tyr Trp Gly Gln
            100                 105                 110

Gly Thr Leu Val Thr Val Ser Ser
        115                 120

<210> SEQ ID NO 85
<211> LENGTH: 106
<212> TYPE: PRT
<213> ORGANISM: Artificial Sequence
<220> FEATURE:
<223> OTHER INFORMATION: Synthetic Construct

<400> SEQUENCE: 85

Asp Ile Val Met Thr Gln Ser Leu Lys Phe Met Ser Thr Ser Val Gly
1               5                   10                  15

Asp Arg Val Ser Ile Thr Cys Lys Ala Ser Gln Asn Val Arg Ser Ala
            20                  25                  30

Val Ala Trp Tyr Gln Gln Lys Pro Gly Gln Ser Pro Lys Val Leu Ile
        35                  40                  45

Tyr Trp Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Leu Thr
                85                  90                  95

Phe Gly Ser Gly Thr Lys Leu Glu Ile Lys
            100                 105

<210> SEQ ID NO 86
<211> LENGTH: 106
<212> TYPE: PRT
<213> ORGANISM: Artificial Sequence
<220> FEATURE:
<223> OTHER INFORMATION: Synthetic Construct

<400> SEQUENCE: 86

Asp Ile Val Leu Thr Gln Ser Pro Ser Ser Leu Ser Ala Ser Val Gly
1               5                   10                  15

Asp Arg Val Thr Ile Thr Cys Arg Ala Ser Gln Asn Val Arg Ser Ala
            20                  25                  30

Leu Ala Trp Tyr Gln Gln Lys Pro Gly Gln Ala Pro Lys Val Leu Ile
        35                  40                  45

Tyr Trp Ala Ser Asn Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Asn Tyr Leu Thr
                85                  90                  95

Phe Gly Gly Gly Thr Lys Val Glu Ile Lys
            100                 105

<210> SEQ ID NO 87
<211> LENGTH: 106
<212> TYPE: PRT
<213> ORGANISM: Artificial Sequence
<220> FEATURE:
<223> OTHER INFORMATION: Synthetic Construct

<400> SEQUENCE: 87

Asp Ile Val Leu Thr Gln Ser Pro Ser Ser Leu Ser Ala Ser Val Gly
1               5                   10                  15

Asp Arg Val Thr Ile Thr Cys Arg Ala Ser Gln Asn Val Arg Ser Ala
            20                  25                  30

Leu Ala Trp Tyr Gln Gln Lys Pro Gly Gln Ala Pro Lys Leu Leu Ile
        35                  40                  45

Tyr Trp Ala Ser Asn Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Asn Tyr Leu Thr
                85                  90                  95

Phe Gly Gly Gly Thr Lys Val Glu Ile Lys
            100                 105

```
<210> SEQ ID NO 88
<211> LENGTH: 106
<212> TYPE: PRT
<213> ORGANISM: Artificial Sequence
<220> FEATURE:
<223> OTHER INFORMATION: Synthetic Construct

<400> SEQUENCE: 88

Asp Ile Val Met Thr Gln Ser Pro Ser Ser Met Ser Ala Ser Val Gly
1               5                   10                  15

Asp Arg Val Thr Ile Thr Cys Gln Ala Ser Gln Asn Val Arg Ser Ala
            20                  25                  30

Val Ala Trp Tyr Gln Gln Lys Pro Gly Lys Ala Pro Lys Leu Leu Ile
        35                  40                  45

Tyr Trp Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Trp Asn Tyr Leu Thr
                85                  90                  95

Phe Gly Gly Gly Thr Lys Val Glu Ile Lys
            100                 105

<210> SEQ ID NO 89
<211> LENGTH: 106
<212> TYPE: PRT
<213> ORGANISM: Artificial Sequence
<220> FEATURE:
<223> OTHER INFORMATION: Synthetic Construct

<400> SEQUENCE: 89

Asp Ile Val Met Thr Gln Ser Pro Ser Ser Leu Ser Thr Ser Val Gly
1               5                   10                  15

Asp Arg Val Thr Ile Thr Cys Arg Ala Ser Gln Asn Val Arg Ser Ala
            20                  25                  30

Leu Ala Trp Tyr Gln Gln Lys Pro Glu Lys Ala Pro Lys Ser Leu Ile
        35                  40                  45

Tyr Trp Ala Ser Asn Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Asn Tyr Leu Thr
                85                  90                  95

Phe Gly Gly Gly Thr Lys Val Glu Ile Lys
            100                 105

<210> SEQ ID NO 90
<211> LENGTH: 106
<212> TYPE: PRT
<213> ORGANISM: Artificial Sequence
<220> FEATURE:
<223> OTHER INFORMATION: Synthetic Construct

<400> SEQUENCE: 90

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asn Val Arg Ser Ala
            20                  25                  30
```

```
Leu Ala Trp Tyr Gln Gln Lys Pro Glu Gln Ala Pro Lys Ser Leu Ile
        35                  40                  45

Tyr Trp Ala Ser Asn Arg His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Asn Tyr Leu Thr
                85                  90                  95

Phe Gly Gly Gly Thr Lys Val Glu Ile Lys
            100                 105
```

<210> SEQ ID NO 91
<211> LENGTH: 106
<212> TYPE: PRT
<213> ORGANISM: Artificial Sequence
<220> FEATURE:
<223> OTHER INFORMATION: Synthetic Construct

<400> SEQUENCE: 91

```
Asp Ile Val Met Thr Gln Ser Pro Ser Ser Leu Ser Ala Ser Val Gly
1               5                   10                  15

Asp Arg Val Thr Ile Thr Cys Gln Ala Ser Gln Asn Val Arg Ser Ala
            20                  25                  30

Leu Asn Trp Tyr Gln Gln Lys Pro Gly Lys Ala Pro Lys Leu Leu Ile
        35                  40                  45

Tyr Trp Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Ser
65                  70                  75                  80

Glu Asp Ile Ala Thr Tyr Tyr Cys Gln Gln His Trp Asn Tyr Leu Thr
                85                  90                  95

Phe Gly Gly Gly Thr Lys Val Glu Ile Lys
            100                 105
```

<210> SEQ ID NO 92
<211> LENGTH: 106
<212> TYPE: PRT
<213> ORGANISM: Artificial Sequence
<220> FEATURE:
<223> OTHER INFORMATION: Synthetic Construct

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Arg Ser Ala
            20                  25                  30

Leu Ala Trp Tyr Gln Gln Lys Pro Glu Gln Ala Pro Lys Ser Leu Ile
        35                  40                  45

Tyr Trp Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Arg His Pro
65                  70                  75                  80

Glu Asp Phe Ala Thr Tyr Tyr Cys Gln Gln His Trp Asn Tyr Leu Thr
                85                  90                  95

Phe Gly Gly Gly Thr Lys Val Glu Ile Lys
            100                 105
```

<210> SEQ ID NO 93

```
<211> LENGTH: 106
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Thr Ser Val Gly
1               5                   10                  15

Asp Arg Val Thr Ile Thr Cys Gln Ala Ser Gln Asn Val Arg Ser Ala
            20                  25                  30

Leu Asn Trp Tyr Gln Gln Lys Pro Gly Lys Ala Pro Lys Leu Leu Ile
        35                  40                  45

Tyr Trp Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Ser
65                  70                  75                  80

Glu Asp Ile Ala Thr Tyr Tyr Cys Gln Gln His Trp Asn Tyr Leu Thr
                85                  90                  95

Phe Gly Gly Gly Thr Lys Val Glu Ile Lys
            100                 105

<210> SEQ ID NO 94
<211> LENGTH: 5
<212> TYPE: PRT
<213> ORGANISM: Artificial Sequence
<220> FEATURE:
<223> OTHER INFORMATION: Synthetic Construct

<400> SEQUENCE: 94

Asn Tyr Trp Met Gln
1               5

<210> SEQ ID NO 95
<211> LENGTH: 17
<212> TYPE: PRT
<213> ORGANISM: Artificial Sequence
<220> FEATURE:
<223> OTHER INFORMATION: Synthetic Construct

<400> SEQUENCE: 95

Ala Thr His Pro Gly His Gly Asp Thr Arg Tyr Thr Gln Lys Phe Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic Construct

<400> SEQUENCE: 96

Ala Thr His Pro Gly His Gly Asp Thr Arg Tyr Ala Gln Lys Phe Gln
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 97

Ala Thr His Pro Gly His Gly Asp Thr Arg Tyr Ser Pro Ser Phe Gln
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic Construct

<400> SEQUENCE: 98

Ala Thr His Pro Gly His Gly Asp Thr Arg Tyr Ala Glu Lys Phe Gln
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Thr Thr Leu Pro Gly His Gly Asp Thr Arg Tyr Ala Gln Lys Phe Gln
1               5                   10                  15

Gly

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Glu Glu Val Tyr Tyr Gly Phe Arg Ser Tyr Trp Tyr Phe Asp Val
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct

<400> SEQUENCE: 101

Glu Glu Val Asp Tyr Gly Phe Arg Ser Tyr Trp Tyr Phe Asp Val
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Glu Glu Val Tyr Tyr Gly Phe Arg Ser Tyr Trp Tyr Phe Asp Leu
1               5                   10                  15

<210> SEQ ID NO 103
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 103

Arg Ala Ser Glu Ser Val Asp Asn Tyr Gly Val Ser Phe Met Asn
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic Construct

<400> SEQUENCE: 104

Arg Ala Ser Glu Ser Val Asp Asn Tyr Gly Val Ser Arg Met Asn
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: Synthetic Construct

<400> SEQUENCE: 105

Gly Ala Ser Asn Gln Gly Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 106

Gly Ala Ser Asn Gln Gln Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Construct

<400> SEQUENCE: 107

Gln Gln Ser Lys Glu Val Pro Pro Thr
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Construct

<400> SEQUENCE: 108

Ser Tyr Trp Ile His
1               5

<210> SEQ ID NO 109
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 109

Asn Ile Asn Pro Thr Asn Gly Gly Thr Asn Tyr Asn Glu Arg Phe Lys
1               5                   10                  15
Ser

<210> SEQ ID NO 110
<211> LENGTH: 17
<212> TYPE: PRT
<213> ORGANISM: Artificial Sequence
<220> FEATURE:
<223> OTHER INFORMATION: Synthetic Construct

<400> SEQUENCE: 110

Asn Ile Asn Pro Thr Asn Gly Gly Thr Asn Tyr Ala Gln Lys Phe Gln
1               5                   10                  15
Gly

<210> SEQ ID NO 111
<211> LENGTH: 17
<212> TYPE: PRT
<213> ORGANISM: Artificial Sequence
<220> FEATURE:
<223> OTHER INFORMATION: Synthetic Construct

<400> SEQUENCE: 111

Asn Ile Asn Pro Thr Asn Gly Gly Thr Asn Tyr Ser Gln Lys Phe Gln
1               5                   10                  15
Gly

<210> SEQ ID NO 112
<211> LENGTH: 11
<212> TYPE: PRT
<213> ORGANISM: Artificial Sequence
<220> FEATURE:
<223> OTHER INFORMATION: Synthetic Construct

<400> SEQUENCE: 112

Ala Tyr Tyr Tyr Gly Ser Ser Leu Phe Ala Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic Construct

<400> SEQUENCE: 113

Lys Ala Ser Gln Asn Val Gly Thr Ala Val Ala
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Ser Ala Ser Tyr Arg His Thr
```

```
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Gln Gln Tyr Ser Thr Tyr Pro Trp Thr
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic Construct

<400> SEQUENCE: 116

Ser Tyr Gly Leu Ser
1               5

<210> SEQ ID NO 117
<211> LENGTH: 17
<212> TYPE: PRT
<213> ORGANISM: Artificial Sequence
<220> FEATURE:
<223> OTHER INFORMATION: Synthetic Construct

<400> SEQUENCE: 117

Trp Ile Asn Thr Tyr Ser Gly Val Pro Thr Tyr Ala Asn Asp Phe Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic Construct

<400> SEQUENCE: 118

Trp Ile Asn Thr Tyr Ser Gly Val Pro Thr Tyr Ala Gln Gly Phe Thr
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic Construct

<400> SEQUENCE: 119

Trp Ile Asn Thr Tyr Ser Gly Val Pro Thr Tyr Ser Gln Lys Phe Gln
1               5                   10                  15

Gly

<210> SEQ ID NO 120
<211> LENGTH: 16
<212> TYPE: PRT
<213> ORGANISM: Artificial Sequence
<220> FEATURE:
```

```
<223> OTHER INFORMATION: Synthetic Construct

<400> SEQUENCE: 120

Ile Asn Thr Tyr Ser Gly Val Pro Thr Tyr Ala Gln Lys Phe Gln Gly
1               5                   10                  15

<210> SEQ ID NO 121
<211> LENGTH: 17
<212> TYPE: PRT
<213> ORGANISM: Artificial Sequence
<220> FEATURE:
<223> OTHER INFORMATION: Synthetic Construct

<400> SEQUENCE: 121

Trp Ile Asn Thr Tyr Ser Gly Val Pro Thr Tyr Ala Gln Lys Phe Gln
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: Synthetic Construct

<400> SEQUENCE: 122

Trp Ile Asn Thr Tyr Ser Gly Val Pro Thr Tyr Ala Gln Gly Phe Ala
1               5                   10                  15

Gly

<210> SEQ ID NO 123
<211> LENGTH: 5
<212> TYPE: PRT
<213> ORGANISM: Artificial Sequence
<220> FEATURE:
<223> OTHER INFORMATION: Synthetic Construct

<400> SEQUENCE: 123

Ser Leu Val Asp Tyr
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic Construct

<400> SEQUENCE: 124

Thr Leu Ala Asp Tyr
1               5

<210> SEQ ID NO 125
<211> LENGTH: 5
<212> TYPE: PRT
<213> ORGANISM: Artificial Sequence
<220> FEATURE:
<223> OTHER INFORMATION: Synthetic Construct

<400> SEQUENCE: 125

Thr Met Val Asp Tyr
1               5

<210> SEQ ID NO 126
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 126

Thr Leu Gly Asp Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Construct

<400> SEQUENCE: 127

Thr Leu Val Asp Tyr
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Construct

<400> SEQUENCE: 128

Ser Leu Ala Asp Tyr
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129

Ser Met Ala Asp Tyr
1               5

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Lys Ser Ser Gln Ser Leu Leu Tyr Ser Asp Gly Lys Thr Tyr Leu Ser
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic Construct

<400> SEQUENCE: 131

Lys Ser Ser Arg Ser Leu Leu Tyr Ser Asp Gly Lys Thr Tyr Leu Ser
1               5                   10                  15

<210> SEQ ID NO 132
<211> LENGTH: 16
<212> TYPE: PRT
```

<213> ORGANISM: Artificial Sequence
<220> FEATURE:
<223> OTHER INFORMATION: Synthetic Construct

<400> SEQUENCE: 132

Lys Ser Ser Arg Ser Leu Leu Tyr Ser Gly Gly Lys Thr Tyr Leu Ser
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic Construct

<400> SEQUENCE: 133

Lys Ser Ser Arg Ser Leu Leu Tyr Ser Glu Gly Lys Thr Tyr Leu Ser
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic Construct

<400> SEQUENCE: 134

Lys Ser Ser Arg Ser Leu Leu Tyr Ser Ala Gly Lys Thr Tyr Leu Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic Construct

<400> SEQUENCE: 135

Lys Ser Ser Arg Ser Leu Leu Tyr Ser Ser Gly Lys Thr Tyr Leu Ser
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Synthetic Construct

<400> SEQUENCE: 136

Lys Ser Ser Arg Ser Leu Leu Tyr Ser Gln Gly Lys Thr Tyr Leu Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic Construct

<400> SEQUENCE: 137

Lys Ala Ser Gln Ser Leu Leu Tyr Ser Asp Gly Lys Thr Tyr Leu Ser
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic Construct

<400> SEQUENCE: 138

Lys Ser Gly Gln Ser Leu Leu Tyr Ser Asp Gly Lys Thr Tyr Leu Ser
1               5                   10                  15

<210> SEQ ID NO 139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 139

Leu Val Ser Lys Leu Asp Ser
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Glu Val Ser Lys Leu Asp Ser
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic Construct

<400> SEQUENCE: 141

Leu Val Ser Arg Leu Asp Ser
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic Construct

<400> SEQUENCE: 142

Leu Val Ser Lys Leu Glu Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 143

Leu Val Ser Lys Leu Ser Ser
1               5

<210> SEQ ID NO 144
<211> LENGTH: 9
<212> TYPE: PRT
<213> ORGANISM: Artificial Sequence
<220> FEATURE:

```
<223> OTHER INFORMATION: Synthetic Construct

<400> SEQUENCE: 144

Trp Gln Gly Ile Asp Phe His Gln Thr
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic Construct

<400> SEQUENCE: 145

Trp Gln Gly Ile Arg Phe His Gln Thr
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic Construct

<400> SEQUENCE: 146

Thr Ser Asp Met Gly Val Gly
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic Construct

<400> SEQUENCE: 147

Thr Ser Asp Met Gly Val Ser
1               5

<210> SEQ ID NO 148
<211> LENGTH: 16
<212> TYPE: PRT
<213> ORGANISM: Artificial Sequence
<220> FEATURE:
<223> OTHER INFORMATION: Synthetic Construct

<400> SEQUENCE: 148

Asp Ile Trp Trp Asp Asp Asn Lys Tyr Tyr Asn Pro Ser Leu Lys Ser
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic Construct

<400> SEQUENCE: 149

Leu Ile Trp Trp Asp Asp Asn Lys Tyr Tyr Ser Thr Ser Leu Lys Thr
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic Construct
```

<400> SEQUENCE: 150

Leu Ile Trp Trp Asp Asp Asn Lys Tyr Tyr Ser Pro Ser Leu Lys Ser
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic Construct

<400> SEQUENCE: 151

His Ile Trp Trp Asp Asp Asn Lys Ser Tyr Ser Thr Ser Leu Lys Ser
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic Construct

<400> SEQUENCE: 152

Ser Ile Trp Trp Asp Asp Asn Lys Tyr Tyr Asn Pro Ser Leu Lys Ser
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic Construct

<400> SEQUENCE: 153

Ser Ile Trp Tyr Asp Asp Asn Lys Tyr Tyr Asn Pro Ser Leu Lys Ser
1               5                   10                  15

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct

<400> SEQUENCE: 154

Arg Ala Asn Tyr Gly Asn Leu Phe Asp Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Synthetic Construct

<400> SEQUENCE: 155

Lys Ala Ser Gln Asn Val Arg Ser Ala Val Ala
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 156

Arg Ala Ser Gln Asn Val Arg Ser Ala Leu Ala
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Synthetic Construct

<400> SEQUENCE: 157

Gln Ala Ser Gln Asn Val Arg Ser Ala Val Ala
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic Construct

<400> SEQUENCE: 158

Gln Ala Ser Gln Asn Val Arg Ser Ala Leu Asn
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Synthetic Construct

<400> SEQUENCE: 159

Trp Ala Ser Asn Arg His Thr
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 160

Trp Ala Ser Asn Arg His Ser
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic Construct

<400> SEQUENCE: 161

Trp Ala Ser Ser Leu Gln Ser
1               5

<210> SEQ ID NO 162
<211> LENGTH: 7
<212> TYPE: PRT
<213> ORGANISM: Artificial Sequence
<220> FEATURE:
<223> OTHER INFORMATION: Synthetic Construct

<400> SEQUENCE: 162
```

Gln His Trp Asn Tyr Leu Thr
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic Construct

<400> SEQUENCE: 163

Gln Gln His Trp Asn Tyr Leu Thr
1               5

<210> SEQ ID NO 164
<211> LENGTH: 124
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Lys Gln Arg Pro Gly Gln Gly Leu Glu Trp Ile
        35                  40                  45

Gly Ala Thr His Pro Gly His Gly Asp Thr Arg Tyr Thr Gln Lys Phe
    50                  55                  60

Lys Gly Lys Ala Thr Leu Ser Ala Asp Lys Ser Ser Ser Thr Ala Tyr
65                  70                  75                  80

Met Gln Leu Ser Asn Leu Ala Ser Glu Asp Ser Ala Val Tyr Tyr Cys
                85                  90                  95

Ala Arg Glu Glu Val Tyr Tyr Gly Phe Arg Ser Tyr Trp Tyr Phe Asp
            100                 105                 110

Val Trp Gly Arg Gly Thr Leu Val Thr Val Ser Ser
        115                 120

<210> SEQ ID NO 165
<211> LENGTH: 111
<212> TYPE: PRT
<213> ORGANISM: Artificial Sequence
<220> FEATURE:
<223> OTHER INFORMATION: Synthetic Construct

<400> SEQUENCE: 165

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Val Ser Phe Met Asn Trp Phe Gln Gln Lys Pro Gly Gln Pro Pro
        35                  40                  45

Lys Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110

<210> SEQ ID NO 166
<211> LENGTH: 120
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Asn Ile Asn Pro Thr Asn Gly Gly Thr Asn Tyr Asn Glu Arg Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Tyr Tyr Tyr Gly Ser Ser Leu Phe Ala Tyr Trp Gly Gln
            100                 105                 110

Gly Thr Leu Val Thr Val Ser Ser
        115                 120

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Ser Gln Gln Lys Pro Gly Gln Ser Pro Lys Leu Leu Ile
        35                  40                  45

Tyr Ser Ala Ser Tyr Arg His Thr Gly Val Pro Asp Arg Phe Thr Gly
    50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Thr Tyr Pro Trp
                85                  90                  95

Thr Phe Gly Gly Gly Thr Lys Leu Glu Ile Lys
            100                 105

<210> SEQ ID NO 168
<211> LENGTH: 114
<212> TYPE: PRT
<213> ORGANISM: Artificial Sequence
<220> FEATURE:
<223> OTHER INFORMATION: Synthetic Construct

<400> SEQUENCE: 168

Gln Ile Gln Leu Val Gln Ser Gly Pro Glu Leu Lys Lys Pro Gly Glu

```
                1               5                   10                  15
        Thr Val Lys Ile Ser Cys Lys Ala Ser Gly Tyr Ile Phe Thr Ser Tyr
                            20                  25                  30

Gly Leu Ser Trp Val Lys Gln Thr Pro Gly Lys Gly Leu Lys Trp Met
                            35                  40                  45

Gly Trp Ile Asn Thr Tyr Ser Gly Val Pro Thr Tyr Ala Asn Asp Phe
                    50                  55                  60

Lys Gly Arg Phe Ala Phe Ser Leu Glu Thr Ser Ala Ser Thr Thr Tyr
        65                  70                  75                  80

Leu Arg Ile Asn Asn Leu Lys Asn Asp Asp Thr Ala Thr Tyr Phe Cys
                            85                  90                  95

Ala Arg Ser Leu Val Asp Tyr Trp Gly Gln Gly Thr Pro Leu Thr Val
                            100                 105                 110

Ser Ser
```

<210> SEQ ID NO 169
<211> LENGTH: 112
<212> TYPE: PRT
<213> ORGANISM: Artificial Sequence
<220> FEATURE:
<223> OTHER INFORMATION: Synthetic Construct

<400> SEQUENCE: 169

```
        Asp Val Val Met Thr Gln Thr Pro Phe Thr Leu Ser Val Thr Ile Gly
        1               5                   10                  15

Gln Ser Ala Ser Ile Ser Cys Lys Ser Ser Gln Ser Leu Leu Tyr Ser
                            20                  25                  30

Asp Gly Lys Thr Tyr Leu Ser Trp Leu Leu Gln Arg Pro Gly Gln Ser
                            35                  40                  45

Pro Lys Arg Leu Ile Tyr Leu Val Ser Lys Leu Asp Ser Gly Val Pro
                    50                  55                  60

Asp Arg Phe Thr Gly Ser Gly Ser Gly Thr Asp Phe Thr Leu Lys Ile
        65                  70                  75                  80

Ser Arg Val Glu Ala Glu Asp Leu Gly Val Tyr Tyr Cys Trp Gln Gly
                            85                  90                  95

Ile Asp Phe His Gln Thr Phe Gly Gly Gly Thr Lys Leu Glu Ile Lys
                            100                 105                 110
```

<210> SEQ ID NO 170
<211> LENGTH: 120
<212> TYPE: PRT
<213> ORGANISM: Artificial Sequence
<220> FEATURE:
<223> OTHER INFORMATION: Synthetic Construct

<400> SEQUENCE: 170

```
        Gln Val Thr Leu Lys Glu Ser Gly Pro Gly Ile Leu Gln Pro Ser Gln
        1               5                   10                  15

Thr Leu Ser Leu Thr Cys Ser Phe Ser Gly Phe Ser Leu Arg Thr Ser
                            20                  25                  30

Asp Met Gly Val Gly Trp Val Arg Gln Pro Ser Gly Glu Gly Leu Glu
                            35                  40                  45

Trp Leu Ala Asp Ile Trp Trp Asp Asp Lys Tyr Tyr Asn Pro Ser
                    50                  55                  60

Leu Lys Ser Arg Leu Thr Ile Ser Lys Asp Thr Ser Asn Gln Val
        65                  70                  75                  80

Phe Leu Lys Ile Thr Ser Val Asp Thr Ala Asp Thr Ala Thr Tyr Tyr
```

```
                    85                  90                  95

Cys Ala Arg Arg Ala Asn Tyr Gly Asn Leu Phe Asp Tyr Trp Gly Gln
                100                 105                 110

Gly Thr Ala Val Thr Val Ser Ser
        115                 120

<210> SEQ ID NO 171
<211> LENGTH: 106
<212> TYPE: PRT
<213> ORGANISM: Artificial Sequence
<220> FEATURE:
<223> OTHER INFORMATION: Synthetic Construct

<400> SEQUENCE: 171

Asp Ile Val Met Thr Gln Ser Leu Lys Phe Met Ser Thr Ser Val Gly
1               5                   10                  15

Asp Arg Val Ser Ile Thr Cys Lys Ala Ser Gln Asn Val Arg Ser Ala
                20                  25                  30

Val Ala Trp Tyr Gln Gln Lys Pro Gly Gln Ser Pro Lys Val Leu Ile
            35                  40                  45

Tyr Trp Ala Ser Asn Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Leu Thr
                85                  90                  95

Phe Gly Ser Gly Thr Lys Leu Glu Ile Lys
                100                 105

<210> SEQ ID NO 172
<211> LENGTH: 171
<212> TYPE: PRT
<213> ORGANISM: Artificial Sequence
<220> FEATURE:
<223> OTHER INFORMATION: Synthetic Construct

<400> SEQUENCE: 172

Met Gly Trp Ser Cys Ile Ile Leu Phe Leu Val Ala Thr Ala Thr Gly
1               5                   10                  15

Val His Ser Met Tyr Gly Lys Leu Asn Asp Leu Leu Glu Asp Leu Gln
                20                  25                  30

Glu Val Leu Lys Asn Leu His Lys Asn Cys Met Ala Ser Asn Thr Tyr
            35                  40                  45

Gly Ser Asn Pro Ile Ser Lys Asp Asn Leu His Asp Val Asp Asn His
        50                  55                  60

Leu Gln Asn Val Ile Glu Asp Ile His Asp Phe Met Gln Gly Gly Gly
65                  70                  75                  80

Ser Gly Gly Lys Leu Gln Glu Met Met Lys Glu Phe Gln Gln Val Leu
                85                  90                  95

Asp Glu Leu Asn Asn His Ser Phe His His Pro Tyr Cys Asn Tyr Tyr
                100                 105                 110

Gly Asn Ser Asn Asn Cys His Gly Thr Met Ser His Thr Val His His
            115                 120                 125

Ile Glu Gln Asn Ile Lys Glu Ile Phe His His Leu Glu Glu Leu Val
        130                 135                 140

His Arg His His His His His His His Gly Gly Gly Leu Asn Asp
145                 150                 155                 160
```

```
Ile Phe Glu Ala Gln Lys Ile Glu Trp His Glu
                165                 170

<210> SEQ ID NO 173
<211> LENGTH: 177
<212> TYPE: PRT
<213> ORGANISM: Artificial Sequence
<220> FEATURE:
<223> OTHER INFORMATION: Synthetic Construct

<400> SEQUENCE: 173

Met Gly Trp Ser Cys Ile Ile Leu Phe Leu Val Ala Thr Ala Thr Gly
1               5                   10                  15

Val His Ser Ala Asp Leu Glu Asp Asn Trp Glu Thr Leu Asn Asp Asn
            20                  25                  30

Leu Lys Val Ile Glu Cys Met Ala Ser Asn Thr Tyr Gly Ser Asn Pro
        35                  40                  45

Ile Ser Ala Ala Gln Val Lys Asp Ala Leu Thr Lys Met Arg Ala Ala
    50                  55                  60

Ala Leu Asp Ala Gln Lys Ala Thr Pro Pro Lys Leu Glu Asp Lys Ser
65                  70                  75                  80

Pro Asp Ser Pro Glu Met Lys Asp Phe Arg His Gly Phe Asp Ile Leu
                85                  90                  95

Val Gly Gln Ile Asp Asp Ala Leu Lys Leu Ala Asn Ser Phe His His
            100                 105                 110

Pro Tyr Cys Asn Tyr Tyr Gly Asn Ser Asn Asn Cys His Gly Thr Met
        115                 120                 125

Ser Val Lys Glu Ala Gln Ala Ala Glu Gln Leu Lys Thr Thr Arg
    130                 135                 140

Asn Ala Tyr Ile Gln Lys Tyr Leu His His His His His His
145                 150                 155                 160

Gly Gly Gly Leu Asn Asp Ile Phe Glu Ala Gln Lys Ile Glu Trp His
                165                 170                 175

Glu

<210> SEQ ID NO 174
<211> LENGTH: 179
<212> TYPE: PRT
<213> ORGANISM: Artificial Sequence
<220> FEATURE:
<223> OTHER INFORMATION: Synthetic Construct

<400> SEQUENCE: 174

Met Gly Trp Ser Cys Ile Ile Leu Phe Leu Val Ala Thr Ala Thr Gly
1               5                   10                  15

Val His Ser Ala Asp Leu Glu Asp Asn Trp Glu Thr Leu Asn Asp Asn
            20                  25                  30

Leu Lys Val Ile Glu Gly Pro Cys Met Ala Ser Asn Thr Tyr Gly Ser
        35                  40                  45

Asn Pro Ile Ser Ala Ala Gln Val Lys Asp Ala Leu Thr Lys Met Arg
    50                  55                  60

Ala Ala Ala Leu Asp Ala Gln Lys Ala Thr Pro Pro Lys Leu Glu Asp
65                  70                  75                  80

Lys Ser Pro Asp Ser Pro Glu Met Lys Asp Phe Arg His Gly Phe Asp
                85                  90                  95

Ile Leu Val Gly Gln Ile Asp Asp Ala Leu Lys Leu Ala Asn Ser Phe
            100                 105                 110
```

```
His His Pro Tyr Cys Asn Tyr Gly Asn Ser Asn Cys His Gly
        115                 120                 125

Thr Met Ser Val Lys Glu Ala Gln Ala Ala Glu Gln Leu Lys Thr
    130                 135                 140

Thr Arg Asn Ala Tyr Ile Gln Lys Tyr Leu His His His His His
145                 150                 155                 160

His His Gly Gly Gly Leu Asn Asp Ile Phe Glu Ala Gln Lys Ile Glu
            165                 170                 175

Trp His Glu
```

<210> SEQ ID NO 175
<211> LENGTH: 146
<212> TYPE: PRT
<213> ORGANISM: Artificial Sequence
<220> FEATURE:
<223> OTHER INFORMATION: Synthetic Construct

<400> SEQUENCE: 175

```
Met Gly Trp Ser Cys Ile Ile Leu Phe Leu Val Ala Thr Ala Thr Gly
1               5                   10                  15

Val His Ser Met Tyr Gly Lys Leu Asn Asp Leu Leu Glu Asp Leu Gln
                20                  25                  30

Glu Val Leu Lys Asn Leu His Lys Asn Trp His Gly Gly Lys Asp Asn
            35                  40                  45

Leu His Asp Val Asp Asn His Leu Gln Asn Val Ile Glu Asp Ile His
        50                  55                  60

Asp Phe Met Gln Gly Gly Gly Ser Gly Gly Lys Leu Gln Glu Met Met
65                  70                  75                  80

Lys Glu Phe Gln Gln Val Leu Asp Glu Leu Asn Asn His Leu Gln Gly
                85                  90                  95

Gly Lys His Thr Val His His Ile Glu Gln Asn Ile Lys Glu Ile Phe
            100                 105                 110

His His Leu Glu Glu Leu Val His Arg His His His His His His His
        115                 120                 125

His Gly Gly Gly Leu Asn Asp Ile Phe Glu Ala Gln Lys Ile Glu Trp
130                 135                 140

His Glu
145
```

<210> SEQ ID NO 176
<211> LENGTH: 150
<212> TYPE: PRT
<213> ORGANISM: Artificial Sequence
<220> FEATURE:
<223> OTHER INFORMATION: Synthetic Construct

<400> SEQUENCE: 176

```
Met Gly Trp Ser Cys Ile Ile Leu Phe Leu Val Ala Thr Ala Thr Gly
1               5                   10                  15

Val His Ser Ala Asp Leu Glu Asp Asn Trp Glu Thr Leu Asn Asp Asn
                20                  25                  30

Leu Lys Val Ile Glu Lys Ala Asp Asn Ala Ala Gln Val Lys Asp Ala
            35                  40                  45

Leu Thr Lys Met Arg Ala Ala Ala Leu Asp Ala Gln Lys Ala Thr Pro
        50                  55                  60

Pro Lys Leu Glu Asp Lys Ser Pro Asp Ser Pro Glu Met Lys Asp Phe
65                  70                  75                  80
```

-continued

Arg His Gly Phe Asp Ile Leu Val Gly Gln Ile Asp Asp Ala Leu Lys
            85                  90                  95

Leu Ala Asn Glu Gly Lys Val Lys Glu Ala Gln Ala Ala Glu Gln
        100                 105                 110

Leu Lys Thr Thr Arg Asn Ala Tyr Ile Gln Lys Tyr Leu His His His
            115                 120                 125

His His His His His Gly Gly Leu Asn Asp Ile Phe Glu Ala Gln
        130                 135                 140

Lys Ile Glu Trp His Glu
145                 150

<210> SEQ ID NO 177
<211> LENGTH: 13
<212> TYPE: PRT
<213> ORGANISM: Homo sapiens

<400> SEQUENCE: 177

Cys Met Ala Ser Asn Thr Tyr Gly Ser Asn Pro Ile Ser
1               5                   10

<210> SEQ ID NO 178
<211> LENGTH: 21
<212> TYPE: PRT
<213> ORGANISM: Homo sapiens

<400> SEQUENCE: 178

Ser Phe His His Pro Tyr Cys Asn Tyr Tyr Gly Asn Ser Asn Asn Cys
1               5                   10                  15

His Gly Thr Met Ser
            20

<210> SEQ ID NO 179
<211> LENGTH: 117
<212> TYPE: PRT
<213> ORGANISM: Artificial Sequence
<220> FEATURE:
<223> OTHER INFORMATION: Synthetic Construct

<400> SEQUENCE: 179

Glu Val Lys Leu Glu Glu Ser Gly Gly Gly Leu Val Gln Pro Gly Arg
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Ser Ser Met Ile Ile Val Asp Tyr Trp Gly Gln Gly Thr Thr
            100                 105                 110

Val Thr Val Ser Ser
        115

<210> SEQ ID NO 180
<211> LENGTH: 111
<212> TYPE: PRT
<213> ORGANISM: Artificial Sequence

```
<220> FEATURE:
<223> OTHER INFORMATION: Synthetic Construct

<400> SEQUENCE: 180

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Ser Ser
            20                  25                  30

Thr Tyr Ser Tyr Leu His Trp Tyr Gln Gln Arg Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Val Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Met Lys
            100                 105                 110

<210> SEQ ID NO 181
<211> LENGTH: 102
<212> TYPE: PRT
<213> ORGANISM: Artificial Sequence
<220> FEATURE:
<223> OTHER INFORMATION: Synthetic Construct

<400> SEQUENCE: 181

Met Tyr Gly Lys Leu Asn Asp Leu Leu Glu Asp Leu Gln Glu Val Leu
1               5                   10                  15

Lys Asn Leu His Lys Asn Trp His Gly Gly Lys Asp Asn Leu His Asp
            20                  25                  30

Val Asp Asn His Leu Gln Asn Val Ile Glu Asp Ile His Asp Phe Met
        35                  40                  45

Gln Gly Gly Gly Ser Gly Gly Lys Leu Gln Glu Met Met Lys Glu Phe
    50                  55                  60

Gln Gln Val Leu Asp Glu Leu Asn Asn His Leu Gln Gly Gly Lys His
65                  70                  75                  80

Thr Val His His Ile Glu Gln Asn Ile Lys Glu Ile Phe His His Leu
                85                  90                  95

Glu Glu Leu Val His Arg
            100

<210> SEQ ID NO 182
<211> LENGTH: 106
<212> TYPE: PRT
<213> ORGANISM: Artificial Sequence
<220> FEATURE:
<223> OTHER INFORMATION: Synthetic Construct

<400> SEQUENCE: 182

Ala Asp Leu Glu Asp Asn Trp Glu Thr Leu Asn Asp Asn Leu Lys Val
1               5                   10                  15

Ile Glu Lys Ala Asp Asn Ala Ala Gln Val Lys Asp Ala Leu Thr Lys
            20                  25                  30

Met Arg Ala Ala Ala Leu Asp Ala Gln Lys Ala Thr Pro Pro Lys Leu
        35                  40                  45

Glu Asp Lys Ser Pro Asp Ser Pro Glu Met Lys Asp Phe Arg His Gly
    50                  55                  60
```

```
Phe Asp Ile Leu Val Gly Gln Ile Asp Asp Ala Leu Lys Leu Ala Asn
 65                  70                  75                  80

Glu Gly Lys Val Lys Glu Ala Gln Ala Ala Glu Gln Leu Lys Thr
                 85                  90                  95

Thr Arg Asn Ala Tyr Ile Gln Lys Tyr Leu
                100                 105

<210> SEQ ID NO 183
<211> LENGTH: 21
<212> TYPE: PRT
<213> ORGANISM: Artificial Sequence
<220> FEATURE:
<223> OTHER INFORMATION: Synthetic Construct

<400> SEQUENCE: 183

Ser Phe His His Ala Tyr Cys Asn Tyr Tyr Gly Asn Ser Asn Cys
 1               5                  10                  15

His Gly Thr Met Ser
                 20

<210> SEQ ID NO 184
<211> LENGTH: 21
<212> TYPE: PRT
<213> ORGANISM: Artificial Sequence
<220> FEATURE:
<223> OTHER INFORMATION: Synthetic Construct

<400> SEQUENCE: 184

Ser Phe His His Pro Tyr Cys Asn Tyr Tyr Gly Asn Ser Ala Asn Cys
 1               5                  10                  15

His Gly Thr Met Ser
                 20

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190
```

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

-continued

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
<400> SEQUENCE: 217
000

<210> SEQ ID NO 218
<400> SEQUENCE: 218
000

<210> SEQ ID NO 219
<400> SEQUENCE: 219
000

<210> SEQ ID NO 220
<400> SEQUENCE: 220
000

<210> SEQ ID NO 221
<400> SEQUENCE: 221
000

<210> SEQ ID NO 222
<400> SEQUENCE: 222
000

<210> SEQ ID NO 223
<400> SEQUENCE: 223
000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255
<211> LENGTH: 13
<212> TYPE: PRT
<213> ORGANISM: Artificial Sequence
<220> FEATURE:
<223> OTHER INFORMATION: Synthetic Construct

<400> SEQUENCE: 255

Ser Met Ala Ser Asn Thr Tyr Gly Ser Asn Pro Ile Ser
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Synthetic Construct

<400> SEQUENCE: 256

Cys Ala Ala Ser Asn Thr Tyr Gly Ser Asn Pro Ile Ser
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Synthetic Construct

<400> SEQUENCE: 257

Cys Met Ser Ser Asn Thr Tyr Gly Ser Asn Pro Ile Ser
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Synthetic Construct

<400> SEQUENCE: 258

Cys Met Ala Ala Asn Thr Tyr Gly Ser Asn Pro Ile Ser
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Synthetic Construct

<400> SEQUENCE: 259

Cys Met Ala Ser Ala Thr Tyr Gly Ser Asn Pro Ile Ser
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthetic Construct

<400> SEQUENCE: 260

Cys Met Ala Ser Asn Ala Tyr Gly Ser Asn Pro Ile Ser
1               5                   10

<210> SEQ ID NO 261
<211> LENGTH: 13
<212> TYPE: PRT
<213> ORGANISM: Artificial Sequence
<220> FEATURE:
<223> OTHER INFORMATION: Synthetic Construct

<400> SEQUENCE: 261

Cys Met Ala Ser Asn Thr Ala Gly Ser Asn Pro Ile Ser
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Synthetic Construct

<400> SEQUENCE: 262

```
Cys Met Ala Ser Asn Thr Tyr Ala Ser Asn Pro Ile Ser
1               5                   10
```

<210> SEQ ID NO 263
<211> LENGTH: 13
<212> TYPE: PRT
<213> ORGANISM: Artificial Sequence
<220> FEATURE:
<223> OTHER INFORMATION: Synthetic Construct

<400> SEQUENCE: 263

```
Cys Met Ala Ser Asn Thr Tyr Gly Ala Asn Pro Ile Ser
1               5                   10
```

<210> SEQ ID NO 264
<211> LENGTH: 13
<212> TYPE: PRT
<213> ORGANISM: Artificial Sequence
<220> FEATURE:
<223> OTHER INFORMATION: Synthetic Construct

<400> SEQUENCE: 264

```
Cys Met Ala Ser Asn Thr Tyr Gly Ser Ala Pro Ile Ser
1               5                   10
```

<210> SEQ ID NO 265
<211> LENGTH: 13
<212> TYPE: PRT
<213> ORGANISM: Artificial Sequence
<220> FEATURE:
<223> OTHER INFORMATION: Synthetic Construct

<400> SEQUENCE: 265

```
Cys Met Ala Ser Asn Thr Tyr Gly Ser Asn Ala Ile Ser
1               5                   10
```

<210> SEQ ID NO 266
<211> LENGTH: 13
<212> TYPE: PRT
<213> ORGANISM: Artificial Sequence
<220> FEATURE:
<223> OTHER INFORMATION: Synthetic Construct

<400> SEQUENCE: 266

```
Cys Met Ala Ser Asn Thr Tyr Gly Ser Asn Pro Ala Ser
1               5                   10
```

<210> SEQ ID NO 267
<211> LENGTH: 13
<212> TYPE: PRT
<213> ORGANISM: Artificial Sequence
<220> FEATURE:
<223> OTHER INFORMATION: Synthetic Construct

<400> SEQUENCE: 267

```
Cys Met Ala Ser Asn Thr Tyr Gly Ser Asn Pro Ile Ala
1               5                   10
```

<210> SEQ ID NO 268
<211> LENGTH: 21
<212> TYPE: PRT
<213> ORGANISM: Artificial Sequence
<220> FEATURE:
<223> OTHER INFORMATION: Synthetic Construct

<400> SEQUENCE: 268

Ala Phe His His Pro Tyr Cys Asn Tyr Tyr Gly Asn Ser Asn Asn Cys

-continued

```
                1               5                  10                  15

His Gly Thr Met Ser
            20

<210> SEQ ID NO 269
<211> LENGTH: 21
<212> TYPE: PRT
<213> ORGANISM: Artificial Sequence
<220> FEATURE:
<223> OTHER INFORMATION: Synthetic Construct

<400> SEQUENCE: 269

Ser Ala His His Pro Tyr Cys Asn Tyr Tyr Gly Asn Ser Asn Asn Cys
1               5                  10                  15

His Gly Thr Met Ser
            20

<210> SEQ ID NO 270
<211> LENGTH: 21
<212> TYPE: PRT
<213> ORGANISM: Artificial Sequence
<220> FEATURE:
<223> OTHER INFORMATION: Synthetic Construct

<400> SEQUENCE: 270

Ser Phe Ala His Pro Tyr Cys Asn Tyr Tyr Gly Asn Ser Asn Asn Cys
1               5                  10                  15

His Gly Thr Met Ser
            20

<210> SEQ ID NO 271
<211> LENGTH: 21
<212> TYPE: PRT
<213> ORGANISM: Artificial Sequence
<220> FEATURE:
<223> OTHER INFORMATION: Synthetic Construct

<400> SEQUENCE: 271

Ser Phe His Ala Pro Tyr Cys Asn Tyr Tyr Gly Asn Ser Asn Asn Cys
1               5                  10                  15

His Gly Thr Met Ser
            20

<210> SEQ ID NO 272
<211> LENGTH: 21
<212> TYPE: PRT
<213> ORGANISM: Artificial Sequence
<220> FEATURE:
<223> OTHER INFORMATION: Synthetic Construct

<400> SEQUENCE: 272

Ser Phe His His Pro Ala Cys Asn Tyr Tyr Gly Asn Ser Asn Asn Cys
1               5                  10                  15

His Gly Thr Met Ser
            20

<210> SEQ ID NO 273
<211> LENGTH: 21
<212> TYPE: PRT
<213> ORGANISM: Artificial Sequence
<220> FEATURE:
<223> OTHER INFORMATION: Synthetic Construct

<400> SEQUENCE: 273
```

Ser Phe His His Pro Tyr Ser Asn Tyr Tyr Gly Asn Ser Asn Asn Cys
1               5                   10                  15

His Gly Thr Met Ser
            20

<210> SEQ ID NO 274
<211> LENGTH: 21
<212> TYPE: PRT
<213> ORGANISM: Artificial Sequence
<220> FEATURE:
<223> OTHER INFORMATION: Synthetic Construct

<400> SEQUENCE: 274

Ser Phe His His Pro Tyr Cys Ala Tyr Tyr Gly Asn Ser Asn Asn Cys
1               5                   10                  15

His Gly Thr Met Ser
            20

<210> SEQ ID NO 275
<211> LENGTH: 21
<212> TYPE: PRT
<213> ORGANISM: Artificial Sequence
<220> FEATURE:
<223> OTHER INFORMATION: Synthetic Construct

<400> SEQUENCE: 275

Ser Phe His His Pro Tyr Cys Asn Ala Tyr Gly Asn Ser Asn Asn Cys
1               5                   10                  15

His Gly Thr Met Ser
            20

<210> SEQ ID NO 276
<211> LENGTH: 21
<212> TYPE: PRT
<213> ORGANISM: Artificial Sequence
<220> FEATURE:
<223> OTHER INFORMATION: Synthetic Construct

<400> SEQUENCE: 276

Ser Phe His His Pro Tyr Cys Asn Tyr Ala Gly Asn Ser Asn Asn Cys
1               5                   10                  15

His Gly Thr Met Ser
            20

<210> SEQ ID NO 277
<211> LENGTH: 21
<212> TYPE: PRT
<213> ORGANISM: Artificial Sequence
<220> FEATURE:
<223> OTHER INFORMATION: Synthetic Construct

<400> SEQUENCE: 277

Ser Phe His His Pro Tyr Cys Asn Tyr Tyr Ala Asn Ser Asn Asn Cys
1               5                   10                  15

His Gly Thr Met Ser
            20

<210> SEQ ID NO 278
<211> LENGTH: 21
<212> TYPE: PRT
<213> ORGANISM: Artificial Sequence
<220> FEATURE:
<223> OTHER INFORMATION: Synthetic Construct

<400> SEQUENCE: 278

Ser Phe His His Pro Tyr Cys Asn Tyr Gly Ala Ser Asn Asn Cys
1               5                   10                  15

His Gly Thr Met Ser
            20

<210> SEQ ID NO 279
<211> LENGTH: 21
<212> TYPE: PRT
<213> ORGANISM: Artificial Sequence
<220> FEATURE:
<223> OTHER INFORMATION: Synthetic Construct

<400> SEQUENCE: 279

Ser Phe His His Pro Tyr Cys Asn Tyr Gly Asn Ala Asn Asn Cys
1               5                   10                  15

His Gly Thr Met Ser
            20

<210> SEQ ID NO 280
<211> LENGTH: 21
<212> TYPE: PRT
<213> ORGANISM: Artificial Sequence
<220> FEATURE:
<223> OTHER INFORMATION: Synthetic Construct

<400> SEQUENCE: 280

Ser Phe His His Pro Tyr Cys Asn Tyr Gly Asn Ser Asn Ala Cys
1               5                   10                  15

His Gly Thr Met Ser
            20

<210> SEQ ID NO 281
<211> LENGTH: 21
<212> TYPE: PRT
<213> ORGANISM: Artificial Sequence
<220> FEATURE:
<223> OTHER INFORMATION: Synthetic Construct

<400> SEQUENCE: 281

Ser Phe His His Pro Tyr Cys Asn Tyr Gly Asn Ser Asn Asn Ser
1               5                   10                  15

His Gly Thr Met Ser
            20

<210> SEQ ID NO 282
<211> LENGTH: 21
<212> TYPE: PRT
<213> ORGANISM: Artificial Sequence
<220> FEATURE:
<223> OTHER INFORMATION: Synthetic Construct

<400> SEQUENCE: 282

Ser Phe His His Pro Tyr Cys Asn Tyr Gly Asn Ser Asn Asn Cys
1               5                   10                  15

Ala Gly Thr Met Ser
            20

<210> SEQ ID NO 283
<211> LENGTH: 21
<212> TYPE: PRT
<213> ORGANISM: Artificial Sequence
<220> FEATURE:
<223> OTHER INFORMATION: Synthetic Construct

<400> SEQUENCE: 283

Ser Phe His His Pro Tyr Cys Asn Tyr Tyr Gly Asn Ser Asn Asn Cys
1               5                   10                  15

His Ala Thr Met Ser
            20

<210> SEQ ID NO 284
<211> LENGTH: 21
<212> TYPE: PRT
<213> ORGANISM: Artificial Sequence
<220> FEATURE:
<223> OTHER INFORMATION: Synthetic Construct

<400> SEQUENCE: 284

Ser Phe His His Pro Tyr Cys Asn Tyr Tyr Gly Asn Ser Asn Asn Cys
1               5                   10                  15

His Gly Ala Met Ser
            20

<210> SEQ ID NO 285
<211> LENGTH: 21
<212> TYPE: PRT
<213> ORGANISM: Artificial Sequence
<220> FEATURE:
<223> OTHER INFORMATION: Synthetic Construct

<400> SEQUENCE: 285

Ser Phe His His Pro Tyr Cys Asn Tyr Tyr Gly Asn Ser Asn Asn Cys
1               5                   10                  15

His Gly Thr Ala Ser
            20

<210> SEQ ID NO 286
<211> LENGTH: 21
<212> TYPE: PRT
<213> ORGANISM: Artificial Sequence
<220> FEATURE:
<223> OTHER INFORMATION: Synthetic Construct

<400> SEQUENCE: 286

Ser Phe His His Pro Tyr Cys Asn Tyr Tyr Gly Asn Ser Asn Asn Cys
1               5                   10                  15

His Gly Thr Met Ala
            20

<210> SEQ ID NO 287
<211> LENGTH: 18
<212> TYPE: PRT
<213> ORGANISM: Artificial Sequence
<220> FEATURE:
<223> OTHER INFORMATION: Synthetic Construct

<400> SEQUENCE: 287

Ser Phe His His Pro Tyr Cys Asn Tyr Tyr Asn Asn Cys His Gly Thr
1               5                   10                  15

Met Ser

<210> SEQ ID NO 288
<211> LENGTH: 16
<212> TYPE: PRT
<213> ORGANISM: Artificial Sequence
<220> FEATURE:
<223> OTHER INFORMATION: Synthetic Construct

<400> SEQUENCE: 288

Ser Phe His His Pro Tyr Cys Asn Asn Cys His Gly Thr Met Ser
1               5                   10                  15

<210> SEQ ID NO 289
<211> LENGTH: 13
<212> TYPE: PRT
<213> ORGANISM: Homo sapiens

<400> SEQUENCE: 289

Cys Met Ala Ser Asn Thr Tyr Gly Ser Asn Pro Ile Ser
1               5                   10

<210> SEQ ID NO 290
<211> LENGTH: 21
<212> TYPE: PRT
<213> ORGANISM: Artificial Sequence
<220> FEATURE:
<223> OTHER INFORMATION: Synthetic Construct

<400> SEQUENCE: 290

Ser Phe His His Pro Tyr Cys Asn Tyr Gly Asn Ser Asn Asn Cys
1               5                   10                  15

His Gly Thr Met Ser
            20

<210> SEQ ID NO 291

<400> SEQUENCE: 291

000

<210> SEQ ID NO 292
<211> LENGTH: 15
<212> TYPE: PRT
<213> ORGANISM: Homo sapiens

<400> SEQUENCE: 292

Ile Thr Met Met Cys Met Ala Ser Asn Thr Tyr Gly Ser Asn Pro
1               5                   10                  15

<210> SEQ ID NO 293
<211> LENGTH: 15
<212> TYPE: PRT
<213> ORGANISM: Homo sapiens

<400> SEQUENCE: 293

Met Met Cys Met Ala Ser Asn Thr Tyr Gly Ser Asn Pro Ile Ser
1               5                   10                  15

<210> SEQ ID NO 294
<211> LENGTH: 15
<212> TYPE: PRT
<213> ORGANISM: Homo sapiens

<400> SEQUENCE: 294

Cys Met Ala Ser Asn Thr Tyr Gly Ser Asn Pro Ile Ser Val Tyr
1               5                   10                  15

<210> SEQ ID NO 295
<211> LENGTH: 15
<212> TYPE: PRT
<213> ORGANISM: Homo sapiens

<400> SEQUENCE: 295

Ala Ser Asn Thr Tyr Gly Ser Asn Pro Ile Ser Val Tyr Ile Gly
1               5                   10                  15

<210> SEQ ID NO 296
<211> LENGTH: 15
<212> TYPE: PRT
<213> ORGANISM: Homo sapiens

<400> SEQUENCE: 296

Leu Ala Phe Tyr Ser Phe His His Pro Tyr Cys Asn Tyr Tyr Gly
1               5                   10                  15

<210> SEQ ID NO 297
<211> LENGTH: 15
<212> TYPE: PRT
<213> ORGANISM: Homo sapiens

<400> SEQUENCE: 297

Phe Tyr Ser Phe His His Pro Tyr Cys Asn Tyr Tyr Gly Asn Ser
1               5                   10                  15

<210> SEQ ID NO 298
<211> LENGTH: 15
<212> TYPE: PRT
<213> ORGANISM: Homo sapiens

<400> SEQUENCE: 298

Ser Phe His His Pro Tyr Cys Asn Tyr Tyr Gly Asn Ser Asn Asn
1               5                   10                  15

<210> SEQ ID NO 299
<211> LENGTH: 15
<212> TYPE: PRT
<213> ORGANISM: Homo sapiens

<400> SEQUENCE: 299

His His Pro Tyr Cys Asn Tyr Tyr Gly Asn Ser Asn Asn Cys His
1               5                   10                  15

<210> SEQ ID NO 300
<211> LENGTH: 15
<212> TYPE: PRT
<213> ORGANISM: Homo sapiens

<400> SEQUENCE: 300

Pro Tyr Cys Asn Tyr Tyr Gly Asn Ser Asn Asn Cys His Gly Thr
1               5                   10                  15

<210> SEQ ID NO 301
<211> LENGTH: 15
<212> TYPE: PRT
<213> ORGANISM: Homo sapiens

<400> SEQUENCE: 301

Cys Asn Tyr Tyr Gly Asn Ser Asn Asn Cys His Gly Thr Met Ser
1               5                   10                  15

<210> SEQ ID NO 302
<211> LENGTH: 15
<212> TYPE: PRT
<213> ORGANISM: Homo sapiens

<400> SEQUENCE: 302

Tyr Tyr Gly Asn Ser Asn Asn Cys His Gly Thr Met Ser Ile Leu

```
<210> SEQ ID NO 303
<211> LENGTH: 15
<212> TYPE: PRT
<213> ORGANISM: Homo sapiens

<400> SEQUENCE: 303

Gly Asn Ser Asn Asn Cys His Gly Thr Met Ser Ile Leu Met Gly
1               5                   10                  15

<210> SEQ ID NO 304
<211> LENGTH: 114
<212> TYPE: PRT
<213> ORGANISM: Artificial Sequence
<220> FEATURE:
<223> OTHER INFORMATION: Synthetic Construct

<400> SEQUENCE: 304

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
                20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser

<210> SEQ ID NO 305
<211> LENGTH: 112
<212> TYPE: PRT
<213> ORGANISM: Artificial Sequence
<220> FEATURE:
<223> OTHER INFORMATION: Synthetic Construct

<400> SEQUENCE: 305

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
                20                  25                  30

Ala Gly Lys Thr Tyr Leu Ser Trp Phe Gln Gln Arg Pro Gly Gln Ser
            35                  40                  45

Pro Arg Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

<210> SEQ ID NO 306
```

```
<211> LENGTH: 114
<212> TYPE: PRT
<213> ORGANISM: Artificial Sequence
<220> FEATURE:
<223> OTHER INFORMATION: Synthetic Construct

<400> SEQUENCE: 306

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser

<210> SEQ ID NO 307
<211> LENGTH: 112
<212> TYPE: PRT
<213> ORGANISM: Artificial Sequence
<220> FEATURE:
<223> OTHER INFORMATION: Synthetic Construct

<400> SEQUENCE: 307

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Ala Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

<210> SEQ ID NO 308
<211> LENGTH: 5
<212> TYPE: PRT
<213> ORGANISM: Artificial Sequence
<220> FEATURE:
<223> OTHER INFORMATION: Synthetic Construct

<400> SEQUENCE: 308

Ser Tyr Gly Leu Ser
1               5

<210> SEQ ID NO 309
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 309

Trp Ile Asn Thr Tyr Ser Gly Val Pro Thr Tyr Ala Gln Gly Phe Thr
1               5                   10                  15
Gly

<210> SEQ ID NO 310
<211> LENGTH: 5
<212> TYPE: PRT
<213> ORGANISM: Artificial Sequence
<220> FEATURE:
<223> OTHER INFORMATION: Synthetic Construct

<400> SEQUENCE: 310

Thr Met Ala Asp Tyr
1               5

<210> SEQ ID NO 311
<211> LENGTH: 5
<212> TYPE: PRT
<213> ORGANISM: Artificial Sequence
<220> FEATURE:
<223> OTHER INFORMATION: Synthetic Construct

<400> SEQUENCE: 311

Ser Tyr Gly Leu Ser
1               5

<210> SEQ ID NO 312
<211> LENGTH: 17
<212> TYPE: PRT
<213> ORGANISM: Artificial Sequence
<220> FEATURE:
<223> OTHER INFORMATION: Synthetic Construct

<400> SEQUENCE: 312

Trp Ile Asn Thr Tyr Ser Gly Val Pro Thr Tyr Ala Gln Gly Phe Lys
1               5                   10                  15
Gly

<210> SEQ ID NO 313
<211> LENGTH: 5
<212> TYPE: PRT
<213> ORGANISM: Artificial Sequence
<220> FEATURE:
<223> OTHER INFORMATION: Synthetic Construct

<400> SEQUENCE: 313

Thr Met Ala Asp Tyr
1               5

<210> SEQ ID NO 314
<211> LENGTH: 16
<212> TYPE: PRT
<213> ORGANISM: Artificial Sequence
<220> FEATURE:
<223> OTHER INFORMATION: Synthetic Construct

<400> SEQUENCE: 314

Lys Ser Ser Arg Ser Leu Leu Tyr Ser Ala Gly Lys Thr Tyr Leu Ser
1               5                   10                  15
```

```
<210> SEQ ID NO 315
<211> LENGTH: 7
<212> TYPE: PRT
<213> ORGANISM: Artificial Sequence
<220> FEATURE:
<223> OTHER INFORMATION: Synthetic Construct

<400> SEQUENCE: 315

Leu Val Ser Lys Leu Asp Ser
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic Construct

<400> SEQUENCE: 316

Trp Gln Gly Ile Asp Phe His Gln Thr
1               5

<210> SEQ ID NO 317
<211> LENGTH: 16
<212> TYPE: PRT
<213> ORGANISM: Artificial Sequence
<220> FEATURE:
<223> OTHER INFORMATION: Synthetic Construct

<400> SEQUENCE: 317

Lys Ser Ser Arg Ser Leu Leu Tyr Ser Ala Gly Lys Thr Tyr Leu Ser
1               5                   10                  15

<210> SEQ ID NO 318
<211> LENGTH: 7
<212> TYPE: PRT
<213> ORGANISM: Artificial Sequence
<220> FEATURE:
<223> OTHER INFORMATION: Synthetic Construct

<400> SEQUENCE: 318

Leu Val Ser Lys Leu Asp Ser
1               5

<210> SEQ ID NO 319
<211> LENGTH: 9
<212> TYPE: PRT
<213> ORGANISM: Artificial Sequence
<220> FEATURE:
<223> OTHER INFORMATION: Synthetic Construct

<400> SEQUENCE: 319

Trp Gln Gly Ile Asp Phe His Gln Thr
1               5

<210> SEQ ID NO 320
<211> LENGTH: 444
<212> TYPE: PRT
<213> ORGANISM: Artificial Sequence
<220> FEATURE:
<223> OTHER INFORMATION: Synthetic Construct

<400> SEQUENCE: 320

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
            20                  25                  30
```

-continued

Gly Leu Ser Trp Val Arg Gln Ala Pro Gly Gln Gly Leu Glu Trp Met
              35                  40                  45

Gly Trp Ile Asn Thr Tyr Ser Gly Val Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
              85                  90                  95

Ala Arg Thr Met Ala Asp Tyr Trp Gly Gln Gly Thr Leu Val Thr Val
                 100                 105                 110

Ser Ser Ala Ser Thr Lys Gly Pro Ser Val Phe Pro Leu Ala Pro Ser
             115                 120                 125

Ser Lys Ser Thr Ser Gly Gly Thr Ala Ala Leu Gly Cys Leu Val Lys
         130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                 165                 170                 175

Tyr Ser Leu Ser Ser Val Val Thr Val Pro Ser Ser Ser Leu Gly Thr
             180                 185                 190

Gln Thr Tyr Ile Cys Asn Val Asn His Lys Pro Ser Asn Thr Lys Val
         195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                 245                 250                 255

Thr Cys Val Val Val Asp Val Ser His Glu Asp Pro Glu Val Lys Phe
             260                 265                 270

Asn Trp Tyr Val Asp Gly Val Glu Val His Asn Ala Lys Thr Lys Pro
         275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                 325                 330                 335

Lys Gly Gln Pro Arg Glu Pro Gln Val Tyr Thr Leu Pro Pro Ser Arg
             340                 345                 350

Asp Glu Leu Thr Lys Asn Gln Val Ser Leu Thr Cys Leu Val Lys Gly
         355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                 405                 410                 415

Gly Asn Val Phe Ser Cys Ser Val Met His Glu Ala Leu His Asn His
             420                 425                 430

Tyr Thr Gln Lys Ser Leu Ser Leu Ser Pro Gly Lys
         435                 440

<210> SEQ ID NO 321
<211> LENGTH: 443
<212> TYPE: PRT
<213> ORGANISM: Artificial Sequence
<220> FEATURE:
<223> OTHER INFORMATION: Synthetic Construct

<400> SEQUENCE: 321

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440
```

<210> SEQ ID NO 322
<211> LENGTH: 444
<212> TYPE: PRT
<213> ORGANISM: Artificial Sequence
<220> FEATURE:
<223> OTHER INFORMATION: Synthetic Construct

<400> SEQUENCE: 322

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285
```

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Ser Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 323
<211> LENGTH: 443
<212> TYPE: PRT
<213> ORGANISM: Artificial Sequence
<220> FEATURE:
<223> OTHER INFORMATION: Synthetic Construct

<400> SEQUENCE: 323

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
                20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

```
Asp Lys Lys Val Glu Pro Lys Ser Cys Asp Lys Thr His Thr Cys Pro
210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
            245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
290                 295                 300
Val Leu His Gln Asp Trp Leu Asn Gly Lys Glu Tyr Lys Cys Lys Val
305                 310                 315                 320
Ser Asn Lys Ala Leu Pro Ala Ser Ile Glu Lys Thr Ile Ser Lys Ala
                325                 330                 335
Lys Gly Gln Pro Arg Glu Pro Gln Val Tyr Thr Leu Pro Pro Ser Arg
                340                 345                 350
Asp Glu Leu Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly
                435                 440

<210> SEQ ID NO 324
<211> LENGTH: 444
<212> TYPE: PRT
<213> ORGANISM: Artificial Sequence
<220> FEATURE:
<223> OTHER INFORMATION: Synthetic Construct

<400> SEQUENCE: 324

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Ala Phe Thr Ser Tyr
                20                  25                  30
Gly Leu Ser Trp Val Arg Gln Ala Pro Gly Gln Gly Leu Glu Trp Met
            35                  40                  45
Gly Trp Ile Asn Thr Tyr Ser Gly Val Pro Thr Tyr Ala Gln Gly Phe
        50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Thr Met Ala Asp Tyr Trp Gly Gln Gly Thr Leu Val Thr Val
                100                 105                 110
Ser Ser Ala Ser Thr Lys Gly Pro Ser Val Phe Pro Leu Ala Pro Ser
            115                 120                 125
```

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Ser Lys Ala Phe Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 325
<211> LENGTH: 443
<212> TYPE: PRT
<213> ORGANISM: Artificial Sequence
<220> FEATURE:
<223> OTHER INFORMATION: Synthetic Construct

<400> SEQUENCE: 325

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Thr Met Ala Asp Tyr Trp Gly Gln Gly Thr Leu Val Thr Val
             100                 105                 110

Ser Ser Ala Ser Thr Lys Gly Pro Ser Val Phe Pro Leu Ala Pro Ser
         115                 120                 125

Ser Lys Ser Thr Ser Gly Gly Thr Ala Ala Leu Gly Cys Leu Val Lys
     130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Ser Lys Ala Phe Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 326
<211> LENGTH: 444
<212> TYPE: PRT

<213> ORGANISM: Artificial Sequence
<220> FEATURE:
<223> OTHER INFORMATION: Synthetic Construct

<400> SEQUENCE: 326

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser

```
                385                 390                 395                 400
        Phe Phe Leu Tyr Ser Lys Leu Thr Val Asp Lys Ser Arg Trp Gln Gln
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Pro Gly Lys
                        435                 440

<210> SEQ ID NO 327
<211> LENGTH: 443
<212> TYPE: PRT
<213> ORGANISM: Artificial Sequence
<220> FEATURE:
<223> OTHER INFORMATION: Synthetic Construct

<400> SEQUENCE: 327

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Thr Ser Tyr
                20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Ala Val
```

|     |     |     |     |     |
| --- | --- | --- | --- | --- |
| 305 | 310 | 315 | 320 | |

Ser Asn Lys Ala Leu Pro Ala Pro Ile Glu Lys Thr Ile Ser Lys Ala
                  325                    330                  335

Lys Gly Gln Pro Arg Glu Pro Gln Val Tyr Thr Leu Pro Pro Ser Arg
                  340                    345                  350

Asp Glu Leu Thr Lys Asn Gln Val Ser Leu Thr Cys Leu Val Lys Gly
                  355                    360                  365

Phe Tyr Pro Ser Asp Ile Ala Val Glu Trp Glu Ser Asn Gly Gln Pro
                  370                    375                  380

Glu Asn Asn Tyr Lys Thr Thr Pro Pro Val Leu Asp Ser Asp Gly Ser
385                        390                    395                  400

Phe Phe Leu Tyr Ser Lys Leu Thr Val Asp Lys Ser Arg Trp Gln Gln
                  405                    410                  415

Gly Asn Val Phe Ser Cys Ser Val Met His Glu Ala Leu His Asn His
                  420                    425                  430

Tyr Thr Gln Lys Ser Leu Ser Leu Ser Pro Gly
                  435                    440

<210> SEQ ID NO 328
<211> LENGTH: 444
<212> TYPE: PRT
<213> ORGANISM: Artificial Sequence
<220> FEATURE:
<223> OTHER INFORMATION: Synthetic Construct

<400> SEQUENCE: 328

Gln Val Gln Leu Val Gln Ser Gly Ser Glu Leu Lys Lys Pro Gly Ala
1                      5                    10                  15

Ser Val Lys Val Ser Cys Lys Ala Ser Gly Tyr Arg Phe Thr Ser Tyr
                  20                    25                  30

Gly Leu Ser Trp Val Arg Gln Ala Pro Gly Gln Gly Leu Glu Trp Met
                  35                    40                  45

Gly Trp Ile Asn Thr Tyr Ser Gly Val Pro Thr Tyr Ala Gln Gly Phe
        50                    55                  60

Lys Gly Arg Phe Val Phe Ser Leu Asp Thr Ser Val Ser Thr Ala Tyr
65                      70                    75                  80

Leu Gln Ile Ser Ser Leu Lys Ala Glu Asp Thr Ala Val Tyr Tyr Cys
                  85                    90                  95

Ala Arg Thr Met Ala Asp Tyr Trp Gly Gln Gly Thr Leu Val Thr Val
                100                  105                110

Ser Ser Ala Ser Thr Lys Gly Pro Ser Val Phe Pro Leu Ala Pro Ser
                115                  120                125

Ser Lys Ser Thr Ser Gly Gly Thr Ala Ala Leu Gly Cys Leu Val Lys
    130                    135                  140

Asp Tyr Phe Pro Glu Pro Val Thr Val Ser Trp Asn Ser Gly Ala Leu
145                      150                  155                160

Thr Ser Gly Val His Thr Phe Pro Ala Val Leu Gln Ser Ser Gly Leu
                165                  170                175

Tyr Ser Leu Ser Ser Val Val Thr Val Pro Ser Ser Ser Leu Gly Thr
                180                  185                190

Gln Thr Tyr Ile Cys Asn Val Asn His Lys Pro Ser Asn Thr Lys Val
                195                  200                205

Asp Lys Lys Val Glu Pro Lys Ser Cys Asp Lys Thr His Thr Cys Pro
    210                    215                  220

Pro Cys Pro Ala Pro Glu Leu Leu Gly Gly Pro Ser Val Phe Leu Phe

```
                225                 230                 235                 240
        Pro Pro Lys Pro Lys Asp Thr Leu Met Ile Ser Arg Thr Pro Glu Val
                        245                 250                 255

Thr Cys Val Val Val Asp Val Ser His Glu Asp Pro Glu Val Lys Phe
                        260                 265                 270

Asn Trp Tyr Val Asp Gly Val Glu Val His Asn Ala Lys Thr Lys Pro
                        275                 280                 285

Arg Glu Glu Gln Tyr Asn Ser Thr Tyr Arg Val Val Ser Val Leu Thr
                        290                 295                 300

Val Leu His Gln Asp Trp Leu Asn Gly Lys Glu Tyr Lys Cys Lys Val
        305                 310                 315                 320

Ser Asn Lys Ala Leu Pro Ala Pro Ile Glu Lys Thr Ile Ser Lys Ala
                        325                 330                 335

Lys Gly Gln Pro Arg Glu Pro Gln Val Tyr Thr Leu Pro Pro Ser Arg
                        340                 345                 350

Asp Glu Leu Thr Lys Asn Gln Val Ser Leu Thr Cys Leu Val Lys Gly
                        355                 360                 365

Phe Tyr Pro Ser Asp Ile Ala Val Glu Trp Glu Ser Asn Gly Gln Pro
                        370                 375                 380

Glu Asn Asn Tyr Lys Thr Thr Pro Pro Val Leu Asp Ser Asp Gly Ser
        385                 390                 395                 400

Phe Phe Leu Tyr Ser Lys Leu Thr Val Asp Lys Ser Arg Trp Gln Gln
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Pro Gly Lys
                        435                 440

<210> SEQ ID NO 329
<211> LENGTH: 443
<212> TYPE: PRT
<213> ORGANISM: Artificial Sequence
<220> FEATURE:
<223> OTHER INFORMATION: Synthetic Construct

<400> SEQUENCE: 329

Gln Val Gln Leu Val Gln Ser Gly Ser Glu Leu Lys Lys Pro Gly Ala
        1               5                   10                  15

Ser Val Lys Val Ser Cys Lys Ala Ser Gly Tyr Arg Phe Thr Ser Tyr
                        20                  25                  30

Gly Leu Ser Trp Val Arg Gln Ala Pro Gly Gln Gly Leu Glu Trp Met
                        35                  40                  45

Gly Trp Ile Asn Thr Tyr Ser Gly Val Pro Thr Tyr Ala Gln Gly Phe
                50                  55                  60

Lys Gly Arg Phe Val Phe Ser Leu Asp Thr Ser Val Ser Thr Ala Tyr
        65                  70                  75                  80

Leu Gln Ile Ser Ser Leu Lys Ala Glu Asp Thr Ala Val Tyr Tyr Cys
                        85                  90                  95

Ala Arg Thr Met Ala Asp Tyr Trp Gly Gln Gly Thr Leu Val Thr Val
                        100                 105                 110

Ser Ser Ala Ser Thr Lys Gly Pro Ser Val Phe Pro Leu Ala Pro Ser
                        115                 120                 125

Ser Lys Ser Thr Ser Gly Gly Thr Ala Ala Leu Gly Cys Leu Val Lys
                        130                 135                 140

Asp Tyr Phe Pro Glu Pro Val Thr Val Ser Trp Asn Ser Gly Ala Leu
```

```
            145                 150                 155                 160
        Thr Ser Gly Val His Thr Phe Pro Ala Val Leu Gln Ser Ser Gly Leu
                            165                 170                 175
        Tyr Ser Leu Ser Ser Val Val Thr Val Pro Ser Ser Leu Gly Thr
                        180                 185                 190
        Gln Thr Tyr Ile Cys Asn Val Asn His Lys Pro Ser Asn Thr Lys Val
                        195                 200                 205
        Asp Lys Lys Val Glu Pro Lys Ser Cys Asp Lys Thr His Thr Cys Pro
                    210                 215                 220
        Pro Cys Pro Ala Pro Glu Leu Leu Gly Gly Pro Ser Val Phe Leu Phe
        225                 230                 235                 240
        Pro Pro Lys Pro Lys Asp Thr Leu Met Ile Ser Arg Thr Pro Glu Val
                        245                 250                 255
        Thr Cys Val Val Val Asp Val Ser His Glu Asp Pro Glu Val Lys Phe
                        260                 265                 270
        Asn Trp Tyr Val Asp Gly Val Glu Val His Asn Ala Lys Thr Lys Pro
                    275                 280                 285
        Arg Glu Glu Gln Tyr Asn Ser Thr Tyr Arg Val Val Ser Val Leu Thr
            290                 295                 300
        Val Leu His Gln Asp Trp Leu Asn Gly Lys Glu Tyr Lys Cys Lys Val
        305                 310                 315                 320
        Ser Asn Lys Ala Leu Pro Ala Pro Ile Glu Lys Thr Ile Ser Lys Ala
                        325                 330                 335
        Lys Gly Gln Pro Arg Glu Pro Gln Val Tyr Thr Leu Pro Pro Ser Arg
                    340                 345                 350
        Asp Glu Leu Thr Lys Asn Gln Val Ser Leu Thr Cys Leu Val Lys Gly
                    355                 360                 365
        Phe Tyr Pro Ser Asp Ile Ala Val Glu Trp Ser Asn Gly Gln Pro
            370                 375                 380
        Glu Asn Asn Tyr Lys Thr Thr Pro Pro Val Leu Asp Ser Asp Gly Ser
        385                 390                 395                 400
        Phe Phe Leu Tyr Ser Lys Leu Thr Val Asp Lys Ser Arg Trp Gln Gln
                        405                 410                 415
        Gly Asn Val Phe Ser Cys Ser Val Met His Glu Ala Leu His Asn His
                        420                 425                 430
        Tyr Thr Gln Lys Ser Leu Ser Leu Ser Pro Gly
                    435                 440

<210> SEQ ID NO 330
<211> LENGTH: 444
<212> TYPE: PRT
<213> ORGANISM: Artificial Sequence
<220> FEATURE:
<223> OTHER INFORMATION: Synthetic Construct

<400> SEQUENCE: 330

Gln Val Gln Leu Val Gln Ser Gly Ser Glu Leu Lys Lys Pro Gly Ala
        1               5                   10                  15
        Ser Val Lys Val Ser Cys Lys Ala Ser Gly Tyr Arg Phe Thr Ser Tyr
                        20                  25                  30
        Gly Leu Ser Trp Val Arg Gln Ala Pro Gly Gln Gly Leu Glu Trp Met
                    35                  40                  45
        Gly Trp Ile Asn Thr Tyr Ser Gly Val Pro Thr Tyr Ala Gln Gly Phe
                50                  55                  60
        Lys Gly Arg Phe Val Phe Ser Leu Asp Thr Ser Val Ser Thr Ala Tyr
```

```
                65                  70                  75                  80
        Leu Gln Ile Ser Ser Leu Lys Ala Glu Asp Thr Ala Val Tyr Tyr Cys
                        85                  90                  95

Ala Arg Thr Met Ala Asp Tyr Trp Gly Gln Gly Thr Leu Val Thr Val
                        100                 105                 110

Ser Ser Ala Ser Thr Lys Gly Pro Ser Val Phe Pro Leu Ala Pro Ser
                        115                 120                 125

Ser Lys Ser Thr Ser Gly Gly Thr Ala Ala Leu Gly Cys Leu Val Lys
                        130                 135                 140

Asp Tyr Phe Pro Glu Pro Val Thr Val Ser Trp Asn Ser Gly Ala Leu
        145                 150                 155                 160

Thr Ser Gly Val His Thr Phe Pro Ala Val Leu Gln Ser Ser Gly Leu
                        165                 170                 175

Tyr Ser Leu Ser Ser Val Val Thr Val Pro Ser Ser Ser Leu Gly Thr
                        180                 185                 190

Gln Thr Tyr Ile Cys Asn Val Asn His Lys Pro Ser Asn Thr Lys Val
                        195                 200                 205

Asp Lys Lys Val Glu Pro Lys Ser Cys Asp Lys Thr His Thr Cys Pro
        210                 215                 220

Pro Cys Pro Ala Pro Glu Leu Leu Gly Gly Pro Ser Val Phe Leu Phe
        225                 230                 235                 240

Pro Pro Lys Pro Lys Asp Thr Leu Met Ile Ser Arg Thr Pro Glu Val
                        245                 250                 255

Thr Cys Val Val Val Asp Val Ser His Glu Asp Pro Glu Val Lys Phe
                        260                 265                 270

Asn Trp Tyr Val Asp Gly Val Glu Val His Asn Ala Lys Thr Lys Pro
                        275                 280                 285

Arg Glu Glu Gln Tyr Asn Ser Thr Tyr Arg Val Val Ser Val Leu Thr
                        290                 295                 300

Val Leu His Gln Asp Trp Leu Asn Gly Lys Glu Tyr Lys Cys Lys Val
        305                 310                 315                 320

Ser Asn Lys Ala Leu Pro Ala Ser Ile Glu Lys Thr Ile Ser Lys Ala
                        325                 330                 335

Lys Gly Gln Pro Arg Glu Pro Gln Val Tyr Thr Leu Pro Pro Ser Arg
                        340                 345                 350

Asp Glu Leu Thr Lys Asn Gln Val Ser Leu Thr Cys Leu Val Lys Gly
                        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
        385                 390                 395                 400

Phe Phe Leu Tyr Ser Lys Leu Thr Val Asp Lys Ser Arg Trp Gln Gln
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Pro Gly Lys
                        435                 440

<210> SEQ ID NO 331
<211> LENGTH: 443
<212> TYPE: PRT
<213> ORGANISM: Artificial Sequence
<220> FEATURE:
<223> OTHER INFORMATION: Synthetic Construct
```

-continued

```
<400> SEQUENCE: 331

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Ser Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
                420                 425                 430

Tyr Thr Gln Lys Ser Leu Ser Leu Ser Pro Gly
            435                 440
```

<210> SEQ ID NO 332
<211> LENGTH: 444
<212> TYPE: PRT
<213> ORGANISM: Artificial Sequence
<220> FEATURE:
<223> OTHER INFORMATION: Synthetic Construct

<400> SEQUENCE: 332

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
                20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
    195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
    275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Ser Lys Ala Phe Pro Ala Pro Ile Glu Lys Thr Ile Ser Lys Ala
                325                 330                 335
```

```
Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 333
<211> LENGTH: 443
<212> TYPE: PRT
<213> ORGANISM: Artificial Sequence
<220> FEATURE:
<223> OTHER INFORMATION: Synthetic Construct

<400> SEQUENCE: 333

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Ser Lys Ala Phe Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 334
<211> LENGTH: 444
<212> TYPE: PRT
<213> ORGANISM: Artificial Sequence
<220> FEATURE:
<223> OTHER INFORMATION: Synthetic Construct

<400> SEQUENCE: 334

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Gln Gly Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

```
Tyr Ser Leu Ser Ser Val Val Thr Val Pro Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 335
<211> LENGTH: 443
<212> TYPE: PRT
<213> ORGANISM: Artificial Sequence
<220> FEATURE:
<223> OTHER INFORMATION: Synthetic Construct

<400> SEQUENCE: 335

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Arg Phe Thr Ser Tyr
                20                  25                  30

Gly Leu Ser Trp Val Arg Gln Ala Pro Gly Gln Gly Leu Glu Trp Met
            35                  40                  45

Gly Trp Ile Asn Thr Tyr Ser Gly Val Pro Thr Tyr Ala Gln Gly Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95
```

Ala Arg Thr Met Ala Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Ala Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 336
<211> LENGTH: 330
<212> TYPE: PRT
<213> ORGANISM: Artificial Sequence
<220> FEATURE:
<223> OTHER INFORMATION: Synthetic Construct

<400> SEQUENCE: 336

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 337
<211> LENGTH: 329
<212> TYPE: PRT
<213> ORGANISM: Artificial Sequence
<220> FEATURE:
<223> OTHER INFORMATION: Synthetic Construct

<400> SEQUENCE: 337

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 338
<211> LENGTH: 330
<212> TYPE: PRT
<213> ORGANISM: Artificial Sequence
<220> FEATURE:
<223> OTHER INFORMATION: Synthetic Construct

<400> SEQUENCE: 338

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 339
<211> LENGTH: 329
<212> TYPE: PRT
<213> ORGANISM: Artificial Sequence
<220> FEATURE:
<223> OTHER INFORMATION: Synthetic Construct

<400> SEQUENCE: 339

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 340
<211> LENGTH: 330
<212> TYPE: PRT
<213> ORGANISM: Artificial Sequence
<220> FEATURE:
<223> OTHER INFORMATION: Synthetic Construct

<400> SEQUENCE: 340

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Ser
            195                 200                 205

Lys Ala Phe Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 341
<211> LENGTH: 329
<212> TYPE: PRT
<213> ORGANISM: Artificial Sequence
<220> FEATURE:
<223> OTHER INFORMATION: Synthetic Construct

<400> SEQUENCE: 341

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Ser
            195                 200                 205

Lys Ala Phe Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 342
<211> LENGTH: 330
<212> TYPE: PRT
<213> ORGANISM: Artificial Sequence
<220> FEATURE:
<223> OTHER INFORMATION: Synthetic Construct

<400> SEQUENCE: 342

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 343
<211> LENGTH: 329
<212> TYPE: PRT
<213> ORGANISM: Artificial Sequence
<220> FEATURE:
<223> OTHER INFORMATION: Synthetic Construct

<400> SEQUENCE: 343

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 344
<211> LENGTH: 107
<212> TYPE: PRT
<213> ORGANISM: Artificial Sequence
<220> FEATURE:
<223> OTHER INFORMATION: Synthetic Construct

<400> SEQUENCE: 344

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 345
<211> LENGTH: 20
<212> TYPE: DNA
<213> ORGANISM: Artificial Sequence
<220> FEATURE:
<223> OTHER INFORMATION: Non-targeting 2

<400> SEQUENCE: 345
gtaggcgcgc cgctctctac                                              20

<210> SEQ ID NO 346
<211> LENGTH: 20
<212> TYPE: DNA
<213> ORGANISM: Artificial Sequence
<220> FEATURE:
<223> OTHER INFORMATION: Non-targeting 2

<400> SEQUENCE: 346
aacccctgat tgtatccgca                                              20

<210> SEQ ID NO 347
<211> LENGTH: 20
<212> TYPE: DNA
<213> ORGANISM: Artificial Sequence

```
<220> FEATURE:
<223> OTHER INFORMATION: MS4A4A-specific guideRNA #1

<400> SEQUENCE: 347
aattgtgtac ccgatataca                                               20

<210> SEQ ID NO 348
<211> LENGTH: 20
<212> TYPE: DNA
<213> ORGANISM: Artificial Sequence
<220> FEATURE:
<223> OTHER INFORMATION: MS4A4A-specific guideRNA #2

<400> SEQUENCE: 348
aaccatgcaa ggaatggaac                                               20

<210> SEQ ID NO 349
<211> LENGTH: 20
<212> TYPE: DNA
<213> ORGANISM: Artificial Sequence
<220> FEATURE:
<223> OTHER INFORMATION: MS4A4A-specific guideRNA #3

<400> SEQUENCE: 349
tattcattcc tagactacct                                               20

<210> SEQ ID NO 350
<211> LENGTH: 20
<212> TYPE: DNA
<213> ORGANISM: Artificial Sequence
<220> FEATURE:
<223> OTHER INFORMATION: MS4A4A-specific guideRNA #4

<400> SEQUENCE: 350
gctctgtact ggctgcatca                                               20

<210> SEQ ID NO 351
<211> LENGTH: 20
<212> TYPE: DNA
<213> ORGANISM: Artificial Sequence
<220> FEATURE:
<223> OTHER INFORMATION: TREM2 #1

<400> SEQUENCE: 351
gccatcacag acgataccct                                               20

<210> SEQ ID NO 352
<211> LENGTH: 20
<212> TYPE: DNA
<213> ORGANISM: Artificial Sequence
<220> FEATURE:
<223> OTHER INFORMATION: TREM2 #2

<400> SEQUENCE: 352 atagggcaa gacacctgca                                                20

<210> SEQ ID NO 353
<211> LENGTH: 20
<212> TYPE: DNA
<213> ORGANISM: Artificial Sequence
<220> FEATURE:
<223> OTHER INFORMATION: TREM2 #3

<400> SEQUENCE: 353
cagcatcccg gtgatccagg                                               20
```

<210> SEQ ID NO 354
<211> LENGTH: 20
<212> TYPE: DNA
<213> ORGANISM: Artificial Sequence
<220> FEATURE:
<223> OTHER INFORMATION: TREM2 #4

<400> SEQUENCE: 354
tggagatctc tggttccccg                                                  20

<210> SEQ ID NO 355
<211> LENGTH: 454
<212> TYPE: PRT
<213> ORGANISM: Artificial Sequence
<220> FEATURE:
<223> OTHER INFORMATION: 4A-313 (huIgG1) sequence

<400> SEQUENCE: 355

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

-continued

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 356
<211> LENGTH: 453
<212> TYPE: PRT
<213> ORGANISM: Artificial Sequence
<220> FEATURE:
<223> OTHER INFORMATION: 4A-313 (huIgG1 heavy chain without C-terminal
      K) sequence

<400> SEQUENCE: 356

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

```
Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
        450

<210> SEQ ID NO 357
<211> LENGTH: 454
<212> TYPE: PRT
<213> ORGANISM: Artificial Sequence
<220> FEATURE:
<223> OTHER INFORMATION: 4A-313 (hIgG1 heavy chain P331S) sequence

<400> SEQUENCE: 357

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met Gln Trp Val Arg Gln Ala Pro Gly Gln Gly Leu Glu Trp Met
            35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
                100                 105                 110
```

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Ser Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 358
<211> LENGTH: 453
<212> TYPE: PRT
<213> ORGANISM: Artificial Sequence
<220> FEATURE:
<223> OTHER INFORMATION: 4A-313 (hIgG1 heavy chain P331S without
     C-terminal K)

<400> SEQUENCE: 358

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
            35                  40                  45

Gly Ala Thr His Pro Gly His Gly Asp Thr Arg Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Ser Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430
```

-continued

Ser Val Met His Glu Ala Leu His Asn His Tyr Thr Gln Lys Ser Leu
        435                 440                 445

Ser Leu Ser Pro Gly
    450

<210> SEQ ID NO 359
<211> LENGTH: 454
<212> TYPE: PRT
<213> ORGANISM: Artificial Sequence
<220> FEATURE:
<223> OTHER INFORMATION: 4A-313 (huIgG1 heavy chain N325S/L328F)
      sequence

<400> SEQUENCE: 359

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Ser Lys Ala Phe Pro

```
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
            355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450
```

<210> SEQ ID NO 360
<211> LENGTH: 453
<212> TYPE: PRT
<213> ORGANISM: Artificial Sequence
<220> FEATURE:
<223> OTHER INFORMATION: 4A-313 (hIgG1 heavy chain N325S/L328F without C-terminal K)

<400> SEQUENCE: 360

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met Gln Trp Val Arg Gln Ala Pro Gly Gln Gly Leu Glu Trp Met
        35                  40                  45
Gly Ala Thr His Pro Gly His Gly Asp Thr Arg Tyr Ala Gln Lys Phe
50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Glu Val Tyr Tyr Gly Phe Arg Ser Tyr Trp Tyr Phe Asp
            100                 105                 110
Leu Trp Gly Arg Gly Thr Leu Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Lys Val Glu Pro
    210                 215                 220
```

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Ser Lys Ala Phe Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
            450

<210> SEQ ID NO 361
<211> LENGTH: 454
<212> TYPE: PRT
<213> ORGANISM: Artificial Sequence
<220> FEATURE:
<223> OTHER INFORMATION: 4A-313 (huIgG1 heavy chain K322A) sequence

<400> SEQUENCE: 361

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Ala Thr His Pro Gly His Gly Asp Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Glu Val Tyr Tyr Gly Phe Arg Ser Tyr Trp Tyr Phe Asp
            100                 105                 110

Leu Trp Gly Arg Gly Thr Leu Val Thr Val Ser Ser Ala Ser Thr Lys
        115                 120                 125
```

-continued

```
Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Ala Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 362
<211> LENGTH: 453
<212> TYPE: PRT
<213> ORGANISM: Artificial Sequence
<220> FEATURE:
<223> OTHER INFORMATION: 4A-313 (huIgG1 heavy chain K322A without
      C-terminal K) sequence

<400> SEQUENCE: 362

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

-continued

Trp Met Gln Trp Val Arg Gln Ala Pro Gly Gln Gly Leu Glu Trp Met
            35                  40                  45
Gly Ala Thr His Pro Gly His Gly Asp Thr Arg Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Glu Val Tyr Tyr Gly Phe Arg Ser Tyr Trp Tyr Phe Asp
            100                 105                 110
Leu Trp Gly Arg Gly Thr Leu Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Lys Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Ala Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445

Ser Leu Ser Pro Gly
            450

<210> SEQ ID NO 363
<211> LENGTH: 219
<212> TYPE: PRT
<213> ORGANISM: Artificial Sequence
<220> FEATURE:
<223> OTHER INFORMATION: 4A-450 - full length light chain

<400> SEQUENCE: 363

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Ala Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ile Asp Phe His Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 364
<211> LENGTH: 219
<212> TYPE: PRT
<213> ORGANISM: Artificial Sequence
<220> FEATURE:
<223> OTHER INFORMATION: 4A-419 - full length light chain

<400> SEQUENCE: 364

Asp Val Val Met Thr Gln Ser Pro Leu Ser Leu Pro Val Thr Leu Gly
1               5                   10                  15

Gln Pro Ala Ser Ile Ser Cys Lys Ser Ser Arg Ser Leu Leu Tyr Ser
            20                  25                  30

Ala Gly Lys Thr Tyr Leu Ser Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Trp Gln Gly
            85                  90                  95

Ile Asp Phe His Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 365
<211> LENGTH: 218
<212> TYPE: PRT
<213> ORGANISM: Artificial Sequence
<220> FEATURE:
<223> OTHER INFORMATION: 4A-313 - full length light chain

<400> SEQUENCE: 365

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Arg Met Asn Trp Tyr Gln Gln Lys Pro Gly Gln Ala Pro
            35                  40                  45

Arg Leu Leu Ile Tyr Gly Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
            85                  90                  95

Glu Val Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```